(12) United States Patent
Bradbury et al.

(10) Patent No.: US 9,999,694 B2
(45) Date of Patent: *Jun. 19, 2018

(54) MULTIMODAL SILICA-BASED NANOPARTICLES

(71) Applicants: SLOAN-KETTERING INSTITUTE FOR CANCER RESEARCH, New York, NY (US); CORNELL UNIVERSITY, Ithaca, NY (US)

(72) Inventors: Michelle S. Bradbury, New York, NY (US); Ulrich Wiesner, Ithaca, NY (US); Oula Penate Medina, Kiel (DE); Andrew Burns, Niskayuna, NY (US); Jason S. Lewis, New York, NY (US); Steven M. Larson, New York, NY (US)

(73) Assignees: Sloan-Kettering Institute for Cancer Research, New York, NY (US); Cornell University, Ithaca, NY (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/215,879

(22) Filed: Mar. 17, 2014

(65) Prior Publication Data
US 2014/0248210 A1 Sep. 4, 2014

Related U.S. Application Data

(63) Continuation-in-part of application No. 13/381,209, filed as application No. PCT/US2010/040994 on Jul. 2, 2010, now Pat. No. 9,625,456.
(Continued)

(51) Int. Cl.
| | |
|---|---|
| *A61K 51/12* | (2006.01) |
| *G01N 33/574* | (2006.01) |
| *G01N 33/543* | (2006.01) |
| *G01N 33/552* | (2006.01) |
| *G01N 33/58* | (2006.01) |
| *G01N 33/60* | (2006.01) |
| *A61K 49/00* | (2006.01) |

(52) U.S. Cl.
CPC ...... *A61K 51/1244* (2013.01); *A61K 49/0002* (2013.01); *A61K 49/0093* (2013.01); *G01N 33/54346* (2013.01); *G01N 33/552* (2013.01); *G01N 33/574* (2013.01); *G01N 33/582* (2013.01); *G01N 33/587* (2013.01); *G01N 33/60* (2013.01)

(58) Field of Classification Search
CPC .......... G01N 33/54346; G01N 33/552; G01N 33/582; G01N 33/587; G01N 33/574; G01N 33/60; A61K 49/0093; A61K 51/1244; A61K 49/0002
See application file for complete search history.

(56) References Cited

U.S. PATENT DOCUMENTS

| | | |
|---|---|---|
| 6,254,852 B1 | 7/2001 | Glajch et al. |
| 8,239,007 B2 | 8/2012 | Voegele et al. |
| (Continued) | | |

FOREIGN PATENT DOCUMENTS

| | | |
|---|---|---|
| WO | WO-2004/108902 A2 | 12/2004 |
| WO | WO-2006/099445 A2 | 9/2006 |
| (Continued) | | |

OTHER PUBLICATIONS

Webb et al., British J. of Cancer (1995) 72, 896-904.*
Ballou, B. et al., Sentinel Lymph Node Imaging Using Quantum Dots in Mouse Tumor Models, Bioconjugate Chem. 18:389-396 (2007).
Bogush, G. H. et al., Preparation of Monodisperse Silica Particles: Control of Size and Mass Fraction, J. Non-Cryst. Solids, 104:95-106 (1988).
Brien, J. F. et al., A Study of the Calcium Carbimide-Ethanol Interaction in Man, Europ. J. Clin. Pharmacol. 14(2):133-41 (1978).
Burns, et al., Fluorescent Silica Nanoparticles with Efficient Urinary Excretion for Nanomedicine, Nano Letters 9(1):442-8 (2009).
Crespi, M. D. et al., Mitroxantrone Affects Topoisomerase Activities in Human Breast Cancer Cells, Biochemical and Biophysical Research Communications, 136(2):521-8 (1986).
(Continued)

*Primary Examiner* — Robert Cabral
(74) *Attorney, Agent, or Firm* — Choate, Hall & Stewart LLP; William R. Haulbrook; Margo R. Monroe

(57) ABSTRACT

The present invention provides a fluorescent silica-based nanoparticle that allows for precise detection, characterization, monitoring and treatment of a disease such as cancer. The nanoparticle has a range of diameters including between about 0.1 nm and about 100 nm, between about 0.5 nm and about 50 nm, between about 1 nm and about 25 nm, between about 1 nm and about 15 nm, or between about 1 nm and about 8 nm. The nanoparticle has a fluorescent compound positioned within the nanoparticle, and has greater brightness and fluorescent quantum yield than the free fluorescent compound. The nanoparticle also exhibits high biostability and biocompatibility. To facilitate efficient urinary excretion of the nanoparticle, it may be coated with an organic polymer, such as poly(ethylene glycol) (PEG). The small size of the nanoparticle, the silica base and the organic polymer coating minimizes the toxicity of the nanoparticle when administered in vivo. In order to target a specific cell type, the nanoparticle may further be conjugated to a ligand, which is capable of binding to a cellular component associated with the specific cell type, such as a tumor marker. In one embodiment, a therapeutic agent may be attached to the nanoparticle. To permit the nanoparticle to be detectable by not only optical fluorescence imaging, but also other imaging techniques, such as positron emission tomography (PET), single photon emission computed tomography (SPECT), computerized tomography (CT), bioluminescence imaging, and magnetic resonance imaging (MRI), radionuclides/radiometals or paramagnetic ions may be conjugated to the nanoparticle.

48 Claims, 50 Drawing Sheets
(13 of 50 Drawing Sheet(s) Filed in Color)

Related U.S. Application Data

(60) Provisional application No. 61/794,414, filed on Mar. 15, 2013, provisional application No. 61/222,851, filed on Jul. 2, 2009, provisional application No. 61/312,827, filed on Mar. 11, 2010.

(56) References Cited

U.S. PATENT DOCUMENTS

| | | | |
|---|---|---|---|
| 8,298,677 | B2 | 10/2012 | Wiesner et al. |
| 8,389,679 | B2 * | 3/2013 | Eckert et al. ............ 530/324 |
| 8,409,876 | B2 | 4/2013 | Wiesner et al. |
| 2003/0219785 | A1 * | 11/2003 | Hallahan ............ A61K 31/70 435/6.17 |
| 2004/0101822 | A1 | 5/2004 | Wiesner et al. |
| 2004/0248856 | A1 | 12/2004 | Lanza et al. |
| 2006/0106306 | A1 * | 5/2006 | Essner ............ A61B 8/0833 600/436 |
| 2006/0183246 | A1 | 8/2006 | Wiesner et al. |
| 2006/0251726 | A1 | 11/2006 | Lin et al. |
| 2008/0097225 | A1 * | 4/2008 | Tearney ............ A61B 18/22 600/478 |
| 2008/0139787 | A1 | 6/2008 | De Jesus et al. |
| 2008/0213377 | A1 | 9/2008 | Bhatia et al. |
| 2008/0292556 | A1 | 11/2008 | Texier-Nogues et al. |
| 2010/0262017 | A1 * | 10/2010 | Frangioni ............ A61B 1/0005 600/476 |
| 2011/0028662 | A1 * | 2/2011 | Wiesner ............ A61K 49/0032 525/478 |
| 2013/0039848 | A1 | 2/2013 | Bradbury et al. |
| 2015/0343091 | A1 | 12/2015 | Yoo et al. |

FOREIGN PATENT DOCUMENTS

| | | |
|---|---|---|
| WO | WO-2007/002540 A2 | 1/2007 |
| WO | WO2007002540 A2 * | 4/2007 |
| WO | WO-2007/149062 A2 | 12/2007 |
| WO | WO-2009/029870 A2 | 3/2009 |
| WO | WO 2009064964 A2 * | 5/2009 |
| WO | WO-2011/084620 A2 | 7/2011 |
| WO | WO-2013/192609 A1 | 12/2013 |

OTHER PUBLICATIONS

Cressman, S. et al., Binding and Uptake of RGD-Containing Ligands to Cellular $\alpha_v\beta 3$ Integrins, Int J Pept Res Ther, 15:49-59 (2009).

Cristy, M. and Eckerman, K. F., Specific absorbed fractions of energy at various ages from internal photon sources (I-VII). Oak Ridge National Laboratory Report ORNL/TM-8381N1-7. Springfield, VA: National Technical Information Service, Dept. of Commerce (1987).

Crow, R. T. and Crothers, D. M., Inhibition of Topoisomerase I by Anthracycline Antibiotics: Evidence for General Inhibition of Topoisomerase I by DNA-Binding Agents, J. Med. Chem. 37(19):3191-3194 (1994).

De Jong, M. et al., Comparison of [111]In-Labeled Somatostatin Analogues for Tumor Scintigraphy and Radionuclide Therapy, Cancer Res., 58:437-41 (1998).

De Jong, M. et al., Internalization of radiolabelled [DTPA[0]]octreotide and [DOTA0,Tyr[3]]ocetreotide:peptides for somatostatin receptor-targeted scintigraphy and radionuclide therapy, Nucl. Med. Commun., 19(3):283-288 (1998).

Denny, W. A. and Baguley, B. C., Dual Topoisomerase I/II Inhibitors in Cancer Therapy, Curr. Top. Med. Chem., 3(3):339-353 (2003).

Doronina, S. O. et al., Novel Peptide Linkers for Highly Potent Antibody Auristatin Conjugate, Bioconjugate Chem., 19(10):1960-1963, (2008).

Foglesong, P. D. et al., Doxorubicin inhibits human DNA topoisomerase I, Cancer Chemother. Pharmacol., 30(2):123-125 (1992).

Gatto, B. et al., Identification of Topoisomerase I as the Cytotoxic Target of the Protoberberine Alkaloid Coralyne, Cancer Res., 15(12):2795-2800 (1996).

Gladson, C. A. and Cheresh, D. A., Glioblastoma Expression of Vitronectin and Alpha v Beta 3 Integrin, Adhesion Mechanism for Transformed Glial Cells, J. Clin. Invest. 88:1924-1932 (1991).

Herz, E. et al., Large Stokes-Shift Fluorescent Silica Nanoparticles with Enhanced Emission over Free Dye for Single Excitation Multiplexing, Macromol Rapid Commun., 30(22):1907-1910 (2009).

Hilderbrand, S. A. and Weissleder, R., Near-infrared fluorescence: application to in vivo molecular imaging, Curr. Opin. Chem. Bioi., 14:71-9 (2010).

International Search Report, PCT/US2010/040994, dated Aug. 30, 2010.

International Search Report, PCT/US2015/032565, 4 pages, dated Aug. 21, 2015.

Kim, S. et al., Near-infrared fluorescent type II quantum dots for sentinel lymph node mapping, Nature Biotechnology 22(1):93-97 (2004).

Koole et al., Paramagnetic lipid-coated silica nanoparticles with a fluorescent quantum dot core: a new contrast agent platform for multimodality imaging, Bioconjugate Chem., 19(12):2471-2479 (2008).

Krenning, E. P. et al, Somatostatin Receptor Scintigraphy with Indium-111-DTPA-D-Phe-1-Octreolide in Man: Metabolism, Dosimetry and Comparison with Iodine-123-Tyr-3-Octreotide, J Nucl. Med. 33:652-8 (1992).

Larson, D. R. et al., Silica Nanoparticle Architecture Determines Radiative Properties of Encapsulated Fluorophores, Chem. Mater. 20:2677-2684 (2008).

Lewis et al. Comparison of Four 64Cu-labeled Somatostatin Analogs in Vitro and in a Tumor-Bearing Rat Model: Evaluation of New Derivatives for Positron Emission Imaging and Targeted Radiotherapy. J Med Chem., 42:1341-7 (1999).

Li, T. et al., Human Topoisomerase I Poisoning by Protoberberines: Potential Roles for Both Drug-DNA and Drug-Enzyme Interactions, Biochemistry, 39(24):7107-7116 (2000).

Li, Z. et al., $^{64}$Cu-labeled Tetrameric and Octomeric RGD Peptides for Small-Animal PET of Tumor $\alpha_v\beta_3$ Integrin Expression, J. Nucl Med. 48:1162-1171 (2007).

Loir, B. et al., Expression of the MC1 Receptor Gene in Normal and Malignant Human Melanocytes. A Semiquantitative RT-PCR Study, Cell Mol. Biol., 45(7):1083-1092 (1999).

Makhey et al., Sbustitute Benzo[i]phenanthridines as Mammalian Topoisomerase-Targeting Agents, Bioorg. Med. Chem. 11(8):1809-1820 (2003).

McKeage et al., Phase I and Pharmacokinetic Study of an Oral Platinum Complex Given Daily for 5 Days in Patients With Cancer, Journal of Clinical Oncology, 15(7):2691-2700 (1997).

Montet, X. et al., Multivalent Effects of RGD Peptides Obtained by Nanoparticle Display, J. Med. Chem. 49:6087-6093 (2006).

Ohnishi, S. et al., Organic Alternatives to Quantum Dots for Intraoperative Near-Infrared Fluorescent Sentinel Lymph Node Mapping, Molecular Imaging 4(3):172-181 (2005).

Ow, H. et al., Bright and Stable Core-Shell Fluorescent Silica Nanoparticles, Nano Letters, 5(1):113-117 (2005).

Papamicheal, D., The Use of Thymidylate Synthase Inhibitors in the Treatment of Advanced Colorectal Cancer: Current Status, The Oncologist, 4:478-487 (1999).

Patel, K. N. et al., MUC1 plays a role in tumor maintenance in aggressive thryroid carcinomas, Surgery 138(6):994-1002 (2005).

Piatyszek, M.A. et al., Iodo-Gen-Mediated Radioiodination of Nucleic Acids, J. Anal. Biochem. 172(2):356-359 (1988).

Pommier, Y., Topoisomerase I inhibitors: camptothecins and beyond, Nat. Rev. Cancer, 6(10):789-802 (2006).

Reubi, J.C. et al., Distribution of Somatostatin Receptors in Normal and Tumor Tissue, Metabolism, 39(9)(2):78-81 (1990).

Reubi, J.C. et al., Somatostatin Receptors and Their Subtypes in Human Tumors and in Peritumoral Vessels, Metabolism, 45(8)(1):39-41 (1996).

Ruoslahti, E. and Pierschbacher, M. D., New Perspectives in Cell Adhesion: RGD and Integrins, Science 238:491 (1987).

(56) References Cited

OTHER PUBLICATIONS

Sadasivan, et al., Alcoholic Solvent Effect on Silica Synthesis-NMR and DLS Investigation, J. Sol-Gel Science and Technology, 12:5-14 (1998).
Seftor, R. E. B. et al., Role of the alpha v beta 3 integrin in human melanoma cell invasion, Proc. Natl. Acad. Sci., 89:1557-1561 (1992).
Seymour, L.W., Passive Tumor Targeting of Soluble Macromolecules and Drug Conjugates, Critical Reviews in Therapeutic Drug Carrier Systems, 9(2):135-187 (1992).
Stabin, M. G. et al., OLINDA/EXM: The Second-Generation Personal Computer Software for Internal Dose Assessment in Nuclear Medicine, J Nucl Med. 46:1023-1027 (2005).
Tanaka, E. et al, Image-Guided Oncologic Surgery Using Invisible Light: Completed Pre-Clinical Development for Sentinel Lymph Node Mapping, Annals of Surgical Oncology 13(12):1671-1681 (2006).
Vejayakumaran, P. et al., Structural and thermal characterizations of silica nanoparticles grafted with pendant maleimide and epoxide grops, Journal of Colloid and Interface Science, 328:81-91 (2008).
Wang, Y. et al., Tumor cell targeted delivery by specific peptide-modified mesoporous silica nanoparticles, J. Mater. Chem., 22:14608-14616, (2012).
Webster, A. et al., Optical calcium sensors: development of a generic method for their introduction to the cell using conjugated cell penetrating peptides, Analyst, 130:163-70 (2005).
Written Opinion, PCT/US2010/040994, dated Aug. 30, 2010.
Written Opinion, PCT/US2015/032565, 6 pages, dated Aug. 21, 2015.
Xu, Z. et al., DNA Minor Groove Biding-Directed Poisoning of Human DNA Topoisomerase I by Terbenzimidazoles, Biochemistry 37(10):3558-3566 (1998).
Zhong, Y. J. et al., Cathepsin B-cleavable doxorubicin prodrugs for targeted cancer therapy (Review), International Journal of Oncology, 42:373-383, (2013).
Chakraborty, M. et al., External Beam Radiation of Tumors Alters Phenotype of Tumor Cells to Render Them Susceptible to Vaccine-Mediated T-Cell Killing, Cancer Research, 64:4328-4337 (2004).
Ding, Y. et al., The performance of thiol-terminated PEG-paclitaxel-conjugated gold nanoparticles, Biomaterials, 34:10217-10227 (2013).
Frauwirth, K. A. and Thompson, C. B., Activation and inhibition of lymphocytes by costimulation, The Journal of clinical Investigation, 109(3):295-299 (2002).
Kalbasi, A. et al., Radiation and immunotherapy: a synergistic combination, Clinical review, The Journal of Clinical Investigation, 127(7):2756-2763 (2013).
Kim, Y. H. et al., In situ vaccination against mycosis fungoides by intratumoral injection of a TLR9 agonist combined with radiation: a phase 1/2 study, Blood, 119(2):355-363 (2012).
Seung, S. K. et al., Phase 1 Study of Stereotactic Body Radiotherapy and Interleukin-2: Tumor and Immunological Responses, Science Translational Medicine 14(137):137ra74 1-7 (2012).
Slowing, I. I. et al., Mesoporous silica nanoparticles as controlled release drug delivery and gene transfection carriers, Advanced Drug Delivery Reviews, 60:1278-1288 (2008).
Takeshima, T. et al., Local Radiation Therapy Inhibits Tumor Growth through the Generation of Tumor-Specific CTL: Its Potentiation by Combination with Th1 Cell Therapy, Cancer Research, 70(7):2697-2706 (2010).
Topalian, S. L. et al., Safety, Activity, and Immune Correlates of Anti-PD-1 Antibody in Cancer, The New England Journal of Medicine, 366(26):2443-2454 (2012).
Wersäll, P.J. et al., Regression of non-irradiated metastases after extracranial stereotactic radiotherapy in metastatic renal cell carcinoma, Acta Oncologica, 45:493-497 (2006).
Zeng, J. et al., Anti-PD-1 Blockade and Stereotactic Radiation Produce Long-Term Survival in Mice With Intracranial Gliomas, Intl. J. Radiation Oncol. Biol. Phys., 86(2):343-349 (2013).
Cho, Y. S. et al., Cetuximab-conjugated magneto-fluorescent silica nanoparticles for in vivo colon cancer targeting and imaging, Cancer Letters, 299:63-71 (2010).
European Extended Search Report, Application No. 14763612.0, 10 pages, dated Oct. 19, 2016.
Prosecution File History of Chinese Application 201080039307.2 as of Oct. 5, 2016, 54 pages.
Prosecution File History of European Application No. 10 794 842.4 as of Jul. 29, 2016, 30 pages.
Soster, M. et al., Targeted dual-color silica nanoparticles provide univocal identification of micrometastases in preclinical models of colorectal cancer, International Journal of Nanomedicine, 7:4797-4807 (2012).
Wang, X. et al., Folate Receptor-Targeted Aggregation-Enhanced Near-IR Emitting Silica Nanoprobe for One-Photon in Vivo and Two-Photon ex Vivo Fluorescence Bioimaging, Bioconjugate Chemistry, 22:1438-1450 (2011).
Wu, P. et al., Imaging Breast Cancer Cells and Tissues Using Peptide-Labeled Fluorescent Silica Nanoparticles, Journal of Nanoscience and Nanotechnology, 8(5):2483-2487 (2008).

* cited by examiner a.

Vehicle control            $^{127}$I-RGDY-PEG dots b.

Tyr³-octreotate = DPhe-Cys-Tyr-DTrp-Lys-Thr-Cys-Thr-OH

"clickable" Tyr³-octreotate: R = N₃ containing group

Tyr³-octreotate: R = H

A

B

A

B

B16F10 mice (1 x 10⁶ cells in 100 ul hindleg injection)
$^{125}$I- MSH-PEG-C dots M21 mice (2.5 x 10⁶ cells in 100 ul hindleg injection)
$^{177}$Lu-α-MSH-PEG-C dots

A

B

MULTIMODAL SILICA-BASED NANOPARTICLES

CROSS REFERENCE TO RELATED APPLICATIONS

This application claims priority to U.S. Provisional Application No. 61/794,414 filed Mar. 15, 2013. This application is also a continuation-in-part of U.S. patent application Ser. No. 13/381,209, which is a 371 national stage filing of International Application No. PCT/US10/40994 filed Jul. 2, 2010, which claims priority to U.S. Provisional Application Nos. 61/222,851 (filed Jul. 2, 2009) and 61/312,827 (filed Mar. 11, 2010). The disclosure of each of the above-identified applications is incorporated by reference in their entirety.

STATEMENT REGARDING FEDERALLY SPONSORED RESEARCH OR DEVELOPMENT

This invention was made with government support under grant numbers CA086438, CA083084, CA008748, RR024996, and CA161280 awarded by National Institutes of Health. The government has certain rights in the invention.

FIELD OF THE INVENTION

The present invention relates to fluorescent silica-based nanoparticles, and methods of using the nanoparticles to detect, diagnose, or treat diseases such as cancer.

BACKGROUND OF THE INVENTION

Early tumor detection and treatment selection is paramount to achieving therapeutic success and long-term survival rates. At its early stage, many cancers are localized and can be treated surgically. However, in surgical settings, the evaluation of metastatic disease spread and tumor margins, particularly in areas of complex anatomy, is limited by a lack of imaging technologies. This has led to a disproportionate number of invasive biopsies. Molecularly-targeted probes incorporating contrast-producing (i.e., optical, PET) labels and offering improved specificity are needed for early imaging detection of molecular differences between normal and tumor cells, such as cancer-specific alterations in receptor expression levels. When combined with higher-sensitivity and higher-resolution imaging tools, specific molecular-targeted probes will greatly improve detection sensitivity, staging, and the monitoring and/or treatment of cancer.

Current fluorescence imaging probes typically consist of single conventional fluorophore (e.g., organic dyes, fluorescent proteins), fluorescent proteins (e.g., GFP) and semiconductor quantum dots (Q-dots). Single fluorophores are usually not stable and have limited brightness for imaging. Similar to dyes, the fluorescent proteins tend to exhibit excited state interactions which can lead to stochastic blinking, quenching and photobleaching. Q-dots are generally made from heavy metal ions such as $Pb^{2+}$ or $Cd^{2+}$ and, therefore, are toxic. Burns et al. "Fluorescent core-shell silica nanoparticles: towards "Lab on a Particle" architectures for nanobiotechnology", *Chem. Soc. Rev.*, 2006, 35, 1028-1042.

Fluorescent nanoparticles having an electrically conducting shell and a silica core are known and have utility in modulated delivery of a therapeutic agent. U.S. Pat. Nos. 6,344,272 and 6,428,811. A shortcoming of existing fluorescent nanoparticles is their limited brightness and their low detectability as fluorescent probes in dispersed systems.

The present multifunctional fluorescent silica-based nanoparticles offer many advantages over other typically larger diameter particle probes. The nanoparticles are non-toxic, exhibit excellent photophysical properties (including fluorescent efficiency and photostability), and demonstrate enhanced binding affinity, potency, as well as a distinct pharmacokinetic signature—one in which bulk renal clearance predominates without significant reticuloendothelial system (RES) uptake. Their relatively small size, and surface PEG coating facilitates excellent renal clearance. The fluorescent nanoparticles of the present invention contain a fluorescent core and silica shell. The core-shell architectures, the great surface area and diverse surface chemistry of the nanoparticle permit multiple functionalities simultaneously delivered to a target cell. For example, the nanoparticle can be functionalized with targeting moieties, contrast agents for medical imaging, therapeutic agents, or other agents. The targeting moieties on the surface of the nanoparticle may be tumor ligands, which, when combined with nanoparticle-conjugated therapeutic agents, makes the nanoparticle an ideal vehicle for targeting and potentially treating cancer. Webster et al. Optical calcium sensors: development of a generic method for their introduction to the cell using conjugated cell penetrating peptides. *Analyst*, 2005; 130: 163-70. The silica-based nanoparticle may be labeled with contrast agents for PET, SPECT, CT, MRI, and optical imaging.

SUMMARY

The present application provides for a method for detecting tumor cells comprising the steps of: (a) administering to a patient a plurality of fluorescent silica-based nanoparticles in a dose ranging from about 0.01 nanomole/kg body weight to about 1 nanomole/kg body weight, the nanoparticle comprising: a silica-based core comprising a fluorescent compound positioned within the silica-based core; a silica shell surrounding at least a portion of the core; an organic polymer attached to the nanoparticle; a ligand attached to the nanoparticle and capable of binding a tumor marker; and at least one therapeutic agent; and (b) detecting the nanoparticles.

The nanoparticle may be administered subdermally, peritumorally, orally, intravenously, nasally, subcutaneously, intramuscularly or transdermally. A fluorescent silica-based nanoparticle comprising:

The present invention also provides for a fluorescent silica-based nanoparticle comprising: a silica-based core comprising a fluorescent compound positioned within the silica-based core; a silica shell surrounding at least a portion of the core; an organic polymer attached to the nanoparticle; and a ligand attached to the nanoparticle, wherein the nanoparticle has a diameter between about 1 nm and about 15 nm, and after administration of the nanoparticle to a subject, renal clearance of the nanoparticle ranges from about 80% ID (initial dose) to about 100% ID in about 24 hours, or from about 90% ID to about 100% ID in about 24 hours.

The present invention provides a fluorescent silica-based nanoparticle comprising a silica-based core having a fluorescent compound positioned within the silica-based core; a silica shell surrounding at least a portion of the core; an organic polymer attached to the nanoparticle; from about 1 to about 30 ligands, or from about 1 to about 20 ligands attached to the nanoparticle; and a contrast agent or a chelate attached to the nanoparticle.

The diameter of the nanoparticle ranges from about 1 nm to about 25 nm, or from about 1 nm to about 8 nm. The organic polymers that may be attached to the nanoparticle include poly(ethylene glycol) (PEG), polylactate, polylactic acids, sugars, lipids, polyglutamic acid (PGA), polyglycolic acid, poly(lactic-co-glycolic acid) (PLGA), Polyvinyl acetate (PVA), or the combinations thereof.

The ligand may be capable of binding to at least one cellular component, such as a tumor marker. The number of ligands attached to the nanoparticle may also range from about 1 to about 30, from about 1 to about 25, or from about 1 to about 10. Examples of the ligand include peptide, protein, biopolymer, synthetic polymer, antigen, antibody, microorganism, virus, receptor, hapten, enzyme, hormone, chemical compound, pathogen, toxin, surface modifier, or combinations thereof. Peptides such as tripeptide RGD, cyclic peptide cRGD, cyclic peptide cRGDYC, octreotate, EPPT1 and peptide analogs of alpha-MSH are encompassed by the present invention. Any linear, cyclic or branched peptide containing the RGD or alpha-MSH sequence is within the scope of the present invention.

A contrast agent, such as a radionuclide including $^{89}$Zr, $^{64}$Cu, $^{68}$Ga, $^{86}$Y, $^{124}$I and $^{177}$Lu, may be attached to the nanoparticle. The nanoparticle may be attached to a chelate, for example, DFO, DOTA, TETA and DTPA, that is adapted to bind a radionuclide.

The nanoparticle of the present invention may be detected by positron emission tomography (PET), single photon emission computed tomography (SPECT), computerized tomography (CT), magnetic resonance imaging (MRI), optical imaging (such as fluorescence imaging including near-infrared fluorescence (NIRF) imaging), bioluminescence imaging, or combinations thereof.

A therapeutic agent may be attached to the nanoparticle. The therapeutic agents include antibiotics, antimicrobials, antiproliferatives, antineoplastics, antioxidants, endothelial cell growth factors, thrombin inhibitors, immunosuppressants, anti-platelet aggregation agents, collagen synthesis inhibitors, therapeutic antibodies, nitric oxide donors, antisense oligonucleotides, wound healing agents, therapeutic gene transfer constructs, extracellular matrix components, vasodialators, thrombolytics, antimetabolites, growth factor agonists, antimitotics, statin, steroids, steroidal and non-steroidal anti-inflammatory agents, angiotensin converting enzyme (ACE) inhibitors, free radical scavengers, PPAR-gamma agonists, small interfering RNA (siRNA), micro-RNA, and anti-cancer chemotherapeutic agents. The therapeutic agents encompassed by the present invention also include radionuclides, for example, $^{90}$Y, $^{131}$I and $^{177}$Lu. The therapeutic agent may be radiolabeled, such as labeled by binding to radiofluorine $^{18}$F.

After administration of the nanoparticle to a subject, blood residence half-time of the nanoparticle may range from about 2 hours to about 25 hours, from about 3 hours to about 15 hours, or from about 4 hours to about 10 hours. Tumor residence half-time of the nanoparticle after administration of the nanoparticle to a subject may range from about 5 hours to about 5 days, from about 10 hours to about 4 days, or from about 15 hours to about 3.5 days. The ratio of tumor residence half-time to blood residence halftime of the nanoparticle after administration of the nanoparticle to a subject may range from about 2 to about 30, from about 3 to about 20, or from about 4 to about 15. Renal clearance of the nanoparticle after administration of the nanoparticle to a subject may range from about 10% ID (initial dose) to about 100% ID in about 24 hours, from about 30% ID to about 80% ID in about 24 hours, or from about 40% ID to about 70% ID in about 24 hours. In one embodiment, after the nanoparticle is administered to a subject, blood residence half-time of the nanoparticle ranges from about 2 hours to about 25 hours, tumor residence half-time of the nanoparticle ranges from about 5 hours to about 5 days, and renal clearance of the nanoparticle ranges from about 30% ID to about 80% ID in about 24 hours.

When the nanoparticles in the amount of about 100 times of the human dose equivalent are administered to a subject, substantially no anemia, weight loss, agitation, increased respiration, GI disturbance, abnormal behavior, neurological dysfunction, abnormalities in hematology, abnormalities in clinical chemistries, drug-related lesions in organ pathology, mortality, or combinations thereof, is observed in the subject in about 10 to about 14 days.

The present invention also provides a fluorescent silica-based nanoparticle comprising a silica-based core comprising a fluorescent compound positioned within the silica-based core; a silica shell surrounding at least a portion of the core; an organic polymer attached to the nanoparticle; and a ligand attached to the nanoparticle, wherein the nanoparticle has a diameter between about 1 nm and about 15 nm. After administration of the nanoparticle to a subject, blood residence half-time of the nanoparticle may range from about 2 hours to about 25 hours, or from about 2 hours to about 15 hours; tumor residence half-time of the nanoparticle may range from about 5 hours to about 2 days; and renal clearance of the nanoparticle may range from about 30% ID to about 80% ID in about 24 hours. The number of ligands attached to the nanoparticle may range from about 1 to about 20, or from about 1 to about 10. The diameter of the nanoparticle may be between about 1 nm and about 8 nm. A contrast agent, such as a radionuclide, may be attached to the nanoparticle. Alternatively, a chelate may be attached to the nanoparticle. The nanoparticle may be detected by PET, SPECT, CT, MRI, optical imaging, bioluminescence imaging, or combinations thereof. A therapeutic agent may be attached to the nanoparticle. After administration of the nanoparticle to a subject, blood residence half-time of the nanoparticle may also range from about 3 hours to about 15 hours, or from about 4 hours to about 10 hours. Tumor residence half-time of the nanoparticle after administration of the nanoparticle to a subject may also range from about 10 hours to about 4 days, or from about 15 hours to about 3.5 days. The ratio of tumor residence half-time to blood residence half-time of the nanoparticle after administration of the nanoparticle to a subject may range from about 2 to about 30, from about 3 to about 20, or from about 4 to about 15. Renal clearance of the nanoparticle may also range from about 45% ID to about 90% ID in about 24 hours after administration of the nanoparticle to a subject.

Also provided in the present invention is a fluorescent silica-based nanoparticle comprising a silica-based core comprising a fluorescent compound positioned within the silica-based core; a silica shell surrounding at least a portion of the core; an organic polymer attached to the nanoparticle; and a ligand attached to the nanoparticle, wherein the nanoparticle has a diameter between about 1 nm and about 8 nm. After administration of the nanoparticle to a subject, the ratio of tumor residence half-time to blood residence half-time of the nanoparticle ranges from about 2 to about 30, and renal clearance of the nanoparticle ranges from about 30% ID to about 80% ID in about 24 hours.

The present invention further provides a method for detecting a component of a cell comprising the steps of: (a) contacting the cell with a fluorescent silica-based nanoparticle comprising a silica-based core comprising a fluorescent compound positioned within the silica-based core; a silica shell surrounding at least a portion of the core; an organic polymer attached to the nanoparticle; from about 1 to about 30 ligands attached to the nanoparticle; and a contrast agent or a chelate attached to the nanoparticle; and (b) monitoring the binding of the nanoparticle to the cell or a cellular component by at least one imaging technique.

The present invention further provides a method for targeting a tumor cell comprising administering to a cancer patient an effective amount of a fluorescent silica based nanoparticle comprising a silica-based core comprising a fluorescent compound positioned within the silica-based core; a silica shell surrounding at least a portion of the core; an organic polymer attached to the nanoparticle; a ligand attached to the nanoparticle and capable of binding a tumor marker; and at least one therapeutic agent. The nanoparticle may be radiolabeled. The nanoparticle may be administered to the patient by, but not restricted to, the following routes: oral, intravenous, nasal, subcutaneous, local, intramuscular or transdermal.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 6a. Schematic representation of the $^{124}$I-cRGDY-PEG-ylated core-shell silica nanoparticle with surface-bearing radiolabels and peptides and core-containing reactive dye molecules (insets).

FIG. 6b. FCS results and single exponential fits for measurements of Cy5 dyes in solution (black), PEGcoated (PEG-dot, red), and PEG-coated, cRGDY-labeled dots (blue, underneath red data set) showing diffusion time differences as a result of varying hydrodynamic sizes.

FIG. 6c. Hydrodynamic sizes (mean±s.d., n=15), and relative brightness comparisons of the free dye with PEG-coated dots and cRGDY-PEG dots derived from the FCS curves, along with the corresponding dye and particle concentrations.

FIG. 8a. High affinity and specific binding of $^{124}$I-cRGDY-PEG-dots to M21 cells by γ-counting. Inset shows Scatchard analysis of binding data plotting the ratio of the concentration receptor-bound (B) to unbound (or free, F) radioligand, or bound-to-free ratio, B/F, versus the receptor-bound receptor concentration, B; the slope corresponds to the dissociation constant, Kd.

FIG. 8b. $\alpha_v\beta_3$-integrin receptor blocking of M21 cells using flow cytometry and excess unradiolabeled cRGD or anti-$\alpha_v\beta_3$ antibody prior to incubation with cRGDY-PEG-dots.

FIG. 8c. Specific binding of cRGDY-PEG-dots to M21 as against M21L cells lacking surface integrin expression using flow cytometry.

FIG. 8d. Specific binding of cRGDY-PEG-dots to HUVEC cells by flow cytometry. Each bar represents mean±s.d. of three replicates.

FIG. 9a. Biodistribution of $^{124}$I-cRGDY-PEG-dots in M21 tumor-bearing mice at various times from 4 to 168 h p.i. The inset shows a representative plot of these data for blood to determine the residence half-time ($T_{1/2}$).

FIG. 9b. Biodistribution of $^{124}$I-PEG-dots from 4 to 96 h postinjection.

FIG. 9c. Clearance profile of urine samples collected up to 168 hr p.i. of unradiolabeled cRGDY-PEG-dots (n=3 mice, mean±s.d.).

FIG. 9d. Corresponding cumulative % ID/g for feces at intervals up to 168 hr p.i. (n=4 mice). For biodistribution studies, bars represent the mean±s.d.

FIG. 10a. Representative H&E stained liver at 400× (upper frames) and stained kidneys at 200× (lower frames). Mice were treated with a single dose of either non-radiolabeled $^{127}$I-RGDY-PEG-dots or $^{127}$I-PEG-coated dots (control vehicle) via intravenous injection and organs collected 14 days later.

FIG. 10b. Average daily weights for each treatment group of the toxicity study. Scale bar in FIG. 10a corresponds to 100 μm.

FIG. 11a. Representative whole-body coronal microPET images at 4 hrs p.i. demonstrating M21 (left, arrow) and M21L (middle, arrow) tumor uptakes of 3.6 and 0.7% ID/g, respectively, and enhanced M21 tumor contrast at 24 hrs (right).

FIG. 11b. In vivo uptake of $^{124}$I-cRGDY-PEG-dots in $\alpha_v\beta_3$ integrin-overexpressing M21 (black, n=7 mice) and non-expressing M21L (light gray, n=5 mice) tumors and $^{124}$I-PEG-dots in M21 tumors (dark gray, n=5).

FIG. 11c. M21 tumor-to-muscle ratios for $^{124}$I-cRGDY-PEG-dots (black) and $^{124}$I-PEG-dots (gray).

FIG. 11d. Correlation of in vivo and ex-vivo M21 tumor uptakes of cRGDY labeled and unlabeled probes. Each bar represents the mean±s.d.

FIG. 12a. Whole body fluorescence imaging of the tumor site (T) and draining inguinal (ILN) and axillary (ALN) nodes and communicating lymphatics channels (bar, LC) 1-hr p.i. in a surgically-exposed living animal.

FIG. 12b. Corresponding co-registered white-light and high-resolution fluorescence images (upper row) and fluorescence images only (lower row) revealing nodal infrastructure of local and distant nodes, including high endothelial venules (HEV). The larger scale bar in (b) corresponds to 500 μm.

FIG. 14a shows whole-body dynamic $^{18}$F-fluorodeoxyglucose ($^{18}$F-FDG) PET scan demonstrating sagittal, coronal, and axial images through the site of nodal disease in the neck.

FIG. 14c shows the whole body miniswine image.

DETAILED DESCRIPTION OF THE INVENTION

Figure 1:
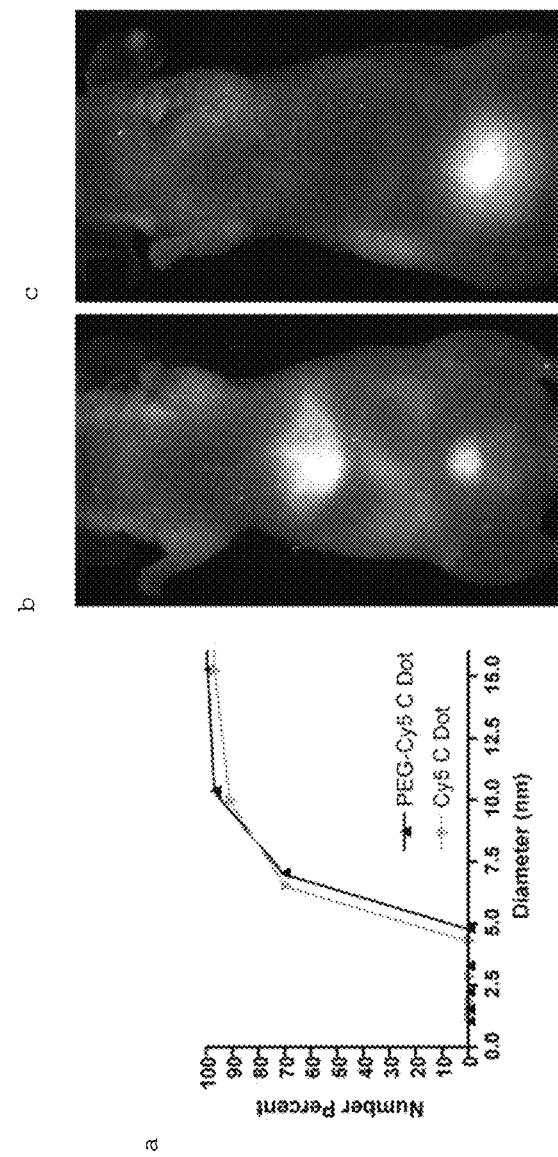
FIG. 1a shows a dynamic light scattering (DLS) plot (number average) of particle size for bare silica (gray) and PEG-coated (black) Cy5-containing silica nanoparticles.
FIG. 1b shows in vivo imaging of spectrally demixed Cy5 particle fluorescence (pseudocolor) overlaid on visible light imaging of nude mice 45 min post-injection with bare silica nanoparticles.
FIG. 1c shows in vivo imaging of spectrally demixed Cy5 particle fluorescence (pseudocolor) overlaid on visible light imaging of nude mice 45 min post-injection with PEG-ylated Cy5 nanoparticles.
FIG. 1d shows in vivo biodistribution study using co-registered PET-CT. Upper row is serial co-registered PET-CT image 24-hr after injection of $^{124}$I-labeled PEG coated nanoparticle, flanked by the independently acquired microCT and microPET scans. Lower row is serial micro-PET imaging.
Figure 1:
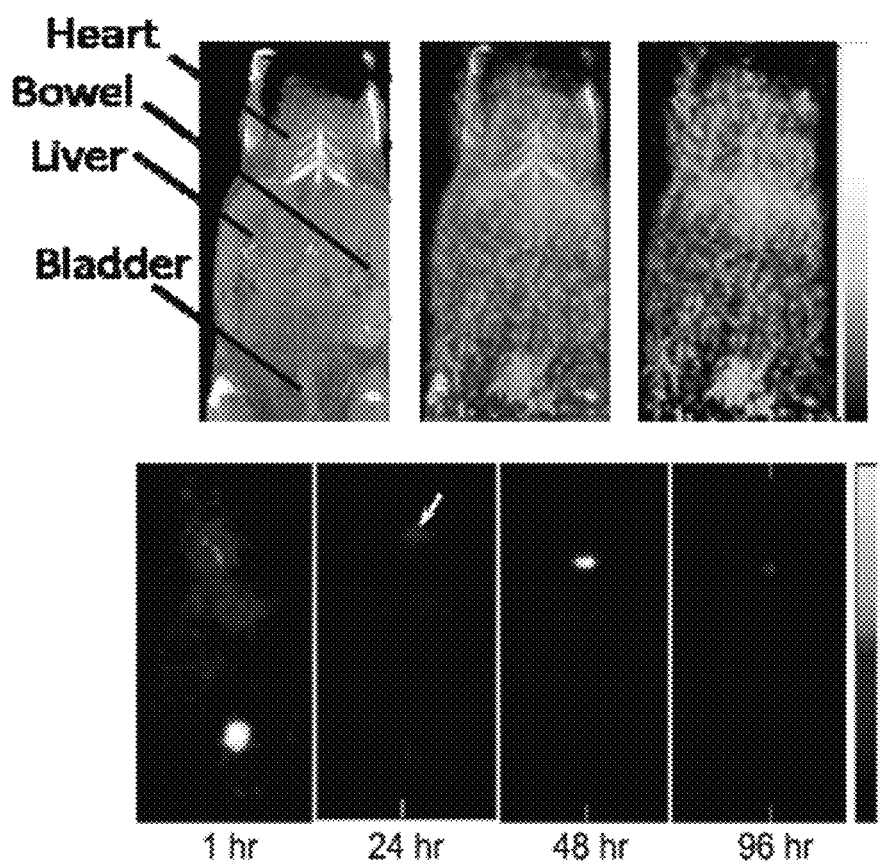

The present invention provides a fluorescent silica-based nanoparticle that allows for precise detection, characterization, monitoring and treatment of a disease such as cancer. The invention also provides for a method for detecting tumor cells. The method may contain the following steps: (a) administering to a patient a plurality of fluorescent silica-based nanoparticles in a dose ranging from about 0.01 nanomole/kg body weight to about 1 nanomole/kg body weight, from about 0.05 nanomole/kg body weight to about 0.9 nanomole/kg body weight, from about 0.1 nanomole/kg body weight to about 0.9 nanomole/kg body weight, from about 0.2 nanomole/kg body weight to about 0.8 nanomole/kg body weight, from about 0.3 nanomole/kg body weight to about 0.7 nanomole/kg body weight, from about 0.4 nanomole/kg body weight to about 0.6 nanomole/kg body weight, or from about 0.2 nanomole/kg body weight to about 0.5 nanomole/kg body weight, and (b) detecting the nanoparticles. In one embodiment, the nanoparticle comprises a silica-based core having a fluorescent compound positioned within the silica-based core; a silica shell surrounding at least a portion of the core; an organic polymer attached to the nanoparticle; a ligand attached to the nanoparticle and capable of binding a tumor marker; and at least one therapeutic agent.

The nanoparticle has a range of diameters including between about 0.1 nm and about 100 nm, between about 0.5 nm and about 50 nm, between about 1 nm and about 25 nm, between about 1 nm and about 15 nm, or between about 1 nm and about 8 nm. The nanoparticle has a fluorescent compound positioned within the nanoparticle, and has greater brightness and fluorescent quantum yield than the free fluorescent compound. The nanoparticle also exhibits high biostability and biocompatibility. To facilitate efficient urinary excretion of the nanoparticle, it may be coated with an organic polymer, such as poly(ethylene glycol) (PEG). The small size of the nanoparticle, the silica base and the organic polymer coating minimizes the toxicity of the nanoparticle when administered in vivo. In order to target a specific cell type, the nanoparticle may further be conjugated to a ligand, which is capable of binding to a cellular component (e.g., the cell membrane or other intracellular component) associated with the specific cell type, such as a tumor marker or a signaling pathway intermediate. In one embodiment, a therapeutic agent may be attached to the nanoparticle. To permit the nanoparticle to be detectable by not only optical imaging (such as fluorescence imaging), but also other imaging techniques, such as positron emission tomography (PET), single photon emission computed tomography (SPECT), computerized tomography (CT), and magnetic resonance imaging (MRI), the nanoparticle may also be conjugated to a contrast agent, such as a radionuclide.

The properties of the nanoparticles lead to bulk excretion through the kidneys, increased potency relative to a native peptide ligand, enhanced uptake, and preferential accumulation in tumors compared with normal tissues. This, along with the lack of in vivo toxicity, has resulted in a unique product resulting in its translation to the clinic.

The present particles can be used to preferentially detect and localize tumors. For example, nanomolar particle tracer doses administered in a microdosing regime accumulate and preferentially localize at sites of disease, although not optimized for targeted detection.

The present nanoparticles may exhibit distinct and reproducible human pharmacokinetic signatures in which renal clearance predominates (e.g., renal clearance of the nanoparticle is greater than about 90% ID in about 24 hours after administration of the nanoparticle to a subject) without significant RES uptake (e.g., less than about 10%).

The present nanoparticles are excellent diagnostic probes, exhibiting optimal physicochemical properties in humans that enable them to "target and clear" the body over relatively short time intervals (e.g., hours, days, etc.).

The present particles bearing multiple actively targeted ligands (e.g., cRGDY and alpha-MSH) demonstrate enhanced binding affinity to the cellular targets compared to the affinity of a ligand alone. In some embodiments, the present particles binds to a cellular target from about 2 to about 20 fold greater, from about 3 to about 15 fold greater, from about 5 to about 10 fold greater than a ligand alone.

In certain embodiments, dual-modality, targeted particles specifically assess tumor burden and can discriminate metastatic tumor from chronic inflammatory disease in large animal models of metastatic melanoma.

Targeted particles may enhance receptor binding affinity and avidity, increase plasma residence times, bioavailability and tumor retention, and/or promote intracellular delivery via internalization. The utilization of such targeted probes within surgical (or medical) oncology settings may enable highly selective treatment of cancer-bearing tissues, potentially reducing attendant complication rates. The present particles may be advantageous over passively targeted nanocarriers, as the latter penetrate and non-specifically accumulate within the tumor interstitium by enhanced permeability and retention (EPR) effects.

Particle-based imaging systems for cancer diagnostics should be non-toxic, and selectively detect sites of primary and metastatic disease while exhibiting relatively rapid renal clearance. Under these conditions, the likelihood of potential toxicity will be reduced given the smaller area under the plasma concentration-time curve. In one embodiment, these renal clearance properties may be achieved by ultrasmall particle-based platforms or macromolecular systems that meet effective renal glomerular filtration size cutoffs of 10 nm or less. Absence of single-dose acute toxicity and the minimization of such risks will also be important. A platform design should maximize safety through rapid whole-body clearance and the selection of biokinetic profiles that minimize non-specific uptake in the reticuloendothelial system (RES), thus reducing potential adverse exposures.

In one embodiment, the present particles are safe and stable in vivo. The particles exhibit distinctly unique and reproducible PK signatures defined by renal excretion. Coupled with preferential uptake and localization of the probe at sites of disease, these particles can be used in cancer diagnostics.

The nanoparticle may have both a ligand and a contrast agent. The ligand allows for the nanoparticle to target a specific cell type through the specific binding between the ligand and the cellular component. This targeting, combined with multimodal imaging, has multiple uses. For example, the nanoparticles can be used to map metastatic disease, such as mapping sentinel lymph nodes (SLN), as well as identifying tumor margins or neural structures, enabling the surgeon to resect malignant lesions under direct visualization and to obviate complications during the surgical procedure. The ligand may also facilitate entry of the nanoparticle into the cell or barrier transport, for example, for assaying the intracellular environment.

The nanoparticle can be coupled with a ligand and a therapeutic agent with or without a radiolabel. The radiolabel can additionally serve as a therapeutic agent for creating a theranostic platform. This coupling allows the therapeutic particle to be delivered to the specific cell type through the specific binding between the ligand and the cellular component. This specific binding of the therapeutic agent ensures selective treatment of the disease site with minimum side effects.

Nanoparticle Structure

The fluorescent nanoparticle of the present invention includes a silica-based core comprising a fluorescent compound positioned within the core, and a silica shell on the core. The silica shell may surround at least a portion of the core. Alternatively, the nanoparticle may have only the core and no shell. The core of the nanoparticle may contain the reaction product of a reactive fluorescent compound and a co-reactive organo-silane compound. In another embodiment, the core of the nanoparticle may contain the reaction product of a reactive fluorescent compound and a co-reactive organo-silane compound, and silica. The diameter of the core may be from about 0.05 nm to about 100 nm, from about 0.1 nm to about 50 nm, from about 0.5 nm to about 25 nm, from about 0.8 nm to about 15 nm, or from about 1 nm to about 8 nm. The shell of the nanoparticle can be the reaction product of a silica forming compound. The shell of the nanoparticle may have a range of layers. For example, the silica shell may be from about 1 to about 20 layers, from about 1 to about 15 layers, from about 1 to about 10 layers, or from about 1 to about 5 layers. The thickness of the shell may range from about 0.01 nm to about 90 nm, from about 0.02 nm to about 40 nm, from about 0.05 nm to about 20 nm, from about 0.05 nm to about 10 nm, or from about 0.05 nm to about 5 nm.

The silica shell of the nanoparticle may cover only a portion of nanoparticle or the entire particle. For example, the silica shell may cover about 1 to about 100 percent, from about 10 to about 80 percent, from about 20 to about 60 percent, or from about 30 to about 50 percent of the nanoparticle. The silica shell can be either solid, i.e., substantially non-porous, meso-porous, such as semi-porous, or porous.

Synthesis of Nanoparticle

The present fluorescent nanoparticle may be synthesized by the steps of: covalently conjugating a fluorescent compound, such as a reactive fluorescent dye, with the reactive moeties including, but not limited to, maleimide, iodoacetamide, thiosulfate, amine, N-Hydroxysuccimide ester, 4-sulfo-2,3,5,6-tetrafluorophenyl (STP) ester, sulfosuccinimidyl ester, sulfodichlorophenol esters, sulfonyl chloride, hydroxyl, isothiocyanate, carboxyl, to an organo-silane compound, such as a co-reactive organo-silane compound, to form a fluorescent silica precursor, and reacting the fluorescent silica precursor to form a fluorescent core; covalently conjugating a fluorescent compound, such as a reactive fluorescent dye, to an organo-silane compound, such as a co-reactive organo-silane compound, to form a fluorescent silica precursor, and reacting the fluorescent silica precursor with a silica forming compound, such as tetraalkoxysilane, to form a fluorescent core; and reacting the resulting core with a silica forming compound, such as a tetraalkoxysilane, to form a silica shell on the core, to provide the fluorescent nanoparticle.

The synthesis of the fluorescent monodisperse core-shell nanoparticles is based on a two-step process. First, the near-infrared organic dye molecules (e.g., tetramethylrhodamine isothiocynate (TRITC)) are covalently conjugated to a silica precursor and condensed to form a dye-rich core. Second, the silica gel monomers are added to form a denser silica network around the fluorescent core material, providing shielding from solvent interactions that can be detrimental to photostability. The versatility of the preparative route allows for the incorporation of different fluorescent compounds, such as fluorescent organic compounds or dyes, depending on the intended nanoparticle application. The fluorescent compounds that may be incorporated in the dye-rich core can cover the entire UV-Vis to near-IR absorption and emission spectrum. U.S. patent application Ser. Nos. 10/306,614, 10/536,569 and 11/119,969. Wiesner et al., PEG-coated Core-shell Silica Nanoparticles and Mathods of Manufactire and Use, PCT/US2008/74894.

For the synthesis of the compact core-shell nanoparticle, the dye precursor is added to a reaction vessel that contains appropriate amounts of ammonia, water and solvent and allowed to react overnight. The dye precursor is synthesized by addition reaction between a specific near-infrared dye of interest and 3-aminopropyltriethoxysilane in molar ratio of 1:50, in exclusion of moisture. After the synthesis of the dye-rich compact core is completed, tetraethylorthosilicate (TEOS) is subsequently added to grow the silica shell that surrounded the core.

The synthesis of the expanded core-shell nanoparticle is accomplished by co-condensing TEOS with the dye precursor and allowing the mixture to react overnight. After the synthesis of the expanded core is completed, additional TEOS is added to grow the silica shell that surrounded the core.

The synthesis of the homogenous nanoparticles is accomplished by co-condensing all the reagents, the dye precursor and TEOS and allowing the mixture to react overnight.

Fluorescent Compound

The nanoparticles may incorporate any known fluorescent compound, such as fluorescent organic compound, dyes, pigments, or combinations thereof. A wide variety of suitable chemically reactive fluorescent dyes are known, see for example MOLECULAR PROBES HANDBOOK OF FLUORESCENT PROBES AND RESEARCH CHEMICALS, 6th ed., R. P. Haugland, ed. (1996). A typical fluorophore is, for example, a fluorescent aromatic or heteroaromatic compound such as is a pyrene, an anthracene, a naphthalene, an acridine, a stilbene, an indole or benzindole, an oxazole or benzoxazole, a thiazole or benzothiazole, a 4-amino-7-nitrobenz-2-oxa-1,3-diazole (NBD), a cyanine, a carbocyanine, a carbostyryl, a porphyrin, a salicylate, an anthranilate, an azulene, a perylene, a pyridine, a quinoline, a coumarin (including hydroxycoumarins and aminocoumarins and fluorinated derivatives thereof), and like compounds, see for example U.S. Pat. Nos. 5,830,912, 4,774, 339, 5,187,288, 5,248,782, 5,274,113, 5,433,896, 4,810,636 and 4,812,409. In one embodiment, Cy5, a near infrared fluorescent (NIRF) dye, is positioned within the silica core of the present nanoparticle. Near infrared-emitting probes exhibit decreased tissue attenuation and autofluorescence. Burns et al. "Fluorescent silica nanoparticles with efficient urinary excretion for nanomedicine", Nano Letters, 2009, 9 (1), 442-448.

Non-limiting fluorescent compound that may be used in the present invention include, Cy5, Cy5.5 (also known as Cy5++), Cy2, fluorescein isothiocyanate (FITC), tetramethylrhodamine isothiocyanate (TRITC), phycoerythrin, Cy7, fluorescein (FAM), Cy3, Cy3.5 (also known as Cy3++), Texas Red, LightCycler-Red 640, LightCycler Red 705, tetramethylrhodamine (TMR), rhodamine, rhodamine derivative (ROX), hexachlorofluorescein (HEX), rhodamine 6G (R6G), the rhodamine derivative JA133, Alexa Fluorescent Dyes (such as Alexa Fluor 488, Alexa Fluor 546, Alexa Fluor 633, Alexa Fluor 555, and Alexa Fluor 647), 4',6-diamidino-2-phenylindole (DAPI), Propidium iodide, AMCA, Spectrum Green, Spectrum Orange, Spectrum Aqua, Lissamine, and fluorescent transition metal complexes, such as europium. Fluorescent compound that can be used also include fluorescent proteins, such as GFP (green fluorescent protein), enhanced GFP (EGFP), blue fluorescent protein and derivatives (BFP, EBFP, EBFP2, Azurite, mKalama1), cyan fluorescent protein and derivatives (CFP, ECFP, Cerulean, CyPet) and yellow fluorescent protein and derivatives (YFP, Citrine, Venus, YPet). WO2008142571, WO2009056282, WO9922026.

The silica shell surface of the nanoparticles can be modified by using known cross-linking agents to introduce surface functional groups. Crosslinking agents include, but are not limited to, divinyl benzene, ethylene glycol dimethacrylate, trimethylol propane trimethacrylate, N,N'-methylenebis-acrylamide, alkyl ethers, sugars, peptides, DNA fragments, or other known functionally equivalent agents. The ligand may be conjugated to the nanoparticle of the present invention by, for example, through coupling reactions using carbodiimide, carboxylates, esters, alcohols, carbamides, aldehydes, amines, sulfur oxides, nitrogen oxides, halides, or any other suitable compound known in the art. U.S. Pat. No. 6,268,222.

Organic Polymer

An organic polymer may be attached to the present nanoparticle, e.g., attached to the surface of the nanoparticle. An organic polymer may be attached to the silica shell of the present nanoparticle. The organic polymer that may be used in the present invention include PEG, polylactate, polylactic acids, sugars, lipids, polyglutamic acid (PGA), polyglycolic acid, poly(lactic-co-glycolic acid) (PLGA), polyvinyl acetate (PVA), and the combinations thereof. The attachment of the organic polymer to the nanoparticle may be accomplished by a covalent bond or non-covalent bond, such as by ionic bond, hydrogen bond, hydrophobic bond, coordination, adhesive, and physical absorption. In one embodiment, the nanoparticle is covalently conjugated with PEG, which prevents adsorption of serum proteins, facilitates efficient urinary excretion and decreases aggregation of the nanoparticle. Burns et al. "Fluorescent silica nanoparticles with efficient urinary excretion for nanomedicine", Nano Letters, 2009, 9 (1), 442-448.

The surface of the nanoparticle may be modified to incorporate at least one functional group. The organic polymer (e.g., PEG) attached to the nanoparticle may be modified to incorporate at least one functional group. For example, the functional group can be a maleimide or N-Hydroxysuccinimide (NHS) ester. The incorporation of the functional group makes it possible to attach various ligands, contrast agents and/or therapeutic agents to the nanoparticle.

Ligand

A ligand may be attached to the present nanoparticle. The ligand is capable of binding to at least one cellular component. The cellular component may be associated with specific cell types or have elevated levels in specific cell types, such as cancer cells or cells specific to particular tissues and organs. Accordingly, the nanoparticle can target a specific cell type, and/or provides a targeted delivery for the treatment and diagnosis of a disease. As used herein, the term "ligand" refers to a molecule or entity that can be used to identify, detect, target, monitor, or modify a physical state or condition, such as a disease state or condition. For example, a ligand may be used to detect the presence or absence of a particular receptor, expression level of a particular receptor, or metabolic levels of a particular receptor. The ligand can be, for example, a peptide, a protein, a protein fragment, a peptide hormone, a sugar (i.e., lectins), a biopolymer, a synthetic polymer, an antigen, an antibody, an antibody fragment (e.g., Fab, nanobodies), an aptamer, a virus or viral component, a receptor, a hapten, an enzyme, a hormone, a chemical compound, a pathogen, a microorganism or a component thereof, a toxin, a surface modifier, such as a surfactant to alter the surface properties or histocompatability of the nanoparticle or of an analyte when a nanoparticle associates therewith, and combinations thereof. In one embodiment, the ligands are antibodies, such as monoclonal or polyclonal antibodies. In another embodiment, the ligands are receptor ligands. In still another embodiment, the ligand is poly-L-lysine (pLysine).

An antigen may be attached to the nanoparticle. The antigen-attached nanoparticle may be used for vaccination.

The terms "component of a cell" or "cellular component" refer to, for example, a receptor, an antibody, a hapten, an enzyme, a hormone, a biopolymer, an antigen, a nucleic acid (DNA or RNA), a microorganism, a virus, a pathogen, a toxin, combinations thereof, and like components. The component of a cell may be positioned on the cell (e.g., a transmembrane receptor) or inside the cell. In one embodiment, the component of a cell is a tumor marker. As used herein, the term "tumor marker" refers to a molecule, entity or substance that is expressed or overexpressed in a cancer cell but not normal cell. For example, the overexpression of certain receptors is associated with many types of cancer. A ligand capable of binding to a tumor marker may be conjugated to the surface of the present nanoparticle, so that the nanoparticle can specifically target the tumor cell.

A ligand may be attached to the present nanoparticle directly or through a linker. The attachment of the ligand to the nanoparticle may be accomplished by a covalent bond or non-covalent bond, such as by ionic bond, hydrogen bond, hydrophobic bond, coordination, adhesive, and physical absorption. The ligand may be coated onto the surface of the nanoparticle. The ligand may be imbibed into the surface of the nanoparticle. The ligand may be attached to the surface of the fluorescent nanoparticle, or may be attached to the core when the shell is porous or is covering a portion of the core. When the ligand is attached to the nanoparticle through a linker, the linker can be any suitable molecules, such as a functionalized PEG. The PEGs can have multiple functional groups for attachment to the nanoparticle and ligands. The particle can have different types of functionalized PEGs bearing different functional groups that can be attached to multiple ligands. This can enhance multivalency effects and/or contrast at the target site, which allows the design and optimization of a complex multimodal platform with improved targeted detection, treatment, and sensing in vivo.

A variety of different ligands may be attached to the nanoparticle. For example, tripeptide Arg-Gly-Asp (RGD) may be attached to the nanoparticle. Alternatively, cyclic peptide cRGD (which may contain other amino acid(s), e.g., cRGDY) may be attached to the nanoparticle. Any linear, cyclic or branched peptide containing the RGD sequence is within the scope of the present invention. RGD binds to $\alpha_v\beta_3$ integrin, which is overexpressed at the surface of activated endothelial cells during angiogenesis and in various types of tumor cells. Expression levels of $\alpha_v\beta_3$ integrin have been shown to correlate well with the aggressiveness of tumors. Ruoslahti et al. New perspectives in cell adhesion: RGD and integrins. *Science* 1987; 238:491. Gladson et al. Glioblastoma expression of vitronectin and alpha v beta 3 integrin. Adhesion mechanism for transformed glial cells. *J. Clin. Invest.* 1991; 88:1924-1932. Seftor et al. Role of the alpha v beta 3 integrin in human melanoma cell invasion. *Proc. Natl. Acad. Sci.* 1992; 89:1557-1561.

Synthetic peptide EPPT1 may be the ligand attached to the nanoparticle. EPPT1, derived from the monoclonal antibody (ASM2) binding site, targets underglycosylated MUC1 (uMUC1). MUC1, a transmembrane receptor, is heavily glycosylated in normal tissues; however, it is overexpressed and aberrantly underglycosylated in almost all human epithelial cell adenocarcinomas, and is implicated in tumor pathogenesis. Moore et al. In vivo targeting of underglycosylated MUC-1 tumor antigen using a multimodal imaging probe. *Cancer Res.* 2004; 64:1821-7. Patel et al. MUC1 plays a role in tumor maintenance in aggressive thyroid carcinomas. *Surgery.* 2005; 138:994-1001. Specific antibodies including monoclonal antibodies against uMUC1 may alternatively be conjugated to the nanoparticle in order to target uMUC1.

In one embodiment, peptide analogues of α-melanotropin stimulating hormone (α-MSH) are the ligands attached to the nanoparticle. Peptide analogues of α-MSH are capable of binding to melanocortin-1 receptors (MC1R), a family of G-protein-coupled receptors overexpressed in melanoma cells. Loir et al. *Cell Mol. Biol.* (Noisy-le-grand) 1999, 45:1083-1092.

In another embodiment, octreotate, a peptide analog of 14-amino acid somatostatin, is the ligand attached to the nanoparticle. Octreotide, which has a longer half-life than somatostatin, is capable of binding to somatostatin receptor (SSTR). SSTR, a member of the G-protein coupled receptor family, is overexpressed on the surface of several human tumors. Reubi et al. Distribution of Somatostatin Receptors in Normal and Tumor-Tissue. *Metab. Clin. Exp.* 1990; 39:78-81. Reubi et al. Somatostatin receptors and their subtypes in human tumors and in peritumoral vessels. *Metab. Clin. Exp.* 1996; 45:39-41. Other somatostatin analogs may alternatively be conjugated to the nanoparticle to target SSTR, such as Tyr3-octreotide (Y3-OC), octreotate (TATE), Tyr3-octreotate (Y3-TATE), and $^{111}$In-DTPA-OC. These somatostatin analogues may be utilized for both PET diagnostic imaging and targeted radiotherapy of cancer. de Jong et al. Internalization of radiolabelled [DTPA$^0$]octreotide and [DOTA$^0$, Tyr$^3$]octreotide: peptides for somatostatin receptor targeted scintigraphy and radionuclide therapy. *Nucl. Med. Commun.* 1998; 19:283-8. de Jong et al. Comparison of $^{111}$In-Labeled Somatostatin Analogues for Tumor Scintigraphy and Radionuclide Therapy. *Cancer Res.* 1998; 58:437-41. Lewis et al. Comparison of four $^{64}$Cu-labeled somatostatin analogs in vitro and in a tumor-bearing rat model: evaluation of new derivatives for PET imaging and targeted radiotherapy. *J Med Chem* 1999; 42:1341-7. Krenning et al. Somatostatin Receptor Scintigraphy with Indium-111-DTPA-D-Phe-1-Octreotide in Man: Metabolism, Dosimetry and Comparison with Iodine-123-Tyr-3-Octreotide. *J Nucl. Med.* 1992; 33:652-8.

Various ligands may be used to map sentinel lymph nodes (SLNs). SLN mapping may be used in diagnosing, staging and treating cancer. J591 is an anti-prostate-specific membrane antigen (i.e., anti-PSMA) monoclonal antibody. J591 has been previously used to detect and stage prostate cancer. Tagawa et al., Anti-prostate-specific membrane antigen-based radioimmunotherapy for prostate cancer, *Cancer,* 2010, 116(4 Suppl):1075-83. Bander et al., Targeting Metastatic Prostate Cancer with Radiolabeled Monoclonal Antibody J591 to the Extracellular Domain of Prostate Specific Membrane Antigen, *The Journal of Urology* 170(5), 1717-1721 (2003). Wernicke et al., (2011) Prostate-Specific Membrane Antigen as a Potential Novel Vascular Target for Treatment of Glioblastoma Multiforme, *Arch Pathol Lab Med.* 2011; 135:1486-1489. The F(ab')2 fragment of J591 may be used as a ligand attached to the present nanoparticle. The nanoparticle may also be radiolabeled to create a dual-modality probe. In one embodiment, nanoparticles bearing the F(ab')2 fragment of J591 (e.g., HuJ591-F(ab')2 fragments, or humanized J591-F(ab')2 fragments) are used in diagnosing prostate cancer or endometrial cancer (e.g., endometrial endometrioid adenocarcinoma). In another embodiment, nanoparticles bearing the F(ab')2 fragment of J591 can be used to target brain tumor neovasculature for treatment, disease progression monitoring. Brain tumor neovasculature has been found to overexpress PSMA, as shown from prior immunohistochemistry evaluations of excised high grade glioma specimens.

Cyclic peptides containing the sequence HWGF are potent and selective inhibitors of MMP-2 and MMP-9 but not of several other MMP family members. Peptide CTTHWGFTLC inhibits the migration of human endothelial cells and tumor cells. Moreover, it prevents tumor growth and invasion in animal models and improves survival of mice bearing human tumors. CTTHWGFTLC-displaying phage specifically targets angiogenic blood vessels in vivo. This peptide and its extension GRENYGHCTTHWGFTLC or GRENYGHCTTHWGFTLS can be used as ligands to be attached to the present nanoparticle. The peptides can also be radiolabelled, e.g., radioiodinated. Koivunen et al., Tumor targeting with a selective gelatinase inhibitor, *Nature Biotechnology* 17, 768-774 (1999). Penate Medina et al., Liposomal tumor targeting in drug delivery utilizing MMP-2- and MMP-9-binding ligands, *J. Drug Delivery*, Volume 2011 (2011), Article ID 160515. *Anticancer Research* 21:4101-4106 (2005). In one embodiment, $^{124}$I labeled matrix metalloproteinase peptide inhibitor (MMPI)-attached nanoparticles are used for SLN mapping to stage endometrioid cancer.

The number of ligands attached to the nanoparticle may range from about 1 to about 30, from about 1 to about 20, from about 2 to about 15, from about 3 to about 10, from about 1 to about 10, or from about 1 to about 6. The small number of the ligands attached to the nanoparticle helps maintain the hydrodynamic diameter of the present nanoparticle which meets the renal clearance cutoff size range. Hilderbrand et al., Near-infrared fluorescence: application to in vivo molecular imaging, *Curr. Opin. Chem. Biol.,* 14:71-9, 2010. The number of ligands measured may be an average number of ligands attached to more than one nanoparticle. Alternatively, one nanoparticle may be measured to determine the number of ligands attached. The number of ligands attached to the nanoparticle can be measured by any suitable methods, which may or may not be related to the properties of the ligands. For example, the number of cRGD peptides bound to the particle may be estimated using FCS-based measurements of absolute particle concentrations and the starting concentration of the reagents for cRGD peptide. Average number of RGD peptides per nanoparticle and coupling efficiency of RGD to functionalized PEG groups can be assessed colorimetrically under alkaline conditions and Biuret spectrophotometric methods. The number of ligands attached to the nanoparticle may also be measured by other suitable methods.

Contrast Agent

A contrast agent may be attached to the present nanoparticle for medical or biological imaging. As used herein, the term "contrast agent" refers to a substance, molecule or compound used to enhance the visibility of structures or fluids in medical or biological imaging. The term "contrast agent" also refers to a contrast-producing molecule. The imaging techniques encompassed by the present invention include positron emission tomography (PET), single photon emission computed tomography (SPECT), computerized tomography (CT), magnetic resonance imaging (MRI), optical bioluminescence imaging, optical fluorescence imaging, and combinations thereof. The contrast agent encompassed by the present invention may be any molecule, substance or compound known in the art for PET, SPECT, CT, MRI, and optical imaging. The contrast agent may be radionuclides, radiometals, positron emitters, beta emitters, gamma emitters, alpha emitters, paramagnetic metal ions, and suprapara-magnetic metal ions. The contrast agents include, but are not limited to, iodine, fluorine, copper, zirconium, lutetium, astatine, yttrium, gallium, indium, technetium, gadolinium, dysprosium, iron, manganese, barium and barium sulfate. The radionuclides that may be used as the contrast agent attached to the nanoparticle of the present invention include, but are not limited to $^{89}$Zr, $^{64}$Cu, $^{68}$Ga, $^{86}$Y, $^{124}$I and $^{177}$Lu.

The contrast agent may be directly conjugated to the nanoparticle. Alternatively, the contrast agent may be indirectly conjugated to the nanoparticle, by attaching to linkers or chelates. The chelate may be adapted to bind a radionuclide. The chelates that can be attached to the present nanoparticle may include, but are not limited to, 1,4,7,10-tetraazacyclododecane-1,4,7,10-tetraacetic acid (DOTA), diethylenetriaminepentaacetic (DTPA), desferrioxamine (DFO) and triethylenetetramine (TETA).

Suitable means for imaging, detecting, recording or measuring the present nanoparticles may also include, for example, a flow cytometer, a laser scanning cytometer, a fluorescence micro-plate reader, a fluorescence microscope, a confocal microscope, a bright-field microscope, a high content scanning system, and like devices. More than one imaging techniques may be used at the same time or consecutively to detect the present nanoparticles. In one embodiment, optical imaging is used as a sensitive, high-throughput screening tool to acquire multiple time points in the same subject, permitting semi-quantitative evaluations of tumor marker levels. This offsets the relatively decreased temporal resolution obtained with PET, although PET is needed to achieve adequate depth penetration for acquiring volumetric data, and to detect, quantitate, and monitor changes in receptor and/or other cellular marker levels as a means of assessing disease progression or improvement, as well as stratifying patients to suitable treatment protocols.

Therapeutic Agent

A therapeutic agent may be attached to the fluorescent nanoparticle, for example, for targeted treatment of a disease. The therapeutic agent may be delivered to a diseased site in a highly specific or localized manner with release of the therapeutic agent in the disease site. Alternatively, the therapeutic agent may not be released. The fluorescent nanoparticle conjugated with the ligand can be used for targeted delivery of a therapeutic agent to a desired location in a variety of systems, such as on, or within, a cell or cell component, within the body of an organism, such as a human, or across the blood-brain barrier.

The therapeutic agent may be attached to the nanoparticle directly or indirectly. The therapeutic agent can be absorbed into the interstices or pores of the silica shell, or coated onto the silica shell of the fluorescent nanoparticle. In other embodiments where the silica shell is not covering the entire surface, the therapeutic agent can be associated with the fluorescent core, such as by physical absorption or by bonding interaction. The therapeutic agent may be associated with the ligand that is attached to the fluorescent nanoparticle. The therapeutic agent may also be associated with the organic polymer or the contrast agent. For example, the therapeutic agent may be attached to the nanoparticle through PEG. The PEGs can have multiple functional groups for attachment to the nanoparticle and therapeutic agent. The particle can have different types of functionalized PEGs bearing different functional groups that can be attached to multiple therapeutic agents. The therapeutic agent may be attached to the nanoparticle covalently or non-covalently.

As used herein, the term "therapeutic agent" refers to a substance that may be used in the diagnosis, cure, mitigation, treatment, or prevention of disease in a human or another animal. Such therapeutic agents include substances recognized in the official United States Pharmacopeia, official Homeopathic Pharmacopeia of the United States, official National Formulary, or any supplement thereof.

Therapeutic agents that can be incorporated with the fluorescent nanoparticles or the ligated-fluorescent nanoparticles of the invention include nucleosides, nucleoside analogs, small interfering RNA (siRNA), microRNA, oligopeptides, polypeptides, antibodies, COX-2 inhibitors, apoptosis promoters, urinary tract agents, vaginal agents, vasodilators neurodegenerative agents (e.g., Parkinson's disease), obesity agents, ophthalmic agents, osteoporosis agents, parasympatholytics, para-sympathometics, antianesthetics, prostaglandins, psychotherapeutic agents, respiratory agents, sedatives, hypnotics, skin and mucous membrane agents, anti-bacterials, anti-fungals, antineoplastics, cardioprotective agents, cardiovascular agents, anti-thrombotics, central nervous system stimulants, cholinesterase inhibitors, contraceptives, dopamine receptor agonists, erectile dysfunction agents, fertility agents, gastrointestinal agents, gout agents, hormones, immunomodulators, suitably functionalized analgesics or general or local anesthetics, anti-convulsants, anti-diabetic agents, anti-fibrotic agents, anti-infectives, motion sickness agents, muscle relaxants, immuno-suppressive agents, migraine agents, non-steroidal anti-inflammatory drugs (NSAIDs), smoking cessation agents, or sympatholytics (see Physicians' Desk Reference, 55th ed., 2001, Medical Economics Company, Inc., Montvale, N.J., pages 201-202).

Therapeutic agents that may be attached to the present nanoparticle include, but are not limited to, DNA alkylating agents, topoisomerase inhibitors, endoplasmic reticulum stress inducing agents, a platinum compound, an antimetabolite, vincalkaloids, taxanes, epothilones, enzyme inhibitors, receptor antagonists, therapeutic antibodies, tyrosine kinase inhibitors, boron radiosensitizers (i.e. velcade), and chemotherapeutic combination therapies.

Non-limiting examples of DNA alkylating agents are nitrogen mustards, such as Mechlorethamine, Cyclophosphamide (Ifosfamide, Trofosfamide), Chlorambucil (Melphalan, Prednimustine), Bendamustine, Uramustine and Estramustine; nitrosoureas, such as Carmustine (BCNU), Lomustine (Semustine), Fotemustine, Nimustine, Ranimustine and Streptozocin; alkyl sulfonates, such as Busulfan (Mannosulfan, Treosulfan); Aziridines, such as Carboquone, ThioTEPA, Triaziquone, Triethylenemelamine; Hydrazines (Procarbazine); Triazenes such as Dacarbazine and Temozolomide; Altretamine and Mitobronitol.

Non-limiting examples of Topoisomerase I inhibitors include Campothecin derivatives including CPT-11 (irinotecan), SN-38, APC, NPC, campothecin, topotecan, exatecan mesylate, 9-nitrocamptothecin, 9-aminocamptothecin, lurtotecan, rubitecan, silatecan, gimatecan, diflomotecan, extatecan, BN-80927, DX-8951f, and MAG-CPT as decribed in Pommier Y. (2006) *Nat. Rev. Cancer* 6(10):789-802 and U.S. Patent Publication No. 200510250854; Protoberberine alkaloids and derivatives thereof including berberrubine and coralyne as described in Li et al. (2000) *Biochemistry* 39(24):7107-7116 and Gatto et al. (1996) *Cancer Res.* 15(12):2795-2800; Phenanthroline derivatives including Benzo[i]phenanthridine, Nitidine, and fagaronine as described in Makhey et al. (2003) *Bioorg. Med. Chem.* 11 (8): 1809-1820; Terbenzimidazole and derivatives thereof as described in Xu (1998) *Biochemistry* 37(10):3558-3566; and Anthracycline derivatives including Doxorubicin, Daunorubicin, and Mitoxantrone as described in Foglesong et al. (1992) *Cancer Chemother. Pharmacol.* 30(2):123-]25, Crow et al. (1994) *J. Med. Chem.* 37(19):31913194, and Crespi et al. (1986) *Biochem. Biophys. Res. Commun.* 136(2):521-8. Topoisomerase II inhibitors include, but are not limited to Etoposide and Teniposide. Dual topoisomerase I and II inhibitors include, but are not limited to, Saintopin and other Naphthecenediones, DACA and other Acridine-4-Carboxamindes, Intoplicine and other Benzopyridoindoles, TAS-I03 and other 7H-indeno[2,1-c]Quinoline-7-ones, Pyrazoloacridine, XR 11576 and other Benzophenazines, XR 5944 and other Dimeric compounds, 7-oxo-7H-dibenz[f,ij]Isoquinolines and 7-oxo-7H-benzo[e]Perimidines, and Anthracenylamino Acid Conjugates as described in Denny and Baguley (2003) *Curr. Top. Med. Chem.* 3(3):339-353. Some agents inhibit Topoisomerase II and have DNA intercalation activity such as, but not limited to, Anthracyclines (Aclarubicin, Daunorubicin, Doxorubicin, Epirubicin, Idarubicin, Amrubicin, Pirarubicin, Valrubicin, Zorubicin) and Antracenediones (Mitoxantrone and Pixantrone).

Examples of endoplasmic reticulum stress inducing agents include, but are not limited to, dimethyl-celecoxib (DMC), nelfinavir, celecoxib, and boron radiosensitizers (i.e. velcade (Bortezomib)).

Non-limiting examples of platinum based compound include Carboplatin, Cisplatin, Nedaplatin, Oxaliplatin, Triplatin tetranitrate, Satraplatin, Aroplatin, Lobaplatin, and JM-216. (see McKeage et al. (1997) *J. Clin. Oncol.* 201: 1232-1237 and in general, CHEMOTHERAPY FOR GYNECOLOGICAL NEOPLASM, CURRENT THERAPY AND NOVEL APPROACHES, in the Series Basic and Clinical Oncology, Angioli et al. Eds., 2004).

Non-limiting examples of antimetabolite agents include Folic acid based, i.e. dihydrofolate reductase inhibitors, such as Aminopterin, Methotrexate and Pemetrexed; thymidylate synthase inhibitors, such as Raltitrexed, Pemetrexed; Purine based, i.e. an adenosine deaminase inhibitor, such as Pentostatin, a thiopurine, such as Thioguanine and Mercaptopurine, a halogenated/ribonucleotide reductase inhibitor, such as Cladribine, Clofarabine, Fludarabine, or a guanine/guanosine: thiopurine, such as Thioguanine; or Pyrimidine based, i.e. cytosine/cytidine: hypomethylating agent, such as Azacitidine and Decitabine, a DNA polymerase inhibitor, such as Cytarabine, a ribonucleotide reductase inhibitor, such as Gemcitabine, or a thymine/thymidine: thymidylate synthase inhibitor, such as a Fluorouracil (5-FU). Equivalents to 5-FU include prodrugs, analogs and derivative thereof such as 5'-deoxy-5-fluorouridine (doxifluroidine), 1-tetrahydrofuranyl-5-fluorouracil (ftorafur), Capecitabine (Xeloda), S-I (MBMS-247616, consisting of tegafur and two modulators, a 5-chloro-2,4dihydroxypyridine and potassium oxonate), ralititrexed (tomudex), nolatrexed (Thymitaq, AG337), LY231514 and ZD9331, as described for example in Papamicheal (1999) The Oncologist 4:478-487.

Examples of vincalkaloids, include, but are not limited to Vinblastine, Vincristine, Vinflunine, Vindesine and Vinorelbine.

Examples of taxanes include, but are not limited to docetaxel, Larotaxel, Ortataxel, Paclitaxel and Tesetaxel. An example of an epothilone is iabepilone.

Examples of enzyme inhibitors include, but are not limited to farnesyltransferase inhibitors (Tipifamib); CDK inhibitor (Alvocidib, Seliciclib); proteasome inhibitor (Bortezomib); phosphodiesterase inhibitor (Anagrelide; rolipram); IMP dehydrogenase inhibitor (Tiazofurine); and lipoxygenase inhibitor (Masoprocol). Examples of receptor antagonists include, but are not limited to ERA (Atrasentan); retinoid X receptor (Bexarotene); and a sex steroid (Testolactone).

Examples of therapeutic antibodies include, but are not limited to anti-HER1/EGFR (Cetuximab, Panitumumab); Anti-HER2/neu (erbB2) receptor (Trastuzumab); Anti-EpCAM (Catumaxomab, Edrecolomab) Anti-VEGF-A (Bevacizumab); Anti-CD20 (Rituximab, Tositumomab, Ibritumomab); Anti-CD52 (Alemtuzumab); and Anti-CD33 (Gemtuzumab). U.S. Pat. Nos. 5,776,427 and 7,601,355.

Examples of tyrosine kinase inhibitors include, but are not limited to inhibitors to ErbB: HER1/EGFR (Erlotinib, Gefitinib, Lapatinib, Vandetanib, Sunitinib, Neratinib); HER2/neu (Lapatinib, Neratinib); RTK class III: C-kit (Axitinib, Sunitinib, Sorafenib), FLT3 (Lestaurtinib), PDGFR (Axitinib, Sunitinib, Sorafenib); and VEGFR (Vandetanib, Semaxanib, Cediranib, Axitinib, Sorafenib); bcr-abl (Imatinib, Nilotinib, Dasatinib); Src (Bosutinib) and Janus kinase 2 (Lestaurtinib).

Chemotherapeutic agents that can be attached to the present nanoparticle may also include amsacrine, Trabectedin, retinoids (Alitretinoin, Tretinoin), Arsenic trioxide, asparagine depleter Asparaginase/Pegaspargase), Celecoxib, Demecolcine, Elesclomol, Elsamitrucin, Etoglucid, Lonidamine, Lucanthone, Mitoguazone, Mitotane, Oblimersen, Temsirolimus, and Vorinostat.

Examples of specific therapeutic agents that can be linked, ligated, or associated with the fluorescent nanoparticles of the invention are flomoxef; fortimicin(s); gentamicin(s); glucosulfone solasulfone; gramicidin S; gramicidin(s); grepafloxacin; guamecycline; hetacillin; isepamicin; josamycin; kanamycin(s); flomoxef; fortimicin(s); gentamicin(s); glucosulfone solasulfone; gramicidin S; gramicidin(s); grepafloxacin; guamecycline; hetacillin; isepamicin; josamycin; kanamycin(s); bacitracin; bambermycin(s); biapenem; brodimoprim; butirosin; capreomycin; carbenicillin; carbomycin; carumonam; cefadroxil; cefamandole; cefatrizine; cefbuperazone; cefclidin; cefdinir; cefditoren; cefepime; cefetamet; cefixime; cefmenoxime; cefminox; cladribine; apalcillin; apicycline; apramycin; arbekacin; aspoxicillin; azidamfenicol; aztreonam; cefodizime; cefonicid; cefoperazone; cefbramide; cefotaxime; cefotetan; cefotiam; cefozopran; cefpimizole; cefpiramide; cefpirome; cefprozil; cefroxadine; cefteram; ceftibuten; cefuzonam; cephalexin; cephaloglycin; cephalosporin C; cephradine; chloramphenicol; chlortetracycline; clinafloxacin; clindamycin; clomocycline; colistin; cyclacillin; dapsone; demeclocycline; diathymosulfone; dibekacin; dihydrostreptomycin; 6-mercaptopurine; thioguanine; capecitabine; docetaxel; etoposide; gemcitabine; topotecan; vinorelbine; vincristine; vinblastine; teniposide; melphalan; methotrexate; 2-p-sulfanilyanilinoethanol; 4,4'-sulfinyldianiline; 4-sulfanilamidosalicylic acid; butorphanol; nalbuphine. streptozocin; doxorubicin; daunorubicin; plicamycin; idarubicin; mitomycin C; pentostatin; mitoxantrone; cytarabine; fludarabine phosphate; butorphanol; nalbuphine. streptozocin; doxorubicin; daunorubicin; plicamycin; idarubicin; mitomycin C; pentostatin; mitoxantrone; cytarabine; fludarabine phosphate; acediasulfone; acetosulfone; amikacin; amphotericin B; ampicillin; atorvastatin; enalapril; ranitidine; ciprofloxacin; pravastatin; clarithromycin; cyclosporin; famotidine; leuprolide; acyclovir; paclitaxel; azithromycin; lamivudine; budesonide; albuterol; indinavir; metformin; alendronate; nizatidine; zidovudine; carboplatin; metoprolol; amoxicillin; diclofenac; lisinopril; ceftriaxone; captopril; salmeterol; xinafoate; imipenem; cilastatin; benazepril; cefaclor; ceftazidime; morphine; dopamine; bialamicol; fluvastatin; phenamidine; podophyllinic acid 2-ethylhydrazine; acriflavine; chloroazodin; arsphenamine; amicarbilide; aminoquinuride; quinapril; oxymorphone; buprenorphine; floxuridine; dirithromycin; doxycycline; enoxacin; enviomycin; epicillin; erythromycin; leucomycin (s); lincomycin; lomefloxacin; lucensomycin; lymecycline; meclocycline; meropenem; methacycline; micronomicin; midecamycin(s); minocycline; moxalactam; mupirocin; nadifloxacin; natamycin; neomycin; netilmicin; norfloxacin; oleandomycin; oxytetracycline; p-sulfanilylbenzylamine; panipenem; paromomycin; pazufloxacin; penicillin N; pipacycline; pipemidic acid; polymyxin; primycin; quinacillin; ribostamycin; rifamide; rifampin; rifamycin SV; rifapentine; rifaximin; ristocetin; ritipenem; rokitamycin; rolitetracycline; rosaramycin; roxithromycin; salazosulfadimidine; sancycline; sisomicin; sparfloxacin; spectinomycin; spiramycin; streptomycin; succisulfone; sulfachrysoidine; sulfaloxic acid; sulfamidochrysoidine; sulfanilic acid; sulfoxone; teicoplanin; temafloxacin; temocillin; tetroxoprim; thiamphenicol; thiazolsulfone; thiostrepton; ticarcillin; tigemonam; tobramycin; tosufloxacin; trimethoprim; trospectomycin; trovafloxacin; tuberactinomycin; vancomycin; azaserine; candicidin(s); chlorphenesin; dermostatin(s); filipin; fungichromin; mepartricin; nystatin; oligomycin(s); perimycin A; tubercidin; 6-azauridine; 6-diazo-5-oxo-L-norleucine; aclacinomycin(s); ancitabine; anthramycin; azacitadine; azaserine; bleomycin(s); ethyl biscoumacetate; ethylidene dicoumarol; iloprost; lamifiban; taprostene; tioclomarol; tirofiban; amiprilose; bucillamine; gusperimus; gentisic acid; glucamethacin; glycol salicylate; meclofenamic acid; mefenamic acid; mesalamine; niflumic acid; olsalazine; oxaceprol; S-enosylmethionine; salicylic acid; salsalate; sulfasalazine; tolfenamic acid; carubicin; carzinophillin A; chlorozotocin; chromomycin(s); denopterin; doxifluridine; edatrexate; eflornithine; elliptinium; enocitabine; epirubicin; mannomustine; menogaril; mitobronitol; mitolactol; mopidamol; mycophenolic acid; nogalamycin; olivomycin(s); peplomycin; pirarubicin; piritrexim; prednimustine; procarbazine; pteropterin; puromycin; ranimustine; streptonigrin; thiamiprine; mycophenolic acid; procodazole; romurtide; sirolimus (rapamycin); tacrolimus; butethamine; fenalcomine; hydroxytetracaine; naepaine; orthocaine; piridocaine; salicyl alcohol; 3-amino-4-hydroxybutyric acid; aceclofenac; alminoprofen; amfenac; bromfenac; bromosaligenin; bumadizon; carprofen; diclofenac; diflunisal; ditazol; enfenamic acid; etodolac; etofenamate; fendosal; fepradinol; flufenamic acid; Tomudex® (N-[[5-[[(1,4-Dihydro-2-methyl-4-oxo-6-quin-azolinyl)methyl]methylamino]-2-thienyl]carbonyl]-L-glutamic acid), trimetrexate, tubercidin, ubenimex, vindesine, zorubicin; argatroban; coumetarol or dicoumarol.

Lists of additional therapeutic agents can be found, for example, in: Physicians' Desk Reference, 55th ed., 2001, Medical Economics Company, Inc., Montvale, N.J.; USPN Dictionary of USAN and International Drug Names, 2000, The United States Pharmacopeial Convention, Inc., Rockville, Md.; and The Merck Index, 12th ed., 1996, Merck & Co., Inc., Whitehouse Station, N.J.

The therapeutic agent may also include radionuclides when the present nanoparticle is used in targeted radiotherapy. In one embodiment, low energy beta-emitting radionuclides, such as $^{177}$Lu-chelated constructs, is associated with the nanoparticle and used to treat relatively small tumor burdens or micrometastatic disease. In another embodiment, higher energy beta emitters, such as yttrium-90 ($^{90}$Y), may be used to treat larger tumor burdens. Iodine-131 ($^{131}$I) may also be used for radiotherapy.

The surface of the nanoparticle may be modified to incorporate at least one functional group. The organic polymer (e.g., PEG) attached to the nanoparticle may be modified to incorporate at least one functional group. For example, the functional group can be a maleimide or N-Hydroxysuccinimide (NHS) ester. The incorporation of the functional group makes it possible to attach various ligands, contrast agents and/or therapeutic agents to the nanoparticle.

In one embodiment, a therapeutic agent is attached to the nanoparticle (surface or the organic polymer coating) via an NHS ester functional group. For example, tyrosine kinase inhibitor such as dasatinib (BMS) or chemotherapeutic agent (e.g., taxol), can be coupled via an ester bond to the nanoparticle. This ester bond can then be cleaved in an acidic environment or enzymatically in vivo. This approach may be used to deliver a prodrug to a subject where the drug is released from the particle in vivo.

We have tested the prodrug approach by coupling small molecule inhibitor dasatinib with the PEG molecules of the nanoparticle. Based on biodistribution results and the human drug dosing calculations, the nanoparticle has been found to have unique biological properties, including relatively rapid clearance from the blood compared to tumors and subsequent tumor tissue accumulation of the therapeutic agent, which suggests that a prodrug approach is feasible. The functionalized nanoparticle permits drugs to be dosed multiple times, ensuring that the drug concentration in the tumor is greater than that specified by the IC-50 in tumor tissue, yet will not be dose-limiting to other organ tissues, such as the heart, liver or kidney. The therapeutic agent and nanoparticle can be radiolabeled or optically labelled separately, allowing independent monitoring of the therapeutic agent and the nanoparticle. In one embodiment, radiofluorinated (i.e., $^{18}$F) dasatinib is coupled with PEG-3400 moieties attached to the nanoparticle via NHS ester linkages. Radiofluorine is crucial for being able to independently monitor time-dependent changes in the distribution and release of the drug from the radioiodinated ($^{124}$I) fluorescent (Cy5) nanoparticle. In this way, we can separately monitor the prodrug (dasatinib) and nanoparticle. This permits optimization of the prodrug design compared with methods in the prior art where no dual-labeling approach is used. In another embodiment, radiotherapeutic iodine molecules (i.e., I-131), or other therapeutic gamma or alpha emitters, are conjugated with PEG via a maleimide functional group, where the therapeutic agent may not dissociate from the PEG in vivo.

A generalizable approach referred herein as "click chemistry" is described below. In order for the present nanoparticle to readily accommodate large ranges of ligands, contrast agents or chelates, the surface of the nanoparticle may be modified to incorporate a functional group. The nanoparticle may also be modified with organic polymers (e.g., PEGs) or chelates that can incorporate a functional group. In the meantime, the ligand, contrast agent, or therapeutic agent is modified to incorporate a functional group that is able to react with the functional group on the nanoparticle, or on the PEGs or chelating agents attached to the nanoparticle under suitable conditions. Accordingly, any ligand, contrast agent or therapeutic agent that has the reactive functional group is able to be readily conjugated to the nanoparticle. This generalizable approach is referred herein as "click chemistry", which would allow for a great deal of versatility to explore multimodality applications. In the chemical reactions of "click chemistry", two molecular components may be joined via a selective, rapid, clean, bioorthogonal, and/or biocompatible reaction. Kolb et al., (2001) Click Chemistry: Diverse Chemical Function from a Few Good Reactions. Angewandte Chemie International Edition 40, 2004-2021. Lim et al., (2010) Bioorthogonal chemistry: recent progress and future directions. Chemical Communications 46, 1589-1600. Sletten et al., (2009) Bioorthogonal chemistry: fishing for selectivity in a sea of functionality. Angewandte Chemie International Edition 48, 6973-6998.

Figure 21A:
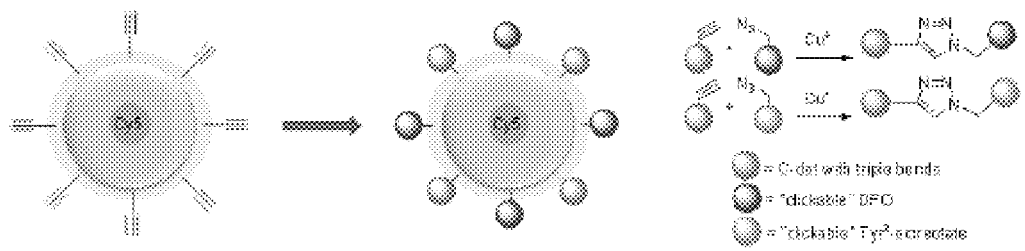
FIG. 21a shows a scheme of the production of functionalized nanoparticle with an NIR fluorescent dye within its core, a PEG surface-coating, DFO chelates and Tyr3-octreotate.
Figure 21B:
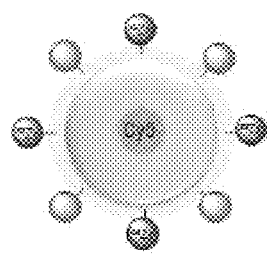
FIG. 21b shows a scheme of the production of a multi-modality $^{89}$Zr-labeled nanoparticle (PET and fluorescence) decorated with Tyr3-octreotate.
Figure 21C:
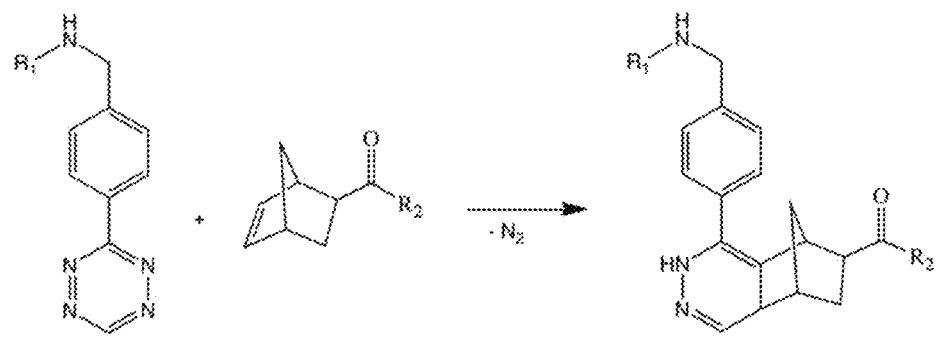
FIG. 21c shows the tetrazine-norbornene ligation.
Figure 21D:
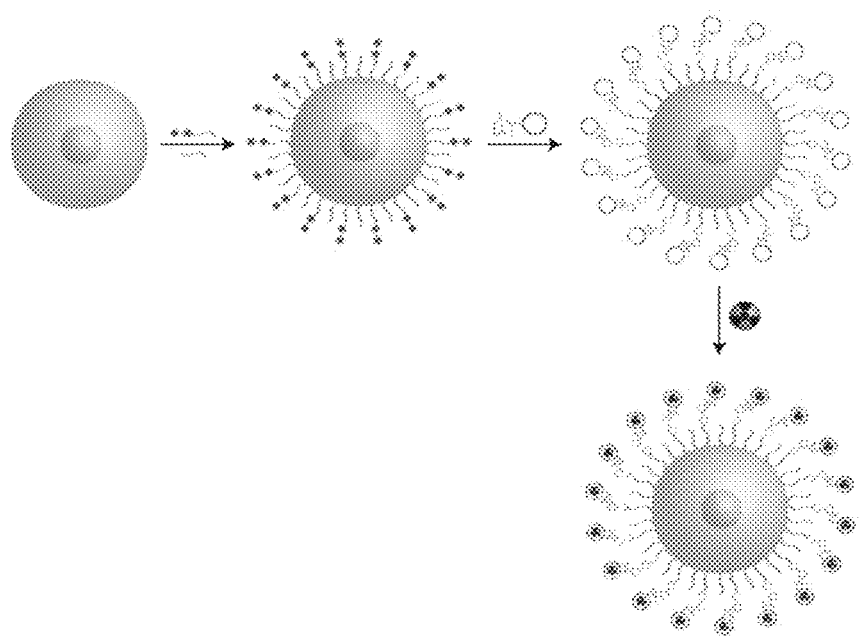
FIG. 21d shows a scheme of the strategy for the creation of radiolabeled core-shell nanoparticles using the tetrazine-norbornene ligation.
Figure 21E:
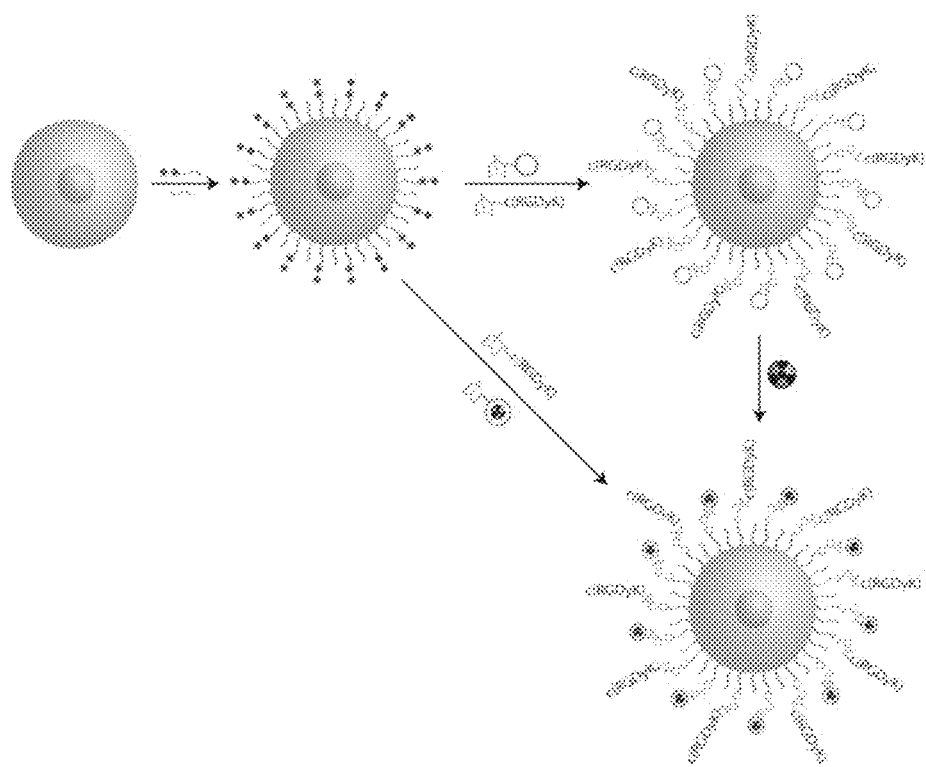
FIG. 21e shows a scheme of the strategy for the creation of peptide-targeted radiolabeled core-shell nanoparticles using the tetrazine-norbornene ligation. Both one-step (in which the pre-metallated chelator-norbornene complex is reacted with the particle) and two-step (in which the chelator is metallated after conjugation) pathways are shown.

Any suitable reaction mechanism may be adapted in the present invention for "click chemistry", so long as facile and controlled attachment of the ligand, contrast agent or chelate to the nanoparticle can be achieved. In one embodiment, a free triple bond is introduced onto PEG, which is already covalently conjugated with the shell of the nanoparticle. In the meantime, an azide bond is introduced onto the desired ligand (or contrast agent, chelate). When the PEGylated nanoparticle and the ligand (or contrast agent, chelate) are mixed in the presence of a copper catalyst, cycloaddition of azide to the triple bond will occur, resulting in the conjugation of the ligand with the nanoparticle. One example of click chemistry is the Cu(I)-catalyzed [3+2] Huisgen cycloaddition between an azide and alkyne. Moses et al., (2007) The growing applications of click chemistry. Chemical Society Reviews 36, 1249-1262. Glaser et al., (2009) 'Click labelling' in PET radiochemistry. Journal of Labelled Compounds & Radiopharmaceuticals 52, 407-414. Mindt et al., (2009) A "Click Chemistry" Approach to the Efficient Synthesis of Multiple Imaging Probes Derived from a Single Precursor. Bioconjugate Chemistry 20, 1940-1949. New et al., (2009) Growing applications of "click chemistry" for bioconjugation in contemporary biomedical research. Cancer Biotherapy and Radiopharmaceuticals 24, 289-301. Wang et al., (2010) Application of "Click Chemistry" in Synthesis of Radiopharmaceuticals. Progress in Chemistry 22, 1591-1602. Schultz et al., (2010) Synthesis of a DOTA-Biotin Conjugate for Radionuclide Chelation via Cu-Free Click Chemistry. Organic Letters 12, 2398-2401. Martin et al., (2010) A DOTA-peptide conjugate by copper-free click chemistry. Bioorganic & Medicinal Chemistry Letters 20, 4805-4807. Lebedev et al., (2009) Clickable bifunctional radiometal chelates for peptide labeling. Chemical Communications 46, 1706-1708. Knor et al., (2007) Synthesis of novel 1,4,7,10-tetraazacyclodecane-1,4,7,10-tetraacetic acid (DOTA) derivatives for chemoselective attachment to unprotected polyfunctionalized compounds. Chemistry—a European Journal 13, 6082-6090. In a second embodiment, a maleimide functional group and a thiol group may be introduced onto the nanoparticle and the desired ligand (or contrast agent, chelate), with the nanoparticle having the maleimide functional group, the ligand (or contrast agent, chelate) having the thiol group, or vice versa. The double bond of maleimide readily reacts with the thiol group to form a stable carbon-sulfur bond. In a third embodiment, an activated ester functional group, e.g., a succinimidyl ester group, and an amine group may be introduced onto the nanoparticle and the desired ligand, contrast agent or chelate. The activated ester group readily reacts with the amine group to form a stable carbon-nitrogen amide bond. In a fourth embodiment, the click chemistry involves the inverse electron demand Diels-Alder reaction between a tetrazine moiety and a strained alkene (FIG. 21c). Devaraj et al., (2009) Fast and Sensitive Pretargeted Labeling of Cancer Cells through a Tetrazine/trans-Cyclooctene Cycloaddition. Angewandte Chemie-International Edition 48, 7013-7016. Devaraj et al., (2008) Tetrazine-Based Cycloadditions: Application to Pretargeted Live Cell Imaging. Bioconjugate Chemistry 19, 2297-2299. Blackman et al., (2008) Tetrazine ligation: fast bioconjugation based on inverse electron demand Diels-Alder reactivity. Journal of the American Chemical Society 130, 13518-13519. The ligation can be selective, fast, biocompatible, and/or bioorthogonal. Unlike many Diels-Alder reactions, the coupling is irreversible, forming a stable pyridazine products after the retro-Diels-Alder release of dinitrogen from the reaction intermediate. A tetrazine moiety and a strained alkene may be introduced onto the nanoparticle and the desired ligand (or contrast agent, chelate), with the nanoparticle having the tetrazine moiety, the ligand (or contrast agent, chelate) having the strained alkene, or vice versa. A number of different tetrazinc strained alkene pairs can be used for the reaction, including, e.g., the combination of 3-(4-benzylamino)-1,2,4,5-tetrazine (Tz) and either norbornene- or trans-cyclooctene-dervatives. Schoch et al., (2010) Post-Synthetic Modification of DNA by Inverse-Electron-Demand Diels-Alder Reaction. Journal of the American Chemical Society 132, 8846-8847. Devaraj et al., (2010) Bioorthogonal Turn-On Probes for Imaging Small Molecules Inside Living Cells. Angewandte Chemie International Edition 49. Haun et al., (2010) Bioorthogonal chemistry amplifies nanoparticle binding and enhances the sensitivity of cell detection. Nature Nanotechnology 5, 660-665. Rossin et al., (2010) In vivo chemistry for pretargeted tumor imaging in live mice. Angewandte Chemie International Edition 49, 3375-3378. Li et al., (2010) Tetrazine-trans-cyclooctene ligation for the rapid construction of 18-F labeled probes. Chemical Communications 46, 8043-8045. Reiner et al., (2011) Synthesis and in vivo imaging of a 18F-labeled PARP1 inhibitor using a chemically orthogonal scavenger-assisted high-performance method. Angewandte Chemie International Edition 50, 1922-1925. For example, the surface of the nanoparticles may be decorated with tetrazine moieties, which can subsequently be conjugated to norbornene-modified ligand (or contrast agent, or chelate) (FIGS. 21d and 21e). In one aspect, the nanoparticles are coated with tetrazine, which can then be modified with the DOTA chelates using the tetrazine-norbornene ligation, and radiolabeled with $^{64}$Cu.

Residence/Clearance Time In Vivo

After administration of the present nanoparticle to a subject, the blood residence half-time of the nanoparticles may range from about 2 hours to about 25 hours, from about 3 hours to about 20 hours, from about 3 hours to about 15 hours, from about 4 hours to about 10 hours, or from about 5 hours to about 6 hours. Longer blood residence half-time means longer circulation, which allows more nanoparticles to accumulate at the target site in vivo. Blood residence half-time may be evaluated as follows. The nanoparticles are first administered to a subject (e.g., a mouse, a miniswine or a human). At various time points post administration, blood samples are taken to measure nanoparticle concentrations through suitable methods.

In one embodiment, after administration of the PEGylated (or control) nanoparticle to a subject, blood residence half-time of the nanoparticle may range from about 2 hours to about 15 hours, or from about 4 hours to about 10 hours. Tumor residence half-time of the nanoparticle after administration of the nanoparticle to a subject may range from about 5 hours to about 2 days, from about 10 hours to about 4 days, or from about 15 hours to about 3.5 days. The ratio of tumor residence half-time to blood residence halftime of the nanoparticle after administration of the nanoparticle to a subject may range from about 2 to about 30, from about 3 to about 20, or from about 4 to about 15. Renal clearance of the nanoparticle after administration of the nanoparticle to a subject may range from about 10% ID (initial dose) to about 100% ID in about 24 hours, from about 30% ID to about 80% ID in about 24 hours, or from about 40% ID to about 70% ID in about 24 hours. In one embodiment, after the nanoparticle is administered to a subject, blood residence half-time of the nanoparticle ranges from about 2 hours to about 25 hours, tumor residence half-time of the nanoparticle ranges from about 5 hours to about 5 days, and renal clearance of the nanoparticle ranges from about 30% ID to about 80% ID in about 24 hours.

After administration of the present nanoparticle to a subject, the tumor residence half-time of the present nanoparticles may range from about 5 hours to about 5 days, from about 10 hours to about 4 days, from about 15 hours to about 3.5 days, from about 20 hours to about 3 days, from about 2.5 days to about 3.1 days, from about 1 day to 3 days, or about 73.5 hours.

The ratio of the tumor residence half-time to the blood residence half-time of the nanoparticle may range from about 2 to about 30, from about 3 to about 20, from about 4 to about 15, from about 4 to about 10, from about 10 to about 15, or about 13.

In one embodiment, the present invention provides a fluorescent silica-based nanoparticle comprising a silica-based core comprising a fluorescent compound positioned within the silica-based core; a silica shell surrounding at least a portion of the core; an organic polymer attached to the nanoparticle; and a ligand attached to the nanoparticle, wherein the nanoparticle has a diameter between about 1 nm and about 15 nm. After administration of the PEGylated (control) nanoparticle to a subject, blood residence half-time of the nanoparticle may range from about 2 hours to about 25 hours, or from about 2 hours to about 15 hours; tumor residence half-time of the nanoparticle may range from about 5 hours to about 2 days; and renal clearance of the nanoparticle may range from about 30% ID to about 80% ID in about 24 hours. The number of ligands attached to the nanoparticle may range from about 1 to about 30, or from about 1 to about 10. The diameter of the nanoparticle may be between about 1 nm and about 8 nm. A contrast agent, such as a radionuclide, may be attached to the nanoparticle. Alternatively, a chelate may be attached to the nanoparticle. The nanoparticle may be detected by PET, SPECT, CT, MRI, optical imaging, bioluminescence imaging, or combinations thereof. A therapeutic agent may be attached to the nanoparticle. After administration of the radiolabeled targeted nanoparticle to a subject, blood residence half-time of the nanoparticle may also range from about 3 hours to about 15 hours, or from about 4 hours to about 10 hours. Tumor residence half-time of the nanoparticle after administration of the nanoparticle to a subject may also range from about 10 hours to about 4 days, or from about 15 hours to about 3.5 days. The ratio of tumor residence half-time to blood residence half-time of the targeted nanoparticle after administration of the nanoparticle to a subject may range from about 2 to about 30, from about 3 to about 20, or from about 4 to about 15. Renal clearance of the nanoparticle may also range from about 45% ID to about 90% ID in about 24 hours after administration of the nanoparticle to a subject.

In one embodiment, to estimate residence (or clearance) half-time values of the radiolabeled nanoparticles ($T_{1/2}$) in blood, tumor, and other major organs/tissues, the percentage of the injected dose per gram (% ID/g) values are measured by sacrificing groups of mice at specified times following administration of the nanoparticles. Blood, tumor, and organs are harvested, weighed, and counted in a scintillation γ-counter. The % ID/g values are corrected for radioactive decay to the time of injection. The resulting time-activity concentration data for each tissue are fit to a decreasing monoexponential function to estimate tissue/organ $T_{1/2}$ values.

After administration of the present nanoparticle to a subject, the renal clearance of the present nanoparticles may range from about 45% ID (initial dose) to greater than 90% ID in about 24 hours, from about 20% ID to about 90% ID in about 24 hours, from about 30% ID to about 80% ID in about 24 hours, from about 40% ID to about 70% ID in about 24 hours, from about 40% ID to about 60% ID in about 24 hours, from about 40% ID to about 50% ID in about 24 hours, about 43% ID in about 24 hours, from about 10% ID to about 100% ID in about 24 hours, from about 40% ID to about 100% ID in about 24 hours, from about 80% ID to about 100% ID in about 24 hours, from about 90% ID to about 95% ID in about 24 hours, from about 90% ID to about 100% ID in about 24 hours, or from about 80% ID to about 95% ID in about 24 hours. Renal clearance may be evaluated as follows. The nanoparticles are first administered to a subject (e.g., a mouse, a miniswine or a human). At various time points post administration, urine samples are taken to measure nanoparticle concentrations through suitable methods.

In one embodiment, renal clearance (e.g., the fraction of nanoparticles excreted in the urine over time) is assayed as follows. A subject is administered with the present nanoparticles, and urine samples collected over a certain time period (e.g., 168 hours). Particle concentrations at each time point are determined using fluorometric analyses and a serial dilution calibration curve generated from background-corrected fluorescence signal measurements of urine samples mixed with known particle concentrations (% ID). Concentration values, along with estimates of average daily mouse urine volumes, are used to compute cumulative % ID/g urine excreted. In another embodiment, renal clearance of radiolabeled nanoparticles is assayed by measuring urine specimen activities (counts per minute) over similar time intervals using, for example, γ-counting, and after nanoparticle administration to compute cumulative urine excretion.

In a third embodiment, to assess cumulative fecal excretion, feces are collected in metabolic cages over similar time intervals after administration of the nanoparticles and specimen activities determined using a γ-counter.

When the nanoparticles in the amount of about 100 times of the human dose equivalent are administered to a subject, substantially no anemia, weight loss, agitation, increased respiration, GI disturbance, abnormal behavior, neurological dysfunction, abnormalities in hematology, abnormalities in clinical chemistries, drug-related lesions in organ pathology, mortality, or combination thereof are observed in about 10 to about 14 days.

When the present nanoparticle contains at least one attached ligand, the multivalency enhancement of the nanoparticle (e.g., compared to the ligand alone) may range from about 1.5 fold to about 10 fold, from about 2 fold to about 8 fold, from about 2 fold to about 6 fold, from about 2 fold to about 4 fold, or about 2 fold.

The nanoparticles of the present invention show unexpected in vitro and in vivo physicochemical and biological parameters in view of the prior art. For example, the blood residence half-time estimated for the ligand-attached nanoparticles (e.g., about 5.5 hrs for cRGD-attached nanoparticles) is substantially longer than that of the corresponding ligand (e.g., about 13 minutes for cRGD). Montet et al. Multivalent effects of RGD peptides obtained by nanoparticle display. *J Med Chem.* 49, 6087-6093 (2006). Extended blood residence half-times may enhance probe bioavailability, facilitate tumor targeting, and yield higher tumor uptake over longer time periods. In one embodiment, the tumor residence half-time for the targeted nanoparticles (i.e., ligand-attached nanoparticles) is about 13 times greater than blood residence half-time, whereas the tumor residence half-time for the non-targeted nanoparticles (i.e., corresponding nanoparticles not attached with ligands) is only about 5 times greater than blood residence half-time. This difference suggests substantially greater tumor tissue accumulation of the targeted nanoparticles compared with the non-targeted nanoparticles. In certain embodiments, given the number of ligands attached to the nanoparticle, the present nanoparticles show unexpected high-affinity binding (e.g., $K_d$ 0.51 nM and $IC_{50}$ 1.2 nM for cRGD-attached nanoparticle), multivalency enhancement (e.g., more than 2 fold enhancement for cRGD-attached nanoparticles compared to cRGD peptide alone), significant differential tumor uptake (e.g., cRGD-attached PEG-nanoparticles show about 3 to 4 fold increase in differential tumor uptake relative to the PEG-coated nanoparticles over 72 hrs post-administration), and significant tumor contrast relative to normal muscle (e.g., about 3 to 5 fold over 72 hrs post-administration) based on tumor-to-muscle uptake ratios.

In one embodiment, three-fold activity-concentration increases were found for ligand-attached nanoparticles in integrin-expressing tumors over controls (e.g., ligand-attached nanoparticles in non-integrin expressing tumors, or corresponding nanoparticles not attached with ligands in integrin-expressing tumors) at the time of maximum tumor uptake (about 4 hrs post-injection of the nanoparticles). In addition, tumor-to-muscle uptake ratios for targeted nanoparticles (i.e., ligand-attached nanoparticles) reveal enhanced tumor tissue contrast relative to normal muscle, compared with decreased tumor tissue contrast relative to normal muscle for non-targeted nanoparticles (i.e., corresponding nanoparticles not attached with ligands), suggesting that the targeted nanoparticles are tumor-selective.

In another embodiment, the targeted and non-targeted nanoparticles both show efficient renal excretion over the same time period. Nearly half of the injected dose is excreted over the first 24 hrs post-injection and about 72% by 96 hrs, suggesting that the bulk of excretion occurred in the first day post-injection. By contrast, fecal excretion profiles of the targeted nanoparticles indicate that, on average, 7% and 15% of the injected dose is eliminated over 24 and 96 hrs, respectively.

The physicochemical and biological parameters of the non-toxic nanoparticles, along with its multimodal imaging capabilities (e.g., PET and optical imaging), expand the range of their potential biomedical applications. The applications include (a) long-term monitoring: the extended blood circulation time and corresponding bioavailability of the nanoparticles highlight their versatility for both early and long-term monitoring of various stages of disease management (such as diagnostic screening, pre-treatment evaluation, therapeutic intervention, and post-treatment monitoring) without restrictions imposed by toxicity considerations; (b) improved tumor penetration: the clearance properties of the targeted nanoparticles (e.g., their renal clearance is slower that of the molecular probes in the prior art) will be useful for various types of biological applications. For example, the nanoparticles would be particularly useful in cases of poorly vascularized and relatively inaccessible solid tumors in which localization of agents is typically slow after systemic administration; (c) multimodal imaging capabilities: these modalities can be combined at multiple scales (i.e., whole body to cellular levels) for acquiring complementary, depth-sensitive biological information. For example, in SLN mapping, deep nodes can be mapped by PET in terms of their distribution and number, while more precise and detailed localization of superficial nodes can be obtained by fluorescence imaging; and (d) targeted therapeutics: longer clearance of the targeted nanoparticles from tumor compared to that from blood may be exploited for combined diagnostic/therapeutic applications, in which the nanoparticles can serve as a radiotherapeutic or drug delivery vehicle.

Pharmaceutical Compositions

The present invention further provides a pharmaceutical composition comprising the present nanoparticle. The pharmaceutical compositions of the invention may be administered orally in the form of a suitable pharmaceutical unit dosage form. The pharmaceutical compositions of the invention may be prepared in many forms that include tablets, hard or soft gelatin capsules, aqueous solutions, suspensions, and liposomes and other slow-release formulations, such as shaped polymeric gels.

Suitable modes of administration for the present nanoparticle or composition include, but are not limited to, oral, intravenous, rectal, sublingual, mucosal, nasal, ophthalmic, subcutaneous, intramuscular, transdermal, intradermal, subdermal, peritumoral, spinal, intrathecal, intra-articular, intra-arterial, sub-arachnoid, bronchial, and lymphatic administration, and other dosage forms for systemic delivery of active ingredients. The present pharmaceutical composition may be administered by any method known in the art, including, without limitation, transdermal (passive via patch, gel, cream, ointment or iontophoretic); intravenous (bolus, infusion); subcutaneous (infusion, depot); transmucosal (buccal and sublingual, e.g., orodispersible tablets, wafers, film, and effervescent formulations; conjunctival (eyedrops); rectal (suppository, enema)); or intradermal (bolus, infusion, depot). The composition may be delivered topically.

Oral liquid pharmaceutical compositions may be in the form of, for example, aqueous or oily suspensions, solutions, emulsions, syrups or elixirs, or may be presented as a dry product for constitution with water or other suitable vehicle before use. Such liquid pharmaceutical compositions may contain conventional additives such as suspending agents, emulsifying agents, non-aqueous vehicles (which may include edible oils), or preservatives.

The nanoparticle pharmaceutical compositions of the invention may also be formulated for parenteral administration (e.g., by injection, for example, bolus injection or continuous infusion) and may be presented in unit dosage form in ampules, pre-filled syringes, small volume infusion containers or multi-dose containers with an added preservative. The pharmaceutical compositions may take such forms as suspensions, solutions, or emulsions in oily or aqueous vehicles, and may contain formulating agents such as suspending, stabilizing and/or dispersing agents. Alternatively, the pharmaceutical compositions of the invention may be in powder form, obtained by aseptic isolation of sterile solid or by lyophilization from solution, for constitution with a suitable vehicle, e.g., sterile, pyrogen-free water, before use.

For topical administration to the epidermis, the pharmaceutical compositions may be formulated as ointments, creams or lotions, or as the active ingredient of a transdermal patch. Suitable transdermal delivery systems are disclosed, for example, in A. Fisher et al. (U.S. Pat. No. 4,788,603), or R. Bawa et al. (U.S. Pat. Nos. 4,931,279; 4,668,506; and 4,713,224). Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The pharmaceutical compositions can also be delivered via ionophoresis, e.g., as disclosed in U.S. Pat. Nos. 4,140,122; 4,383,529; or 4,051,842.

Pharmaceutical compositions suitable for topical administration in the mouth include unit dosage forms such as lozenges comprising a pharmaceutical composition of the invention in a flavored base, usually sucrose and acadia or tragacanth; pastilles comprising the pharmaceutical composition in an inert base such as gelatin and glycerin or sucrose and acacia; mucoadherent gels, and mouthwashes comprising the pharmaceutical composition in a suitable liquid carrier.

For topical administration to the eye, the pharmaceutical compositions can be administered as drops, gels (S. Chrai et al., U.S. Pat. No. 4,255,415), gums (S. L. Lin et al., U.S. Pat. No. 4,136,177) or via a prolonged-release ocular insert (A. S. Michaels, U.S. Pat. No. 3,867,519 and H. M. Haddad et al., U.S. Pat. No. 3,870,791).

When desired, the above-described pharmaceutical compositions can be adapted to give sustained release of a therapeutic compound employed, e.g., by combination with certain hydrophilic polymer matrices, e.g., comprising natural gels, synthetic polymer gels or mixtures thereof.

Pharmaceutical compositions suitable for rectal administration wherein the carrier is a solid are most preferably presented as unit dose suppositories. Suitable carriers include cocoa butter and other materials commonly used in the art, and the suppositories may be conveniently formed by admixture of the pharmaceutical composition with the softened or melted carrier(s) followed by chilling and shaping in molds.

Pharmaceutical compositions suitable for vaginal administration may be presented as pessaries, tampons, creams, gels, pastes, foams or sprays containing, in addition to the nanoparticles and the therapeutic agent, such carriers are well known in the art.

For administration by inhalation, the pharmaceutical compositions according to the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the pharmaceutical compositions of the invention may take the form of a dry powder composition, for example, a powder mix of the pharmaceutical composition and a suitable powder base such as lactose or starch. The powder composition may be presented in unit dosage form in, for example, capsules or cartridges or, e.g., gelatin or blister packs from which the powder may be administered with the aid of an inhalator or insufflator.

For intra-nasal administration, the pharmaceutical compositions of the invention may be administered via a liquid spray, such as via a plastic bottle atomizer. Typical of these are the Mistometer® (isoproterenol inhaler-Wintrop) and the Medihaler® (isoproterenol inhaler—Riker).

Pharmaceutical compositions of the invention may also contain other adjuvants such as flavorings, colorings, antimicrobial agents, or preservatives.

It will be further appreciated that the amount of the pharmaceutical compositions required for use in treatment will vary not only with the therapeutic agent selected but also with the route of administration, the nature of the condition being treated and the age and condition of the patient and will be ultimately at the discretion of the attendant physician or clinician. For evaluations of these factors, see J. F. Brien et al., Europ. J. Clin. Pharmacol., 14, 133 (1978); and Physicians' Desk Reference, Charles E. Baker, Jr., Pub., Medical Economics Co., Oradell, N.J. (41st ed., 1987). Generally, the dosages of the therapeutic agent when used in combination with the fluorescent nanoparticles of the present invention can be lower than when the therapeutic agent is administered alone or in conventional pharmaceutical dosage forms. The high specificity of the fluorescent nanoparticle for a target site, such as a receptor situated on a cell's surface, can provide a relatively highly localized concentration of a therapeutic agent, or alternatively, a sustained release of a therapeutic agent over an extended time period.

The present nanoparticles or compositions can be administered to a subject. The subject can be a mammal, preferably a human. Mammals include, but are not limited to, murines, rats, rabbits, simians, bovines, ovine, swine, canines, feline, farm animals, sport animals, pets, equine, and primates.

Uses of Nanoparticles

The present invention further provides a method for detecting a component of a cell comprising the steps of: (a) contacting the cell with a fluorescent silica-based nanoparticle comprising a silica-based core comprising a fluorescent compound positioned within the silica-based core; a silica shell surrounding at least a portion of the core; an organic polymer attached to the nanoparticle; from about 1 to about 25 ligands (from about 1 to about 20 ligands, or from about 1 to about 10 ligands, or other ranges; see discussions herewithin) attached to the nanoparticle; and a contrast agent or a chelate attached to the nanoparticle; and (b) monitoring the binding of the nanoparticle to the cell or a cellular component (and/or its potential intracellular uptake) by at least one imaging technique. The imaging technique may be PET, SPECT, CT, MRI, optical bioluminescence or fluorescence imaging, and combinations thereof.

The location of the cellular component can be detected and determined inside a metabolically active whole cell, in a whole cell lysate, in a permeabilized cell, in a fixed cell, or with a partially purified cell component in a cell-free environment. The amount and the duration of the contacting can depend, for example, on the diagnostic or therapeutic objectives of the treatment method, such as fluorescent or antibody-mediated detection of upregulated signaling pathway intermediates (i.e., Akt, NF-κB), disease states or conditions, the delivery of a therapeutic agent, or both. The amount and the duration of the contacting can also depend on the relative concentration of the fluorescent nanoparticle to the target analyte, particle incubation time, and the state of the cell for treatment.

The present invention further provides a method for targeting a tumor cell comprising administering to a cancer patient an effective amount of a fluorescent silica-based nanoparticle comprising a silica-based core comprising a fluorescent compound positioned within the silica-based core; a silica shell surrounding at least a portion of the core; an organic polymer attached to the nanoparticle; a ligand attached to the nanoparticle and capable of binding a tumor marker; and at least one therapeutic agent.

The nanoparticle may be radiolabeled. The nanoparticle may be radiolabelled using any suitable techniques. The radiolabelling may be automated. In one embodiment, the nanoparticle is radiolabelled using the FASTlab radiochemistry synthesis platform (GE Healthcare). The synthesis parameters may be fine-tuned to achieve high reproducibility, radiochemical yield/purity, labeling efficiency, and relatively short synthesis times. New particle tracers may be accommodated on the same FASTlab module.

The nanoparticle may be administered to the patient by, but not restricted to, the following routes: oral, intravenous, nasal, subcutaneous, local, intramuscular or transdermal.

In certain embodiments, it may be desirable to use a mixture of two or more types of fluorescent nanoparticles having different properties to evaluate different tissue types.

The methods and compositions of the invention can be used to help a physician or surgeon to identify and characterize areas of disease, such as cancers and inflammatory/infectious processes, including, but not restricted to, cancers of the skin (melanoma), head & neck, prostate, brain, and bowels, to distinguish diseased and normal tissue, such as detecting tumor margins that are difficult to detect using an ordinary operating microscope, e.g., in brain surgery, to help dictate a therapeutic or surgical intervention, e.g., by determining whether a lesion is cancerous and should be removed or non-cancerous and left alone, or in surgically staging a disease, e.g., intraoperative lymph node staging, sentinel lymph node (SLN) mapping, e.g., nerve-sparing procedures for preserving vital neural structures (intraparotid nerves).

The methods and compositions of the invention may be used in metastatic disease detection, treatment response monitoring, SLN mapping/targeting, nerve sparing procedures, residual disease detection, targeted delivery of therapeutics (combined diagnostic/therapeutic platform), local delivery of non-targeted, drug-bearing nanoparticles (catheter delivery), blood-brain barrier therapeutics, treatment of inflammatory/ischemic diseases (i.e., brain, heart, urinary tract, bladder), combined treatment and sensing of disease (e.g., Ratiometric pH sensing, oxygen sensing), etc.

The methods and compositions of the invention can also be used in the detection, characterization and/or determination of the localization of a disease, especially early disease, the severity of a disease or a disease-associated condition, the staging of a disease, and/or monitoring a disease. The presence, absence, or level of an emitted signal can be indicative of a disease state. The methods and compositions of the invention can also be used to monitor and/or guide various therapeutic interventions, such as surgical and catheter-based procedures, and monitoring drug therapy, including cell based therapies. The methods of the invention can also be used in prognosis of a disease or disease condition. Cellular subpopulations residing within or marginating the disease site, such as stem-like cells ("cancer stem cells") and/or inflammatory/phagocytic cells may be identified and characterized using the methods and compositions of the invention. With respect to each of the foregoing, examples of such disease or disease conditions that can be detected or monitored (before, during or after therapy) include cancer (for example, melanoma, thyroid, colorectal, ovarian, lung, breast, prostate, cervical, skin, brain, gastrointestinal, mouth, kidney, esophageal, bone cancer), that can be used to identify subjects that have an increased susceptibility for developing cancer and/or malignancies, i.e., they are predisposed to develop cancer and/or malignancies, inflammation (for example, inflammatory conditions induced by the presence of cancerous lesions), cardiovascular disease (for example, atherosclerosis and inflammatory conditions of blood vessels, ischemia, stroke, thrombosis), dermatologic disease (for example, Kaposi's Sarcoma, psoriasis), ophthalmic disease (for example, macular degeneration, diabetic retinopathy), infectious disease (for example, bacterial, viral, fungal and parasitic infections, including Acquired Immunodeficiency Syndrome), immunologic disease (for example, an autoimmune disorder, lymphoma, multiple sclerosis, rheumatoid arthritis, diabetes mellitus), central nervous system disease (for example, a neurodegenerative disease, such as Parkinson's disease or Alzheimer's disease), inherited diseases, metabolic diseases, environmental diseases (for example, lead, mercury and radioactive poisoning, skin cancer), bone-related disease (for example, osteoporosis, primary and metastatic bone tumors, osteoarthritis) and a neurodegenerative disease.

The methods and compositions of the invention, therefore, can be used, for example, to determine the presence and/or localization of tumor and/or co-resident stem-like cells ("cancer stem cells"), the presence and/or localization of inflammatory cells, including the presence of activated macrophages, for instance in peritumoral regions, the presence and in localization of vascular disease including areas at risk for acute occlusion (i.e., vulnerable plaques) in coronary and peripheral arteries, regions of expanding aneurysms, unstable plaque in carotid arteries, and ischemic areas. The methods and compositions of the invention can also be used in identification and evaluation of cell death, injury, apoptosis, necrosis, hypoxia and angiogenesis. PCT/US2006/049222.

The following examples are presented for the purposes of illustration only and are not limiting the invention.

Example 1 Preparation and Characterization of PEG-Coated Nanoparticles

Nanoparticles containing an NIR-emitting dye (Cy-5) were synthesized and functionalized by PEGylation according to well-established protocols as disclosed in PCT/US2008/074894 and Stober et al. Controlled growth of monodispersed silica spheres in the micron size range. *Colloid Interface Sci.* 1968; 26:62-69. Ohnishi et al. *J. Mol. Imaging* 2005, 4:172-181. Cy5 malemide was reacted with a co-reactive organo silane compound, (3-Mercaptopropyl) tromethoxysilane to form a fluorescent silica precursor. This fluorescent silica precursor was co-condensed with tetraethylorthosilicate to form a fluorescent silica based core. A PEG-silane compound, with methoxy-terminated poly(ethylene glycol) chains (PEG, ~0.5 kDa) Methoxy(Polyethyleneoxy) Propyl]-Trimethoxysilane, was added to the fluorescent silica based core to form a PEG coating on the core. PEG-coated nanoparticles were dialyzed to physiological saline (0.15M NaCl in H2O) through 3500 MWCO Snakeskin Dialysis Membranes and sterile-filtered. All samples were optical density-matched at their peak absorption wavelength (640 nm) prior to injection. Hydrodynamic size measurements were achieved by Dynamic Light Scattering (DLS) and Fluorescence Correlation Spectroscopy (FCS). Briefly, particles dialyzed to water were measured on a Brookhaven Instruments Company 200SM static/DLS system using a HeNe laser ($\lambda$=632.8 nm). Due to overlap of the dye absorption with the excitation source, 15-min integration times were used to achieve acceptable signal-to-noise ratios. For FCS, particles were dialyzed to water, diluted into 0.15M NaCl, and measured on a Zeiss LSM 510 Confocor 2 FCS (HeNe 633 nm excitation). The instrument was calibrated for size prior to all measurements. Comparison of the relative brightness of PEGylated nanoparticles with free dye was determined from FCS curves, measured as count rate per molecule/particle.

Example 2 Renal Clearance of PEG Coated Nanoparticles

Fluorescent core-shell silica nanoparticles, having a hydrodynamic radius of about 3 nm, were synthesized. These nanoparticles were found to be in the 6-10 nm diameter range, as shown by dynamic light scattering (DLS) results (FIG. 1a). In vivo whole-body NIR fluorescence imaging of bare (no PEG coat) silica nanoparticles, on the order of 6-nm and 3.3-nm, in nude mice showed considerable renal clearance 45 min post-injection with a significant accumulation remaining in the liver (FIG. 1b). Eventual excretion into the enterohepatic circulation occurred during the ensuing 24 h. On the basis of these results, particles were covalently coated with methoxy-terminated poly(ethylene glycol) chains (PEG, ~0.5 kDa), per protocols in PCT/US2008/074894, to prevent opsonization and further enhance particle clearance while maintaining a small hydrodynamic size. This treatment decreased liver retention and resulted in increased renal filtration into the bladder at 45 min post-injection by NIR fluorescence imaging (FIG. 1c), with bladder fluorescence visible out to 24 h. The probes were well tolerated, with no adverse effects or animal deaths observed over the course of the study. Serial co-registered PET-CT imaging 24-hr after injection of [124]I-labeled PEG coated nanoparticles (FIG. 1 d, upper row) demonstrated a small amount of residual bladder activity, as well as activity overlying the liver/gastrointestinal tract (center), flanked by independently acquired microCT and microPET scans. Serial microPET images confirmed findings on NIR fluorescence imaging. The half-time of blood residence of the [124]I-labeled PEGylated nanoparticles based on time-dependent changes in blood activity over a 96-hour period was found to be 7.3 hours. For the [124]I-labeled, RGD-bound nanoparticles, the half-time of blood residence was found to be 5.6 hours.

Figure 2:
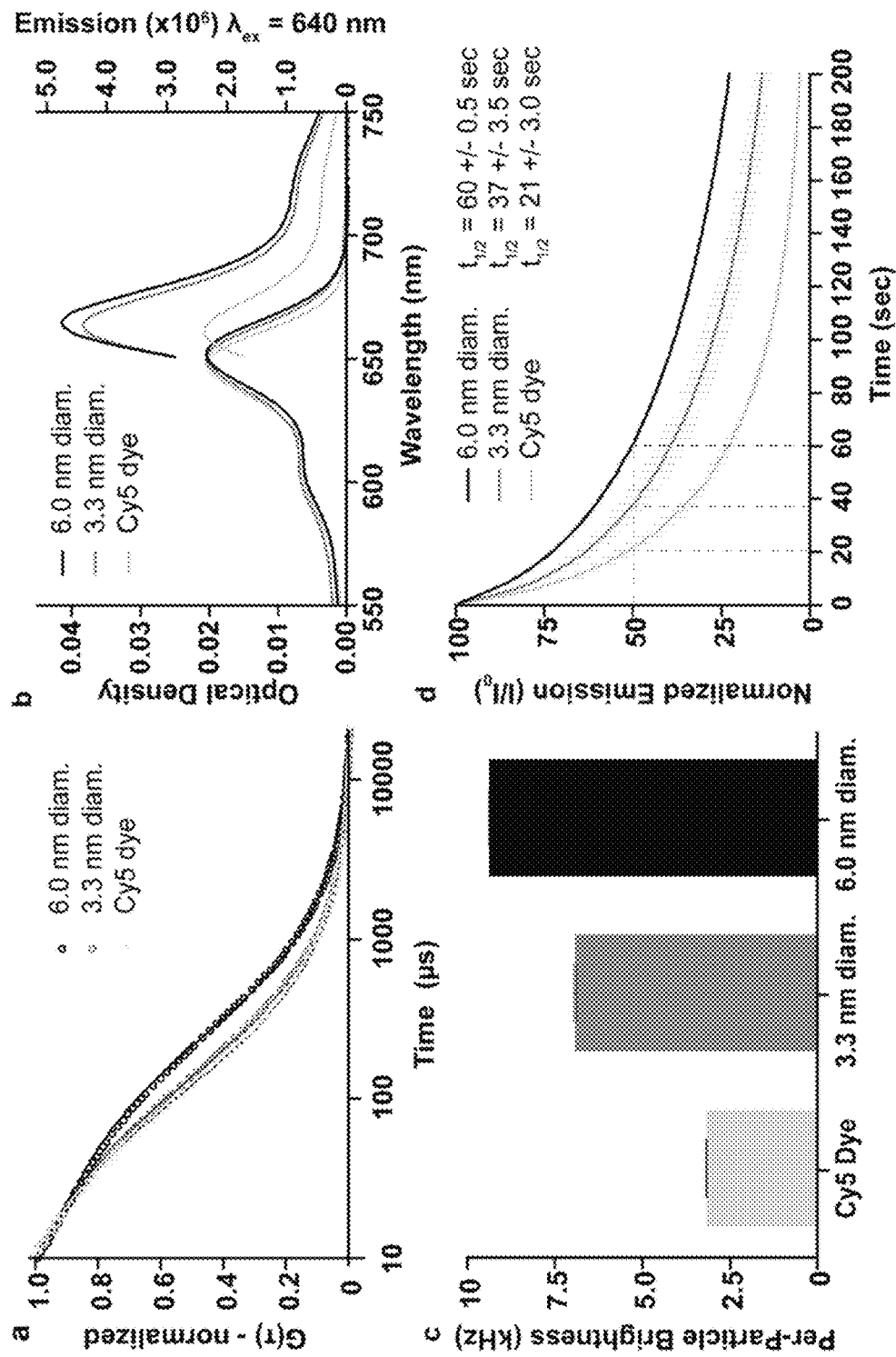
FIG. 2a shows fluorescence correlation spectroscopy (FCS) data and single exponential fits for Cy5 dye (light gray), 3.3±0.06 nm diameter (dark gray, mean±standard deviation, n=9) and 6.0±0.1 nm diameter (black, mean±standard deviation, n=6) Cy5-containing PEG-coated nanoparticles showing the differences in diffusion time resulting from the different hydrodynamic sizes of the different species.
FIG. 2b shows absorption and emission spectra of Cy5 dye (light gray), 3.3 nm diameter (dark gray) and 6.0 nm diameter (black) PEG-coated nanoparticles.
FIG. 2c shows relative brightness comparison of free dye (light gray) with 3.3 nm (dark gray) and 6.0 nm diameter (black) nanoparticles, measured as count rate per molecule/particle as determined from the FCS curves.
FIG. 2d shows photobleaching data for Cy5 dye (light gray), 3.3 nm diameter (dark gray), and 6.0 nm diameter (black) PEG-coated nanoparticles under ~3.5 mW laser excitation.

Based on these in vivo data, a more detailed biodistribution and clearance study of coated nanoparticles was undertaken on two sets of PEGylated Cy5-containing particles to assess the effects of probe size on biodistribution. Nanoparticles with hydrodynamic diameters of 3.3±0.06 and 6.0±0.1 nm, as measured by fluorescence correlation spectroscopy (FCS), were generated (FIG. 2a). Prior to in vivo studies, particle photophysical properties were investigated to establish their performance levels versus free dye. Despite the extremely small particle size, silica-encapsulated dye molecules exhibited photophysical enhancements over free dye that scaled with particle size, including significant increases in brightness, as determined by absorption and emission spectroscopy (FIG. 2b) and FCS (FIG. 2c). Compared to the free dye, the 3.3 and 6.0 nm diameter nanoparticles exhibited 2- and 3-fold increases in photobleaching half-life, respectively, when irradiated with a high power 635 nm laser (FIG. 2d). Thus, these nanoparticle probes were found to be both brighter and more photostable than their free dye counterparts.

Figure 3:
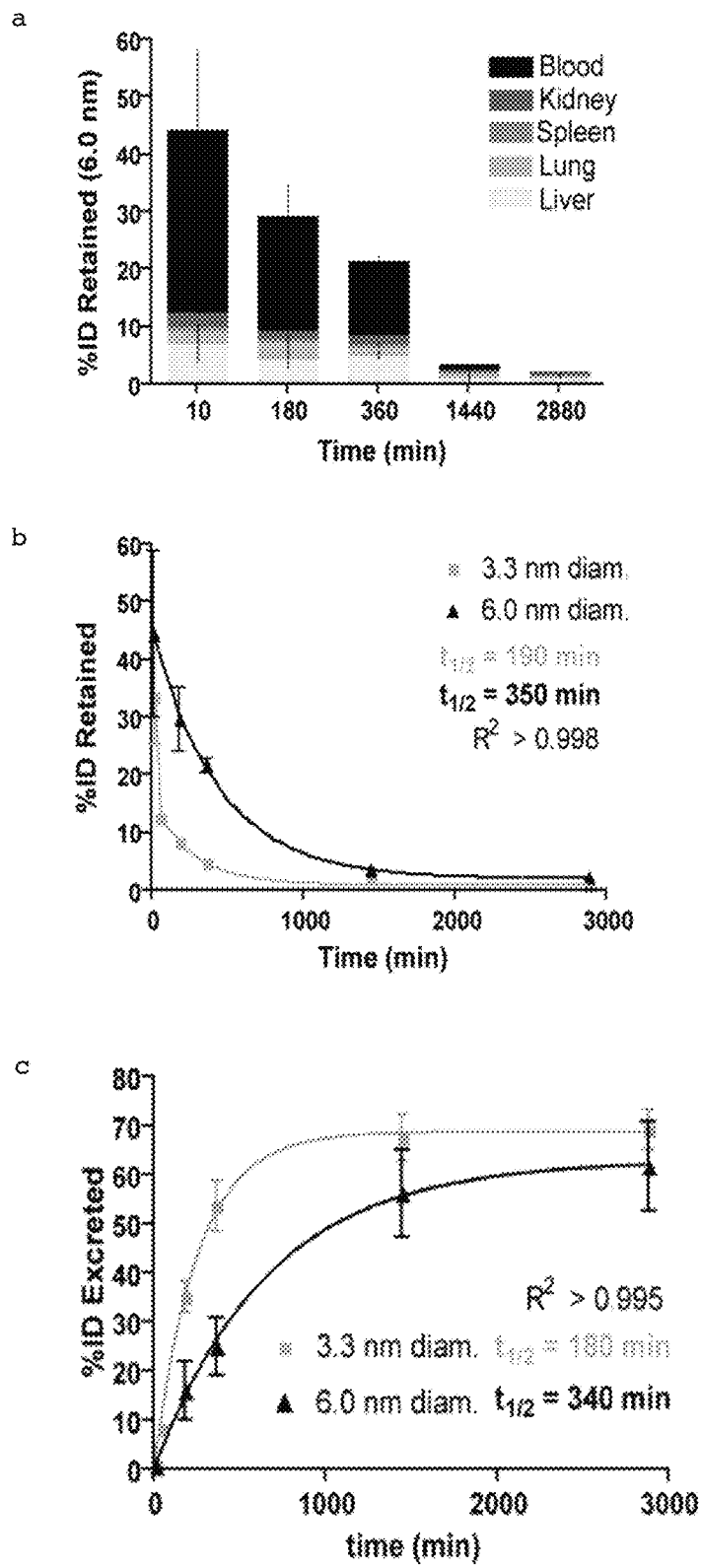
FIG. 3a shows percent of initial particle dose (% ID) retained by blood (black) and tissues: liver (light gray), lung (mid-low gray), spleen (midgray), and kidney (mid-high gray) for 6.0 nm diameter nanoparticles at various time points from 10 min to 48 h post-injection (n=3 mice, mean±standard deviation).
FIG. 3b shows plot of retained particle concentration for 3.3 nm (light gray) and 6.0 nm (black) diameter nanoparticles and the associated logarithmic decay fits and half-lives.
FIG. 3c shows plot of estimated particle excretion for 3.3 nm (light gray) and 6.0 nm (black) diameter nanoparticles and the associated logarithmic fits and half-lives (mean±standard deviation, n=9 (three mice per time point)).

In addition to semiquantitative evaluation of in vivo nanoparticle behavior from whole-body imaging, ex-vivo analysis of tissue homogenates and fluids was performed using a fluorescence plate reader, which allowed calibrated quantitation of variations observed in NIR fluorescence imaging. Samples were grouped as "retained" (liver, kidney, lung, spleen homogenates, and blood) and "excreted" (urine) sources of particle fluorescence, were background-corrected and were converted to percent of the initial dose (% ID) per animal based on calibration curves. Tissue analysis showed minimal particle retention in major organs, with most of the fluorescence attributed to circulating blood (FIG. 3a). Net particle retention, calculated as the sum of the "retained" components, was fit with an exponential decay curve to determine the kinetics of excretion (FIG. 3b). Larger particles exhibited a longer tissue half-life ($t_{1/2}$(3.3 nm)=190 min, $t_{1/2}$(6.0 nm)=350 min) and greater initial organ retention. After 48 h, the 6-nm particle exhibited minimal retention in the body ($R_{total}$(6.0 nm)=2.4±0.6% ID). Urine samples collected at the time of sacrifice, in conjunction with serial dilution calibration data, was used to estimate the total renal clearance based on a conservative estimate of the average urine volume excreted per unit time. By this method, the % ID excreted over time for both particle sizes (FIG. 3c) was estimated.

Example 3 Fluorescent Silica Nanoparticles Conjugated with $\alpha_v\beta_3$ Integrin-Targeting Peptide (Melanoma Model)

Figure 4:
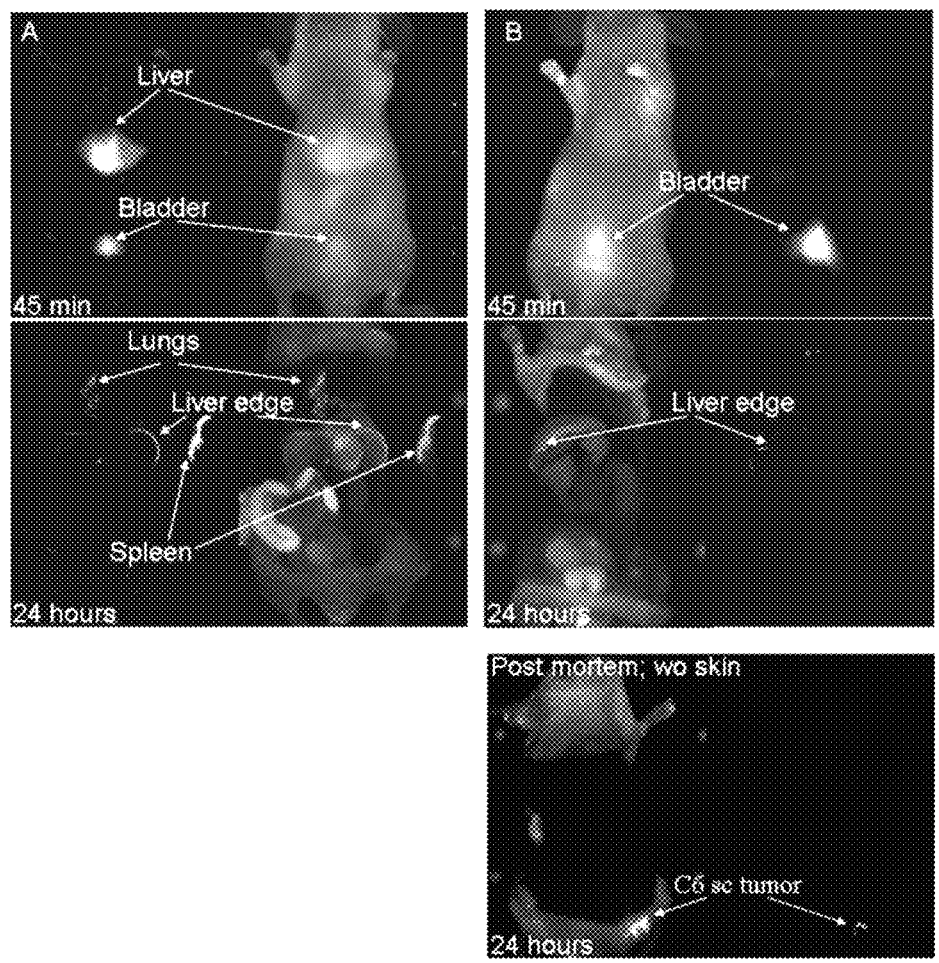
FIG. 4 shows in vivo biodistribution of the nanoparticles in non-tumor-bearing and tumor-bearing mice with subcutaneous C6 xenografts. (A) Bare silica particles; (B) PEGylated RGD particles.

To synthesize a multimodal (optical-PET) nanoparticle with high affinity for tumor marker $\alpha_v\beta_3$ integrin, cyclic RGD pentapeptide (RGDYC) was conjugated to the nanoparticle via a Cys-maleimide linkage. The tyrosine linker, Y, was used to subsequently attach a radiolabel. Male athymic nude mice were injected subcutaneously into their flanks with C6 rat glioma cells. At ~0.5 cm in diameter, mice were IV-injected with either bare silica nanoparticles (FIG. 4A) or PEG-ylated RGD nanoparticles (FIG. 4B, ~500 nm/kg). FIG. 4 shows the in vivo biodistribution in non-tumor-bearing and tumor-bearing mice using whole body optical imaging.

Figure 5:
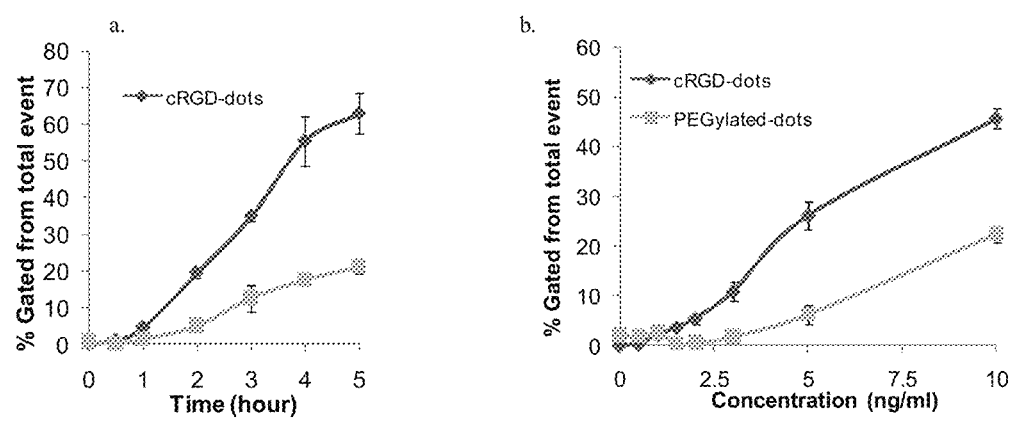
FIG. 5 shows total specific binding data for cRGD- and PEG-ylated dots (i.e., nanoparticles) using flow cytometry in the Cy5 channel as a function of time (a) and particle concentration (b).

In vitro binding of targeted (RGD-bound) and non-targeted (PEG-coated) nanoparticles to $\alpha_v\beta_3$-integrin-positive human melanoma cell lines (M21) was investigated as part of a dose response study using flow cytometry (FIGS. 5A, 5B). Particle binding/uptake was evaluated as a function of time (FIG. 5A) and concentration (FIG. 5B).

Example 4 Fluorescent Silica Nanoparticles Conjugated with $\alpha_v\beta_3$ Integrin-Targeting Peptide and Nodal Mapping (Melanoma Model)

We utilized a biocompatible material, silica, which has an architecture that could be precisely tuned to particle sizes optimized for renal clearance. We attached small targeting peptides and a radioactive label to the particle surface for serial PET imaging measurements in a well-characterized in vivo human melanoma model, and mapped draining lymph nodes and lymphatic channels using an encapsulated near infrared (NIR) dye and multi-scale optical fluorescence imaging methods. Ballou et al., Sentinel lymph node imaging using quantum dots in mouse tumor models. *Bioconjugate Chem.* 18, 389-396 (2007). Kim et al., Near-infrared fluorescent type II quantum dots for sentinel lymph node mapping. *Nat. Biotechnol.* 22, 93-97 (2003). Tanaka et al, Image-guided oncologic surgery using invisible light: completed pre-clinical development for sentinel lymph node mapping. *J Surg Oncol.* 13, 1671-1681 (2006). Toxicity testing was also performed and human normal-organ radiation doses derived. Specifically, we synthesized about 7 nm diameter, near-infrared (NIR) dye-encapsulating core-shell silica nanoparticles, coated with PEG chains and surface-functionalized with a small number (about 6-7) of targeting peptides and radiolabels.

We demonstrate that these probes simultaneously are non-toxic, exhibit high-affinity/avidity binding, efficient excretion, and significant differential uptake and contrast between tumor and normal tissues using multimodal molecular imaging approaches. The sensitive detection, localization, and interrogation of lymph nodes and lymphatic channels, enabled by the NIR dye fluorescence, highlights the distinct potential advantage of this multimodal platform for detecting and staging metastatic disease in the clinical setting, while extending the lower range of nodal sizes that can be detected.

Materials and Methods

Synthesis of cRGDY-PEG-Nanoparticles and PEG-Nanoparticles

Particles were prepared by a modified Stober-type silica condensation as described previously. Wiesner et al., PEG-coated Core-shell Silica Nanoparticles and Mathods of Manufactire and Use, PCT/US2008/74894. Larson, et al., Silica nanoparticle architecture determines radiative properties of encapsulated chromophores. *Chem. Mater.* 20, 2677-2684 (2008). Bogush, et al., Preparation of Monodisperse Silica Particles: Control of Size and Mass Fraction. *J. Non-Cryst. Solids*, 104, 95-106 (1988). Sadasivan, et al., Alcoholic Solvent Effect on Silica Synthesis—NMR and DLS Investigation. *J. Sol-Gel Sci. Technol.* 12, 5-14 (1998). Herz, et al., Large Stokes-Shift Fluorescent Silica Nanoparticles with Enhanced Emission over Free Dye for Single Excitation Multiplexing. *Macromol Rapid Commun.* 30, 1907-1910 (2009). Tyrosine residues were conjugated to PEG chains for attachment of radioiodine or stable iodine moieties. Hermanson, *Bioconjugate Techniques*, (Academic Press, London, ed. 2, 2008). All samples were optical density-matched at their peak absorption wavelength (640 nm) prior to radiolabeling. cRGD peptides were attached to functionalized PEG chains via a cysteine-maleimide linkage, and the number of cRGD peptides bound to the particle was estimated using FCS-based measurements of absolute particle concentrations and the starting concentration of the reagents for cRGD peptide.

Hydrodynamic Size and Relative Brightness Comparison Measurements by Fluorescence Correlation Spectroscopy (FCS)

Particles dialyzed to water were diluted into physiological saline (0.15 M NaCl in $H_2O$) and measured on a Zeiss LSM 510 Confocor 2 FCS using HeNe 633-nm excitation. The instrument was calibrated for size prior to all measurements. Diffusion time differences were used to evaluate variations in the hydrodynamic sizes of the dye and particle species. Relative brightness comparisons of the free dye and the PEG- and the RGDY-PEG nanoparticles were performed using count rates per molecule/particle.

Radiolabeling of C Dot Conjugates

Radiolabeling of the cRGDY-PEG and PEG-nanoparticles was performed using the IODOGEN method (Pierce, Rockford, Ill.). Piatyszek, et al., Iodo-gen mediated radioiodination of nucleic acids. *J. Anal. Biochem.* 172, 356-359 (1988). Activities were measured by gamma (γ)-counting and fluorescence measured using a Varian fluorometer (excitation 650 nm/emission 680).

Cells and Cell Culture

Human melanoma M21 and M21 variant (M21-L, $\alpha_v$ negative) cell lines were maintained in RPMI 1640 media/10% fetal BSA, 2 mM L-glutamine penicillin, and streptomycin (Core Media Preparation Facility, Memorial Sloan Kettering Cancer Center, New York). Human umbilical venous cord endothelial cells (HUVECs) were cultured in M199 media/10% fetal bovine serum, 20 μg/ml endothelial cell growth factor, 50 μg/ml heparin, penicillin and streptomycin.

In Vitro Cell-Binding and Molecular Specificity of $^{124}$I-cRGD-PEG-Nanoparticles To assay particle binding and specificity for M21 cells, 24-well plates were coated with 10 μg/ml collagen type I (BD Biosciences, Bedford, Mass.) in phosphate buffered saline (PBS) and incubated (37° C., 30 min). M21 cells (3.0-4.0×105 cells/well) were grown to confluency and washed with RPMI 1640 media/0.5% bovine serum albumin (BSA). $^{124}$I-cRGD-PEG-nanoparticles (0-4.0 ng/ml) were added to wells and cells incubated (25° C., 4 hours), washed with RPMI 1640 media/0.5% BSA, and dissolved in 0.2 M NaOH. Radioactivity was assayed using a 1480 Automatic Gamma Counter (Perkin Elmer) calibrated for iodine-124. Nonspecific binding was determined in the presence of a 1000-fold excess of cRGD (Peptides International, Louisville, Ky.). Scatchard plots of the binding data were generated and analyzed using linear regression analyses (Microsoft Excel 2007) to derive receptor-binding parameters (Kd, Bmax, IC50).

In Vitro Cell-Binding Studies Using Optical Detection Methods

Maximum differential binding of cRGDY-PEG-nanoparticles and PEG-nanoparticles to M21 cells was determined for a range of incubation times and particle concentrations using flow cytometry, with optimum values used in competitive binding and specificity studies. Cells (3.0×10⁵ cells/well) were washed with RPMI 1640 media/0.5% BSA, detached using 0.25% trypsin/EDTA, and pelleted in a microcentrifuge tube (5 min at 1400 rpm, 25° C.). Pellets were resuspended in BD FACSFlow solution (BD Biosciences, San Jose, Calif.) and analyzed in the Cy5 channel to determine the percentage of particle-bound probe (FACSCalibur, Becton Dickinson, Mountain View, Calif.). Competitive binding studies were additionally performed following incubation of cRGDY-PEG-nanoparticles (2.5 ng/ml) with M21, M21L, and HUVEC cells in the presence of excess cRGD and/or mouse monoclonal anti-human integrin $\alpha_v\beta_3$ fluorescein-conjugated antibody (Millipore, Temecula, Calif.) and analyzed by flow cytometry. To assess potency of the RGDY-PEG nanoparticles relative to the cRGD peptide, anti-adhesion assays were performed. Ninety-six-well microtiter plates were coated with vitronectin in PBS (5 μg/ml), followed by 200 μl of RPMI/0.5% BSA (1 h, 37° C.). Cells (3×10⁴/100 μl/well) were incubated in quadruplicate (30 min, 25° C.) with various concentrations of cRGDY-PEG-nanoparticles or cRGD peptide in RPMI/0.1% BSA, and added to vitronectin-coated plates (30 min, 37° C.). Wells were gently rinsed with RPMI/0.1% BSA to remove non-adherent cells; adherent cells were fixed with 4% PFA (20 min, 25° C.) and stained with methylene blue (1 h, 37° C.) for determination of optical densities, measured using a Tecan Safire plate reader ($\lambda ex$=650 nm, $\lambda em$=680 nm, 12 nm bandwidth). The multivalent enhancement factor was computed as the ratio of the cRGD peptide to cRGDY-PEG-dot IC50 values. Montet, et al., Multivalent effects of RGD peptides obtained by nanoparticle display. *J Med Chem.* 49, 6087-6093 (2006).

Animal Models and Tumor Innoculation

All animal experiments were done in accordance with protocols approved by the Institutional Animal Care and Use Committee of Memorial Sloan-Kettering Cancer Center and followed National Institutes of Health guidelines for animal welfare. Male athymic nu/nu mice (6-8 weeks old, Taconic Farms Inc, Hudson, N.Y.) were provided with water containing potassium iodide solution to block uptake by the thyroid gland of any free radioiodine in vivo, and maintained on a Harlan Teklad Global Diet 2016, ad libitum, as detailed elsewhere10. To generate M21 or M21L xenografts, equal volumes of cells (~5×10⁶/100 μl) and matrigel were co-injected subcutaneously into the hindleg in different mice. Tumor sizes were regularly measured with calipers, yielding average tumor volumes of 200 mm³.

In Vivo Pharmacokinetic and Residence Half-Time ($T_{1/2}$) Measurements

Time-dependent activity concentrations (% ID/g), corrected for radioactive decay to the time of injection, were measured by sacrificing groups of mice at specified times following i.v. injection of $^{124}$I-cRGDY-PEG-nanoparticles or $^{124}$I-PEG-nanoparticles (~20 μCi/mouse) and harvesting, weighing, and counting blood, tumor, and organs in a scintillation γ-counter calibrated for $^{124}$I. The resulting time-activity concentration data for each tissue were fit to a decreasing monoexponential function to determine the values of $T_{1/2}$ and A, the tissue/organ residence half time and zero-time intercept, respectively, of the function.

The fraction of particles excreted in the urine over time was estimated using previously described methods. Burns, et al., Fluorescent Silica Nanoparticles with Efficient Urinary Excretion for Nanomedicine, *Nano Letters* 9, 442-8 (2009). Briefly, mice were injected i.v. with either 200 μl unlabeled cRGDY-PEG-nanoparticles or PEG-nanoparticles, and urine samples collected over a 168-hr period (n=3 mice per time point). Particle concentrations at each time point were determined using fluorometric analyses and a serial dilution calibration curve generated from background-corrected fluorescence signal measurements of urine samples mixed with known particle concentrations (% ID). Concentration values, along with estimates of average daily mouse urine volumes, were then used to compute the cumulative % ID/g urine excreted over time. To assess cumulative fecal excretion, metabolic cages were used to collect feces over a similar time interval after i.v. injection of 200 μl $^{124}$I-cRGDY-PEG-nanoparticles (n=4 mice per time point). Specimen activities were measured using a γ-counter calibrated for $^{124}$I.

Dosimetry

Time-activity functions derived for each tissue were analytically integrated (with inclusion of the effect of radioactive decay) to yield the corresponding cumulative activity (i.e. the total number of radioactive decays). $^{124}$I mouse organ absorbed doses were then calculated by multiplying the cumulative activity by the $^{124}$I equilibrium dose constant for non-penetrating radiations (positrons), assuming complete local absorption of such radiations and ignoring the contribution of penetrating radiations (i.e., γ-rays). Eckerman, et al., *Radionuclide Data and Decay Schemes*, 2nd ed. Reston, Va.: Society of Nuclear Medicine; 1989. The mouse normal-organ cumulated activities were converted to human normal-organ cumulated activities by adjustment for the differences in total-body and organ masses between mice and humans (70-kg Standard Man). Cristy, et al., Specific absorbed fractions of energy at various ages from internal photon sources (I-VII). *Oak Ridge National Laboratory Report ORNL/TM-8381/V1-7*. Springfield, Va.: National Technical Information Service, Dept of Commerce; 1987. The human normal-organ cumulated activities calculated were entered into the OLINDA dosimetry computer program to calculate, using the formalism of the Medical Internal Dosimetry (MIRD) Committee of the Society of Nuclear Medicine, the Standard-Man organ absorbed doses. Loevinger, et al., *MIRD Primer for Absorbed Dose Calculations* (Society of Nuclear Medicine, New York, 1991). Stabin, et al., OLINDA/EXM: the second-generation personal computer software for internal dose assessment in nuclear medicine. *J Nucl Med.* 46, 1023-1027 (2005).

Acute Toxicity Studies and Histopathology

Figure 10:
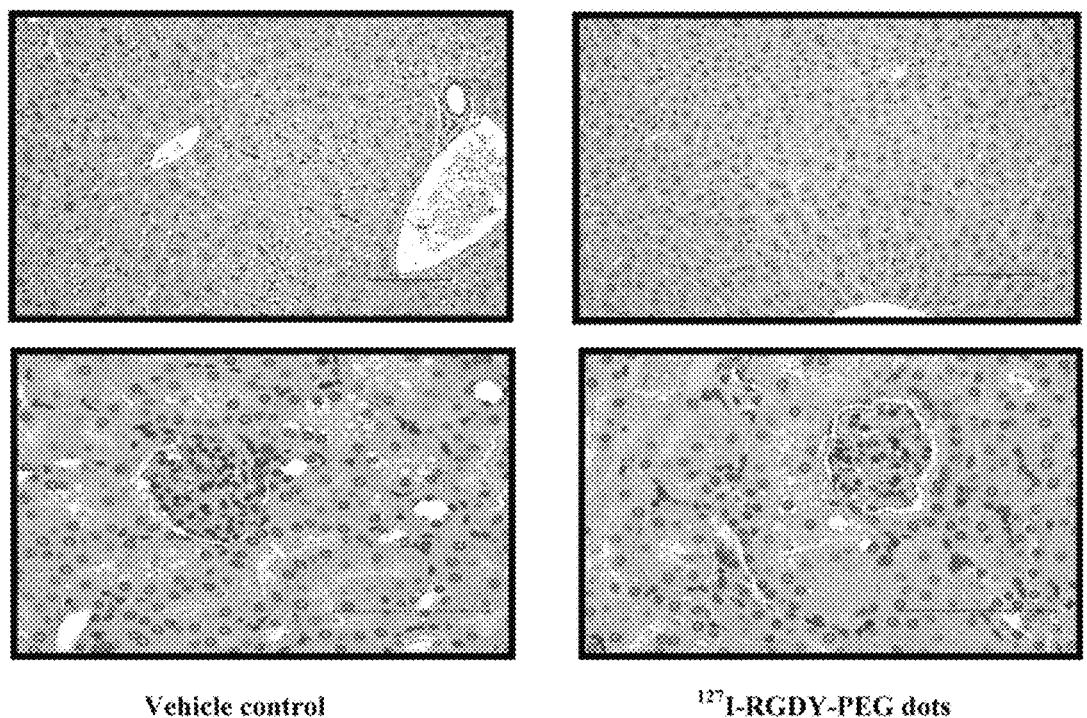
FIG. 10 shows acute toxicity testing results.
Figure 10:
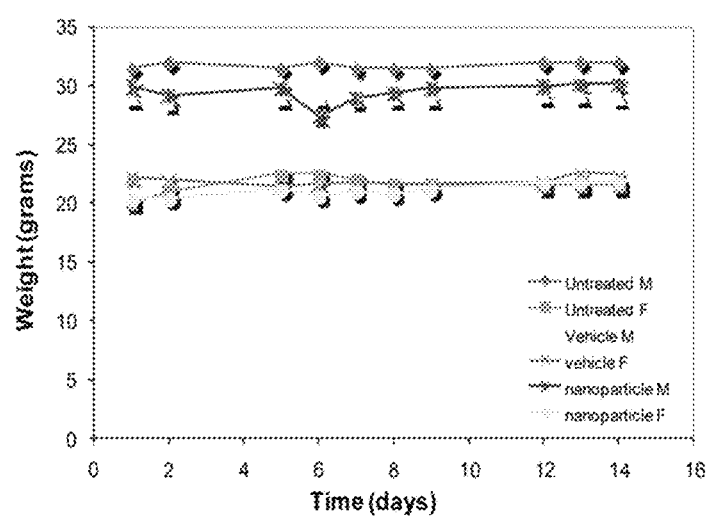

Acute toxicity testing was performed in six groups of male and female B6D2F1 mice (7 wks old, Jackson Laboratories, Bar Harbor, Me.). The treatment group (n=6 males, n=6 females) received unlabeled targeted probe ($^{127}$I-RGDY-PEG-nanoparticles) and the control group (n=6 males, n=6 females) unlabeled iodinated PEG-nanoparticles (vehicle, $^{127}$I-RGDY-PEG-nanoparticles) in a single i.v. injection (200 μl). Untreated controls (n=2 males, n=2 females) were additionally tested. Mice were observed daily over 14 days p.i. for signs of morbidity/mortality and weight changes, and gross necropsy, histopathology, and blood sampling for hematology and serum chemistry evaluation was performed at 7- and 14-days p.i (FIG. 10 and Table 3).

Serial PET Imaging of Tumor-Specific Targeting

Imaging was performed using a dedicated small-animal PET scanner (Focus 120 microPET; Concorde Microsystems, Nashville, Tenn.). Mice bearing M21 or M21L hindleg tumors were maintained under 2% isoflurane anesthesia in oxygen at 2 L/min during the entire scanning period. One-hour list-mode acquisitions were initiated at the time of i.v. injection of 200 μCi of $^{124}$I-cRGDY-PEG-nanoparticles or $^{124}$I-PEG-nanoparticles in all mice, followed by serial 30 min static images over a 96-hour interval. Image data were corrected for non-uniformity of the scanner response, dead time count losses, random counts, and physical decay to the time of injection. Voxel count rates in the reconstructed images were converted to activity concentrations (% ID/g) by use of a measured system calibration factor. Three-dimensional region-of-interest (ROI) analysis of the reconstructed images was performed by use of ASIPro software (Concorde Microsystems, Nashville, Tenn.) to determine the mean, maximum, and SD of probe uptake in the tumors. Tumor-to-muscle activity concentration ratios were derived by dividing the image-derived tumor % ID/g values by the γ-counter muscle % ID/g values.

Nodal Mapping Using Combined NIR Fluorescence Imaging and Microscopy

Nude mice bearing hindleg tumors were injected by 4-quadrant, peritumoral administration using equal volumes of a 50-μl cRGDY-PEG-dot sample and allowed to perambulate freely. Following a 30 min to 1-hr interval, mice were anesthetized with a 2% isofluorine/98% oxygen mixture, and a superficial paramidline incision was made vertically along the ventral aspect of the mouse to surgically expose the region from the hindlimb to the axilla ipsilateral to the tumor. In situ optical imaging of locoregional nodes (i.e., inguinal, axillary) and draining lymphatics (including axillary region) was performed using a macroscopic fluorescence microscope fitted with 650±20 nm NIR excitation and 710-nm long-pass emission filters. Whole-body optical images (Cambridge Research Instruments Maestro imager) were additionally acquired and spectrally deconvolved as reported previously. Burns, et al., Fluorescent Silica Nanoparticles with Efficient Urinary Excretion for Nanomedicine, *Nano Letters* 9, 442-8 (2009).

Statistical Analysis

Statistical analyses comparing groups of tumor mice receiving targeted/non-targeted probes or bearing M21/M21L tumors, were performed using a one-tail Mann-Whitney U test, with P<0.05 considered statistically significant. For biodistribution studies, the tissue-specific mean % ID/g values of $^{124}$I-cRGDY-PEG-(n=7 mice) and $^{124}$I-PEG-nanoparticles (control, n=5 mice) were compared at each time point, with statistically significant differences in tracer activities observed in blood, tumor, and major organs at 4 and 96 hrs p.i., as well as at 24 hrs p.i. for tumor and other tissues (Table 1). For tumor targeting studies, differences in mean % ID/g values between M21 (n=7) and M21L tumor mice (n=5), as well as mice receiving control probes (n=5), were found to be maximal at 4 hrs p.i. (p=0.0015 for both controls), remaining significantly elevated at 24 hrs (p=0.0015 and p=0.004, respectively), 48 hrs (p=0.001 and p=0.003, respectively), 72 hrs (p=0.015 and 0.005, respectively), and 96 hrs (p=0.005 for M21-M21L). Tumor-to-muscle ratios for $^{124}$I-cRGDY-PEG-nanoparticles (n=7) versus $^{124}$I-PEG-nanoparticles (n=5) were found to be statistically significant at 24 hrs p.i. (p=0.001) and 72 hrs p.i. (p=0.006), but not at 4 hrs p.i. (p=0.35). Goodness of fit values (R2), along with their associated p values, were determined for the urine calibration curve (R2=0.973, p=0.01), as well as for the urine (R2>0.95, p=0.047) and fecal (R2>0.995, p<0.002) cumulative % ID excretion curves using non-linear regression analyses (SigmaPlot, Systat, v. 11.0).

Results

Nanoparticle Design and Characterization

Figure 6:
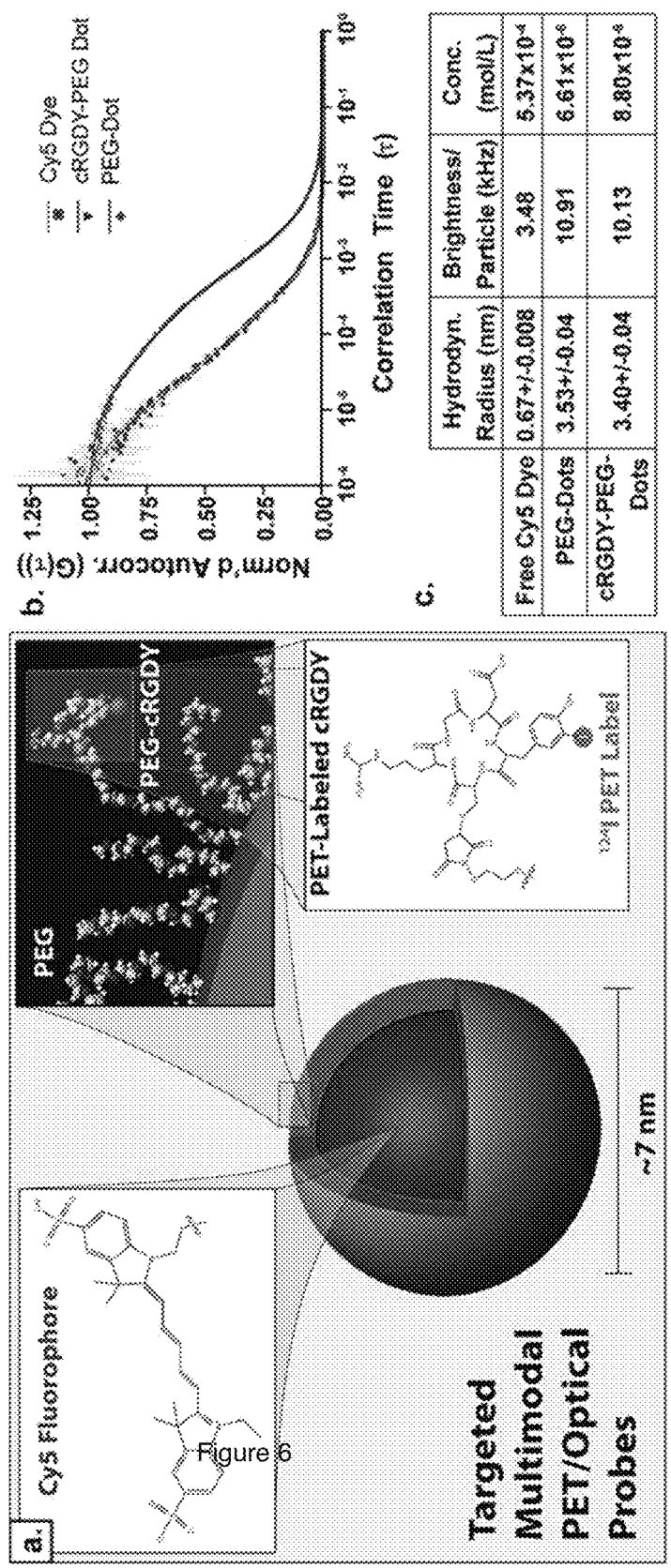
FIG. 6 shows multimodal C dot design for $\alpha_v\beta_3$-integrin targeting and characterization.
Figure 7:
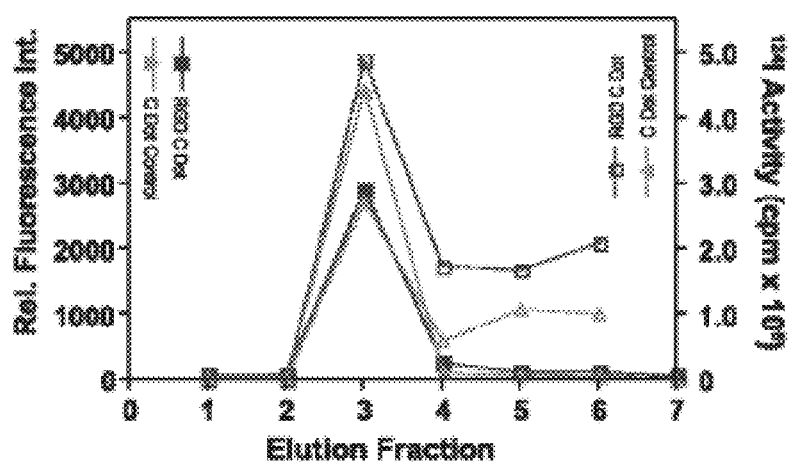
FIG. 7 shows purification and quality control of $^{124}$I-RGDY-PEG-dots using size exclusion column chromatography. Radioactivity (right column) of $^{124}$I-RGDdots and $^{124}$I-PEG-dots detected by γ-counting and corresponding fluorescence signal intensity (Cy5, left column) of $^{124}$I-RGDY-PEG-dots and $^{124}$I-PEG-dots in each eluted fraction.

Cy5 dye encapsulating core-shell silica nanoparticles (emission maxima >650 nm), coated with methoxy-terminated polyethylene glycol (PEG) chains (PEG ~0.5 kDa), were prepared according to previously published protocols. Burns, et al., Fluorescent Silica Nanoparticles with Efficient Urinary Excretion for Nanomedicine, *Nano Letters*, 9, 442-8 (2009). Ow, et al., Bright and stable core-shell fluorescent silica nanoparticles. *Nano Lett.* 5, 113-117 (2005). The neutral PEG coating prevented non-specific uptake by the reticuloendothelial system (opsonization). The use of bifunctional PEGs enabled attachment of small numbers (~6-7 per particle) of $\alpha_v\beta_3$ integrin-targeting cyclic arginine-glycine-aspartic acid (cRGDY) peptide ligands to maintain a small hydrodynamic size facilitating efficient renal clearance. Peptide ligands were additionally labeled with $^{124}$I through the use of a tyrosine linker to provide a signal which can be quantitatively imaged in three dimensions by PET ($^{124}$I-cRGDY-PEG-dots, FIG. 6A); an important practical advantage of relatively long-lived $^{124}$I (physical half-life: 4.2 d) is that sufficient signal persists long enough to allow radiodetection up to at least several days postadministration, when background activity has largely cleared and tumor-to-background contrast is maximized. Purity of the radiolabeled targeted nanoparticle was >95% by radio thin layer chromatography. Stability of the non-radiolabeled targeted nanoparticle is about 1 year by FCS measurements. Particle is excreted intact in the urine by FCS analyses. As used herein, "dot" and "nanoparticle" are used interchangeably. A PEG-coated particle containing a tyrosine residue for $^{124}$I labeling served as the control probe ($^{124}$I-PEG-dots). Purification of the radiolabeled samples by size exclusion chromatography (FIG. 7) resulted in radiochemical yields of >95%. Hydrodynamic diameters of ~7 nm i.d. were measured for non-radioactive cRGDY-PEG-dots and PEG-dots by fluorescence correlation spectroscopy (FCS) (FIGS. 6B and 6C). The relative brightness of the cRGDY-PEG-dots was determined, on average, to be 200% greater than that of the free dye (FIG. 6C), consistent with earlier results. Burns, et al., Fluorescent Silica Nanoparticles with Efficient Urinary Excretion for Nanomedicine, *Nano Letters,* 9, 442-8 (2009). Larson, et al., Silica nanoparticle architecture determines radiative properties of encapsulated chromophores. *Chem. Mater.* 20, 2677-2684 (2008). Based on these physicochemical properties, we anticipated achieving a favorable balance between selective tumor uptake and retention versus renal clearance of the targeted particle, thus maximizing target-tissue localization while minimizing normal-tissue toxicity and radiation doses.

In Vitro Receptor Binding Studies

Figure 8:
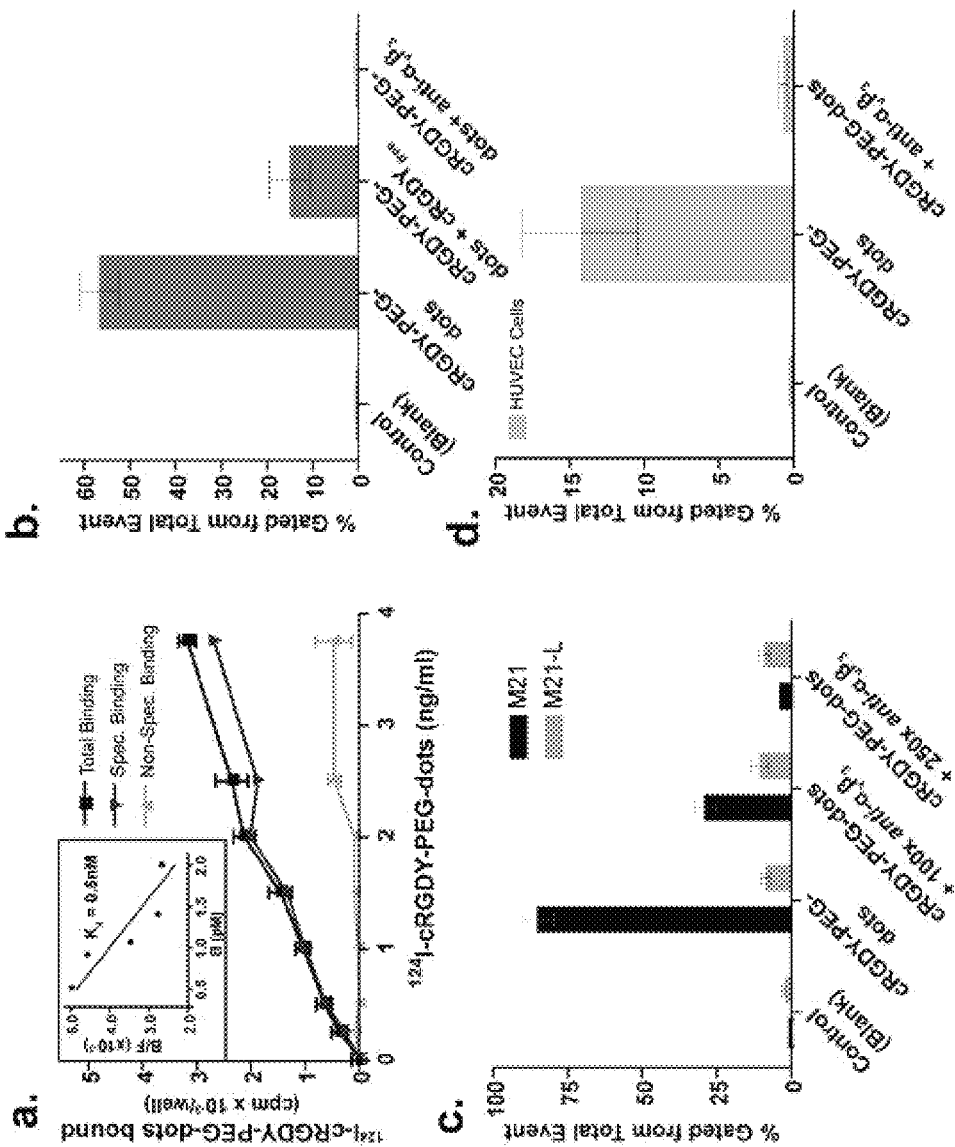
FIG. 8 shows competitive integrin receptor binding studies with $^{124}$I-cRGDY-PEG-dots, cRGDY peptide, and anti-$\alpha_v\beta_3$ antibody using two cell types.

To examine in vitro binding affinity and specificity of $^{124}$I-cRGDY-PEG-dots and $^{124}$I-PEGdots to tumor and vascular endothelial surfaces, $\alpha_v\beta_3$ integrin-overexpressing (M21) and nonexpressing (M21L) melanoma and human umbilical vein endothelial (HUVECs) cell lines were used. Highly specific linear and saturable binding of the cRGDY-PEG-dots was observed over a range of particle concentrations (0 to 8 ng/ml) and incubation times (up to 5-hrs), with maximum differential binding at 4-hr and ~2.0 ng/ml particle concentration (data not shown) using flow cytometry. Receptor-binding specificity of $^{124}$I-cRGDY-PEG dots was tested using γ-counting methods after initially incubating M21 cells with excess non-radiolabeled cRGD and then adding various concentrations of the radiolabeled targeted probe (FIG. 8A). Scatchard analysis of the binding data yielded a dissociation equilibrium constant, Kd, of 0.51 nM (FIG. 8A, inset) and receptor concentration, Bmax, of 2.5 pM. Based on the Bmax value, the $\alpha_v\beta_3$ integrin receptor density was estimated to be $1.0 \times 10^4$ per M21 cell, in reasonable agreement with the previously published estimate of $5.6 \times 10^4$ for this cell line. Cressman, et al., Binding and uptake of RGD-containing ligands to cellular $\alpha_v\beta_3$ integrins. *Int J Pept Res Ther.* 15, 49-59 (2009). Incremental increases in integrin-specific M21 cellular uptake were also observed over a temperature range of 4 to 37° C., suggesting that receptor-mediated cellular internalization contributed to overall uptake (data not shown). Additional competitive binding studies using the targeted probe showed complete blocking of receptor-mediated binding with anti-$\alpha_v\beta_3$ integrin antibody (FIG. 8B) by flow cytometry. No significant reduction was seen in the magnitude of receptor binding (~10% of M21) with M21L cells (FIG. 8C) using either excess cRGDY or anti-$\alpha_v\beta_3$ integrin antibody. These results were confirmed by additional γ-counting studies, and a 50% binding inhibition concentration, IC50, of 1.2 nM was determined for the $^{124}$I-cRGDY-PEG-dot. An associated multivalent enhancement factor of greater than 2.0 was found for the cRGDY-PEG-dot relative to the monomeric cRGD peptide using an anti-adhesion assay and M21 cells (data not shown). Montet, et al., Multivalent effects of RGD peptides obtained by nanoparticle display. *J Med Chem.* 49, 6087-6093 (2006). Li, et al., $^{64}$Cu-labeled tetrameric and octomeric RGD peptides for small-animal PET of tumor $\alpha_v\beta_3$ integrin expression. *J. Nucl Med.* 48, 1162-1171 (2007). Similar to M21 cells, excess antibody effectively blocked cRGDY-PEG-dot receptor binding to HUVEC cells by flow cytometry (FIG. 8D).

Biodistribution and Clearance Studies

Figure 9:
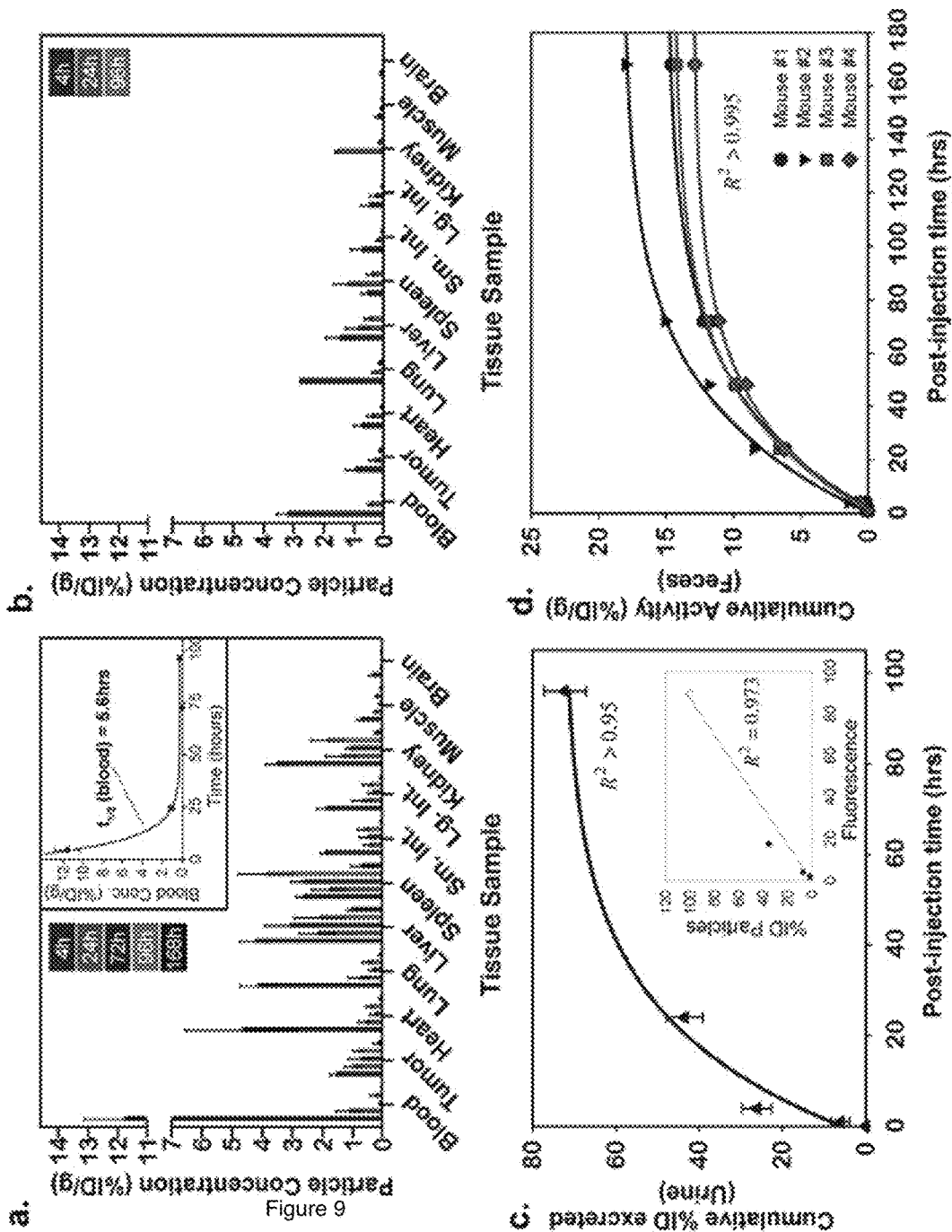
FIG. 9 shows pharmacokinetics and excretion profiles of the targeted and non-targeted particle probes.

The time-dependent biodistribution, as well as renal and hepatobiliary clearance were evaluated by intravenously administering tracer doses (~0.2 nanomoles) of $^{124}$I-cRGDY-PEGdots and $^{124}$I-PEG-dots to M21 tumor xenograft mouse models (FIG. 9). Although tissue activity-concentrations (percent of the injected dose per gram (% ID/g)) for the targeted probe were measured over a 196-hr post-injection (p.i.) time interval, comparison of the $^{124}$I-cRGDY-PEGdot (FIG. 9A) and $^{124}$I-PEG-dot tracers (FIG. 9B) was restricted to a 96-hr window, as data for the latter was not acquired at 1 week. Statistically significant (p<0.05) differences in tracer activities were observed for blood, tumor, and major organs at 4 and 96 hrs p.i., as well as at 24 hrs p.i. for the tumor and several other tissues (Table 1). The targeted probe was almost entirely eliminated from the carcass at 1 week p.i (~3% ID). The residence half times ($T_{1/2}$) for blood, tumor, and major organs for these tracers are shown in Table 2 (columns 2 and 5). A representative data set (blood residence) is shown in the inset of FIG. 9A. A relatively long blood $T_{1/2}$ value of 7.3±1.2 hrs was determined for the $^{124}$I-PEG-dot. Upon attachment of the cRGDY peptide to synthesize the $^{124}$I-cRGDY-PEG-dot, the $T_{1/2}$ value decreased slightly to 5.6±0.15 hrs, but was accompanied by greater probe bioavailability (Table 2, column 3). The tumor $T_{1/2}$ value for the $^{124}$I-cRGDY-PEG-dot was found to be about 13 times greater than that for blood, versus only a 5-fold difference for the $^{124}$I-PEG-dot (Table 2, columns 2 and 5).

TABLE 1

Biodistribution study p-values comparing
$^{124}$I-cRGDY-PEG- and $^{124}$I-PEG-dots†

| Tissue | Post-injection times (hours) | | |
|---|---|---|---|
| | 4 | 24 | 96 |
| Blood | 0.001 | 0.113 | 0.010 |
| Tumor | 0.045 | 0.012 | 0.001 |
| Heart | 0.019 | 0.231 | 0.001 |
| Lungs | — | 0.039 | 0.006 |
| Liver | 0.001 | 0.033 | 0.028 |
| Spleen | 0.001 | 0.208 | 0.001 |
| Small Intestine | 0.001 | 0.046 | 0.002 |
| Large Intestine | 0.001 | 0.137 | 0.003 |
| Kidneys | — | 0.356 | 0.001 |
| Muscle | 0.001 | 0.007 | 0.001 |
| Brain | 0.001 | 0.074 | 0.001 |

TABLE 2

| | Mouse | | | | | | Human[†] | |
|---|---|---|---|---|---|---|---|---|
| | [124]I-RGDY-PEG | | | [124]I-PEG | | | [124]I RGDY-PEG | [124]I-PEG |
| Target Organ | $T_{1/2}$ (h) | A (% ID/g) | Absorbed Dose (rad/mCi) | $T_{1/2}$ (h) | A (% ID/g) | Absorbed Dose (rad/mCi) | Absorbed Dose (rad/mCi) | |
| Blood | 5.9 | 18.8 | 626 | 7.3 | 4.7 | 189 | (see red marrow below) | |
| Heart | 6.8 | 7.0 | 266 | 34.1 | 0.8 | 120 | 0.307 (Wall) | 0.087 |
| Lungs | 8.5 | 5.7 | 267 | 37.7 | 3.0 | 498 | 0.298 | 0.263 |
| Liver | 65.9 | 3.9 | 935 | 52.5 | 1.4 | 294 | 0.486 | 0.234 |
| Spleen | 42.3 | 45.6 | 1071 | 27.4 | 45.7 | 410 | 3.20 | 0.254 |
| | 195. | | | 286 | | | | |
| Small Intestine | 30.3 | 1.8 | 251 | 13.2 | 0.9 | 61 | 0.304 | 0.115 |
| Large Intestine | 23.9 | 2.0 | 228 | 49.2 | 0.5 | 99 | 0.427 (U) | 0.209 |
| | | | | | | | 0.724 (L) | 0.416 |
| Kidneys | 66.0 | 3.0 | 712 | 33.0 | 2.0 | 388 | 2.50 | 0.320 |
| Muscle | 27.7 | 0.8 | 105 | 47.1 | 0.2 | 38 | 0.227 | 0.060 |
| Brain | 13.9 | 0.4 | 29 | 8.5 | 0.2 | 8 | 0.187 | 0.149 |
| [§]Tumor | 73.5 | 1.5 | 380 | 37.0 | 0.9 | 146 | n/a | n/a |
| [ʦ]Bone | | | | | | | (see osteogenic cells) | |
| Adrenals | | | | | | | 0.400 | 0.083 |
| Breasts | | | | | | | 0.141 | 0.042 |
| Gallbladder Wall | | | | | | | 0.289 | 0.097 |
| Stomach Wall | | | | | | | 0.265 | 0.065 |
| Ovaries | | | | | | | 0.303 | 0.124 |
| Pancreas | | | | | | | 0.389 | 0.081 |
| Red Marrow | | | | | | | 1.07 | 0.084 |
| Osteogenic Cells | | | | | | | 0.203 | 0.127 |
| Skin | | | | | | | 0.158 | 0.038 |
| Testes | | | | | | | 0.186 | 0.073 |
| Thymus | | | | | | | 0.173 | 0.052 |
| Thyroid | | | | | | | 0.188 | 0.043 |
| Urinary Bladder Wall | | | | | | | 2.01 | 1.65 |
| Uterus | | | | | | | 0.333 | 0.171 |
| Total Body | | | | | | | 0.034 | 0.075 |
| Effective Dose Equivalent (rem/mCi) | | | | | | | 0.863 | 0.256 |
| Effective Dose (rem/mCi) | | | | | | | 0.599 | 0.232 |

[†]70-kg Standard Man, U (upper), L (lower),
[§]mouse melanoma model,
[ʦ]bone activity much lower than other tissues (not reported)

By appropriate mass-adjusted translation of the foregoing biodistribution data to man, human normal-organ radiation doses were derived and found to be comparable to those of other commonly used diagnostic radiotracers (Table 2, columns 8, 9). Along with the finding that the targeted probe was non-toxic and resulted in no tissue-specific pathologic effects (i.e., no acute toxicity) (FIG. 10 and Table 3), first-in-man targeted and nontargeted molecular imaging applications with these agents are planned.

TABLE 3

Organ Histopathology for [127]I-RGDY-PEG-DOTS vs [127]I-PEG-DOTS

| | Treatment | | | | | | | | | |
|---|---|---|---|---|---|---|---|---|---|---|
| | UNTREATED | | [127]I-PEG-DOTS | | | | [127]I-RGDY-PEG-DOTS | | | |
| | Sex | | | | | | | | | |
| | M | F | M | M | F | F | M | M | F | F |
| Heart | N | N | N | N | N | N | N | N | N | N |
| Thymus | N | N | N | N | N | N | N | N | N | N |
| Trachea | N | N | N | N | N | N | N | N | N | N |
| Lungs | N | N | N | N | N | N | N | N | N | N |
| Kidneys | N | N | N | N | N | N | N | N | N | N |
| Liver | N | N | N | N | N | N | N | N | N | N |
| Random cellular clusters | | | | | 1 | | | | | |
| Gall bladder | NP | N | N | N | N | NP | N | NP | N | N |
| Pancreas | N | N | N | N | N | N | N | N | N | N |
| Chronic lymph | | | | 2F | | | N | N | N | N |
| Spleen | N | N | N | N | N | N | N | N | N | N |
| Salivary gland | N | N | N | N | N | N | N | N | N | N |
| Esophagus | N | N | N | N | N | N | N | N | N | N |
| Stomach | N | N | N | N | N | N | N | N | N | N |
| Small intestine | N | N | N | N | N | N | N | N | N | N |
| Follic lymph. hyperplasia | | | | | | 1 MF | | | | |

TABLE 3-continued

Organ Histopathology for $^{127}$I-RGDY-PEG-DOTS vs $^{127}$I-PEG-DOTS

| | UNTREATED | | $^{127}$I-PEG-DOTS | | | | $^{127}$I-RGDY-PEG-DOTS | | | |
|---|---|---|---|---|---|---|---|---|---|---|
| | M | F | M | M | F | F | M | M | F | F |
| Large intestine | N | N | N | N | N | N | N | N | N | N |
| Mesenteric lymph node | N | N | N | N | N | N | N | N | N | NP |
| Submandibular lymph | NP | NP | N | NP | N | N | N | N | N | N |
| Adrenals | N | N | N | N | N | N | N | N | N | N |
| Thyroid | N | N | N | N | N | N | N | N | N | N |
| Testes | N | U | N | N | U | U | N | N | U | U |
| Epididymides | N | U | N | N | U | U | N | N | U | U |
| Seminal vesicles | N | U | N | N | U | U | N | N | U | U |
| Coagulating glands | N | U | N | N | U | U | N | N | U | U |
| Prostate | N | U | N | N | U | U | N | N | U | U |
| Ovary | U | N | U | U | N | N | U | U | N | N |
| Uterus | U | N | U | U | N | N | U | U | N | N |
| Cervix | U | N | U | U | N | N | U | U | N | N |
| Mammary gland | NP | NP | N | NP | N | N | NP | NP | N | NP |
| Urinary bladder | N | N | N | N | N | N | N | N | N | N |
| Bones joint | N | N | N | N | N | N | N | N | N | N |
| Bone marrow | N | N | N | N | N | N | N | N | N | N |
| Spinal cord | N | N | N | N | N | N | N | N | N | N |
| Brain | N | N | N | N | N | N | N | N | N | N |
| Pituitary | N | NP | N | N | N | N | N | N | N | N |
| Skin | N | N | N | N | N | N | N | N | N | N |
| Subcut. inflammation | | 1 | | | | | | | | |
| Skeletal muscle | N | N | N | N | N | N | N | N | N | N |
| Peripheral nerves | N | N | N | N | N | N | N | N | N | N |

N: normal, U: unavailable, NP: not present, 1: minimal, 2: mild F: focal, MF: multifocal In another study to confirm that $^{127}$I-RGD-PEG dots are non-toxic after intravenous administration in mice, formal single dose toxicity testing was performed over the course of 2 weeks using $^{127}$I-RGD-PEG dots at about 100 times of the human dose equivalent. $^{127}$I-PEG dots served as the control particle. In summary, the procedure was as follows. Twenty-eight, 8 week old B6D2F1 mice were used in the acute toxicity study and were divided into a treatment and control group. The treatment group (n=6 males+6 females) received one dose $^{127}$I-PEGylated RGD silica nanoparticles at a dose of $1 \times 10^{-9}$ moles/mouse intravenously, and the control group (n=6 males+6 females) received the same amount of vehicle. Two mice/group (one male and one female/group) were sacrificed on day 7 post dose and clinical chemistry, hematology and tissue specific histopathology were done at autopsy. All remaining animals (n=5 males+5 females/group) were observed for 14 days following treatment. Four untreated mice (two males and two females) were used as reference. The conclusion of the studies was that no adverse events were observed during dosing or the following 14-days observation period. No mortality or morbidity was observed. Clinical observations included the absence of the following: anemia, weight loss, agitation, increased respiration, GI disturbance, abnormal behavior, neurological dysfunction, abnormalities in hematology, abnormalities in clinical chemistries, or drug-related lesions in terms of organ pathology. Thus, a single injection of $^{127}$I-PEGylated RGD silica nanoparticles at $1 \times 10^{-9}$ moles/mouse, a dose equivalent to an excess of 100 times the PEGylated RGD silica nanoparticles dose required for Phase 0 imaging studies, is safe and nontoxic in B6D2F1 mice.

Efficient renal excretion was found for the ~7-nm diameter targeted and non-targeted probes over a 168-hr time period by fluorometric analyses of urine samples. Fluorescence signals were background-corrected and converted to particle concentrations (% ID/µl) based on a serial dilution calibration scheme (FIG. 9C, inset; Table 4, column 2). Burns, et al., Fluorescent Silica Nanoparticles with Efficient Urinary Excretion for Nanomedicine, Nano Letters, 9, 442-8 (2009). Concentration values, along with age-dependent conservative estimates of the average urine excretion rate, permitted the cumulative % ID excreted to be computed (Table 4, column 4). Drickamer, Rates of urine excretion by house mouse (mus domesticus): differences by age, sex, social status, and reproductive condition. J. Chem. Ecol. 21, 1481-1493 (1995). Nearly half of the injected dose (about 43% ID) was observed to be excreted over the first 24 hrs p.i. and ~72% ID by 96 hrs, FIG. 9C), suggesting that the bulk of excretion has occurred in the first day p.i. No significant particle fluorescence in urine could be detected 168 hrs p.i. Fecal excretion profiles of the $^{124}$I-cRGDY-PEG-dot indicated that, on average, 7% ID and 15% ID of the injected dose was eliminated over 24 and 96 hrs, respectively (FIG. 9D). FCS analysis of urine samples obtained at multiple time points after injection of the targeted probe revealed that the particle was excreted intact and without release of the encapsulated dye (data not shown).

TABLE 4

Urine Concentration and Cumulative Excretion Data

| | Time (hr) | Concentration (% ID/ul) | Avg. Urine Volume (µl) | Computed Cumulative % ID Excreted |
|---|---|---|---|---|
| 7.0 mm RGDY-PEG dot | 0 | 0.0 | 0.0 | 0 |
| | 1 | 0.292 | 41.6 | 6.07 |
| | 4 | 0.026 | 166.7 | 26.1 |
| | 24 | 0.016 | 1000. | 43.4 |
| | 96 | 0.004 | 3974. | 72.2 |

Serial Whole Body PET Studies

Figure 11:
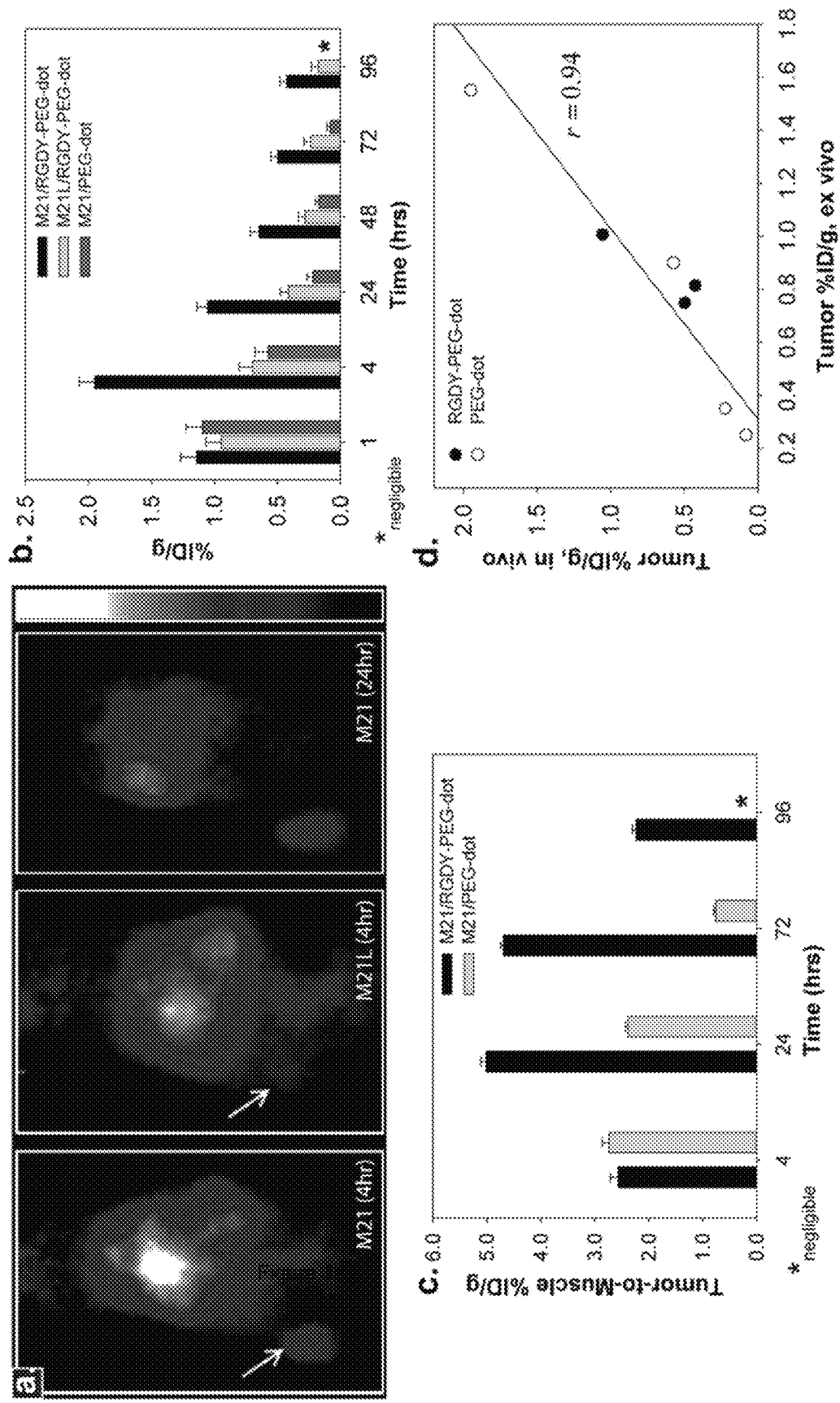
FIG. 11 shows serial in vivo PET imaging of tumor-selective targeting.

PET imaging of integrin expression in M21 and M21L subcutaneous hindleg xenograft mouse models was performed at multiple time points p.i. following i.v. injection of $^{124}$I-cRGDY-PEG-dots or $^{124}$I-PEG-dots (control). Representative whole-body coronal microPET images at 4 hrs (left: M21 tumor; middle: M21L tumor) and 24 hrs (right: M21 tumor) p.i. are shown in FIG. 11A. The specific targeting of the $\alpha_v\beta_3$ integrin-overexpressing M21 tumor is clearly visible from these images. Average tumor % ID/g and standard deviations are shown for groups of M21 (n=7) and M21L (control) tumors (n=5) receiving the targeted $^{124}$I-cRGDY-PEG-dots, as well as for M21 tumor mice (n=5) receiving non-targeted $^{124}$I-PEG-dot tracer (FIG. 11B). At the time of maximum tumor uptake (~4 hrs p.i.), three-fold activity-concentration increases (in % ID/g) were seen in the M21 tumors over the controls. Differences were statistically significant at all time points p.i. (p<0.05) except at 1 hr (p=0.27).

Image-derived tumor-to-muscle uptake (% ID/g) ratios for the $^{124}$I-cRGDY-PEG-dots revealed enhanced tumor contrast at later times (~24-72 hrs p.i.), while that for $^{124}$I-PEG-dots declined (FIG. 11C). This finding suggested that $^{124}$I-cRGDY-PEG-dots were, in fact, tumor-selective, which became more apparent as the blood activity was cleared during the initial 24-hr period (compare FIG. 11C with inset of FIG. 9A). A statistically significant correlation was found between PET-derived tumor tissue % ID/g values for both $^{124}$I-cRGDY-PEG-dots and $^{124}$I-PEGdots, and the corresponding ex-vivo γ-counted tumor % ID/g values (correlation coefficient r=0.94, P<0.0016; FIG. 11D), confirming the accuracy of PET for non-invasively deriving quantitative biodistribution data.

In Vivo NIR Fluorescence Imaging and Microscopy

We performed in vivo fluorescence imaging studies using our small, targeted nanoparticles for mapping local/regional nodes and lymphatic channels, thus overcoming the foregoing limitation. Importantly, the multimodal nature and small size of our targeted particle probe can be exploited to visualize a range of nodal sizes and lymphatic branches in our melanoma model following 4-quadrant, peritumoral administration, simulating intraoperative human sentinel lymph node mapping procedures. Initially, serial NIR fluorescence microscopy was performed in intact mice over a 4-hr time period using either the targeted or non-targeted particle probes. Peritumoral administration of the targeted probe revealed drainage into and persistent visualization of adjacent inguinal and popliteal nodes over this interval, with smaller and/or more distant nodes and lymphatics more difficult to visualize. By contrast, the non-targeted probe yielded shorter-term (~1 hr) visualization of local nodes with progressively weaker fluorescence signal observed (data not shown). Upon surgical exposure, this observation was found to be the result of more rapid particle diffusion from the tumor site, as compared with the extended retention observed with the targeted probe.

Figure 12:
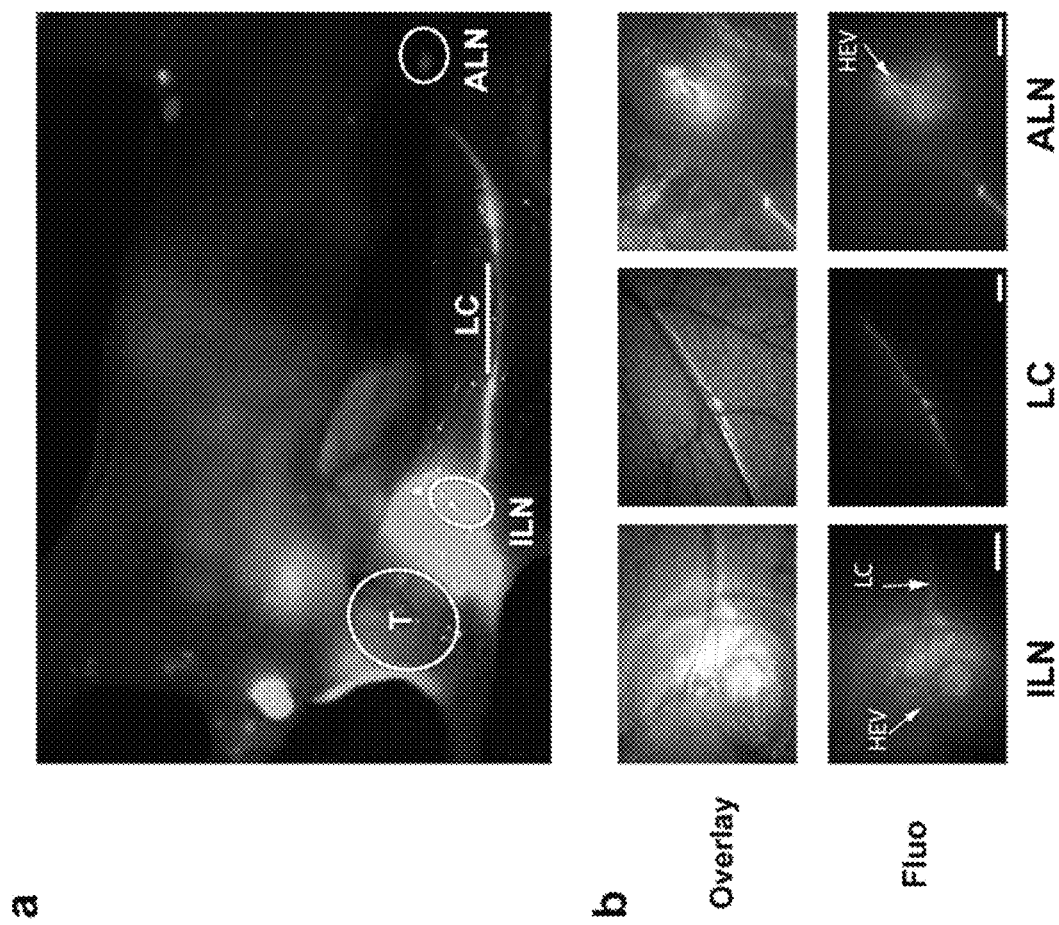
FIG. 12 shows nodal mapping using multi-scale near-infrared optical fluorescence imaging.

We next performed representative lymph node mapping over multiple spatial scales using live-animal whole-body optical imaging (FIG. 12A) and NIR fluorescence microscopy techniques (FIG. 12B) to visualize lymphatic drainage from the peritumoral region to the inguinal and axillary nodes in surgically exposed living animals. In addition, higher-resolution fluorescence images (FIG. 12B, lower row) permitted more detailed intranodal architecture to be visualized, including high endothelial venules, which facilitate passage of circulating naïve lymphocytes into the node, and which may have important implications for nodal staging and the ability to detect micrometastases at earlier stages of disease. Smaller, less intense lymphatic branches were also visualized by fluorescence microscopy in the axillary region (data not shown). Thus, the small size of the targeted probe not only permits the first draining (or sentinel node), proximal to the tumor to be visualized, but also enables visualization of more distant nodes and of the pattern of lymphatic drainage to be visualized.

Discussion

We report on non-toxic, high-affinity, and efficiently cleared silica nanoparticles for tumor-selective targeting and nodal mapping, having successfully addressed a number of the current challenges associated with other particle technologies. This is the first targeted nanoparticle that, on the basis of its favorable properties, can be said to be clinically translatable as a combined optical-PET probe. The complementary nature of this multimodal probe, coupled with its small size (~7-nm diameter), may facilitate clinical assessment by enabling the seamless integration of imaging data acquired at different spatial, temporal, and sensitivity scales, potentially providing new insights into fundamental molecular processes governing tumor biology.

Our in vitro results show receptor-binding specificity of the ~7-nm targeted particle probe to M21 and HUVEC cells. Similar findings have been reported with receptor-binding assays using the same cell types, but with the monovalent form of the peptide. Cressman, et al., Binding and uptake of RGD-containing ligands to cellular $\alpha_v\beta_3$ integrins. *Int J Pept Res Ther.* 15, 49-59 (2009). Importantly, the multivalency enhancement of the cRGDY-bound particle probe, along with the extended blood and tumor residence time $T_{1/2}$ values, are key properties associated with the particle platform that are not found with the monovalent form of the peptide.

The relatively long blood $T_{1/2}$ value of 7.3±1.2 hrs estimated for the $^{124}$I-PEG-dot tracer may be related to the chemically neutral PEG-coated surface, rendering the probe biologically inert and significantly less susceptible to phagocytosis by the reticuloendothelial system. That a reduction in the $T_{1/2}$ value to 5.6±0.15 hrs was found for the $^{124}$I-cRGDY-PEG-dot tracer is most likely the result of recognition by target integrins and/or more active macrophage activity. However, it is substantially longer than published blood $T_{1/2}$ values of existing cRGDY peptide tracers (~13 minutes), and results in greater probe bioavailability, facilitating tumor targeting and yielding higher tumor uptakes over longer periods of time. Montet, et al., Multivalent effects of RGD peptides obtained by nanoparticle display. *J Med Chem.* 49, 6087-6093 (2006). In addition, the tumor $T_{1/2}$ value for the $^{124}$I-cRGDY-PEG-dot was about 13 times greater than that for blood, versus only a fivefold difference for the $^{124}$I-PEG-dot, suggesting substantially greater target-tissue localization of the former than the latter. Such mechanistic interpretations of the in vivo data can be exploited to refine clinical diagnostic, treatment planning, and treatment monitoring protocols.

The results of this study underscore the clear-cut advantages offered by PET, a powerful, quantitative, and highly sensitive imaging tool for non-invasively extracting molecular information related to receptor expression levels, binding affinity, and specificity. The greater accumulation in and slower clearance from M21 tumors, relative to surrounding normal structures, allows discrimination of specific tumor uptake mechanisms from non-specific mechanisms (i.e., tissue perfusion, leakage) in normal tissues. A small component of the M21 tumor uptake, however, presumably can be attributed to vascular permeability alterations (i.e., enhanced permeability and retention effects). Seymour, Passive tumor targeting of soluble macromolecules and drug conjugates. *Crit. Rev. Ther. Drug Carrier Syst.* 9, 135-187 (1992). This non-specific mode of uptake reflects a relatively small portion of the overall tumor uptake at earlier p.i. time points based on the observed % ID/g increases in mice receiving the control tracer ($^{124}$I-PEG-dots, FIG. 11B). At 1-hr p.i., no significant % ID/g increases were seen in the M21 tumors over the controls. This observation may reflect the effects of differential perfusion in the first hour, with tumor accumulation and retention primarily seen at later p.i. times (i.e., 24 hrs). Further, in comparison with the clinically approved peptide tracer, $^{18}$F-galacto RGD, nearly two-fold greater uptake in M21 tumors was found for the $^{124}$I-cRGDY-PEG-dots34, while additionally offering advantages of multivalent binding, extended blood circulation times, and greater renal clearance.

One advantage of a combined optical-PET probe is the ability to assess anatomic structures having sizes at or well below the resolution limit of the PET scanner (i.e., the so-called partial-volume effect), which may undermine detection and quantitation of activity in lesions. For instance, in small-animal models, assessment of metastatic disease in small local/regional nodes, important clinically for melanoma staging and treatment, may not be adequately resolved by PET imaging, given that the size of the nodes observed are typically on the order of system spatial resolution (1-2 mm). By utilizing a second complementary and sensitive imaging modality, near-infrared (NIR) fluorescence imaging, functional maps revealing nodal disease and lymphatic drainage patterns can be obtained. Ballou, et al., Sentinel lymph node imaging using quantum dots in mouse tumor models. *Bioconjugate Chem.* 18, 389-396 (2007). While further studies investigating the distribution of intranodal cRGDY-PEG-dot fluorescence in relation to metastatic foci are needed to determine whether sensitive localization of such foci can be achieved, these results clearly demonstrate the advantages of working with such a combined optical-PET probe.

In the clinic, the benefits of such a combined platform for tumor staging and treatment cannot be overstated. The extended blood circulation time and resulting bioavailability of this nanoprobe highlights its use as a versatile tool for both early and long-term monitoring of the various stages of disease management (diagnostic screening, pre-treatment evaluation, therapeutic intervention, and post-treatment monitoring) without restrictions imposed by toxicity considerations. An additional important advantage is that while rapidly cleared probes may be useful for certain applications where target tissue localization is itself rapid, localization of many agents in often poorly vascularized and otherwise relatively inaccessible solid tumors will likely be slow following systemic administration. Thus, the current nanoparticle platform expands the range of applications of such agents, as the kinetics of target tissue localization are no longer limiting. Furthermore, deep nodes can be mapped by PET in terms of their distribution and number while more precise and detailed localization of superficial nodes can be obtained by NIR fluorescence imaging. Finally, the relatively prolonged residence of the targeted probe from tumor relative to that from blood, in addition to its multivalency enhancement, may be exploited for future theranostic applications as a radiotherapeutic or drug delivery vehicle.

Example 5 Fluorescent Silica Nanoparticles Conjugated with $\alpha_v\beta_3$ Integrin-Targeting Peptide and/or uMUC1-Targeting Peptide (Thyroid Cancer and Squamous Cell Carcinoma (SCC) Models)

A cRGD peptide (Peptides International), having a cysteine end functionality, will be attached to the PEG-ylated nanoparticle via a thiol-maleimide linkage. The nanoparticles can optionally further be functionalized by a synthetic peptide ligand, EPPT1. The nanoparticles will be characterized on the basis of particle size, size distribution, and photobleaching.

Characterization of Nanoparticle-Peptide Conjugates

For assessing photophysical properties on a per-particle basis, spectrophotometry, spectrofluorometry, and multiphoton fluorescence correlation spectroscopy (FCS) will be used to determine the particle size, brightness, and size distribution. Size data will be corroborated by scanning electron microscopy and dynamic light scattering (DLS) measurements. Ow et al. Bright and stable core-shell fluorescent silica nanoparticles. *Nano Letters* 2005; 5, 113. Average number of RGD peptides per nanoparticle and coupling efficiency of RGD to functionalized PEG groups will be assessed colorimetrically under alkaline conditions and Biuret spectrophotometric methods ($\lambda$=450 nm, maximum absorbance).

The nanoparticle conjugates will be iodinated via tyrosine linkers to create a radiolabeled ($^{124}$I)($T_{1/2}$~4 d) and stable ($^{127}$I) form by using Iodogen (Pierce, Rockford, Ill.). The end product will be purified by using size exclusion chromatography.

Evaluation of In Vitro Targeting Specificity and Biodistribution Patterns of the RGD- and RGD-EPPT-Nanoparticles.

$\alpha_v\beta_3$ integrin and uMUC1 expression patterns in thyroid and squamous cell carcinoma (SCC) cell lines will be evaluated against known $\alpha_v\beta_3$ integrin-negative and $\alpha_v\beta_3$ integrin-positive (M21-L and M21 human melanoma cell lines, respectively) and uMUC1-negative and uMUC1-positive (U87[28], H-29 cell lines, respectively) controls using anti-integrin and anti-uMUC 1 antibodies. Cell lines highly expressing $\alpha_v\beta_3$-integrin and/or MUC1 will be selected for differential binding studies with RGD- and RGD-EPPT-nanoparticles, as well as for in vivo imaging.

Quantitative cell binding assays will assess the labeling efficiency of tumor cells, and biodistribution studies assaying uptake in tumor, organs, and fluids will be performed using radioiodinated nanoparticle conjugates ($^{124}$I-RGD-nanoparticles, $^{124}$I-RGD-EPPT-nanoparticles). To compare PET uptake data of nanoparticle conjugates with that observed initially using optical NIRF imaging, each nanoparticle conjugate will also be iodinated to create a radiolabeled ($^{124}$I) and stable ($^{127}$I) form.

Fluorescence Microscopy with RGD- and RGD-EPPT-C-dots. Differential binding of RGD-nanoparticles and RGD-EPPT-nanoparticles to thyroid carcinoma/SCC cell lines highly expressing $\alpha_v\beta_3$-integrin and/or MUC1, versus control lines will be visualized by fluorescence microscopy.

Animal models. All animal experiments will be done in accordance with protocols approved by the Institutional Animal Care and Use Committee and following NIH guidelines for animal welfare.

In vivo Biodistribution: Male athymic nude mice (6-8 week old, n=5 per tumor) will be subcutaneously (s.c.) injected in both flanks with integrin-negative/-positive or uMUC1-negative/-positive tumors of different tissue origins (n=3/each tumor). At 0.5 cm in diameter (i.d.), mice will be injected intravenously (IV) with $^{124}$I-labeled nanoparticle conjugates (~500 nm/kg). Animals are sacrificed at 0.5, 1, and 24-hrs later, with removal of tumors, organs, and fluids for weighing and counting (gamma counter). Biodistribution results will be expressed as the percentage of injected dose per gram of tissue.

Quantitative Cell Binding Assay. Labeling efficiency will be assessed by incubating fixed numbers of carcinoma cells highly expressing $\alpha_v\beta_3$-integrin and/or MUC1, with preselected concentrations of $^{124}$I-labeled nanoparticle conjugates for 1-hr in a humidified $CO_2$ atmosphere at 37° C. Cells are extensively washed, lysed with 0.1% Triton X, with cell lysates counted in a gamma counter.

Assess of Relative Differences in Tumor-Specific Targeting Using In Vivo Multimodality (PET-NIRF) Imaging.

As a high-throughput diagnostic screening tool, optical NIRF imaging can be used to evaluate relative differences in the biodistribution of progressively functionalized nanoparticle conjugates in vivo with increased sensitivity and temporal resolution. Semi-quantitative data on tumor-specific targeting can also be derived. These preliminary studies facilitate the selection of cell lines strongly expressing markers of interest for further detailed quantitation of biodistribution and tumor-specific targeting using PET.

Whole-body microPET™ and NIRF optical imaging will be performed over a 1-week period to assess differential uptake in flank tumors. The results of these studies will be validated with fluorescence microscopy of tumors ex-vivo.

Serial In Vivo NIRF Imaging. Mice will be injected bilaterally with $\alpha_v\beta_3$ integrin-negative and $\alpha_v\beta_3$ integrin-positive cells or with uMUC1-negative and uMUC1-positive cells (n=5/tumor). After tumors reach ~0.5 cm i.d., stable iodinated and non-iodinated nanoparticle conjugates (RGD, $^{127}$I-RGD, RDG-EPPT, $^{127}$I-RGD-EPPT) will be injected IV. Serial imaging will be performed using the Maestro™ In Vivo Fluorescence Imaging System (CRI, Woburn, Mass.) at 0, 0.5, 1, 2, 4, 6, 12, and 24 hrs. At 24-h, mice are euthanized, and major tissues/organs dissected, weighed, and placed in 6-well plates for ex-vivo imaging. Fluorescence emission will be analyzed using regions-of-interest (ROIs) over tumor, selected tissues, and reference injectates, employing spectral unmixing algorithms to eliminate autofluorescence. Dividing average fluorescence intensities of tissues by injectate values will permit comparisons to be made among the various tissues/organs for each injected nanoparticle conjugate.

Dynamic MicroPET Imaging Acquisition and Analysis. Two groups of tumor-bearing mice (n=5/tumor) will be injected with radiolabeled $^{124}$I-nanoparticle conjugates (radiotracers), and dynamic PET imaging performed for 1-hr using a Focus 120 microPET™ (Concorde Microsystems, TN). One-hour list-mode acquisitions are initiated at the time of IV injection of ~25.9 MBq (700 µCi) radiotracers. Resulting list-mode data are reconstructed in a 128×128×96 matrix by filtered back-projection. ROI analysis of reconstructed images is performed using ASIPro™ software (Concorde Microsystems, TN) to determine the mean and SD of radiotracer uptake (% ID/g) in tumors, other organs/tissues, and left ventricle (LV). Additional data will be obtained from static images at 24-, 48-, and 72-hr post-injection time points. A three-compartment, four-parameter kinetic model will be used to characterize tracer behavior in vivo. For this analysis, arterial input is measured using an ROI placed over the LV.

Example 6 Nodal Mapping in Miniswine

Real-time intraoperative scanning of the nodal basin cannot be practically achieved at the present time, as these systems are generally too cumbersome and expensive for use in the operating suite or may be unable to provide the necessary field-of-view or tissue contrast. Further, there are no clinically promising, biostable fluorophore-containing agents, offering improved photophysical features and longer circulation lifetimes over parent dyes, available to enhance tissue contrast for extended nodal mapping/resection procedures. With this animal study, we will show that advances in both multimodal particle probes and real-time molecular imaging device technologies can be readily translated to a variety of future human clinical trials. Such transformative technologies can significantly impact standard intraoperative cancer care by providing state-of-the-art targeted visualization tools for facilitating metastatic SLN detection and enabling accurate delineation of node(s) from adjoining anatomy to minimize risk of injury to crucial structures. Benefits include extended real-time in vivo intraoperative mapping of nodal disease spread and tumor extent in the head and neck. Deep nodes can be mapped by PET, while precise and detailed localization of superficial nodes can be obtained by NIR fluorescence imaging. The small size of the particle probe may also extend the lower limit of nodal sizes that can be sensitively detected. The net effect of the proposed non-toxic, multimodal platform, along with the application of combined diagnostic/treatment procedures, has important implications for disease staging, prognosis, and clinical outcome for this highly lethal disease.

Disease Target.

In addition to melanoma, a number of other tumors (i.e., breast, lung, and brain) overexpress $\alpha v\beta 3$ integrin receptors and could serve as disease targets. Metastatic melanoma has a very poor prognosis, with a median survival of less than 1 year. Successful management relies on early identification with adequate surgical excision of the cancer. Surgical removal of the primary disease, screening, and treatment for regional lymph node spread is standard-of-care in the US to accurately stage disease and tailor treatment. The recently revised staging guidelines recognize the presence of microscopic nodal metastases as a hallmark of advanced stage disease leading to dramatically reduced survival. Knowledge of pathologic nodal status is critical for early risk stratification, improved outcome predictions, and selection of patient subgroups likely to benefit from adjuvant treatment (therapeutic nodal dissection, chemotherapy) or clinical trials.

Sentinel Lymph Node (SLN) Mapping.

SLN mapping techniques, routinely used in staging melanoma, identify the specific node(s) that are at highest risk of tumor metastases. This procedure identifies patients harboring metastatic disease for further treatment. Standard-of-care techniques rely on injection of radioactive technetium ($^{99m}$Tc) sulfur colloid dye around the primary tumor for SLN localization, followed by the intraoperative use of a gamma probe to measure radioactivity in lymphatic structures within an exposed nodal basin. Blue dye injected about the primary tumor can help delineate small SLN(s) from adjacent tissue, but the technique is unreliable and liable to complications. Current SLN mapping and biopsy techniques have limitations, and account for higher rates of non-localization of SLN(s) in the head and neck compared to other anatomic sites. The head and neck region is notorious for its unpredictable patterns of metastatic disease. The close proximity of the primary disease to nodal metastases in this region makes intraoperative use of the gamma probe difficult due to interference from the injection site. Importantly, current technology does not allow the surgeon to visualize the sentinel node and reliably differentiate it from adjoining fat or other tissues, placing vital structures (i.e., nerves) at risk for injury during dissection to identify and harvest this node. The small size of nodes and wide variation in drainage patterns provides additional challenges, resulting in a non-localization rate of around 10%.

Nanoparticles.

The majority of preclinical studies have used RGD peptide or peptide-conjugate radiotracers as targeting ligands for imaging αvβ3-integrin expression. $^{18}$F-galacto-RGD and $^{99m}$Tc-NC100692 are peptide tracers that have been used successfully in patients to diagnose disease. Peptide tracers clear rapidly, which may result in reduced receptor binding and increased background signal from non-specific tissue dispersal. These properties limit the potential of peptide tracers for longer-term monitoring. By contrast, nanoparticle probes (~10-100 nm), which have also been used for imaging integrin expression along tumor neovasculature, have extended circulation half times for performing longer-term monitoring (i.e., days). Nanoparticles are typically larger than antibodies and radiopharmaceuticals (<10 kDa), and are associated with slower transmembrane transport, increased reticuloendothelial system (RES) uptake, and enhanced non-specific uptake due to altered tumor vascular permeability. The 7 nm diameter targeted nanoparticles used for this SLN mapping study are roughly comparable to the average diameter of an albumin molecule and 2-3 times smaller than the average diameter of a typical antibody. Relative to peptide tracers, the targeted particle probe is less prone to extravasation and is associated with extended circulation half times that enhance tumor targeting. Importantly, 124I-cRGDY-PEG-dots demonstrate key in vitro and in vivo properties in M21 tumors necessary for clinical translation.

Materials and Methods.

Spontaneous melanoma Sinclair miniature swine (10-12 kg, Sinclair Research Center, MO) were injected intravenously with 5 mCi $^{18}$F-fluoro-deoxyglucose ($^{18}$F-FDG) for whole-body screening of nodal and/or organ metastases. Miniswine underwent 1-hr dynamic $^{18}$F-FDG PET whole body PET scan using a clinical PET scanner 40 minutes after injection to screen for metastatic disease, followed by CT scan acquisition for anatomic localization. Then miniswine were subdermally injected in a 4-quadrant pattern about the tumor site (head and neck sites preferentially) with multimodal $^{124}$I-RGD-PEG-dots 48 hrs after $^{18}$F-FDG PET, and a second dynamic PET-CT scan performed to assess for additional nodal metastases.

Miniswine were taken to the operating room for identification of nodes. Optical fluorescence imaging was performed using large field-of-view near infrared fluorescence camera system, smaller field-of-view modified endoscope, and a modified stereomacroscope for obtaining higher resolution fluorescence images within the exposed surgical bed.

Validation of the fluorescent signal was performed intraoperatively by gamma counting with a clinically-approved hand-held PET device within the operative bed to localize targeted dots transdermally, acquired intraoperatively from skin and the nodes within and nodal basin.

The primary melanoma skin lesion was excised, and an incision made to allow access to the sentinel node(s). Nodal identity was confirmed using hand held PET and multi-scale optical imaging systems, and the nodes in question excised. Specimens were sent for histological assessment for metastases and optical confocal microscopy to confirm the presence of both malignancy and nanoparticle fluorescence.

Following harvest of the sentinel nodes, the entire lymph node basin was excised and further evaluated using histological methods (with immunohistochemical markers for melanoma as needed), fluorescence microscopy, and the hand-held PET probe for correlative purposes. This step helped identify any other malignant nodes within the nodal basin and the number of $^{124}$I-RGD-PEG-dots present in adjacent nodes by their appearance on imaging.

$^{124}$I-RGD-PEG-dots was administered subcutaneously into the limbs of the animal sequentially. Transit of the $^{124}$I-RGD-PEG-dots to the inguinal/axillary nodes was followed using the optical imaging system and hand held PET probes to confirm the duration of transit along the lymphatic pathways. The draining nodal basins was exposed surgically and the pattern of lymph node drainage observed. The sentinel lymph node was harvested from each site to confirm the lymphatic nature of the tissue. Animals were euthanized, and any further lesions noted on imaging were excised in the necropsy room of the animal facility.

Discussion

A whole-body $^{18}$F-fluorodeoxyglucose ($^{18}$F-FDG) PET-CT scan revealed a primary melanomatous lesion adjacent to the spine on the upper back, as well as a single node in the neck, posteriorly on the right side of the animal, which were both FDG-avid, and suspicious for metastatic disease. This finding was confirmed after subdermal, 4-quadrant injection of $^{124}$I-RGD-PEG-dots about the tumor site, which additionally identified two more hypermetabolic nodes, as well as the draining lymphatics. Final scan interpretation pointed to 3 potential metastatic nodes. Surgical excision of the primary lesion, hypermetabolic nodes, and tissue from other nodal basins in the neck bilaterally was performed after hand-held PET probes identified and confirmed elevated count rates at the location of sentinel node(s). Patchy fluorescence signal measured in the excised right posterior sentinel node tissue correlated with sites of melanoma metastases by histologic analysis. All hypermetabolic nodal specimens were black-pigmented, and found to correlate with the presence of distinct clusters of melanoma cells. Thus, the results of surgically resected tissue submitted to pathology for H&E and staining for other known melanoma markers confirmed multimodal imaging findings.

Figure 13:
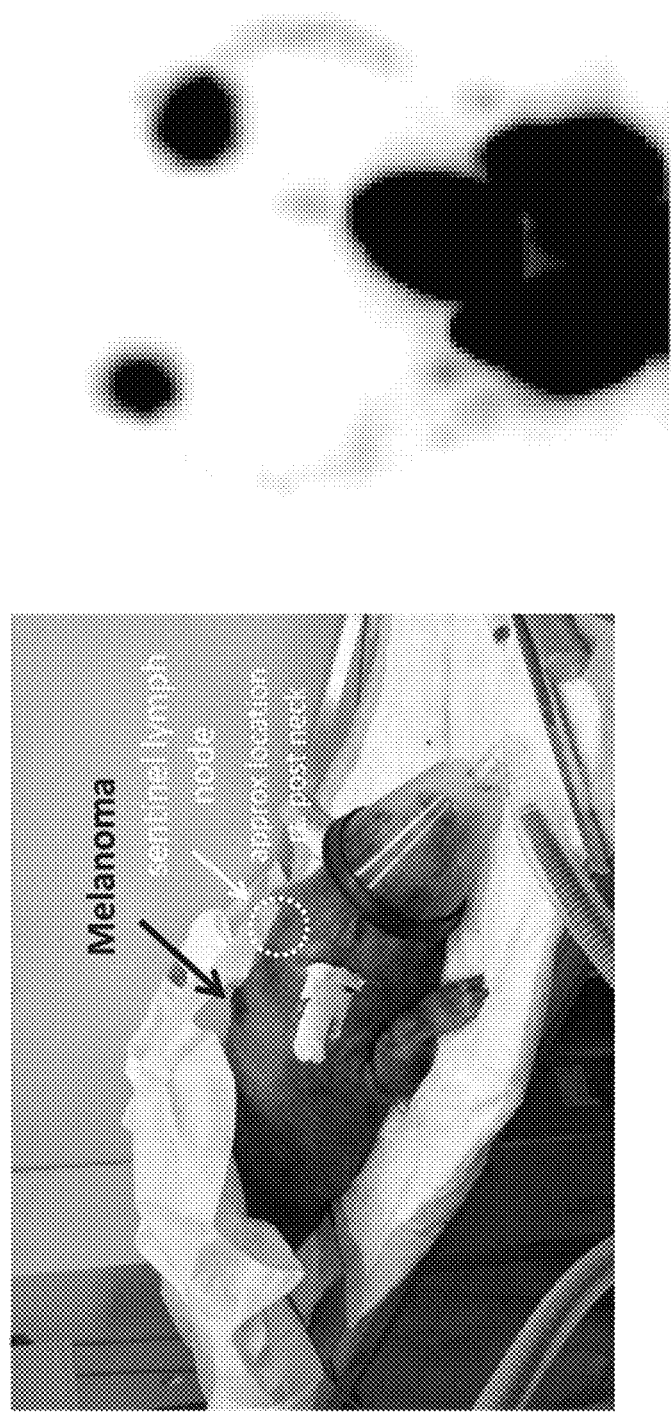
FIG. 13a shows the experimental setup of using spontaneous miniswine melanoma model for mapping lymph node basins and regional lymphatics draining the site of a known primary melanoma tumor.
FIG. 13b shows small field-of-view PET image 5 minutes after subdermal injection of multimodal particles ($^{124}$I-RGD-PEG-dots) about the tumor site.

FIG. 13a shows the experimental setup of using spontaneous miniswine melanoma model for mapping lymph node basins and regional lymphatics draining the site of a known primary melanoma tumor. This intermediate size miniswine model is needed to simulate the application of sentinel lymph node (SLN) biopsy procedures in humans, and more accurately recapitulates human disease. FIG. 13b shows small field-of-view PET image 5 minutes after subdermal injection of multimodal particles ($^{124}$I-RGD-PEG-dots) about the tumor site. The tumor region, lymph nodes, and the lymphatics draining the tumor site are seen as areas of increased activity (black).

Figure 14:
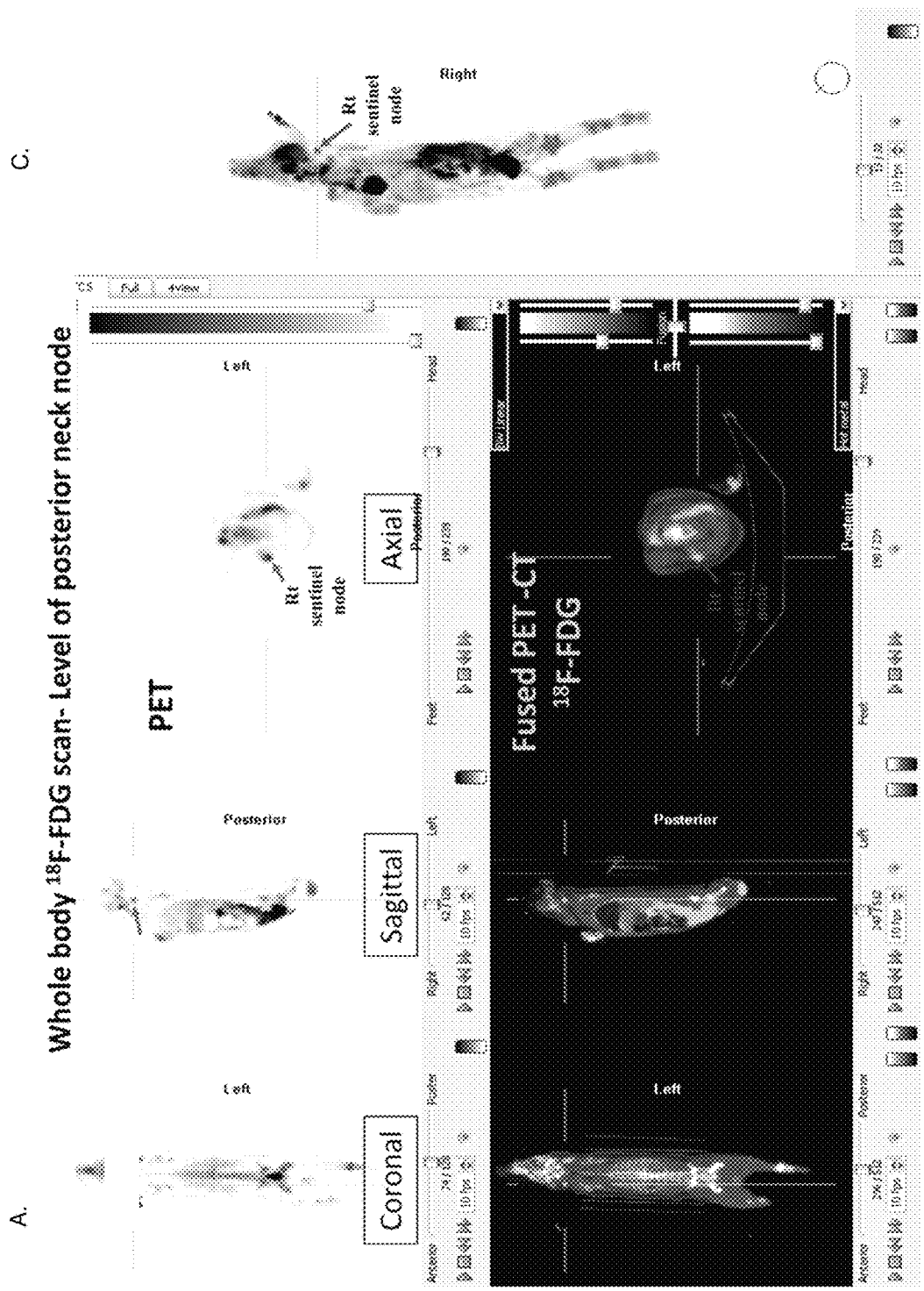
FIG. 14 b shows fused $^{18}$F-FDG PET-CT scans demonstrating sagittal, coronal, and axial images through the site of nodal disease in the neck.

FIG. 14 shows whole-body dynamic $^{18}$F-fluorodeoxyglucose ($^{18}$F-FDG) PET scan (FIG. 14a) and fused $^{18}$F-FDG PET-CT scans (FIG. 14b) demonstrating sagittal, coronal, and axial images through the site of nodal disease in the neck. The $^{18}$F-FDG PET scan was performed to map sites of metastatic disease after intravenous administration and prior to administration of the radiolabeled nanoparticle probe. A single hypermetabolic node is seen in the neck posteriorly on the right side of the animal (arrows, axial images, upper/lower panels), also identified on the whole body miniswine image (FIG. 14c).

Figure 15:
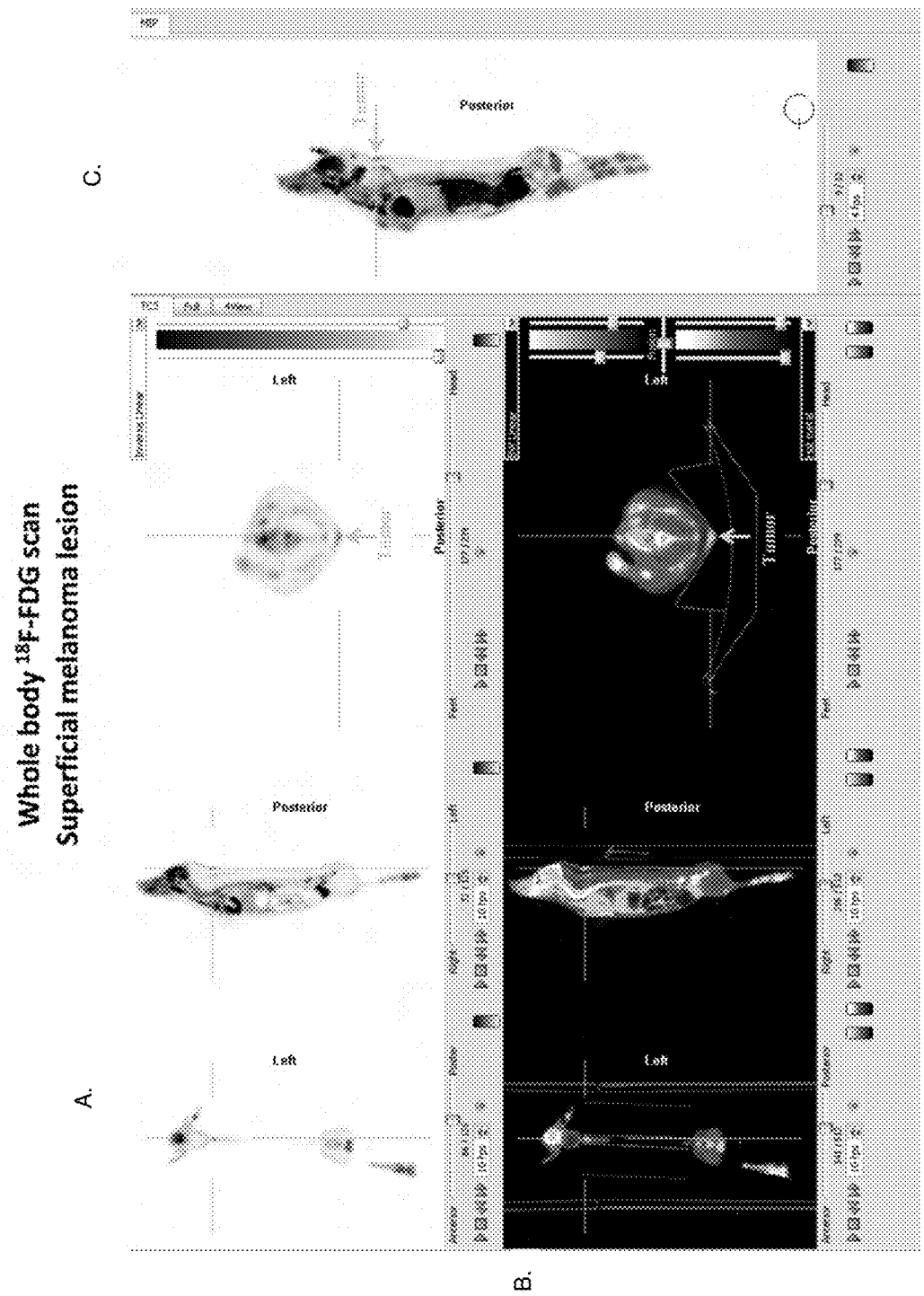
FIG. 15 shows the same image sets as in FIG. 14, but at the level of the primary melanoma lesion, adjacent to the spine on the upper back.

FIG. 15 shows the same image sets as in FIG. 14, but at the level of the primary melanoma lesion, adjacent to the spine on the upper back. The PET-avid lesion is identified (arrows, axial images, upper/lower panels), as well as on the whole body miniswine image (FIG. 15c).

Figure 16:
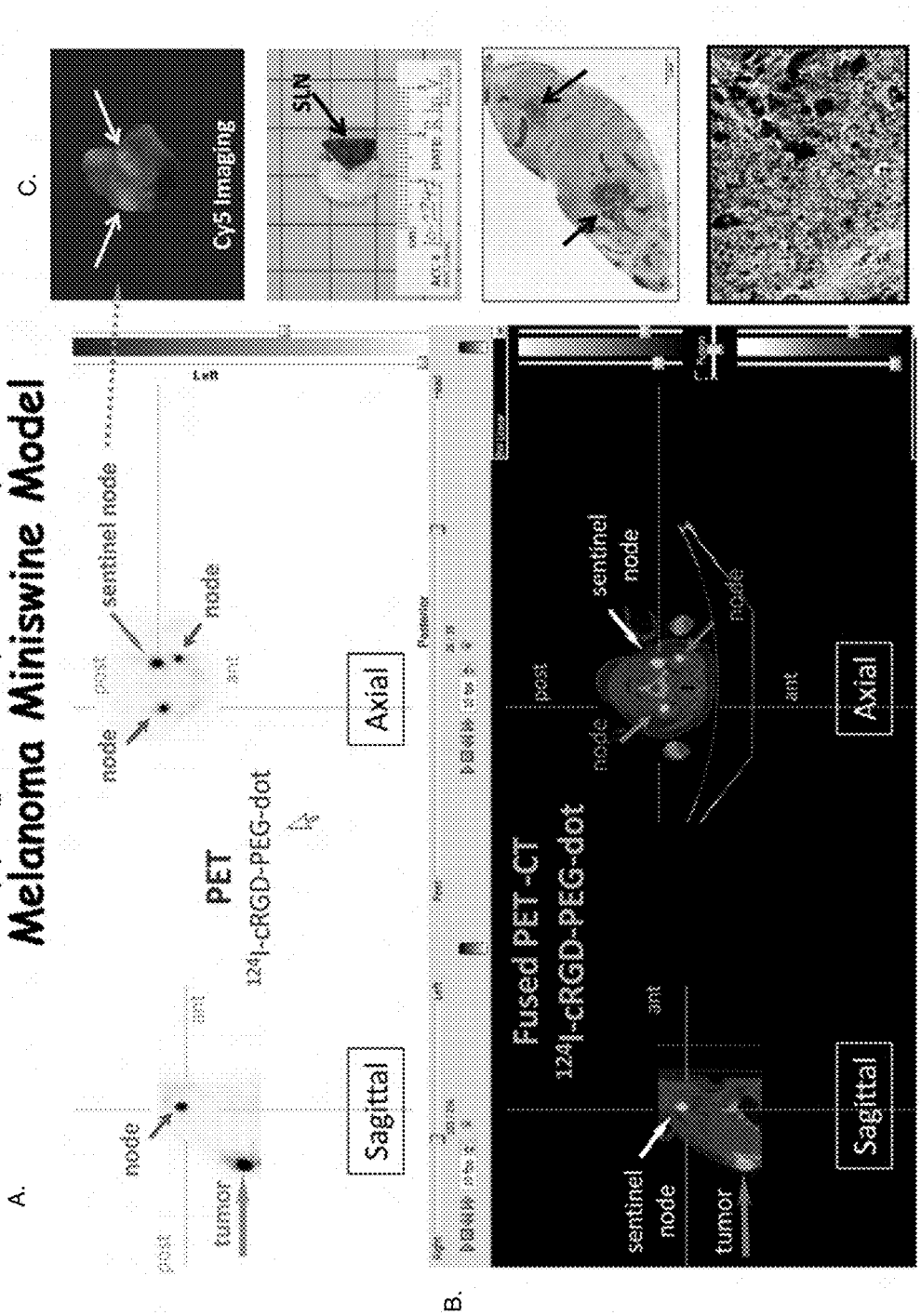
FIG. 16a shows high resolution dynamic PET images following subdermal, 4-quadrant injection of $^{124}$I-RGD-PEG-dots about the tumor site over a 1 hour time period.
FIG. 16b shows fused PET-CT images following subdermal, 4-quadrant injection of $^{124}$I-RGD-PEG-dots about the tumor site over a 1 hour time period.
FIG. 16c shows Cy5 imaging (top image), the resected node (second to top image), and H&E staining (lower two images).

FIG. 16 shows high resolution dynamic PET (FIG. 16a) and fused PET-CT images (FIG. 16b) following subdermal, 4-quadrant injection of $^{124}$I-RGD-PEG-dots about the tumor site, simulating clinical protocol, over a 1 hour time period. Three hypermetabolic lymph nodes (arrows) were found in the neck, suggesting metastatic disease. The excised right posterior SLN was excised and whole body near infrared (NIR) fluorescence imaging was performed. Cy5 fluorescence signal was detectable within the resected node (FIG. 16c, top, Cy5 imaging) on whole-body optical imaging. Pathological analysis of this black-pigmented node (arrow, SLN) demonstrated clusters of invading melanoma cells on low-(arrows) and high-power cross-sectional views of the node by H&E staining (lower two images), and we expect melanoma specificity to be further confirmed using special stains (Melan A, HMB45, PNL2, and "melanoma associated antigen" biogenex clone NKI/C3). We additionally expect colocalization of the particle with these metastatic clusters of cells on confocal fluorescence microscopy and high resolution digital autoradiography, confirming metastatic disease detection.

Example 7 Fluorescent Silica Nanoparticles Conjugated with MC1R-Targeting Peptide (Melanoma Model)

For the multimodality (PET-NIRF) diagnostic imaging experiments, the targeting peptide and the radiolabel on the nanoparticle surface will be exchanged to determine target specificity, binding affinity/avidity, and detection sensitivity. Subsequent therapeutic particles will also be synthesized using therapeutic radiolabels (lutetium-177, $^{177}$Lu, $t^{1/2}$=6.65 d) for targeted killing of MC1R-expressing melanoma cells. Combined quantitative PET and optical imaging findings will be correlated with tumor tissue autoradiography and optical imaging across spatial scales. For cellular microscopy, an in vivo confocal fluorescence scanner for combined reflectance and fluorescence imaging will be used.

Example 8 Fluorescent Nanoparticles for Targeted Radiotherapy

Dose escalation studies with $^{131}$I-RGD nanoparticles will be performed and treatment response will be monitored weekly, over the course of six weeks, using $^{18}$F-FDG PET. Time-dependent tumor uptake and dosimetry of the nanoparticle platform will be performed using planar gamma camera imaging. In vivo imaging data will be correlated with gamma counting of excised tumor specimens.

Male nude mice (6-8 wks, Charles River Labs, MA) will be used for generating hind leg xenograft models after injection of M21 human melanoma cells (5×10$^5$ in PBS). Tumors will be allowed to grow 10-14 days until 0.5-0.9 cm$^3$ in size.

$^{131}$I-based targeted radiotherapy studies. The therapeutic radionuclide $^{131}$I will be used as a radiolabel for targeted radiotherapy. In estimating the highest possible $^{131}$I dose resulting in no animal deaths and less than 20% weight loss (MTD), a dose escalation study will be carried out in tumor-bearing nude mice. For a 200 rad dose to blood 54, an administered activity of 10 MBq is required, which would deliver a dose of 270 rad to tumor. 4 doses of 10 MBq each will be administered to achieve a tumor dose greater than 1000 rad with dose fractionation designed to allow repair and sparing of bone marrow. $^{131}$I allows for planar gamma camera imaging using a pinhole collimator to measure the time-dependent tumor uptake and dosimetry of the nanoparticles. $^{18}$F-FDG PET allows for quantitative monitoring of tumor response, thus providing complementary information.

Based on this data, and in vivo data on the effect of nanoparticles loaded with paclitaxel, a therapy study with the $^{131}$I-RGD-nanoparticle conjugate will be conducted. Two groups of tumor-bearing mice (n=10 per group) will receive either four, 10.4-MBq activities once per week for 4 weeks, of i.v.-administered $^{131}$I-RGD-nanoparticle conjugates or saline vehicle (control, n=10), and will be monitored over a 6-week period. Treatment response/progression will be quantified on the basis of tumor volume (via caliper measurements). All mice from the treatment groups will also be imaged once per week (~1 hr sessions) by SPECT imaging (Gamma Medica) over a 6 week period.

$^{18}$F-FDG PET Imaging Acquisition and Analysis. Two groups of tumor-bearing mice (n=10/group) will undergo initial PET scanning prior to and then, on a weekly basis after treatment over a 6 week interval. Mice will be injected intravenously (i.v.) with 500 µCi $^{18}$F-FDG and static 10-minute PET images will be acquired using a Focus 120 microPET™ (Concorde Microsystems, TN) before and after treatment. Acquired data will be reconstructed in a 128× 128×96 matrix by filtered back-projection. Region-of-interest (ROI) analyses of reconstructed images will be performed using ASIPro™ software (Concorde Microsystems, TN) to determine the mean and SD of radiotracer uptake (% ID/g) in tumors. Animals will be sacrificed at the termination of the study and tumors excised for gamma counting.

Example 9 Fluorescent Nanoparticles Conjugated with Radionuclide Chelate and MC1R-Targeting Peptide PEG-ylated nanoparticles will be conjugated with targeting peptides and macrocyclic chelates binding high-specific activity radiolabels.

High purity two-arm activated commercially available PEGs, derivatized with NHS esters or maleimide, will be attached to the silica shell of the nanoparticle using standard procedures. Either of the two functionalized PEG groups (NHS esters or maleimide) will be available for further conjugation with either the peptide-chelate construct, cyclic peptide Re-[Cys3,4,10,D-Phe7]α-MSH3-13 (ReCCMSH (Arg11)), or 1,4,7,10-tetraazacyclododecane-N,N',N'',N'''-tetraacetic acid (DOTA) linker chelators. The covalent attachment of derivatized PEGs to the nanoparticle surface will be performed in such a manner as to expose different functional groups for linking DOTA and peptide-chelate constructs, as discussed below.

Synthesis and Physicochemical Characterization of Functionalized Nanoparticles.

Functionalized nanoparticles will be synthesized by establishing covalent linkages of the following moieties with the derivatized PEG groups:

(A) DOTA chelates for subsequent high-specific activity radiolabeling with positron-emitting radiometals (i.e., $^{64}$Cu) to permit diagnostic detection with PET imaging. DOTA will be conjugated to the functionalized PEGs using standard Fmoc chemistry, and purification of the chelated nanoparticles will be performed by chromatography. $^{64}$Cu and $^{177}$Lu will be attached to DOTA by incubation of the reaction mixture at 60° C. for 30 min followed by gel filtration or high pressure liquid chromatography purification. Alternatively, PET nuclides, such as $^{124}$I, $^{86}$Y, $^{68}$Ga and $^{89}$Zr, may be conjugated to the nanoparticle, either via the DOTA-functionalized PEG (radiometals) or tyrosine-functionalized PEG ($^{124}$I). The single photon emitter, $^{177}$Lu, obtained in the form of $^{177}$LuCl$_3$ will be complexed to DOTA for radiotherapy.

(B) αMSH melanoma targeting peptide analogue (ReCCMSH(Arg11)) is cyclized by rhenium. It is necessary to confirm the ratio of DOTA chelates to ReCCMSH(Arg11) moieties on the PEG-ylated nanoparticle surface.

Characterization of the functionalized nanoparticle preparations will be performed as follows:

(A) Average number of DOTA chelates per nanoparticle will be determined by standard isotopic dilution assays with $^{64}$Cu. Briefly, $^{64}$Cu will be added to solutions containing a known amount of ReCCMSH(Arg11)-nanoparticles. Incubated solutions will be spotted on silica gel-coated glass plates, developed in 1:1 10% ammonium acetate-to-methanol (with EDTA), and analyzed by radio-TLC. While $^{64}$Cu-labeled ReCCMSH(Arg11)-Nanoparticles will remain at the origin, $^{64}$Cu bound to EDTA will migrate. The percent labeling efficiency will be plotted against total nanomoles of $^{64}$Cu added to the reaction mixture. The number of chelates attached per nanoparticle can be determined from the inflection point of this curve.

(B) Average number of ReCCMSH(Arg11) peptides per nanoparticle and coupling efficiency of the ReCCMSH(Arg11) to the functionalized PEG groups will be assessed using spectrophotometric methods ($\lambda$=435 nm, maximum absorbance) and the known extinction coefficient of ReCCMSH(Arg11). The incorporation of rhenium offers the advantage that highly sensitive absorbance measurements of rhenium concentrations can be made on a small sample of product.

In Vitro and In Vivo Optical-PET Imaging of Multifunctional Nanoparticle Nanoparticles in Melanoma Models to Assess Tumor-Specific Targeting and Treatment Response.

$^{64}$Cu-DOTA-ReCCMSH(Arg11)-nanoparticles will be compared with the native $^{64}$Cu-DOTA-ReCCMSH(Arg11) construct to test targeting capabilities of the nanoparticles.

Competitive binding assays. The MC1R receptor-positive B16/F1 murine melanoma lines will be used. The $IC_{50}$ values of ReCCMSH(Arg11) peptide, the concentration of peptide required to inhibit 50% of radioligand binding, will be determined using $^{125}$I-(Tyr2)-NDP7, a radioiodinated α-MSH analog with picomolar affinity for the MC1R. Single wells will be incubated at 25° C. for 3 h with approximately 50,000 cpm of $^{125}$I-(Tyr2)-NDP in 0.5 ml binding medium with 25 mmol/L N-(2-hydroxyethyl)-piperazine-N-(2-ethanesulfonic acid), 0.2% BSA and 0.3 mmol/L 1,10-phenanthroline], with concentrations of (Arg11)CCMSH ranging from 10-13 to 10-5 mol/L. Radioactivity in cells and media will be separately collected and measured, and the data processed to compute the $IC_{50}$ value of the Re(Arg11) CCMSH peptide with the Kell software package (Biosoft, MO).

Receptor Quantitation Assay. Aliquots of 5×105 B16/F1 cells will be added to wells, cultured in 200 μL RPMI media, and incubated at 37° C. for 1.5 h in the presence of increasing concentrations of $^{125}$I-(Tyr2)-NDP (from 2.5 to 100 nCi) in 0.5 mL of binding media (MEM with 25 mM HEPES, pH 7.4). Cells will be washed with 0.5 mL of ice-cold, pH 7.4, 0.2% BSA/0.01 M PBS twice, and the level of activity associated with the cellular fraction measured in a γ-counter. Nonspecific binding will be determined by incubating cells and $^{125}$I-(Tyr2)-NDP with non-radioactive NDP at a final concentration of 10 μM. Scatchard plots will be obtained by plotting the ratio of specific binding to free $^{125}$I-(Tyr2)-NDP vs. concentration of specific binding (fmol/million cells); Bmax, the maximum number of binding sites, is the X intercept of the linear regression line.

B16/F1 murine melanoma lines (5×10$^5$ in PBS) will be injected subcutaneously into the hind legs of Male nude mice (6-8 week old). The tumors will be allowed to grow 10-14 days until 0.5-0.9 cm$^3$ in size.

Biodistribution: A small amount of the $^{64}$Cu-DOTA-ReCCMSH(Arg11)-nanoparticle conjugate (~10 μCi, 0.20 μg) will be injected intravenously into each of the mice bearing palpable B16/F1 tumors. The animals will be sacrificed at selected time points after injection (2, 4, 24, 48, 72 hours; n=4-5/time point) and desired tissues removed, weighed, and counted for accumulated radioactivity. Additional mice (n=5) injected with the native radiolabeled construct, $^{64}$Cu-DOTA-ReCCMSH(Arg11) (~10 μCi, 0.20 μg) will serve as the control group, and evaluated 1 h post-injection. To examine in vivo uptake specificity, an additional group of mice (2-h time point) will be pre-injected with 20 μg of NDP to act as a receptor block immediately prior to the injection of the $^{64}$Cu-DOTA-ReCCMSH(Arg11) nanoparticle conjugate. Major organs and tissues will be weighed and gamma-counted, and the percentage-injected dose per gram (% ID/g) determined.

Serial In Vivo NIRF Imaging. In parallel with the PET studies below, NIR (fluorescence tomographic imaging, FMT 225, Visen, Woburn, Mass.) will be performed using a tunable 680 nm scanning NIR laser beam and CCD before and after i.v. injection of tumor-bearing animals (n=10). Mice will be kept under continuous isoflurane anesthesia, and placed in a portable multimodal-imaging cassette (compatible with both our FMT 2500 and Focus 120 microPET) for FMT scanning before and after injection (1, 2, 4, 6, 12, 24, 48 and 72 hours). The NIR fluorescence image, measured over a 1-10 minute period, will be reconstructed using the Visen proprietary software and superimposed onto a normal photograph of the mouse. The imaging data is quantitative, as the measured intensity is directly related to the NIR fluorophore concentration, enabling parametric maps of absolute fluorophore concentrations to be generated for co-registration with the acquired PET imaging data.

Dynamic PET Imaging Acquisition and Analysis. Two groups of tumor-bearing mice (n=5/group) will be placed in the imaging cassette for co-registering sequential PET-optical studies. Mice will be injected intravenously (i.v.); one with radiolabeled $^{64}$Cu-DOTA-ReCCMSH(Arg11) nanoparticle conjugates and the second with native $^{64}$Cu-DOTA-ReCCMSH(Arg11) constructs. Following injection, dynamic 1-hr PET images will be acquired using a Focus 120 microPET™ (Concorde Microsystems, TN). One-hour list-mode acquisitions are initiated at the time of IV injection of radiolabeled probe (~1 mCi). Resulting list-mode data will be reconstructed in a 128×128×96 matrix by filtered back-projection. Region-of-interest (ROI) analyses of reconstructed images are performed using ASIPro™ software (Concorde Microsystems, TN) to determine the mean and SD of radiotracer uptake (% ID/g) in tumors, other organs/tissues, and left ventricle (LV). Tracer kinetic modeling of the data will permit estimation of pharmacokinetic parameters, including delivery, clearance, and volume of distribution. As noted, an arterial blood input is measured using an ROI placed over the LV (as a measure of blood activity). Additional data will be obtained from static images at 24 hr, 48 hr, 72 hr post-injection time points.

Fluorescence microscopy and autoradiography of tissues. A combination of optical imaging technologies exhibiting progressively smaller spatial scales (i.e., whole body fluorescence imaging, fluorescence macroscopy, and in vivo fluorescence confocal laser scanning microscopy) will be utilized for imaging tumors in live, intact animals at 72-h post-injection. Mice will be maintained under continuous isofluorane anesthesia, thus enabling detection and localization of fluorescence signal from the whole animal/organ level to the cellular level over a range of magnifications. Whole animal/macroscopic imaging will be performed with fluorescence stereomicroscope (Visen; Nikon SMZ1500) fitted with Cy5 fluorescence filter sets and CCD cameras. Fluorescence confocal laser scanning microscopy capabilities will be developed. Mice will subsequently be euthanized for autoradiography in order to map tracer biodistributions at high resolution throughout the tumor volume. Tumors will be excised, flashfrozen, serially sectioned (100μ sections) and slide-mounted, with alternating slices placed in contact with a phosphor plate in a light-tight cassette (up to 1 wk). H&E staining will be performed on remaining consecutive sections. Autoradiographic findings will be correlated with PET imaging data and histological results.

The therapeutic radionuclides $^{177}$Lu or $^{90}$Y may alternatively be used for targeted radiotherapy. In estimating the highest possible $^{177}$Lu dose resulting in no animal deaths and less than 20% weight loss (MTD), a dose escalation study will be carried out in tumor-bearing nude mice. Doses of radiopharmaceutical suspected to be at (or near) the MTD based on literature values for $^{177}$Lu will be evaluated.

Example 10 Fluorescent Nanoparticles Functionalized to Conjugate with Ligand and Contrast Agent Via "Click Chemistry"

Synthesis of Nanoparticles Containing Versatile Functional Groups for Subsequent Conjugation of Ligand e.g., Peptides) and Contrast Agent (e.g., Radionuclides).

Figure 17:
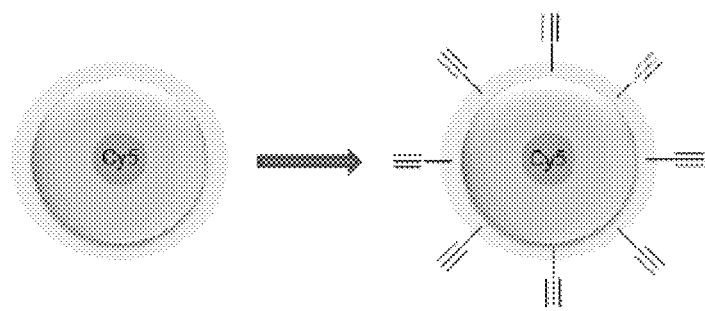
FIG. 17 shows a scheme for a nanoparticle with a fluorescent dye within the core and a PEG surface-coating. The nanoparticle is decorated with triple bonds for subsequent "click chemistry" with both DFO and Tyr3-octreotate functionalized with azide groups.

In order to synthesize an array of nanoparticle-peptide-chelate constructs suitable for high-specific activity radiolabeling, a "click-chemistry" approach may be used to functionalize the nanoparticle surface (FIG. 17). This method is based on the copper catalyzed cycloaddition of azide to a triple bond. Such an approach would allow for a great deal of versatility to explore multimodality applications.

Nanoparticle synthesis and characterization. The PEG groups that will be covalently attached will be produced following the scheme in FIG. 14. PEG will be covalently attached to the nanoparticle via the silane group. Standard chemical pathways will be used for the production of the functionalized PEG with triple bonds.

Figure 18:
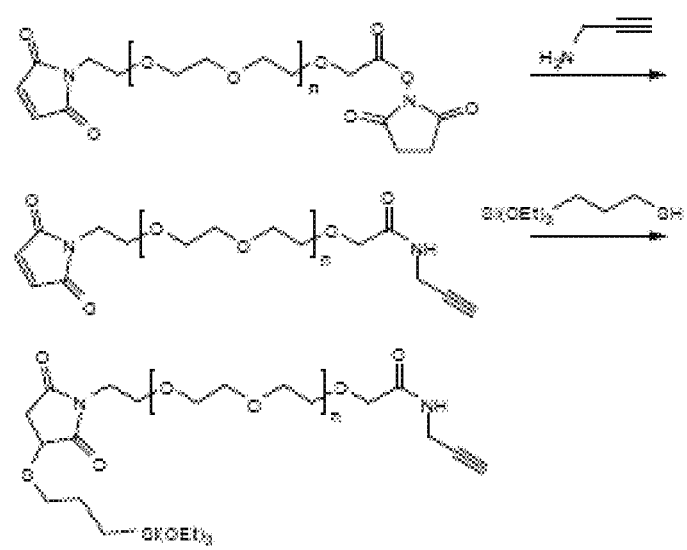
FIG. 18 shows structures of PEG derivative. Standard chemical reactions are used for the production of the functionalized PEG with triple bonds, which will then be covalently attached to the nanoparticle via the silane group.

Functionalization of nanoparticles with triple bonds. To synthesize the bifunctionalized PEGs, the first step will employ the well studied reaction of activated carboxylic ester with aliphatic amine (FIG. 18). Alternatively, another suitable triple-bond bearing amine, for example, p-aminophenylacetylene, can be used. The second step of the synthesis also relies on a well-known conjugation reaction. Synthesis and Physicochemical Characterization of Functionalized Nanoparticles Conjugated with Model Peptides and Chelates.

The functionalized nanoparticle contains both (A) desferrioxamine B (DFO) for subsequent high-specific activity radiolabeling with the positron-emitter zirconium-89 ($^{89}$Zr) and (B) the SSTR-targeting peptide, octreotate.

Figure 19:
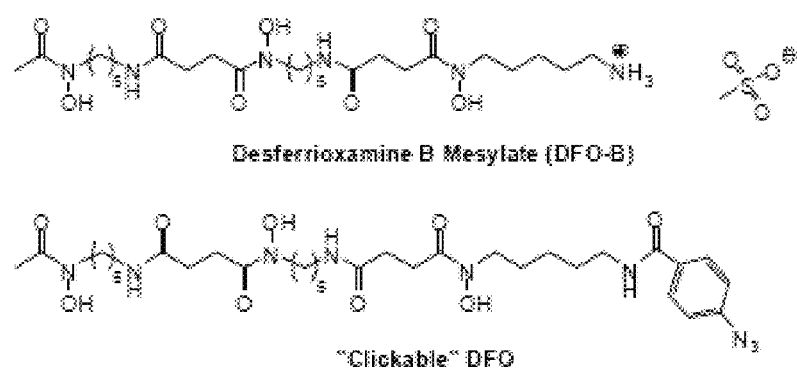
FIG. 19 shows structures of DFO derivatives.

Synthesis of DFO with an azide bond. DFO with an azide group will be produced by reaction of DFO-B with pazido benzoic acid) (FIG. 19) and purified. The "click chemistry" reaction is a 1,3-dipolar cycloaddition at room temperature and the conditions are often referred to as "Huigsen Conditions". Although the reactions can generally be completed at room temperature in ethanol, it may be appropriate to heat the reaction. The catalyst is often Cu(I)Br, but alternatives include Cu(I)I or Cu(II)SO4 (with a reductant). Knor et al. Synthesis of novel 1,4,7,10-tetraazacyclodecane-1,4,7,10-tetraacetic acid (DOTA) derivatives for chemoselective attachment to unprotected polyfunctionalized compounds. *Chemistry*, 2007; 13:6082-90. Click reactions may also be run in the absence of any catalyst. Alternatively, the NH$^{3+}$ group in DFO-B may be converted directly into an azide group.

Figure 20A:
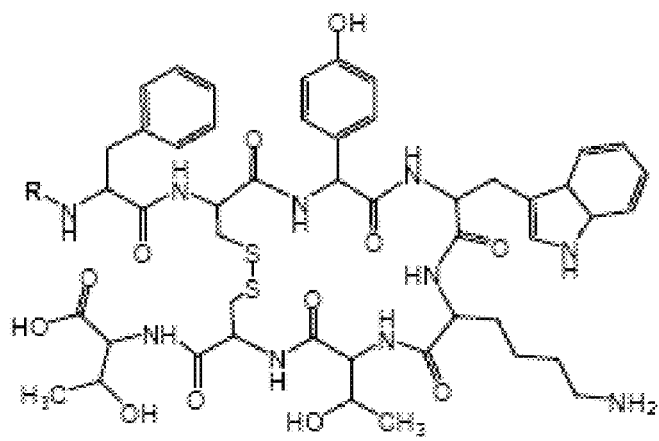
FIG. 20a shows structures of Tyr3-octreotate.
Figure 20B:
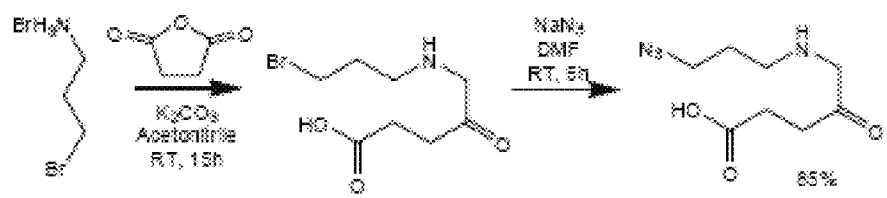
FIG. 20b shows synthesis of the azide-containing acid for incorporation into Tyr3-Octreotate.

Synthesis of Tyr3-octreotate with an azide. Solid phase peptide synthesis (SPPS) of Tyr3-octreotate (FIG. 20A) will be performed on a peptide synthesizer. Briefly, the synthesis will involve the Fmoc (9-fluorenylmethoxycarbonyl) method as previous described for this peptide. Briefly, the instrument protocol requires 25 μmol of subsequent Fmoc-protected amino acids activated by a combination of 1-hydroxybenzotriazole (HOBt) and 2-(1Hbenzotriazol-1-yl)-1,1,3,3-tetramethyluronium hexafluorophosphate (HBTU). The Fmoc-protected amino acids will be purchased commercially unless otherwise stated; the pre-packed amino acids will be obtained from Perkin-Elmer (Norwalk, Conn.), while those unavailable in pre-packed form, such as the Damino acids and Fmoc-Cys(Acm) will be supplied by BACHEM Bioscience, Inc. (King of Prussia, Pa.) or Novabiochem (San Diego, Calif.). The azide group (for the "click" chemistry) will be introduced into the peptide backbone via coupling of an azide-containing acid to the N-terminus of the peptide, while the peptide is still protected and attached to the resin (FIG. 20B).

Synthesis of functionalized nanoparticles. The next step will be to conjugate both the DFO having an azide bond and Tyr3-octreotate having an azide bond (FIGS. 21A and B) to the nanoparticle. "Click chemistry" is highly selective, quantitative and can be performed very fast and using mild conditions. The number of combined azide groups from DFO and Tyr3-octreotate will be controlled to never exceed the number of available triple-bonds; the triple bonds will always be in <5% excess.

Functionalized nanoparticle characterization. Average number of DFO chelates peptide per nanoparticle will be determined by performing a standard isotopic dilution assay with $^{89}$Zr (or $^{68}$Ga). $^{89}$Zr will be produced on cyclotron and purified. Briefly, 10 concentrations of 89Zr-oxalate will be added to solutions containing a known amount of DFO-derived nanoparticles. Following a 30 min. room temperature incubation, the solutions will be spotted on silica gel coated glass plates, developed in 1:1 10% ammonium acetate-to-methanol (with EDTA) and analyzed by radio-TLC. Whereas the $^{89}$Zr-DFO-derived nanoparticles will remain at the origin, nonspecifically bound $^{89}$Zr bound to EDTA will migrate. The percent labeling efficiency will be plotted as a function of total nanomoles of $^{89}$Zr added to the reaction mixture. The number of chelates attached to the nanoparticle can then be determined from the inflection point of this curve.

Average number of Tyr3-octreotate peptide per nanoparticle will be determined by assaying the disulfide bridge of Tyr3-octreoate. Briefly, the disulfide bonds of the Tyr3-octreotate can be cleaved quantitatively by excess sodium sulfite at pH 9.5 and room temperature. DTNB or Elman's reagent can be used to quantitate thiols in proteins by absorption measurements. It readily forms a mixed disulfide with thiols, liberating the chromophore 5-merapto-2-nitrobenzoic acid (absorption maximum 410 nm). Only protein thiols that are accessible to this water-soluble reagent are modified. Alternatively, the Measure-iT™ Thiol Assay Kit from Invitrogen can be used.

In Vivo Testing in Suitable Tumor Models.

Subcutaneous xenograft models using AR42J tumor-bearing female SCID mice will be generated. Briefly, AR42J cells (1×10$^7$), will be injected subcutaneously into the flanks of female SCID mice. The tumors will be allowed to grow 10-12 days until 0.5-0.9 cm$^3$ in size.

Radiolabeling of the DFO-nanoparticle by $^{89}$Zr is expected to proceed in <15 min. at room temperature. Non-specifically bound $^{89}$Zr will be removed by addition of EDTA followed by a gel filtration step.

Receptor binding assays. The receptor binding assays will be performed using $^{89}$Zr-DFO-nanoparticles on membranes obtained from AR42J tumors. The competing ligands, natZr-DFO-Nanoparticles and natZr-DFO-octreotate will be prepared by the reaction of high purity natural zirconium oxalate with DFO-octreotate and DFO-Nanoparticles, respectively. Purity of the final products will be confirmed by HPLC. IC50 values will be determined according to previously published methods, using the Millipore Multi-Screen assay system (Bedford, Mass.). Data analysis will be performed using the programs GraFit (Erithacus Software, U.K.), LIGAND (NIH, Bethesda, Md.), and GraphPad PRISM™ (San Diego, Calif.).

In vitro assays. The AR42J cells will be harvested from monolayers with Cell Dissociation Solution (Sigma Chemical Co., St. Louis, Mo.) and resuspended in fresh DMEM media at a concentration of 2×106 cells/mL. An aliquot of about 0.3 pmol of $^{89}$Zr-DFO-nanoparticles will be added to 10 mL of cells, incubated at 37° C. with continuous agitation. At 1, 5, 15, 30, 45, 60 and 120 min triplicate 200-μL aliquots will be removed and placed in ice. The cells will immediately be isolated by centrifugation, and the % uptake of the compound into the cells will be calculated.

Biodistribution. A small amount of the $^{89}$Zr-DFO-nanoparticles (~10 μCi, 0.20 μg) will be injected intravenously into each of the mice bearing palpable AR42J-positive tumors. The animals will be sacrificed at selected time points after injection (1, 4, 24, 48, 72 hours; n=4-5) and desired tissues will be removed, weighed, and counted for radioactivity accumulation. Two additional control groups will be studied at 1 h post-injections: (A) mice injected with the native radiolabeled peptide $^{89}$Zr-DFO-octreotate (~10 μCi, 0.20 μg), and (B) mice pre-injected with a blockade of Tyr3-octreotate (150 μg) to demonstrate receptor-mediated accumulation of the $^{89}$Zr-DFO-nanoparticles. Tissues including blood, lung, liver, spleen, kidney, adrenals (STTR positive) muscle, skin, fat, heart, brain, bone, pancreas (STTR positive), small intestine, large intestine, and AR42J tumor will be counted. The percentage injected dose per gram (% ID/g) and percentage injected dose per organ (% ID/organ) will be calculated by comparison to a weighed, counted standard solution.

In vivo NIRF imaging. Serial imaging will be performed using the Maestro™ In Vivo Fluorescence Imaging System (CRI, Woburn, Mass.) at 0, 0.5, 1, 2, 4, 6, 12, 24, 48 and 72 hrs. At 72-hr, mice will be euthanized, and major tissues/organs dissected, weighed, and placed in 6-well plates for ex-vivo imaging. Fluorescence emission will be analyzed using regions-of-interest (ROIs) over tumor, selected tissues, and reference injectates, employing spectral unmixing algorithms to eliminate autofluorescence. Fluorescence intensities and standard deviations (SD) will be averaged for groups of 5 animals. Dividing average fluorescence intensities of tissues by injectate values will permit comparisons to be made among the various tissues/organs for each injected nanoparticle conjugate.

In vivo small animal PET imaging. Small animal PET imaging will be performed on a microPET®-FOCUS™ system (Concorde Microsystems Inc, Knoxville Tenn.). Mice bearing the AR42J tumors (n=5 per group) will be anesthetized with 1-2% isoflurane, placed in a supine position, and immobilized in a custom prepared cradle. The mice will receive 200 μCi of the $^{89}$Zr-DFO-octreotate-nanoparticle complex via the tail vein and will be imaged side by side. Animals will initially be imaged by acquiring multiple, successive 10-minute scans continuously from the time of injection over a 1-hr time frame, followed by 10-min static data acquisitions at 2, 4, 24, 48 and 72-hrs post-injection. Standard uptake values (SUVs) will be generated from regions of interest (ROIs) drawn over the tumor and other organs of interest. Co-registration of the PET images will be achieved in combination with a microCAT-II camera (Imtek Inc., Knoxville, Tenn.), which provides high-resolution X-ray CT anatomical images. The image registration between microCT and PET images will be accomplished by using a landmark registration technique and AMIRA image display software (AMIRA, TGS Inc, San Diego, Calif.). The registration method proceeds by rigid transformation of the microCT images from landmarks provided by fiducials directly attached to the animal bed.

Pharmacokinetic measurements. The biodistribution and dynamic PET data will provide the temporal concentration of $^{89}$Zr-DFO-octreotate-nanoparticle in tissue which will allow for characterization of pharmacokinetic parameters of the agent.

Fluorescence microscopy and autoradiography of tissues ex vivo. Localization of nanoparticle conjugates in tissues will be performed on frozen sections. Imaging by microPET will allow us to evaluate fully the global distribution in tumors and other non-target tissues. Following the acute stage of the imaging trial, autoradiography will also be performed on the tumors, and this data will be correlated to both the PET imaging and histological results. Consecutive slices (~10 μm) will be taken, alternating slices for autoradiography and for histological analysis. These sections will also be analyzed by multichannel fluorescence microscopy in the NIR channel.

Example 11 Particle Internalization Studies

The goal of this study is to evaluate the binding and internalization of the present nanoparticles to assess their localization in subcellular organelles and exocytosis. This will help study the fate of functionalized particles with different targeting moieties and attached therapies. For example, both diagnostic nanoparticles (e.g., non-targeted PEG-coated versus cRGD-PEG-coated nanoparticles) and therapeutic nanoparticles (e.g., cRGD-PEG-nanoparticles attached to iodine for radiotherapy, attached to tyrosine kinase inhibitors, or attached to chemotherapeutic drugs such as Taxol.)

Materials and Methods

Internalization/uptake studies. Internalization assays and colocalization studies were performed for identifying specific uptake pathways.

Melanoma cells, including human M21 and mouse B16 cells (~2×10$^5$ cells/well), were plated in 8-well chamber slides (1.7 cm$^2$/well) slides or 24 well plates (1.9 cm$^2$/well) with a 12 mm rounded coverglass and incubated at 37° C. overnight. To monitor targeted nanoparticle internalization, cells were incubated with cRGD-PEG dots (0.075 mg/ml) for 3 hrs at 37° C. To remove unbound particles in the medium, cells were rinsed twice with PBS. Confocal microscopy was performed on a Leica inverted confocal microscope (Leica TCS SP2 AOBS) equipped with a HCX PL APO: 63×1.2NA Water DICD objective to assess co-localization of cRGD-PEG-dots with organelle-specific stains or antibodies. Images were analyzed using ImageJ software version 1.37 (NIH Image; http://rsbweb.nih.gov/ij/).

Co-localization Assays/Dye-bound markers. In order to identify endocytic vesicles involved in C dot internalization, colocalization assays in living cells were performed using dye-bound markers. Cells were coincubated with nanoparticles and different dyes. The dyes include: 100 nM Lysotracker red for 30 min to label acidic organelles along endosomal pathway; 2 µg/mL transferrin Alexa 488 conjugate to label recycling and sorting endosomes (clathrin-dependent pathway); 1 mg/mL 70 kDa dextran-FITC conjugate at 37° C. for 30 min to label macropinosomes.

Co-localization/Organelle-specific antibodies. Immunocytochemistry will be performed with known markers for Golgi and lysosomes. For Golgi, Giantin (Abcam, rabbit polyclonal, 1:2000) will be used for human cells; GM-130 (BD Pharmingen, 1 µg/ml) will be used for mouse cells. For Lysosomes, LC3B (Cell Signaling, rabbit polyclonal, 0.5 µg/ml) will be used.

For Giantin or LC3B staining, cells will be blocked for 30 minutes in 10% normal goat serum/0.2% BSA in PBS. Primary antibody incubation (rabbit polyclonal anti-Giantin antibody (Abcam catalog # ab24586, 1:2000 dilution) or LC3B (Cell Signaling, C#2775, 0.5 ug/ml) will be done for 3 hours, followed by 60 minutes incubation with biotinylated goat anti-rabbit IgG (Vector labs, cat#:PK6101) in 1:200 dilution. Detection will be performed with Secondary Antibody Blocker, Blocker D, Streptavidin-HRP D (Ventana Medical Systems) and DAB Detection Kit (Ventana Medical Systems) according to manufacturer instructions.

For GM-130 staining, cells will be blocked for 30 min in Mouse IgG Blocking reagent (Vector Labs, Cat#: MKB-2213) in PBS. The primary antibody incubation (monoclonal anti-GM130, from BD Pharmingen; Cat#610822, concentration 1 ug/mL) will be done for 3 hours, followed by 60 minutes incubation of biotinylated mouse secondary antibody (Vector Labs, MOM Kit BMK-2202), in 1:200 dilution. Detection will be performed with Secondary Antibody Blocker, Blocker D, Streptavidin-HRP D (Ventana Medical Systems) and DAB Detection Kit (Ventana Medical Systems) according to manufacturer instructions.

For temperature-dependent studies, nanoparticles will be incubated with cRGD-PEG-nanoparticles at 4° C., 25° C., and 37° C. to assess fraction of surface bound versus internalized particles.

For exocytosis studies, nanoparticles (0.075 mg/ml) will be incubated for 4 hours and chamber slides washed with PBS, followed by addition of fresh media. At time intervals of 0.5, 1.0, 1.5, 2.5, 4.5, 8.0 hrs, cells will be washed, typsinized, and fluorescence signal of cells and media measured by fluorimetry. In dose-response studies, cells will be incubated over a range of concentrations and incubation times, and assayed using flow cytometry. In viability studies, cell viability will be measured using a trypan blue exclusion assay before and after incubation to assess for toxicity. In time-lapse studies, mechanism of nanoparticle internalization in living cells will be investigated after incubating cells with nanoparticle conjugates at different temperatures of incubation (4° C., 25° C., and 37° C.) using an inverted confocal microscope over a 12-hr period at 20 min intervals.

Figure 22:
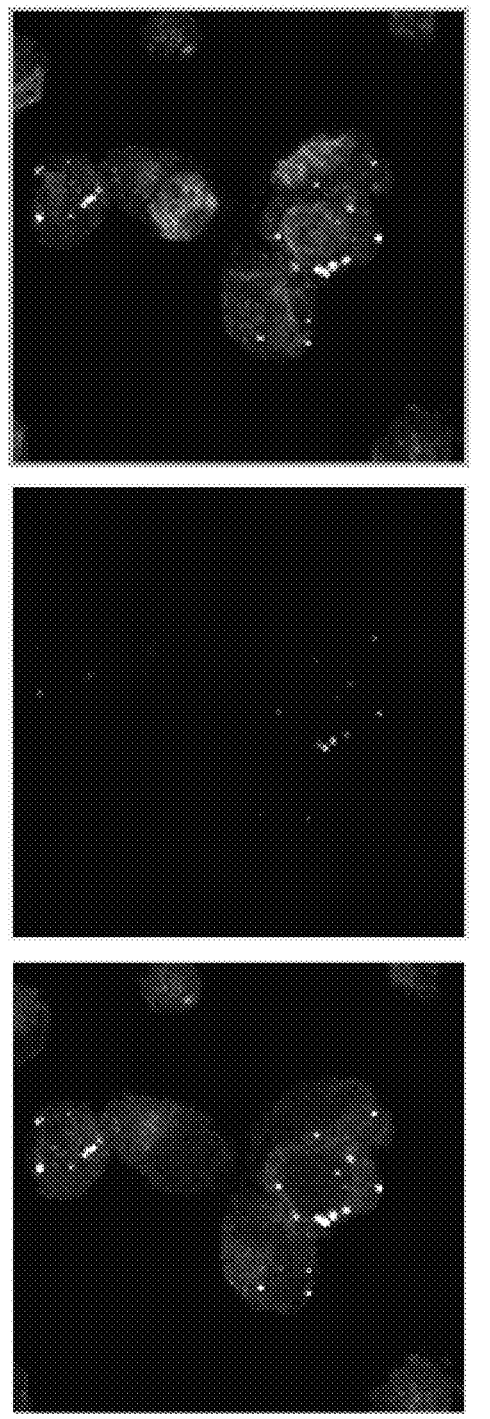
FIG. 22 shows microscopic images demonstrating co-localization between cRGF-PEG-nanoparticles and lysotracker red in the endocytotic pathway.

Discussion cRGD-PEG-dots and PEG-dots were found to co-localize with Lysotracker Red in M21 and B16 cells suggesting uptake in the endosomal pathway (FIG. 22). Data showed that these particles strongly colocalize with transferrin and dextran. Regardless of surface functionality and total charge, nanoparticles (6-7 nm in hydrodynamic diameter) studied appeared to follow the same route. Time lapse imaging in both cell types demonstrated internalization of functionalized nanoparticles within a small fraction of the plated cells. Particles were eventually delivered to vesicular structures in the perinuclear region. Colocalization assays with Giantin (or GM-130) is not expected to show nanoparticle fluorescent signal in the Golgi.

Figures 23A, 23B, 23C, 23D, 23E, 23F, 23G, 23H, 23I:
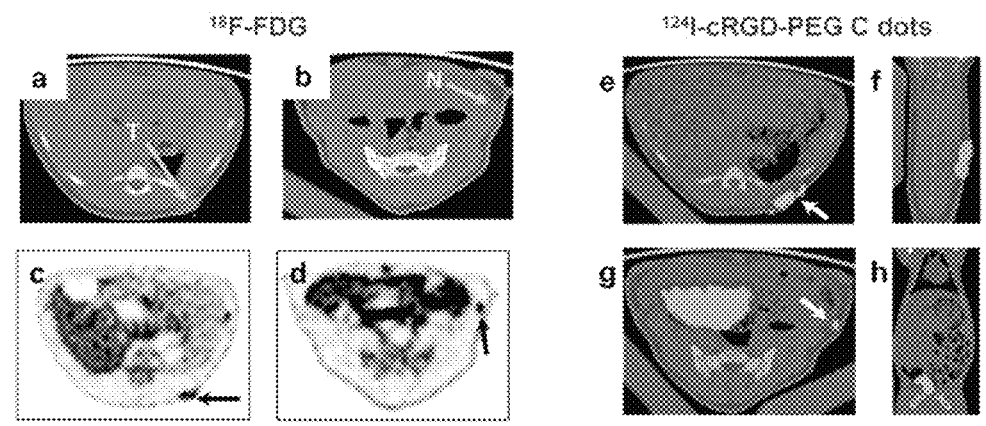
FIGS. 23a-23i Image-guided SLN (sentinel lymph node) Mapping: Pre-operative PET imaging. (a,b) Axial CT images reveal a left pelvic soft tissue mass (a, arrow) and left flank SLN (b, arrow). (c,d) Axial $^{18}$F-FDG PET images show localized activity within the tumor (c, arrow) and left flank SLN (d, arrow) following i.v. tracer injection. (e) Axial and (f) coronal $^{124}$I-cRGDY-PEG-C dot co-registered PET-CT images show site of local injection about the pelvic lesion (e, arrow). (g) Corresponding axial and (h) coronal co-registered PET-CT images localize activity to the SLN (g, arrow). (i) Radioactivity levels of the primary tumor, SLN (in vivo, ex vivo), and a site remote from the primary tumor (i.e., background), using a handheld gamma probe.

Example 12 Dual-Modality Silica Nanoparticles for Image-Guided Intraoperative SLN Mapping and Interventions Dual-Modality Silica Nanoparticles for Image-Guided Intraoperative SLN Mapping These studies were expanded to include optical imaging using the portable ArteMIS™ fluorescence camera system, along with radiodetection using the gamma probe, for performing real-time assessments of the draining tumor lymphatics and nodal metastases, as well as assessment of tumor burden. In a representative miniswine (FIGS. 23a-23i), initial preoperative PET-CT scanning was performed using $^{18}$F-FDG and $^{124}$I-cRGDY-PEG-C dots using the foregoing imaging procedure. Axial CT images revealed a primary pelvic tumor (FIG. 23a) and draining SLN (FIG. 23b), which were seen as areas of increased activity on the corresponding $^{18}$F-FDG PET scan (FIGS. 23c, 23d). These findings were confirmed 2 days later by dynamic PET-CT imaging about 5 minutes after subdermal, 4-quadrant injection of the particle tracer about the tumor site; coregistered axial (FIGS. 23e, 23g) and coronal (arrows, 23f, 23h) views demonstrate these findings. Following pre-operative scanning, the skin overlying the SLN site was marked for intraoperative localization, and the miniswine was transported to the intraoperative suite. Baseline activity measurements, made over the primary tumor and SLN sites using the portable gamma probe (FIG. 23i), showed a 20-fold increase in activity within the SLN relative to background signal.

Figures 24A, 24Q:
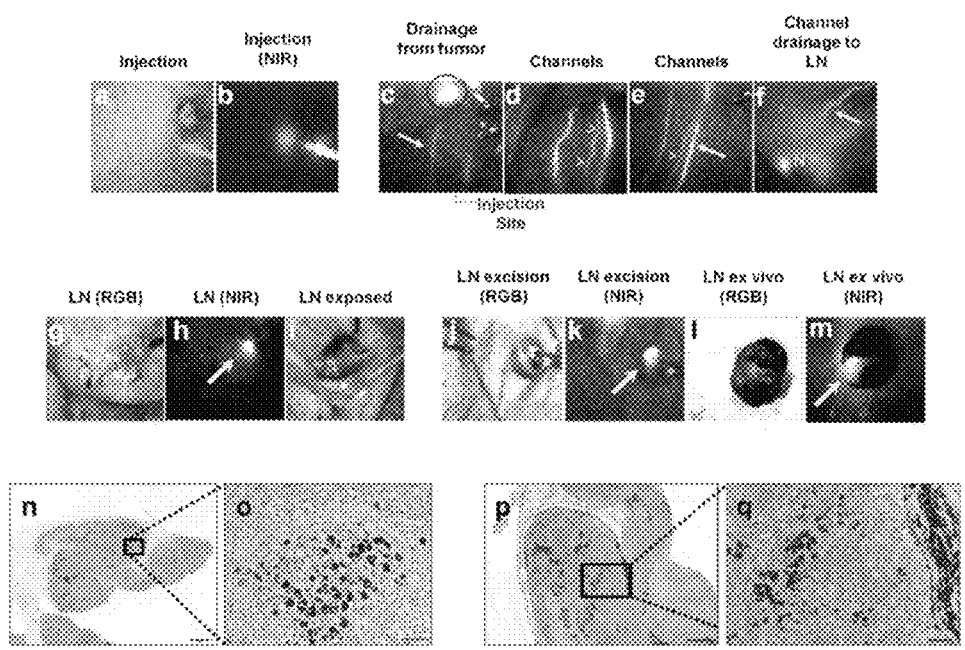
FIGS. 24a-24q Image-guided SLN mapping: Real-time intraoperative optical imaging with correlative histology. Intraoperative SLN mapping was performed on the animal shown in FIGS. 23a-23i. (a-i) Two-channel NIR optical imaging of the exposed nodal basin. Local injection of Cy5.5-incorporated particles displayed in dual-channel model (a) RGB color and (b) NIR fluorescent channels (white). (c-f) Draining lymphatics distal to the site of injection. Fluorescence signal within the main draining proximal (c,d), mid (e), and distal (f) lymphatic channels (arrows) extending toward the SLN ('N'). Smaller caliber channels are also shown (arrowheads). Images of the SLN displayed in the (g) color and (h) NIR channels. (i) Image of the exposed SLN. (j-m) Images of SLN in the color and NIR channels during (j,k) and following (l,m) excision, respectively. (n) Low power view of H&E stained SLN shows cluster of pigmented cells (black box) (bar=1 mm). (o) Higher magnification of (n) reveals rounded pigmented melanoma cells and melanophages (bar=50 μm). (p) Low power view of HMB45-stained SLN confirms presence of metastases (black box, bar=500 μm). (q) Higher magnification in (p) reveals clusters of HMB45+ expressing melanoma cells (bar=100 μm).

For real-time optical imaging of the lymphatic system, a second subdermal injection of $^{124}$I-cRGDY-PEG-C dots was administered about the tumor site with the skin intact, and the signal viewed in the color (FIG. 24a) and Cy5.5 fluorescent channels (FIG. 24b). The adjacent nodal basin was exposed, and fluorescent signal was seen in the NIR channel flowing from the injection site (FIG. 24c) into the main proximal (FIGS. 24c, 24d), mid (FIG. 24e), and distal (FIG. 24f) lymphatic branches, which drained towards the SLN (FIG. 24f). Smaller caliber lymphatic channels were also visualized (FIGS. 24d, 24e). The black-pigmented SLN, viewed in dual-channel mode (FIGS. 24g, 24h), was further exposed (FIG. 24i) prior to successive nodal excision (FIGS. 24j-24m). Fluorescence signal within the in situ (FIG. 24k) and ex vivo (FIG. 24m) nodal specimen was confirmed by gamma emissions using the gamma probe (FIG. 24i), and seen to correspond to scattered clusters of tumor cells on low-power (box, FIG. 24n) and high-power (FIG. 24o) views from H&E-stained tissue sections. Positive expression of HMB45 was identified on low-power (FIG. 24p) and high-power (FIG. 24q) views, consistent with metastatic melanoma.

Surprisingly, and by contrast to the observed $^{18}$F-FDG findings, $^{124}$I-RGD-PEG-C dots were found to specifically discriminate between metastatic tumor infiltration and inflammatory processes in these miniswine. Mechanistic differences in the behavior of these agents at the cellular and subcellular levels, as well as the presence of an integrin-targeting moiety on the particle surface, may account for the observed imaging findings. In multiple miniswine harboring pathologically-proven inflammatory changes due to granulomatous disease (n=3), $^{18}$F-FDG failed to detect metastatic disease, while identifying inflammatory and other metabolically active sites. These discrepant findings highlighted the ability of the particle tracer to selectively target, localize, and stage metastatic disease, while $^{18}$F-FDG failed in many cases to accurately stage cancer spread, instead identifying sites of inflammation.

Figures 25A, 25B, 25C, 25D, 25E, 25F, 25G, 25H, 25I, 25J, 25K:
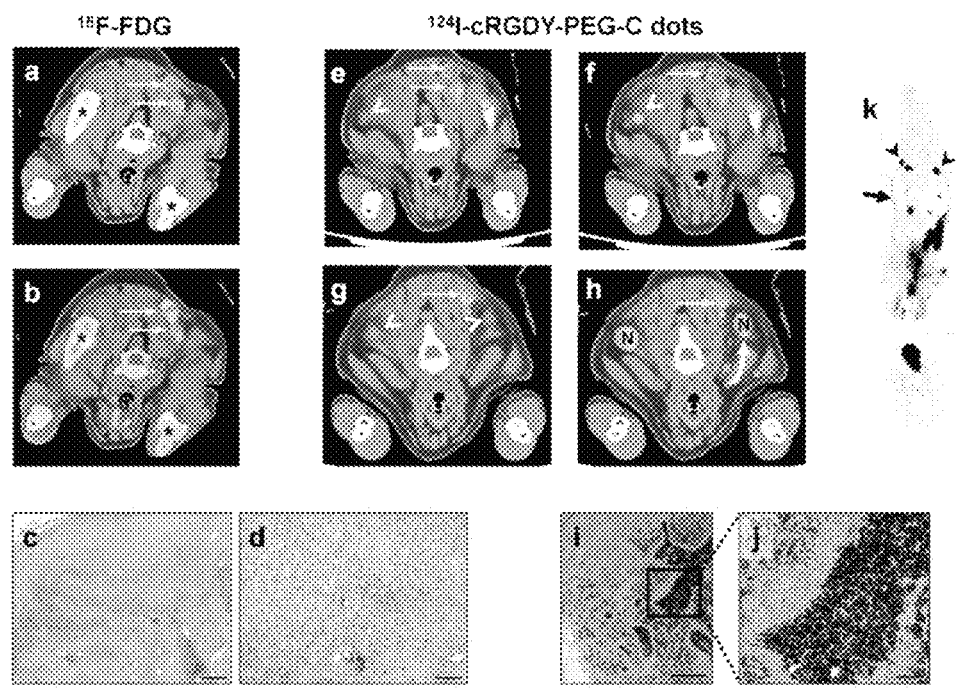
FIGS. 25a-25k Discrimination of inflammation from metastatic disease: Comparison of $^{18}$F-FDG and $^{124}$I-cRGDY-PEG C dot tracers. (a-d) Imaging of inflammatory changes using $^{18}$F-FDG-PET with tissue correlation. (a) Axial CT scan of the $^{18}$F-FDG PET study shows calcification within the left posterior neck (arrows). (b) Fused axial $^{18}$F-FDG PET-CT reveals hypermetabolic activity at this same site (arrows). Increased PET signal is also seen in metabolically active osseous structures (asterisks). (c) Low- and (d) high-power views of H&E-stained calcified tissue demonstrate extensive infiltration of inflammatory cells. (e-k) Metastatic disease detection following injection of $^{124}$I-cRGDY-PEG C dots about the tumor site. (e) Preinjection axial CT scan of $^{124}$I-cRGDY-PEG-C dots shows calcified soft tissues within the posterior neck (arrows). (f) Co-registered PET-CT shows no evident activity corresponding to calcified areas (arrow), but demonstrates a hypermetabolic node on the right (arrowhead). (g) Axial CT at a more superior level shows nodes (arrowheads) bilaterally and a calcified focus (arrow). (h) Fused PET-CT demonstrates PET-avid nodes (N) and lymphatic drainage (curved arrow). Calcification shows no activity (arrow). (i) Low- and (j) high-power views confirm the presence of nodal metastases. (k) Single frame from a three-dimensional (3D) PET image reconstruction shows multiple bilateral metastatic nodes (arrowheads) and lymphatic channels (arrow). Bladder activity is seen with no significant tracer accumulation in the liver. Scale bars: 500 μm (c,d); 100 μm (i,j).

In a representative miniswine study illustrating these findings, initial axial $^{18}$F-FDG PET-CT scans showed calcification within the left posterior neck on CT (FIG. 25a), corresponding to an area of intense activity on the $^{18}$F-FDG PET (FIG. 25b). Low-power (FIG. 25c) and high-power (FIG. 25d) views of H&E stained tissue sections revealed diffuse inflammatory changes, consistent with granulomatous disease. Intense $^{18}$F-FDG PET activity was additionally seen within the metabolically active bone marrow compartment of these young miniswine (FIGS. 25a, 25b). By contrast, the particle tracer imaging study identified bilateral metastatic neck nodes. A right neck node on axial CT imaging (FIG. 25e) was seen to be PET-avid on co-registered PET-CT (FIG. 25f); additional bilateral nodes on a more superior CT image (FIG. 25g) were also hypermetabolic on fused PET-CT (FIG. 25h). Moreover, left neck calcifications (FIGS. 25e, 25g) showed no PET activity on co-registered scans (FIG. 25f, 25h). Corresponding H&E-stained SLN tissue sections revealed dark melanomatous clusters on low-power (box, FIG. 25i) and high-power views (FIG. 25j), seen to be comprised of melanoma cells and melanophages. A single frame (FIG. 25k) selected from 3D PET reconstructed images again illustrated multiple, bilateral PET-avid neck nodes and associated draining lymphatic channels. Importantly, bulk activity was seen in the bladder 1 hr post-injection without significant tracer accumulation over the liver region.

Figures 26A, 26B, 26C:
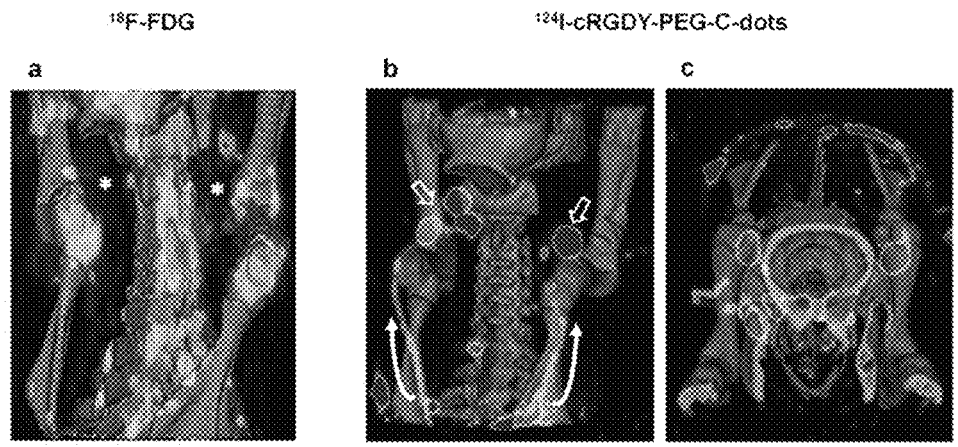
FIGS. 26a-26c show 3D Integrated $^{18}$F-FDG and $^{124}$I-cRGDY-PEG-C dot PET-CT. (a-c) 3D Volume rendered images were generated from CT and PET imaging data shown in FIGS. 7a-7k. (a) PET-CT fusion image (coronal view) shows no evident nodal metastases (asterisks). Increased activity within bony structures is identified. (b, c) High-resolution PET-CT fusion images showing coronal (b) and superior views (c) of bilateral metastatic nodes (open arrows) and lymphatic channels (curved arrows) within the neck following local particle tracer injection.

The above findings were seen to better advantage on PET-CT fusion MIP images generated from dynamic imaging data sets acquired over a 1 hour period after $^{18}$F-FDG (FIG. 26a) or local particle tracer administration (FIGS. 26b, 26c). For $^{18}$F-FDG, a clear absence of nodal metastases is noted, with diffusely increased activity seen within metabolically-active bony structures. In contrast to these findings, $^{124}$I-cRGDY-PEG-C dots detected bilateral metastatic neck nodes, along with draining lymphatic channels.

Dual-Modality Silica Nanoparticles for Image-Guided Interventions: Treatment Response.

The ability of the particle tracer to discriminate metastatic disease from tissue inflammatory changes could potentially be exploited in a variety of therapeutic settings—either surgically-based or interventionally-driven—as treatment response assessments are often confounded by the presence of inflammatory changes, making interpretation difficult. Image-guided interventions, such as therapeutic tumor ablations, may specifically benefit from the innovative coupling of new particle platform and imaging device technologies to (1) enable earlier post-procedural evaluation of response; (2) verify complete ablation or detect residual tumor representing treatment failure, and (3) improve tumor surveillance strategies. Locally ablative therapies, including microwave ablation, cryoablation, radiofrequency ablation (RFA), and laser interstitial therapy, induce local thermal injury via an energy applicator insertion into tumors. These methods are typically employed as alternative options in patients deemed ineligible for surgical excision. Further, patients undergoing ablative therapies are often poor surgical candidates due to co-morbidities. Widely used in clinical practice, they offer a distinct advantage, as they can be performed percutaneously as outpatient procedures with significantly less morbidity, and may improve quality of life and survival in selected patient cohorts.

Accurate post-therapy imaging, typically acquired 1-3 months after an ablation procedure, traditionally utilized contrast enhanced volumetric imaging, such as CT or MRI. These techniques suffer from a number of drawbacks. First, they are limited to identifying the presence of abnormal enhancement or growth in the size of the tumor area, considered primary indicators of residual tumor or recurrent disease. Diffuse rim enhancement about the ablation zone on post-procedural evaluations may be related to inflammation and hyperemia in the ablation zone, and often does not necessarily represent residual tumor. Increasing enhancement, notably irregular or nodular, is considered suspicious for tumor. However, these interpretations are controversial, as an ablation zone can look larger than expected for several months post-procedure, and enhancement might also reflect granulation or scar tissue formation.

Functional methods, such as $^{18}$F-FDG PET, have also been used to assess the efficacy and effects of locally ablative procedures, but may suffer from an inability to accurately discriminate tumor from inflammatory changes. Thus, interpretation of imaging changes (i.e., inflammation, tumor) at the tissue level in response to ablative procedures using current morphologic or functional assessments, particularly at early time intervals, is a significant challenge. What is needed are reliable endpoints for ablation success and unequivocal detection of residual disease in the postablation period.

Figures 27A, 27O:
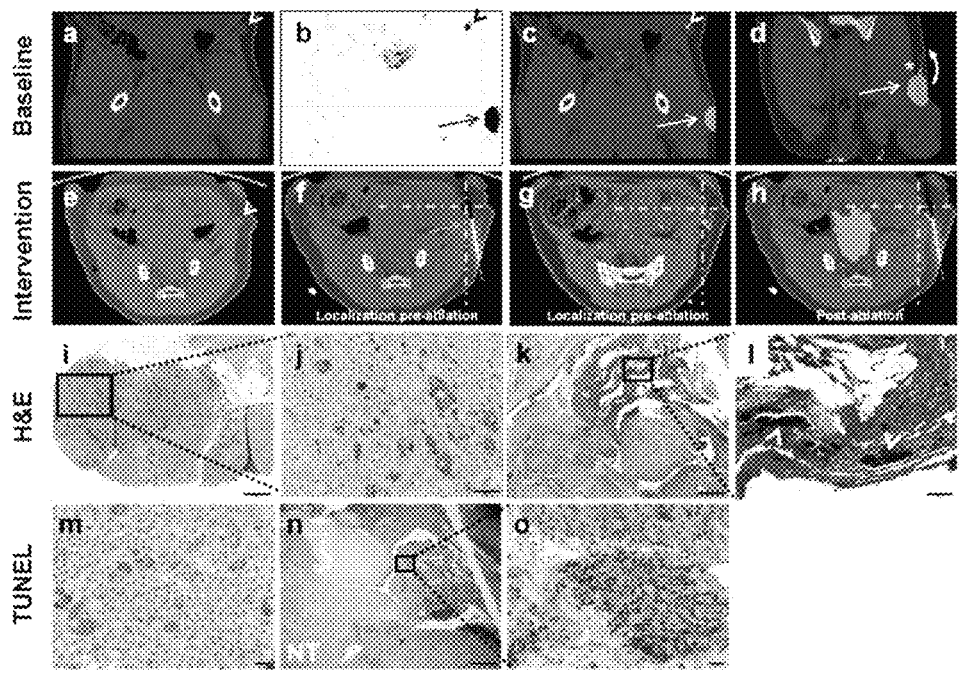
FIGS. 27a-27o Assessment of treatment response after radiofrequency ablation (RFA) using $^{124}$I-cRGDY-PEG-C dots. (a-c) Single-dose particle radiotracer localization of the SLN. (a) Baseline coronal CT (white arrowhead), (b) PET (black arrowhead), and (c) fused PET-CT images (white arrowhead) following a peritumoral injection. (b-d) Tumor particle tracer activity. (b) PET-avid exophytic left pelvic mass (black arrow). (c, d) Combined PET-CT images showing a hypermetabolic lesion (white arrow) and particle tracer flow within a draining lymphatic channel (asterisk) towards the SLN (curved arrow). (e,f) Pre-ablation axial CT images locate the SLN (e, white arrowhead) prior to RFA electrode placement (f, arrow) into the node (below crosshairs). (g) Pre-ablation fused PET-CT reveals increased SLN activity (posterior to cross-hairs). (h) Post-ablation PET-CT scan shows mildly reduced activity at the SLN site, anterior to the needle tip. (i) Corresponding pre-ablation H&E staining of core biopsy tissue from the SLN confirms pigmented tumor infiltration (bar=200 μm). (j) High magnification of boxed area in (i) reveals large, rounded pigmented clusters of melanoma cells (bar=50 μm). (k) Post-ablation H&E staining shows necrotic changes within a partially tumor-infiltrated node (box) and multifocal hemorrhages (bar=500 μm). (l) High magnification of (k) reveals significant tissue necrosis (arrowheads) within the metastatic node, in addition to lymphoid tissue (bar=50 μm). (m) TUNEL staining of metastatic SLN before ablation (bar=20 μm). (n) Post-ablation TUNEL staining demonstrating focal areas of necrosis with adjacent scattered tumor foci and normal nodal tissue (NT) (bar=500 μm). (o) High magnification of boxed area in (n) shows positive TUNEL staining, consistent with necrosis (bar=20 μm).

As a forerunner to performing future ablations of metastatic liver lesions, a proof-of-concept radiofrequency ablation (RFA) study of a larger (i.e., 1-2 cm) SLN was performed in a miniswine with metastatic melanoma to evaluate early treatment response in the presence of the particle tracer. PET-CT imaging findings prior to and after RFA were correlated histologically. Following subdermal injection of $^{124}$I-cRGDY-PEG-C dots (~0.6 mCi) about the primary left pelvic tumor, an initial baseline coronal CT showed a 2.2×1.6 cm SLN (FIG. 27a) superior to the tumor site, which was PET-avid (FIGS. 27b, 27c). The hypermetabolic left pelvic tumor is also shown (FIG. 27b), noting additional particle tracer flow within a draining lymphatic channel on fused PET-CT images (FIG. 27c, 27d). Additional serial CT scans were acquired to localize the node (FIG. 27e) prior to the ablation procedure and guide RFA probe insertion (FIG. 27f) into the node (below level of crosshairs). On the corresponding pre-ablation co-registered PET-CT scan, the PET-avid SLN was seen just posterior to crosshairs (FIG. 27g). A partial node ablation was performed for 12 minutes using a 2 cm active tip RFA probe (Cool-tip ablation system, Covidien plc, Dublin, Ireland). Post-ablation PET-CT showed mildly reduced tracer activity in the ablation zone, anterior to the electrode tip (FIG. 27h). Pre- and post-ablation imaging findings were confirmed histologically. H&E staining of pre-ablated core biopsy tissue from the SLN confirmed diffuse metastatic tumor infiltration on low-power (FIG. 27i) and high-power (FIG. 27j) views. Post ablation, the extent of metastatic infiltration decreased on H&E stained nodal tissue, seen on corresponding low- (FIG. 27k) and high-power views (FIG. 27l). Coagulative necrosis and lymphoid tissue were also identified, along with multifocal hemorrhages (FIGS. 27k, 27l, respectively). TUNEL stained high-power views prior to ablation reveal scattered neoplastic cells (FIG. 27m). On post-ablation TUNEL staining, focal areas of necrosis (red) were seen on both low- (FIG. 27n) and high-power (FIG. 27o) views.

CONCLUSIONS

Lymph node metastases are a powerful predictor of outcome for melanoma. Early detection of micrometastases in regional lymph nodes using SLN mapping may permit the timely stratification of patients to appropriate treatment arms, and can potentially improve patient outcomes. Although the current standard-of-care SLN mapping and biopsy techniques rely on the use of radioactivity-based identification of SLNs, a number of limitations of this technology exist. These include low spatial resolution, reduced staging accuracy, absence of target specificity, slow tracer clearance that may obscure the surgical field, and the lack of accurate intraoperative visualization to prevent injury to vital structures lying in close proximity to SLNs.

The recent introduction of newer generation, biocompatible particle platforms that can be actively tailored and refined to overcome these drawbacks according to key design criteria, while enabling selective probing of critical cancer targets, can offer important insights into cellular and molecular processes governing metastatic disease spread. The additional adaptation of such platforms for multimodality imaging could be used to advantage by the operating surgeon or interventionalist to explore these processes in a variety of image-guided procedural settings.

One such dual-modality platform, a clinically-translated integrin-targeting silica nanoparticle developed for both optical and PET imaging, meets a number of key design criteria—small size, superior brightness, enhanced tumor tissue retention, and low background signal—that make it an ideal agent for SLN localization and staging during SLN biopsy procedures when coupled with portable, real-time optical camera systems. The ability to discriminate metastatic disease from tissue inflammatory changes in melanoma models, which are often co-existing processes, may provide a more accurate and reliable marker for the assessment of treatment response in the future. Further investigation in a broader set of cancer types and treatments is warranted using either surgically-based or interventionally-driven therapies.

Example 13 SLN Mapping of Prostate Cancer

Multimodal nanoparticle bearing HuJ591-F(ab')2 fragments are novel diagnostic probes for binding prostate specific membrane antigen (PSMA). By synthesizing particles bearing multiple F(ab')2 fragments, we can (1) enhance binding affinity/potency due to multivalency effects and (2) alter in vivo distributions, as clearance and uptake will be dominated by particle kinetic behavior, rather than the antibody itself. By maintaining particle size below or just at the renal cut-off of 10-nm diameter, renal clearance is promoted. Further, target-to-background ratios will increase on the basis of improvements in (1) and (2), potentially improving diagnostic specificity and disease staging. Synthesis/Characterization of $^{124}$I-J591 F(Ab')2-Bound Particles.

To generate PEGylated F(ab')2 constructs, 100 ug of F(ab')2 was added to an eppendorf tube in 100 μl PBS, followed by incubation with 4 μl of 2 mg/ml Traut's reagent for 1 h at room temperature. Maleimide-PEG (6 mg) dissolved in buffer solution was then added. The solution was incubated overnight and purified with a PD-10 column prior to particle attachment. F(ab')2 fragments are being radiolabeled with iodine-124 ($^{124}$I) to create a dual-modality particle platform, and the specific activity, purity, and radiochemical yield will be derived. Particle size and concentration will additionally be assessed by FCS.

Example 14 In-Human Dual-Modality Silica Nanoparticles for Integrin-Targeting in Melanoma Nanomaterials, in particular nanoparticle probes, possess unique physicochemical and biological properties, as well as surface versatility. By exploiting their surface versatility, biocompatible, multifunctional particles can be selectively modified with molecular markers that recognize and localize key cancer targets. Of increasing importance in operative settings is the need for more robust optically-driven multifunctional particle probes which can improve real-time targeted detection of local/regional disease spread about the primary tumor site, thus facilitating treatment. Real-time delineation of disease from critical neural and/or vascular structures in intraoperative settings will also be paramount. Duncan, R, The dawning era of polymer therapeutics, Nat Rev Drug Discov 2, 347-360 (2003). Wagner, et al., The emerging nanomedicine landscape, Nat Biotechnol 24, 1211-1217 (2006). Scheinberg, et al., Conscripts of the infinite armada: systemic cancer therapy using nanomaterials, Nat Rev Clin Oncol 7, 266-276 (2010). Miyata et al., Polymeric micelles for nano-scale drug delivery, React. Func. Polym. 71, 227-234 (2011). Lee et al., Multifunctional mesoporous silica nanocomposite nanoparticles for theranostic applications, Acc Chem Res 44, 893-902 (2011). Schroeder et al., Treating metastatic cancer with nanotechnology, Nat Rev Cancer 12, 39-50 (2012). Rosenholm et al., Nanoparticles in targeted cancer therapy: mesoporous silica nanoparticles entering preclinical development stage, Nanomedicine (Lond) 7, 111-120 (2012). Ashley et al. The targeted delivery of multicomponent cargos to cancer cells by nanoporous particle-supported lipid bilayers, Nat Mater 10, 389-397 (2011). Vivero-Escoto et al., Silica-based nanoprobes for biomedical imaging and theranostic applications, Chem Soc Rev 41, 2673-2685 (2012). Tada et al., In vivo real-time tracking of single quantum dots conjugated with monoclonal anti-HER2 antibody in tumors of mice, Cancer Res 67, 1138-1144 (2007). Yet, despite extensive particle developments to date, no inorganic fluorescent particle imaging probe has successively made the transition to the clinic as a targeted multifunctional platform technology. Altinoglu et al., Near-infrared emitting fluorophore-doped calcium phosphate nanoparticles for in vivo imaging of human breast cancer, ACS Nano 2, 2075-2084 (2008). Hilderbrand et al., Near-infrared fluorescence: application to in vivo molecular imaging, Curr Opin Chem Biol 14, 71-79 (2010). Choi et al., Design considerations for tumour-targeted nanoparticles, Nat Nanotechnol 5, 42-47 (2010). He et al., Near-infrared fluorescent nanoprobes for cancer molecular imaging: status and challenges, Trends Mol Med 16, 574-583 (2010).

Here we describe that a first, ~7-nm fluorescence nanoparticle, modified as a hybrid (optical/PET) targeted platform by the attachment of radiolabels and cyclic arginine-glycine-aspartic acid-tyrosine (cRGDY) peptide, is not only well-tolerated in metastatic melanoma patients, but may preferentially detect and localize presumed integrin-expressing tumors in a microdosing regime with high signal-tonoise ratios. No significant serum protein binding is observed, and the integrity of the particle and its surface components are maintained in vivo. Results on safety, pharmacokinetics, dosimetry and targeting suggest general utility of this renally-excreted particle in cancer diagnosis and for potentially guiding treatment planning. This dual modality probe constitutes a platform that can be tailored to specific tumor types which may improve optical and/or PET-based lesion detection and cancer staging in humans, as well as drug delivery, potentially leading to better and more personalized cancer care.

Figures 28A, 28B, 28C:
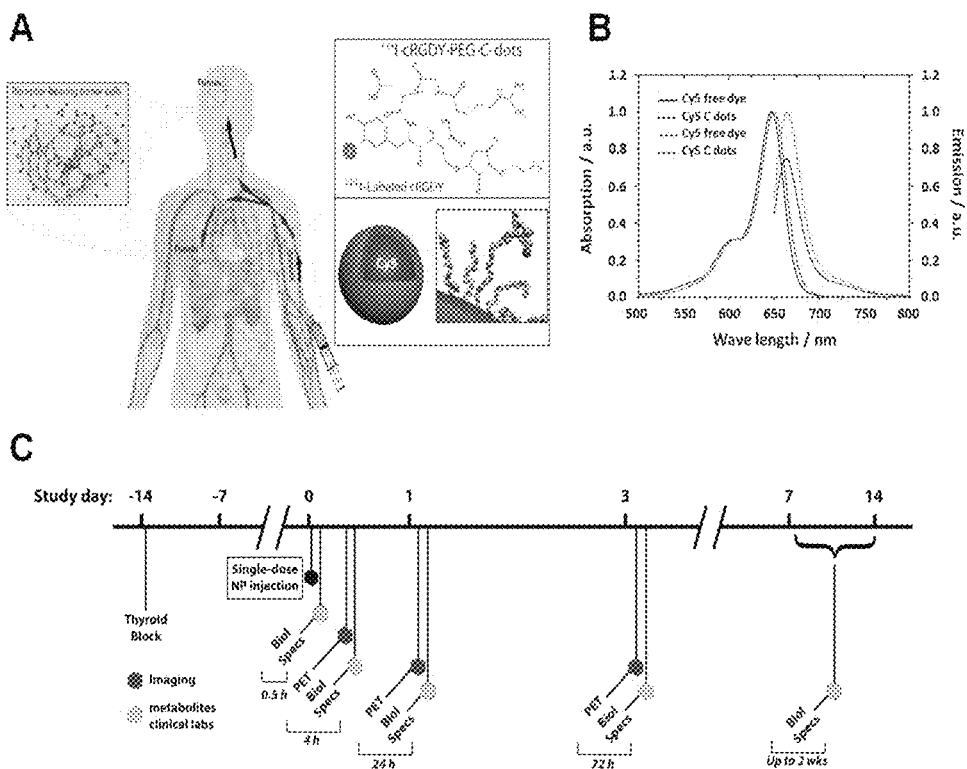
FIGS. 28A-28C. Core-shell hybrid silica nanoparticle platform ($^{124}$I-cRGDY-PEG-C dots) and overview of study design. (A) Schematic of the hybrid (PET-optical) inorganic imaging probe (right) showing the core-containing deep-red dye and surface-attached polyethylene glycol (PEG) chains that bear cRGDY peptide ligands and radiolabels for detecting human $\alpha_v\beta_3$ integrin-expressing tumors (left). (B) Absorption-matched spectra (left: red, black curves) and emission spectra (right) for free (blue curve) and encapsulated (green curve) dyes revealing increased fluorescence of encapsulated fluorophores. (C) Timeline of clinical trial events. Biol specs, biological specimens (blood, urine).

We used an ultra-small (~7-nm diameter), dual-modality (optical/PET) inorganic nanoparticle probe for targeted molecular imaging of $\alpha_v\beta_3$ integrin-expressing cancers. This nanoparticle probe is the first FDA-investigational new drug of its class and properties approved for first-in-human studies (FIG. 28a). The fluorescent silica nanoparticle (Cornell, or C dots) covalently sequesters dye molecules in a core encapsulated by a silica shell to prevent dye leaching and to enhance brightness and photostability. Ow, et al. Bright and stable core-shell fluorescent silica nanoparticles, *Nano Lett* 5, 113-117 (2005). Burns, et al. Fluorescent silica nanoparticles with efficient urinary excretion for nanomedicine, *Nano Lett,* 9, 442-448 (2009). Absorption-matched spectra demonstrate this per dye brightness enhancement as differences in intensity between the emissions of the encapsulated and free dyes (FIG. 28b). A neutral layer of surface poly (ethylene glycol) (PEG) chains enables attachment of a small number of cyclic arginine-glycine-aspartic acid-tyrosine (cRGDY) peptides for potent and selective integrin receptor binding. Benezra, et al. Multimodal silica nanoparticles are effective cancer-targeted probes in a model of human melanoma, *J Clin Invest,* 121, 2768-2780 (2011). Activated integrins induce many structural and signaling changes within the cell, in addition to regulating differentiation pathways, mediating adhesion properties, and promoting cell migration, survival, and cell cycle progression. Hood et al., Role of integrins in cell invasion and migration, *Nat Rev Cancer,* 2, 91-100 (2002). The attachment of nuclear imaging labels, such as $^{124}$I, via tyrosine residues amplifies signal sensitivity for serial PET imaging. The final product, a highly biocompatible and biostable tumor-selective particle tracer ($^{124}$I-cRGDY-PEG-C-dots), has previously provided a read-out of integrin receptor status by PET imaging in human melanoma xenografts, thus defining a distinct class of renally-cleared theranostic platforms for nanomedicine. Jokerst et al., Molecular imaging with theranostic nanoparticles, *Acc Chem Res,* 44, 1050-1060 (2011).

A first-in-human clinical trial was initiated, employing PET to quantitatively assess the time-dependent tumor uptake and biodistribution, radiation dosimetry, and safety of this agent in a cohort of five patients with metastatic melanoma. Implicit in the rationale of using PET imaging is the preclinical evidence that the particle radiotracer has no pharmacologic, radiogenic, or other demonstrable biologic effect. Collins, J. M. Phase 0 clinical studies in oncology, *Clin Pharmacol Ther,* 85, 204-207 (2009). Kummar et al., Phase 0 clinical trials: recommendations from the Task Force on Methodology for the Development of Innovative Cancer Therapies, *Eur J Cancer,* 45, 741-746 (2009). Following a single dose intravenous (i.v.) injection of approximately 185 megabequerels (MBq) (~3.4-6.7 nanomoles, nmol) of the $^{124}$I-cRGDY-PEG-particle tracer (specific activity range 27.8-57.4 GBq/μmol) into human subjects (FIG. 28a), three whole-body PET-CT scans were acquired over a 72-hour period to assess pharmacokinetics, in addition to analyzing metabolites in blood and urine specimens over a two week interval by gamma counting and radio thin layer chromatography (radioTLC).

Five patients had no adverse events and the agent was well tolerated over the study period. Pharmacokinetic behavior, expressed as the percentage of the injected dose per gram of tissue (% ID/g), versus time post-injection and the corresponding mean organ absorbed doses (FIG. 28d), were comparable to those found for other commonly used diagnostic radiotracers. Serial PET imaging of this representative patient (FIG. 28d) showed progressive loss of presumed blood pool activity from major organs and tissues, with no appreciable activity seen by 72-hour post-injection (p.i.). Whole-body clearance half-times in these patients were estimated to range from 13-21 hours. Interestingly, there was no notable localization in the liver, spleen, or bone marrow, in contrast to many hydrophobic molecules, proteins, and larger particle platforms (>10 nm). Although patients were pretreated with potassium iodide (KI) to block thyroid tissue uptake, a higher average absorbed thyroid dose was obtained in this patient relative to other tissues. Particles were also primarily excreted by the kidneys, with both kidney and bladder wall (after thyroid and tumor, see below), demonstrating one of the highest % ID/g values by 72 hrs p.i. (FIG. 28d); as is often the case for renally excreted radiopharmaceuticals, the bladder wall received a higher average absorbed dose than other major organs and tissues. The detailed clinical protocol (FIG. 28C) and the rationale for its design, is further described in Materials and Methods.

These findings highlight the fact that renal, rather than hepatobiliary, excretion is the predominant route of clearance from the body. Efficient renal clearance will be contingent upon the design of ultra-small particle-based platforms or macromolecular systems that are on the order of the effective renal glomerular filtration size cutoffs of about 10 nm or less. Choi, et al., Targeting kidney mesangium by nanoparticles of defined size, *Proc Natl Acad Sci USA,* 108, 6656-6661 (2011). A small fraction of the administered activity (less than 5%) was seen as uptake in the stomach and salivary glands of this patient, consistent with free iodine, which was progressively cleared over the imaging period. The particle does not exhibit properties typical of reticuloendothelial agents (i.e., technetium-99m sulfur colloid), whose uptake reflects macrophage function, principally in liver. Based on prior data acquired for cRGD radiotracers, no unexpected foci of activity were observed. Haubner, R., et al. Synthesis and biological evaluation of a (99m)Tc-labelled cyclic RGD peptide for imaging the alphavbeta3 expression, *Nuklearmedizin,* 43, 26-32 (2004).

Figure 29:
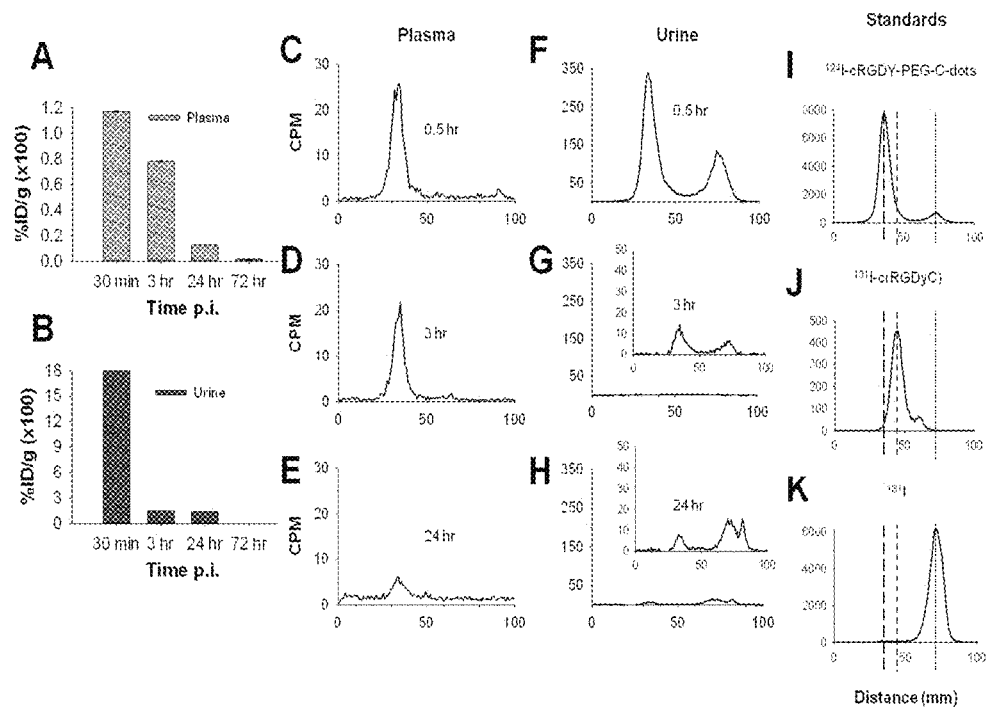
FIG. 29 Metabolic analyses of biological specimens. (A, B) Time-dependent activity concentrations (% ID/g×100) in plasma and urine, respectively, decay-corrected to the time of injection. (C-H) RadioTLC (4:1 acetic acid:methanol as mobile phase) of plasma and urine specimens (decay-corrected counts per minute, cpm). (C-E) Chromatograms of plasma show a single peak at 0.5—(C), 3—(D) and 24—(E) hours p.i. (F-H). Chromatograms of urine specimens reveal two peaks at 0.5—(F), 3—(G), 24—(H) hours p.i. Insets (G, H) show respective data scaled to a maximum of 50 cpm. (I-K) Chromatograms of standards: injectate (I), radio-iodinated ($^{131}$I) peptide (J) and free $^{131}$I (K). Vertical lines discriminate peaks corresponding to the particle tracer (long dashes; $R_f$=0.04), $^{131}$I-cRGDY (short dashes; $R_f$=0.2) and $^{131}$I (dotted; $R_f$=0.7).

Importantly, these properties point to the rather unique pharmacokinetic behavior exhibited by this inorganic dual-modality imaging particle as a renally cleared agent. Metabolic analyses of blood (FIG. 29a) and urine (FIG. 29b) specimens by gamma counting revealed at least an order of magnitude drop in tracer activity over a 72-hour period, with essentially no activity remaining at the end of this interval. Particle activity was largely confined to the blood plasma fraction without evidence of significant serum protein binding (data not shown). RadioTLC analyses of plasma samples revealed a single peak through 24 h p.i. (FIGS. 29c-29e), corresponding to the intact radiolabeled nanoparticle. In urine specimens, two peaks, one corresponding to the intact nanoparticle and the other to a more mobile species (identified as free iodine), were seen over a 24-hour period (FIGS. 29f-29h). RadioTLC analyses of the particle tracer (FIG. 29i), radioiodinated peptide ($^{131}$I-cRGDY, FIG. 29j), and free radioiodine ($^{131}$I, FIG. 29k) confirmed that the first and second peaks in the radiochromatograms corresponded to the intact nanoparticle and free iodine, respectively. Thus, these findings suggested that no measurable loss of particle integrity occurred over the course of the study, even after excretion through the kidneys.

Figure 30:
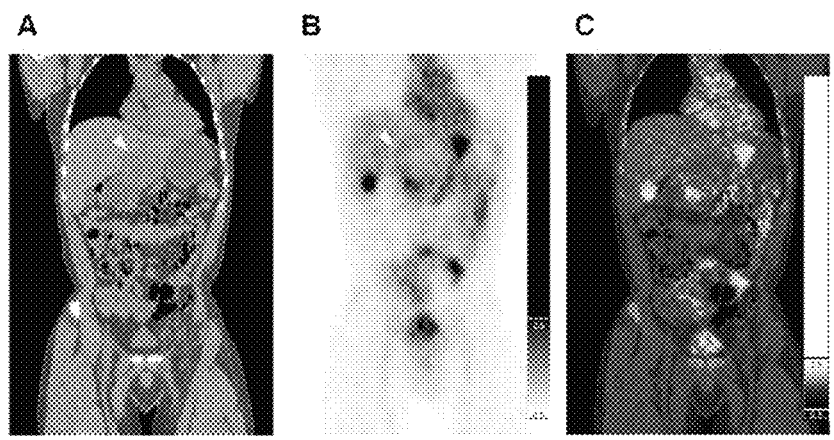
FIG. 30 Whole-body PET-CT imaging of particle biodistribution and preferential tumor uptake following systemic injection of $^{124}$I-cRGDY-PEG-C dots (A) Reformatted coronal CT demonstrates a well-defined, hypodense left hepatic lobe metastasis (arrowhead). (B) Coronal PET image at 4 hours p.i. demonstrates increased activity along the peripheral aspect of the tumor (arrowhead), in addition to the bladder, gastrointestinal tract (stomach, intestines), gallbladder, and heart. (C) Co-registered PET-CT localizes activity to the tumor margin.

Although tumor detection was not the goal of this PET microdosing study, surprisingly, despite the low injected dose, there was evidence of tumor localization of the particle tracer. In the first case, a whole-body PET-CT scan was acquired four hours after i.v. administration of $^{124}$I-cRGDY-PEG-C-dots in a patient with anorectal mucosal melanoma. On coronal CT images (FIG. 30a), a large rounded area of decreased density (arrowhead) was seen in the inferior left lobe of the liver, the site of a known metastatic lesion by prior fluorodeoxyglucose ($^{18}$F-FDG) PET/CT imaging (data not shown). On the coronal PET (FIG. 30b) and co-registered PET and CT scans (FIG. 30c), a rim of higher uptake circumscribed this lesion (FIG. 30b arrowhead; FIG. 30c) and subsequently cleared by the time of the 24-hour PET scan, suggesting some preferential localization in this presumed integrin-expressing metastasis. Significant activity was seen within the bladder, gastrointestinal tract (stomach, intestines), heart, and the gallbladder. In a second subject, a well-defined cystic lesion was seen in the right anterior lobe of the pituitary gland by axial (FIG. 31a) and sagittal (FIG. 31b) magnetic resonance imaging (MRI).

Figure 31:
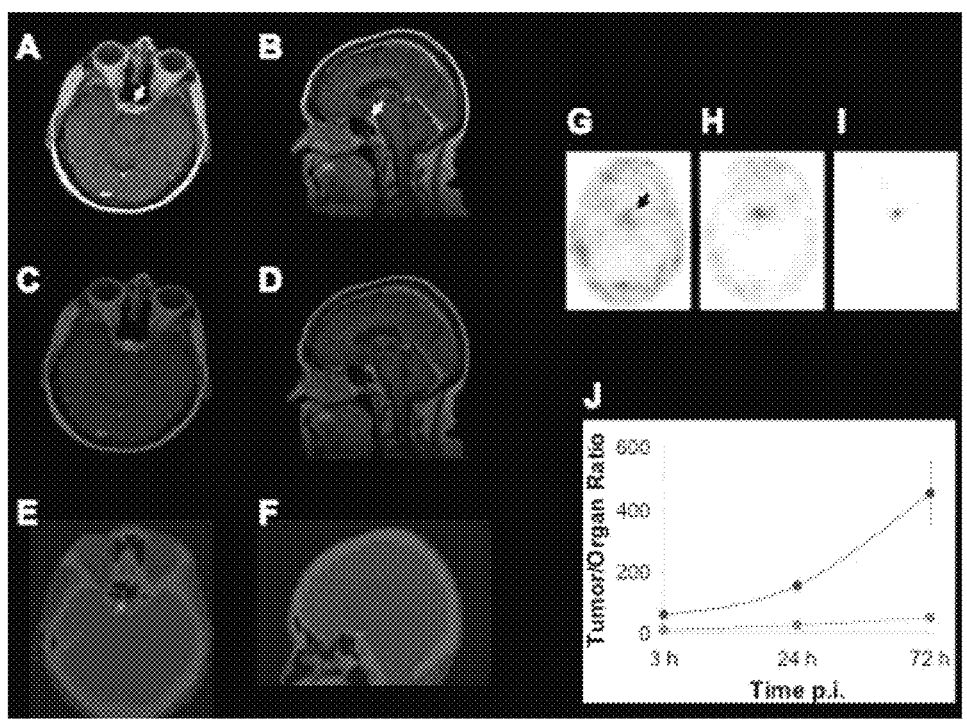
FIG. 31 Multimodal imaging of particle uptake in a pituitary lesion. (A-B) Multiplanar contrast-enhanced MR axial (A) and sagittal (B) images at 72 hours p.i. demonstrate a subcentimeter cystic focus (arrows) within the right aspect of the anterior pituitary gland. (C-D) Co-registered axial (C) and sagittal (D) MRI-PET images reveal increased focal activity (red) localized to the lesion site. (E-F) Axial (E) and sagittal (F) PET-CT images localize activity to the right aspect of the sella. (G-I) Axial PET images at 3 hours (G), 24 hours (H) and 72 hours (I) p.i. demonstrate progressive accumulation of activity (SUVmax) within the sellar region along with a corresponding decline in background activity about the lesion. (J) Tumor-to-brain (T/B) and tumor-to-liver (T/L) activity ratios increasing as a function of post-injection times.

This lesion, a stable finding on prior MRI scans, was presumed to be a pituitary microadenoma, an intracranial neoplasm known to exhibit malignant properties, such as neoangiogenesis and progression into peritumoral tissues. Precise co-registration of this tracer-avid focus with multi-planar MRI (FIGS. 31c, 31d) and CT (FIG. 31e, 31f) images confirmed its location within the anterior pituitary gland. Initially seen as a focus of intense activity, it progressively increased in intensity over a 72-hour interval (arrow, FIGS. 31g-31i), accompanied by a corresponding decrease in surrounding background marrow signal, thus yielding higher tumor-to-background ratios (i.e., tumor-to-brain (T/B)~6) and tumor-to-liver (T/L)~2)) (FIG. 31j). PET imaging results may be explained on the basis of findings in a prior study showing increased $\alpha_v\beta_3$ integrin-expression in the parenchyma of a subset of adenomas, as well as enhanced integrin expression levels in adenomatous stromal cells in relation to normal connective tissue cells. Farnoud, et al., Adenomatous transformation of the human anterior pituitary is associated with alterations in integrin expression, *Int J Cancer*, 67, 45-53 (1996).

Figures 28D, 28E:
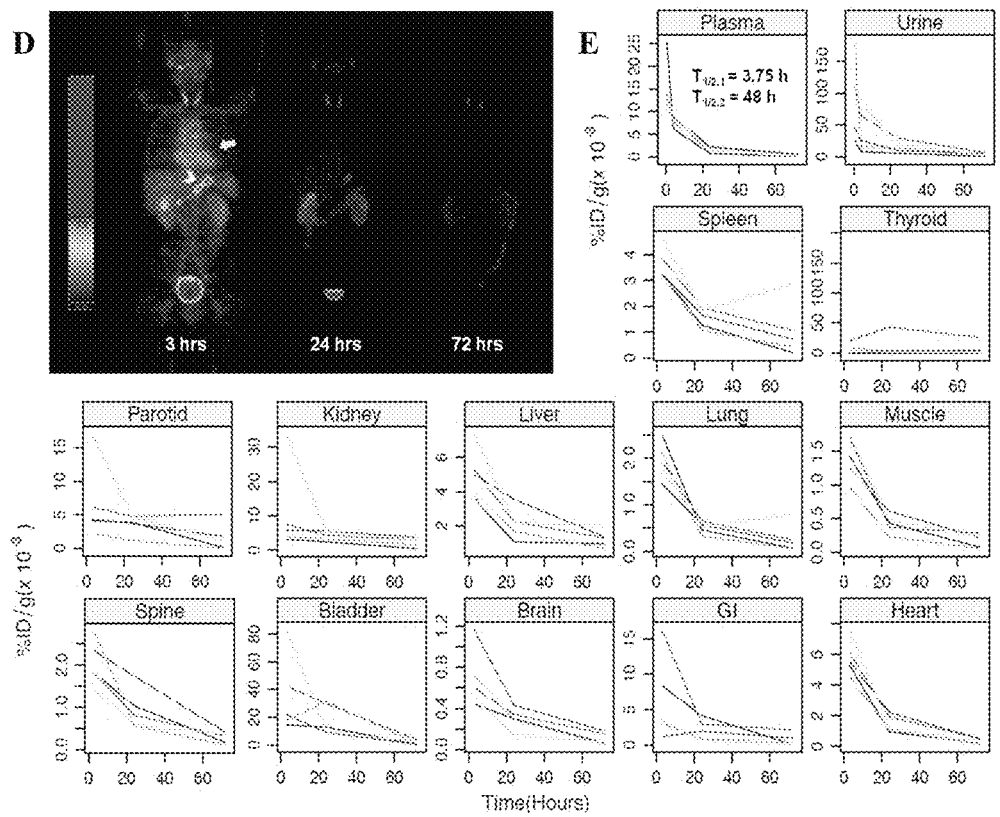
FIGS. 28D-28E. Whole body distribution and pharmacokinetics of $^{124}$I-cRGDY-PEG-C dots. (D) Maximum intensity projection (MIP) PET images at 2-(left), 24-(middle) and 72-(right) hours p.i. of $^{124}$I-cRGDY-PEG-C dots reveal activity in bladder (*), heart (yellow arrow), and bowel (white arrowhead). (E) Decay-corrected percent injected dose per gram (% ID/g) of urine and plasma collected at approximately 30 min, 4 h, 24 h and 72 h following injection of the particles was determined by gamma-counting; individual plots were generated for each patient. ROIs were drawn on major organs for each patient's PET scans for each patient to derive standardized uptake values and % ID/g.

Our initial data support the notion that human PET studies with this targeted imaging vehicle are a rationale approach towards detection and localization of presumed integrin-expressing tumors. We are planning dose escalation methods to determine an optimal balance among safety, whole-body clearance, and tumor targeting efficiency in more advanced clinical trials. Such PET-driven studies may also permit accurate quantification of integrin receptor expression levels for achieving maximum targeting efficiency, as well as detection of alterations in these levels. Further, the use of these quantitative molecular imaging tools can yield information on time-dependent changes in particle uptake and accumulation within tumors. Kelloff, G. J., et al., The progress and promise of molecular imaging probes in oncologic drug development, *Clin Cancer Res*, 11, 7967-7985 (2005). For the case of the pituitary adenoma, we were able to compute the cumulative uptake of particles within this lesion. Specifically, we computed the fraction of the total injected activity and the number of particles that accumulated at this site over a 72-hour imaging period. Using the measured maximum standardized uptake value ($SUV_{max}$, see Methods) of the lesion (i.e., 46.5) at 72 hours post-injection (nearly a factor of ten higher than that in normal pituitary tissue), corrected for partial volume effects, as well as the approximate mass of the lesion (i.e., product of the lesion volume and an assumed density of 1 g/cm$^3$), and the patient's body mass, we found that, relative to an injected particle load of $2\times10^{15}$, roughly $1.78\times10^{11}$ particles (0.01% of the injected dose, % ID) or 1 part per 10,000 accumulated at the lesion site. The standard uptake values (SUV) is defined as the activity per gram of tissue divided by the administered activity per gram of body mass. Time-dependent changes in the % ID/g and dosimetry of this lesion, in relation to major organs and tissues, are shown in FIGS. 28c and 28d.

The results suggest that the systemically injected particle tracer was well-tolerated and safe. Safety measures included monitoring of uptake in normal organs, as well as laboratory toxicity indicators. Secondary objectives were to estimate radiation doses and assess plasma and urine metabolic activity. Safety assessments were based on dosimetry, lack of clinical symptoms, and the absence of any laboratory indications of particle (drug) toxicity.

The results obtained from this first-in-human clinical trial point to a systemically injected particle tracer that exhibited favorable and reproducible PK signatures defined by renal excretion. In contrast to reticuloendothelial agents (i.e., technetium-99m sulfur colloid) and macromolecules, such as antibodies, there was no appreciable particle tracer accumulation within the liver, spleen, or bone marrow. Our data clearly indicate that a large proportion of the administered activity was eliminated via the urinary system (FIGS. 28E, 29B); activity concentrations in the urinary bladder were up to an order of magnitude higher than those in the liver, for example. Based on the conservative assumption that all hepatic activity is ultimately excreted via the hepatobiliary route, these data are consistent with ~90% of the administered activity being excreted via the urinary system and only ~10% via the hepatobiliary route. In remaining organs/tissues, notably at early time points (2-4 hrs), residual activity largely reflects that of the blood pool.

Targeted detection did not serve as a study endpoint, and dose escalation procedures to achieve maximum uptake at sites of disease were therefore not incorporated into the trial design (i.e., no attempt was made to adjust particle doses to optimize tumor targeting). However, despite the low nano-molar amounts used, preferential localization and accumulation of the particle tracer occurred in several tumors. In one of the patients with a presumed pituitary adenoma, PET imaging results showed progressive net accumulation of particle tracer activity at the site of the lesion. The results of this study suggest that our systemically injected particles are well tolerated and exhibit a distinctly unique 'macromolecular' PK signature, where bulk renal clearance predominates without significant RES uptake. This is in contrast to many hydrophobic molecules, proteins, and larger-particle platforms (>10 nm). This feature is highly atypical for nanoparticles (which generally exhibit diameters greater than estimated renal cut-off values, and therefore little renal excretion and slower clearance) and warrants clinical evaluation of our ultrasmall nanoparticle platform.

These results, along with essential data on safety, pharmacokinetics, and dosimetry of the dual-modality C dot imaging platform, suggest the general utility of this human microdosing technique in terms of yielding key tumor-specific read-outs for cancer diagnostics. Such estimated tumor-accumulated particle tracer loads (or concentrations), along with knowledge of cellular inhibitory response (i.e., $IC_{50}$ or 50% inhibitory concentration), can potentially be used to predict therapeutic dosing requirements for a given drug.

Methods

Synthesis and Characterization of cRGDY-PEG-C-dots.

For details regarding the synthesis and characterization of PEGylated and cRGDY (Peptides International, Louisville Ky.) surface-functionalized fluorescent core-shell silica nanoparticles (cRGDY-PEG-C-dots) encapsulating the organic dye, Cy5 (emission maxima ~650 nm, 2 dye equivalents within the particle core), see an earlier publication of this group and references therein. Benezra, M., et al., Multimodal silica nanoparticles are effective cancer-targeted probes in a model of human melanoma, *J Clin Invest,* 121, 2768-2780 (2011). In brief, particles were prepared by a modified Stöber-type silica condensation. Bogush, et al., Preparation of monodisperse silica particles: Control of size and mass fraction, *J Non-Cryst Solids,* 104, 95-106 (1988). Herz, et al., Large stokes-shift fluorescent silica nanoparticles with enhanced emission over free dye for single excitation multiplexing, *Macromol Rapid Commun,* 30, 1907-1910 (2009). Sadasivan, et al., Alcoholic solvent effect on silica synthesis—NMR and DLS investigation, *J Sol-Gel Sci Technol,* 12, 5-14 (1998). Bifunctional PEGs were derivatized with silanes for attachment to the silica surface and for peptide coupling. cRGDY peptides containing the sequence cyclo-(Arg-Gly-Asp-Tyr) and bearing cysteine residues (Peptide International) were attached to functionalized PEG chains via a cysteine-maleimide linkage. Hydrodynamic radius, brightness, and concentrations of cRGDY-PEG-Cdots, as against free Cy5 dye, were analyzed on a Zeiss LSM 510 Confocor 2 FCS using HeNe 633-nm excitation.

Radiolabeling of cRGDY-PEG-C-dots.

Tyrosine residues were conjugated to PEG chains for attachment of radioiodine moieties (i.e., $^{124}I$, $^{131}I$). Hermanson, G, *Bioconjugate Techniques,* (Academic Press, London, UK, 2008). Yoon, T. J., et al. Specific targeting, cell sorting, and bioimaging with smart magnetic silica core-shell nanomaterials. *Small,* 2, 209-215 (2006). Radiolabeling of cRGDY-PEG-C-dots was performed using the IODOGEN method (Pierce). Piatyszek, et al., Iodo-Gen-mediated radioiodination of nucleic acids, *Anal Biochem,* 172, 356-359 (1988). The radiolabeled product was eluted from PD-10 columns and assayed using a dose calibrator (Capintec, Ramsey N.J.) and radioTLC; specific activities of the $^{124}I$-bound particle fractions were on the order of 1450 millicuries (mCi)/µmole and radiochemical purity was greater than 95%.

Patient Selection.

Metastatic melanoma subjects with histological confirmation of disease and harboring newly diagnosed or recurrent tumor were eligible for the trial. Individuals who had medical illness unrelated to melanoma, which would preclude administration of the particle tracer, were excluded from the study. Potassium iodide solution (SSKI, 130 mg per day) was administered 2 days prior to and up to 2 weeks after intravenous injection of the radio-iodinated particle tracer ($^{124}I$-cRGDY-PEG-C-dots, 185 MBq/5 ml) to block thyroid function. This protocol was approved by the Institutional Review Board of the Memorial Sloan Kettering Cancer Center. Patients were tested for hemotologic, renal, and liver function before and after PET and provided signed informed consent.

Image Acquisition and Processing.

Low-dose spiral CT scans were obtained per standard procedure, followed by the acquisition of three whole-body PET scans on a dedicated GE Discovery STE PET/CT scanner 4, 24, and 72 hours post-injection of the particle tracer. Positron emission data was reconstructed using the ordered subsets expectation maximization (OSEM) algorithm. Images were corrected for attenuation using the CT transmission data collected over the same region as for emission imaging, and registration of the serial data set was performed using CT data sets.

Imaging and Metabolic Analyses.

For pharmacokinetic and dosimetric analyses, regions-of-interest (ROIs) were drawn on PET imaging data (AW Workstation, GE Healthcare, Ridgewood, N.J.) to extract mean and maximum standard uptake values (SUVs) for all major normal organs and tissues, including brain, lung, left ventricle, liver, spleen, intestine, kidneys, bladder, muscle, breast, and tumor(s). For pharmacokinetic evaluation, SUVs were converted to % ID/g values (i.e., SUV=% ID/g tissue× patient body mass/100). Organ/tissue uptake data was supplemented by time-activity data from the blood and urine. Venous blood and urine specimens were collected at approximately 30-min, 3-hr, 24-hr, 72-hr, and up to 2 weeks p.i. of $^{124}I$-cRGDYPEG-C-dots. Following centrifugation of whole blood specimens (4000 rpm, 10 min), plasma supernatant, along with urine specimens, were assayed in a scintillation well counter (1480 Automatic Gamma Counter, Perkin Elmer, Shelton Conn.) calibrated for $^{124}I$. RadioTLC analyses were additionally performed on biological specimens. RadioTLC analyses of the particle tracer, native peptide (cRGDY) labeled with $^{131}I$, and free iodine ($^{131}I$) served as controls to facilitate interpretation. Activities (counts per minute, cpm) were converted to microcuries, decay-corrected, and adjusted for volumes aliquoted. Final values were expressed as % ID/g. Retention factor ($R_f$) values for the tracer were obtained and used for identification of the parent compound and possible metabolites.

Radiation Dosimetry.

The standard radiation dosimetry method is an adaptation of that promulgated by the MIRD (Medical Internal Radionuclide Dosimetry) Committee, accounting for the physical properties of the administered radionuclides ($^{124}I$) as well as the biological properties (pharmacokinetics and biodistribution) of the radiopharmaceutical in individual patients. The $^{124}I$ emissions and their respective frequencies and energies are obtained from the MIRD Radionuclide Data and Decay Scheme publications. Serial whole-body PET scans enabled derivation of normal-organ absorbed dose (rad and rad/mCi) estimates using ROI-derived time-activity data. PET scans were acquired with all parameters identical, including the scan time. Using the patient's total-body mass (in kg) and the 70-kg Standard Man organ masses, the total-body and organ ROI data (i.e., mean standard uptake values (SUVs) were converted to activities (i.e., fraction of the injected dose). The foregoing image-derived time-activity data were fit to exponential functions using a least-squares fitting algorithm and the resulting time-activity functions analytically integrated, incorporating the effect of physical decay of $^{124}I$ to yield the cumulated activities (or residence times) in µCi-hr/µCi in the organs and total body. Cumulated activities were used to calculate $^{124}I$-labeled particle mean absorbed doses to the organs (rad/mCi) and effective dose (rem/mCi) for the 70-kg Standard Man anatomic model by employing the OLINDA EXM MIRD program. Loevinger et al., *MIRD Primer for Absorbed Dose Calculations,* Society of Nuclear Medicine, New York, N.Y., 1991.

Serum Protein Binding Assays.

Whole-blood specimens were collected in serum separator tubes from a metastatic melanoma miniswine model (Sinclair Research Center, MO), followed by centrifugation (4000 rpm, 10 min) to isolate the plasma fraction. An aliquot of serum was set aside for gamma counting; the remaining fraction was treated with ethanol (200 proof, Decon Labs, King of Prussia, Pa.), vortexed until cloudy, and placed on dry ice (5 min) to promote precipitation of serum proteins. Following centrifugation, supernatant was collected for gamma counting and the pellet was washed repeatedly with phosphate buffered saline and centrifuged (4000 rpm, 10 min) to collect 100 µL aliquots of supernatant for gamma-counting (1480 Wizard 3").

Example 15 Alpha-MSH-PEG-Cy5-Particles (MSH Peptide-Bound Particles)

Figure 32:
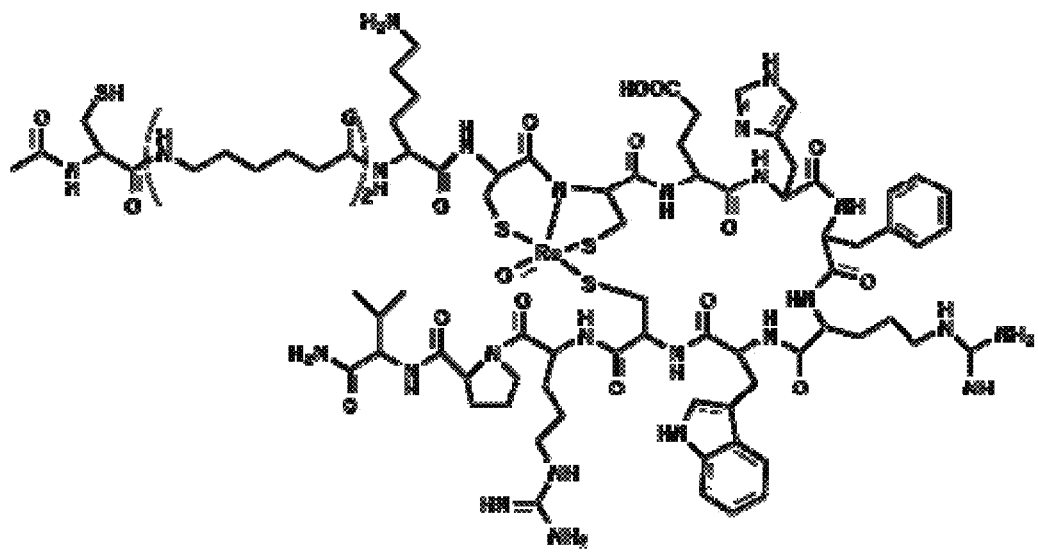
FIG. 32. Structure of N-Ac-Cys-(Ahx)$_2$-D-Lys-ReCC-MSH (or alpha MSH) peptide used for nanoparticle conjugation.
Figure 33:
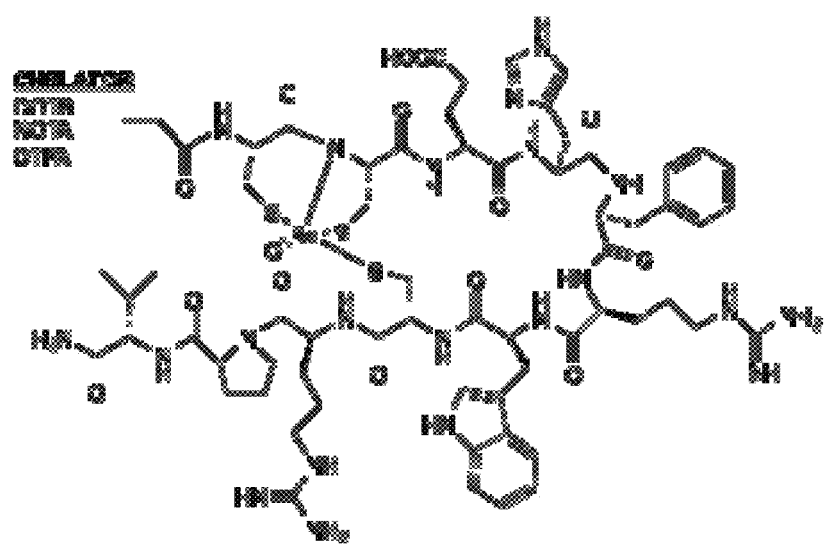
FIG. 33. Structure of the original ReCCMSH targeting molecule.

The N-Ac-Cys-(Ahx)$_2$-D-Lys-ReCCMSH (or alpha MSH) peptide used for nanoparticle conjugation has the structure shown in FIG. 32. It is attached to the nanoparticle via the N-terminal cysteine thiol. A spacer of two amino hexanoic acid units separates the nanoparticle attachment point from the D-Lys-ReCCMSH targeting molecule. The original ReCCMSH targeting molecule is shown in FIG. 33. It was designed to target radionuclide to melanoma tumors for imaging and therapy. The MSH peptide analog could be directly radiolabeled with $^{99m}$Tc or $^{188}$Re (at the site of the Re) or via a metal chelator appended to the amino terminus. The alpha MSH peptide analog shown in FIG. 32 is quite different from the original MSH analog shown in FIG. 33. The original MSH molecule could not be attached to a nanoparticle. The nanoparticle MSH peptide contains a free amino group containing side chain for radiolabeling. This is currently a D-Lysine but could be an amino group terminated side chain of 1 to many carbons in length.

The conjugation of the N-Ac-Cys-(Ahx)$_2$-D-Lys-ReCCMSH (or alpha-MSH) to the nanoparticle allows the nanoparticle to target and bind melanoma cells and tumors. The resulting particles, or alpha-MSH-PEG-Cy5-C dots were about 6-7 nm i.d. using FCS and contained, on average, about 2.6 dyes per particle. The number of alpha-MSH ligands per particle was estimated at <10.

Figure 34:
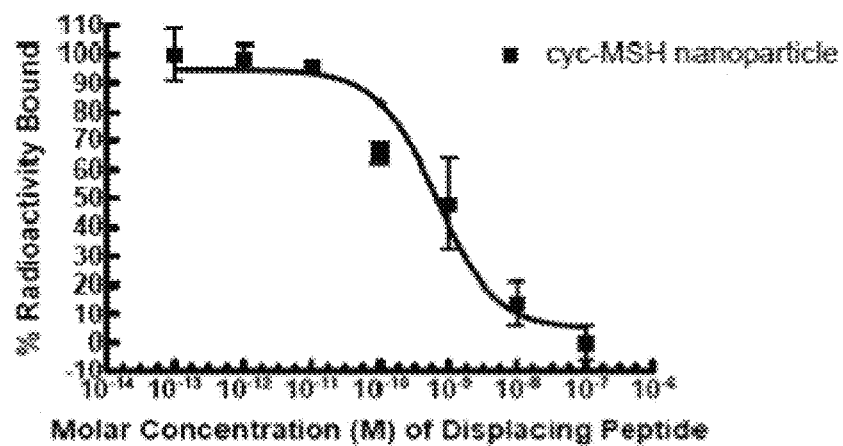
FIGS. 34A and 34B. Competitive binding studies using a melanocortin-1 receptor agonist ($^{125}$I-NDP). N-Ac-Cys-(Ahx)$_2$-D-Lys-ReCCMSH (or alpha-MSH) conjugated particles (FIG. 34A) had stronger affinity for cultured B16/F1 melanoma cells than a scrambled sequence version of the molecule (FIG. 34B).
Figure 34:
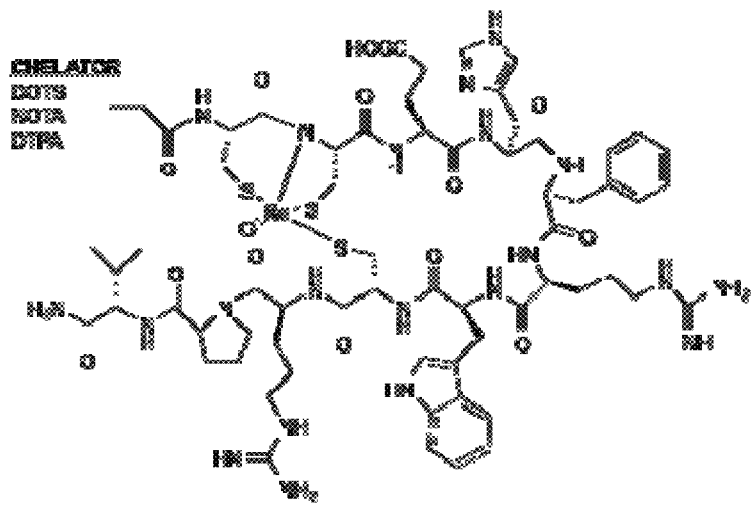

Competitive binding studies using N-Ac-Cys-(Ahx)$_2$-D-Lys-ReCCMSH (or alpha-MSH) conjugated particles: In a competitive binding assay with a melanocortin-1 receptor agonist ($^{125}$I-NDP), the alpha MSH conjugated nanoparticles had an IC$_{50}$ for cultured B16/F1 melanoma cells of $6.6 \times 10^{-10}$ M (FIG. 34A), while a scrambled sequence version of the molecule had an IC$_{50}$ of $2.3 \times 10^{-7}$ M (FIG. 34B). In addition, there was a 3 order of magnitude difference in binding. For reference in the same type of competitive binding assay, the original DOTA-ReCCMSH had an IC$_{50}$ of $2.1 \times 10^{-9}$ M.

The N-Ac-Cys-(Ahx)$_2$-D-Lys-ReCCMSH (or alpha-MSH) peptide-bound nanoparticle conjugate had better affinity for the B16/F1 cells than the original DOTA-ReCCMSH and much larger affinity than the scramble peptide nanoparticle.

Figure 35:
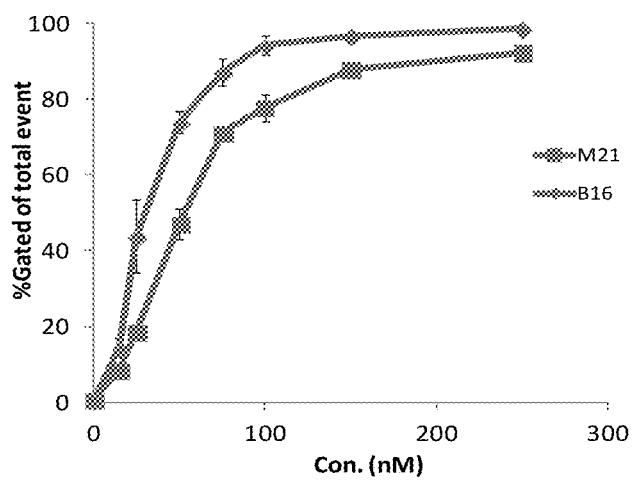
FIGS. 35A and 35B. Dose-response data was obtained as a function of targeted particle concentrations (FIG. 35A) and incubation times (FIG. 35B) for both B16F10 and M21 melanoma cell lines.
Figure 35:
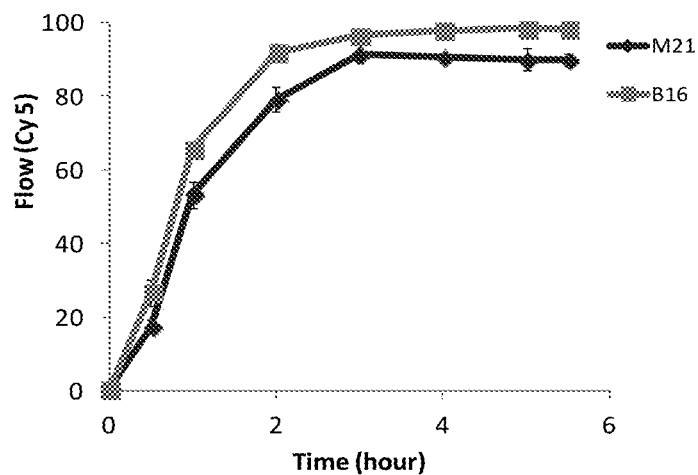

Dose-response data was additionally obtained as a function of targeted particle concentrations (FIG. 35A) and incubation times (FIG. 35B) for both B16F10 and M21 melanoma cell lines. Saturation concentrations for these lines, based on flow cytometry studies, were found to be on the order of ~100 nM for these two cell types, and at least 2 hr incubation times were needed to maximize binding.

Figure 36:
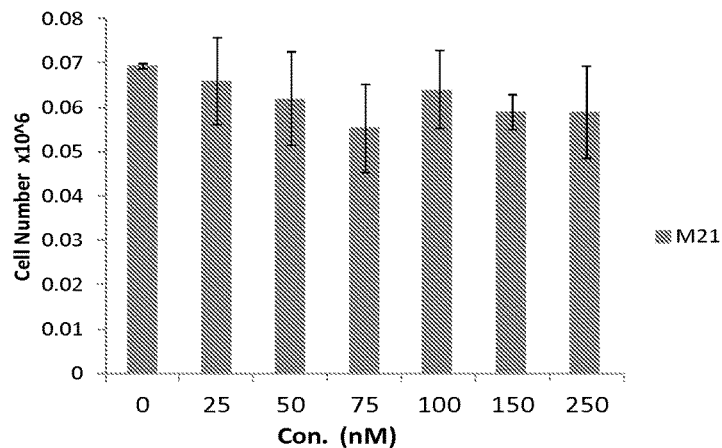
FIG. 36. Human M21 cell survival studies, performed over a range of particle concentrations for a fixed incubation time of 48 hr demonstrated no significant loss of cell viability.

Human M21 cell survival studies, performed over a range of particle concentrations for a fixed incubation time of 48 hr demonstrated no significant loss of cell viability (FIG. 36).

Figure 37A:
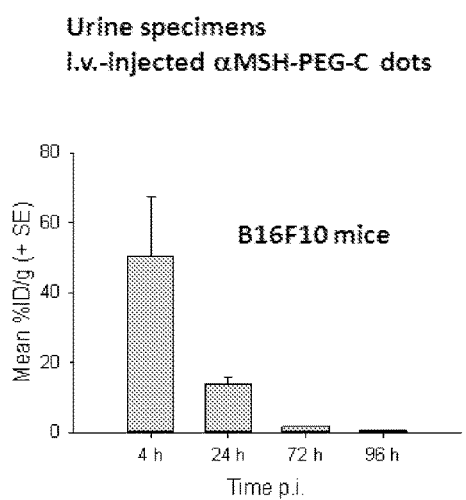
FIGS. 37A and 37B. $^{125}$I-radiolabeled alpha-MSH conjugated nanoparticles demonstrated bulk renal excretion over a 24 hr period in both B16F10 and M21 murine xenograft models.
Figure 37B:
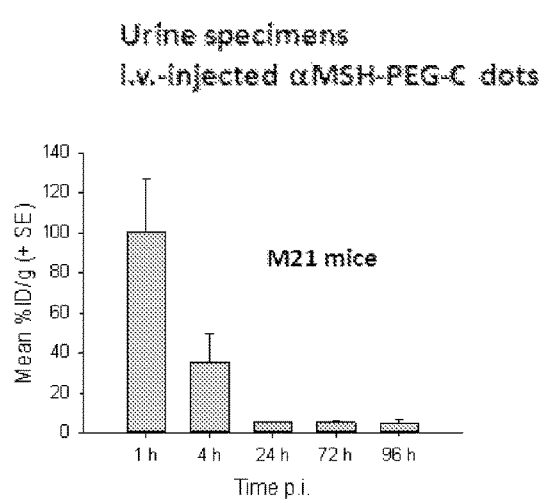
Figure 38A:
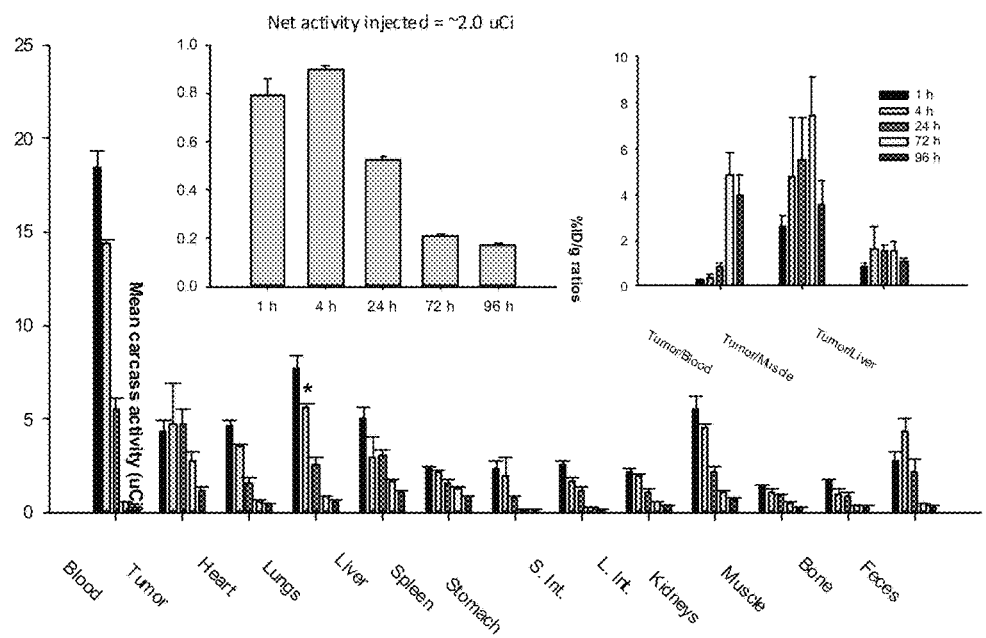
FIGS. 38A and 38B. Neither B16F10 or M21 xenograft models showed significant accumulation of the targeted particle probe in the reticuloendothelial system (i.e., not an RES agent), nor in the kidney.
Figure 38B:
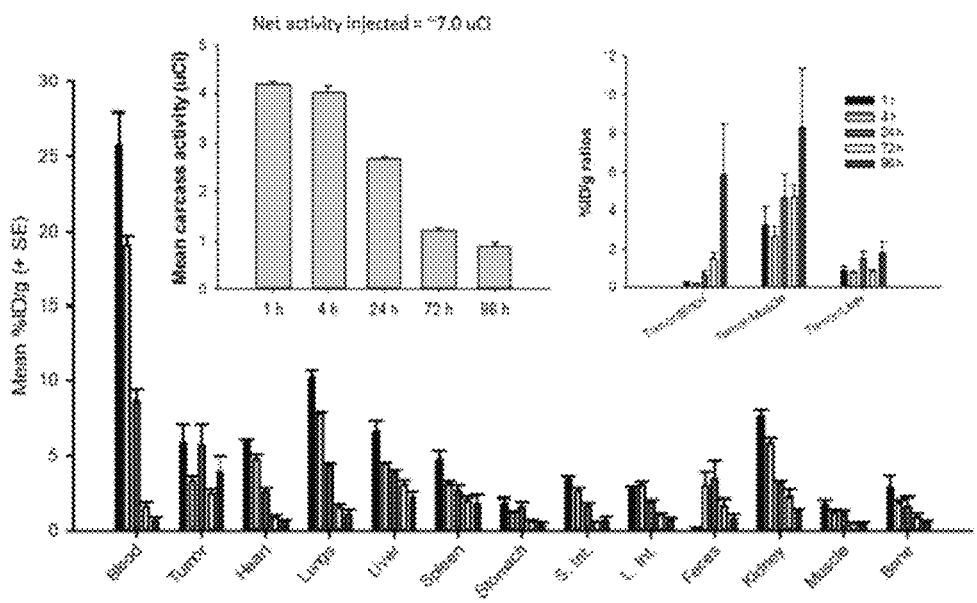

$^{125}$I-radiolabeled alpha-MSH conjugated nanoparticles demonstrated bulk renal excretion over a 24 hr period in both B16F10 and M21 murine xenograft models (FIGS. 37A, 37B); no appreciable particle tracer was measured at later time points (i.e., >24 hrs). In addition, neither B16F10 nor M21 xenograft models showed significant accumulation of the targeted particle probe in the reticuloendothelial system (i.e., not an RES agent), nor in the kidney (FIGS. 38A, 38B), the latter organ typically a site that accumulates alpha-MSH non-specifically given its net positive charge. Thus, the attachment of alpha-MSH to the particle probe significantly improved its renal clearance properties and eliminated accumulation within the kidneys.

Example 16 Integrin-Mediated Signaling and Modulation of Tumor Biology

Integrin signaling regulates diverse functions in tumour cells, including adhesion/spreading, migration, invasion, proliferation and survival. In several tumor types, including melanoma, the expression of particular integrins correlates with increased disease progression and decreased patient survival. Integrin-mediated adhesive interactions have identified novel integrin functions in cell survival mechanisms and in the activation of divergent signaling pathways. It is well known that binding of peptides (or clusters of peptides), containing the RGD sequence, to integrin receptors leads to cross-linking or clustering of integrins which, in turn, modulates the above processes. It is not clear, however, whether nanoparticles bearing multiple RGD peptide ligands can additionally trigger such integrin signaling events, as this will reflect a complex dependency on multiple particle-based factors (size, charge, composition, surface chemistry, ligand number/type), tumor (or endothelial) cell type, cell receptor density, and particle dosing. Our dose-response studies demonstrate modest activation of divergent signaling pathways upon cell exposure to particle concentrations greater than 100 nM which, in turn, promote M21 and HUVEC cell migration, proliferative activity, and alter adhesion properties.

Binding of cRGDY-PEG-C-dots to M21 and HUVEC Cells

Figure 39:
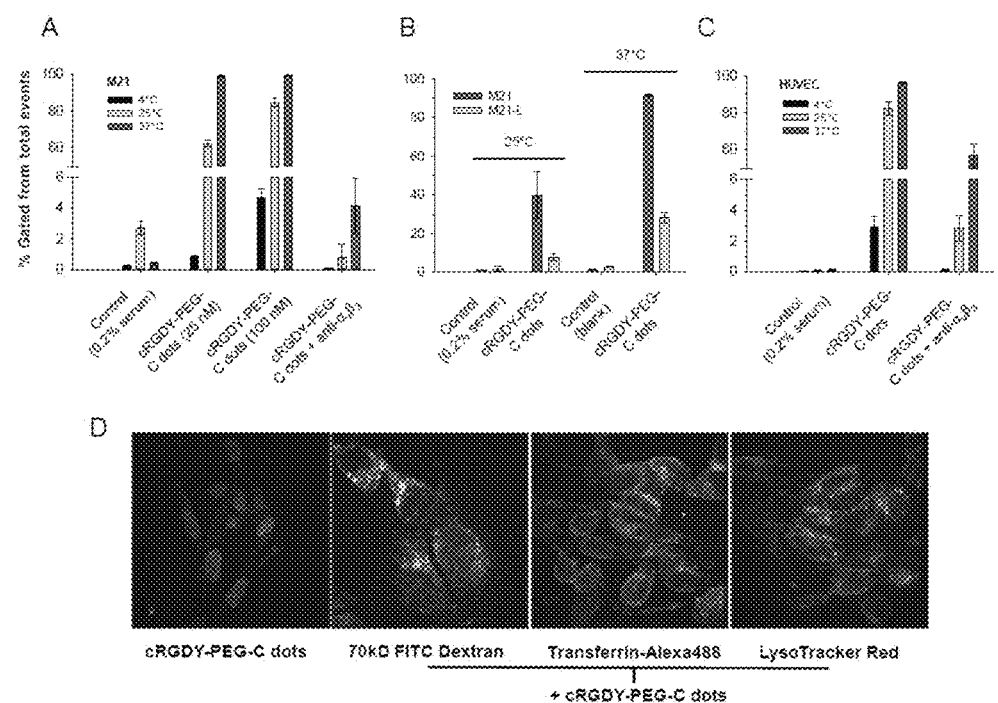
FIG. 39. Competitive integrin receptor binding and temperature-dependent uptake using cRGDY-PEG-C dots and anti-$\alpha_v\beta_3$ antibody for 2 cell types. A. Specific binding and uptake of cRGDY-PEG-C dots in M21 cells as a function of temperature (4° C., 25° C., 37° C.) and concentration (25 nM, 100 nM) using anti-$\alpha_v\beta_3$ integrin receptor antibody and flow cytometry. Anti-$\alpha_v\beta_3$ integrin receptor antibody concentrations were 250 times (i.e., 250×) the particle concentration. B. Uptake of cRGDY-PEG-C dots in M21 cells, as against M21L cells lacking normal surface integrin expression by flow cytometry. C. Selective particle uptake in HUVECs using anti-$\alpha_v\beta_3$ integrin receptor antibody and flow cytometry. D. cRGDY-PEG-C dot (1 µM, red) colocalization assay with endocytic (transferrin-Alexa-488, FITC-dextran, green) and lysosomal markers (LysoTracker Red) after 4 h particle incubation using M21 cells. Colocalized vesicles (yellow), Hoechst counterstain (blue). Scale bar=15 µm. Each data point (A-C) represents the mean±SD of 3 replicates.
Figure 47:
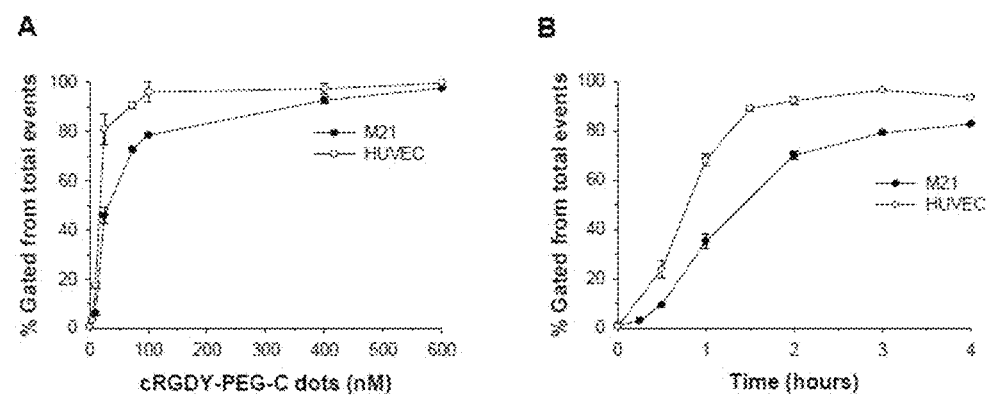
FIG. 47. Dose-response effects and saturation binding kinetics using cRGDY-PEG-C dots and $\alpha_v\beta_3$ integrin-expressing cells. A, B. Cellular binding/uptake as a function of particle concentration (A) and incubation time (B) by flow cytometry. Monolayers of M21 and HUVEC cells were incubated (4 h, 25° C.) with increasing concentrations of particles (5-600 nM), as well as over a range of incubation times (0.5-4 h; 100 nM) and assayed by fluorescence-activated cell sorting (FACS) analysis. The percentage of the total events detected is displayed. Each data point represents mean±SD of 3 replicates.

The $\alpha_v\beta_3$ integrin receptor plays a key role in vascular remodeling and angiogenesis, demonstrating increased expression on endothelial and tumor cell surfaces for a variety of tumor cell lines. This leads to the use of this receptor as a target for diagnostic and therapeutic purposes. In our case, the cRGDY-PEG-C dots were tested for their ability to bind to melanoma cells (M21) or to human umbilical vascular endothelial cells (HUVEC) as a function of concentration and time. Initial dose-response studies showed a progressive increase in the binding of cRGDY-PEG-C dots to M21 and HUVEC cells as a function of concentration by flow cytometry (FIG. 39, FIG. 47A). Particle binding demonstrated saturation at about 100 nM for both cell lines, with mean % gated values of about 80% for M21 cells and 96% for HUVEC cells. Dose-response behavior was additionally investigated as a function of particle incubation times for both cell types after incubating with 100 nM cRGDY-PEG-C dots. Maximum binding was observed at 2 hours post-incubation, remaining relatively constant thereafter (FIG. 47B).

Endocytosis and Intracellular Trafficking of cRGDY-PEG-C-dots

To elucidate the nature of the pathway/s utilized by cRGDY-PEG-C-dots following their incubation in M21 cells—whether this is an $\alpha_v\beta_3$ integrin receptor-mediated and/or non-specific uptake process, we examined the temperature-dependent uptake of these particles for a 4 hour incubation time at three temperatures: 4°, 25° C. and 37° C. The results, summarized in FIG. 39A, C indicate an increase in cell-associated cRGDY-PEG-C-dots at 37° C. as compared to 25° C. or to 4° C. in both cells line tested. Moreover, internalization of cRGDY-PEG-C-dots was partially blocked in the presence of excess (×250) antibody to $\alpha_v\beta_3$ receptor in M21 and HUVEC cells (FIGS. 39A, 39C), suggesting a component of receptor-mediated binding. Additionally, uptake in $\alpha_v\beta_3$-negative M21L cells was roughly a factor of 4- to 8-fold lower than that seen with $\alpha_v\beta_3$-expressing cells at both 37° C. and 25° C. (FIG. 39B), respectively.

To further characterize the cellular compartments involved in cRGDY-PEG-C dot internalization, we performed colocalization assays in M21 cells with cRGDY-PEG-C dots and biomarkers of different endocytotic vesicles. Internalization of the targeted particle (~1 µM, red, 4-hr incubation) was sensitively detected by an inverted confocal microscope (Leica TCS SP2 AOBS) equipped with a HCX PL APO objective (63×1.2NA Water DIC D) (FIG. 39D). Using endocytotic markers LysoTracker Red (100 nM, green) (FIG. 39D) and transferrin-Alexa488, uptake into acidic endocytic structures was confirmed, suggesting clathrin-dependent pathway activity and gradual acidification of vesicles. FIG. 39D shows co-localization data between the particle and acidic endocytic 30 vesicles (yellow puncta). Uptake into macropinocytes was also observed with 70-kDa dextran-FITC which co-localized with cRGDY-PEG-C dots; this finding suggested a second pathway of internalization. Nuclear counterstaining (blue) was done with Hoechst. No particles entered the nucleus. Time lapse imaging confirms particle uptake into M21 cells and co-localization with the lysosomal marker, Lamp1.

Figure 48:
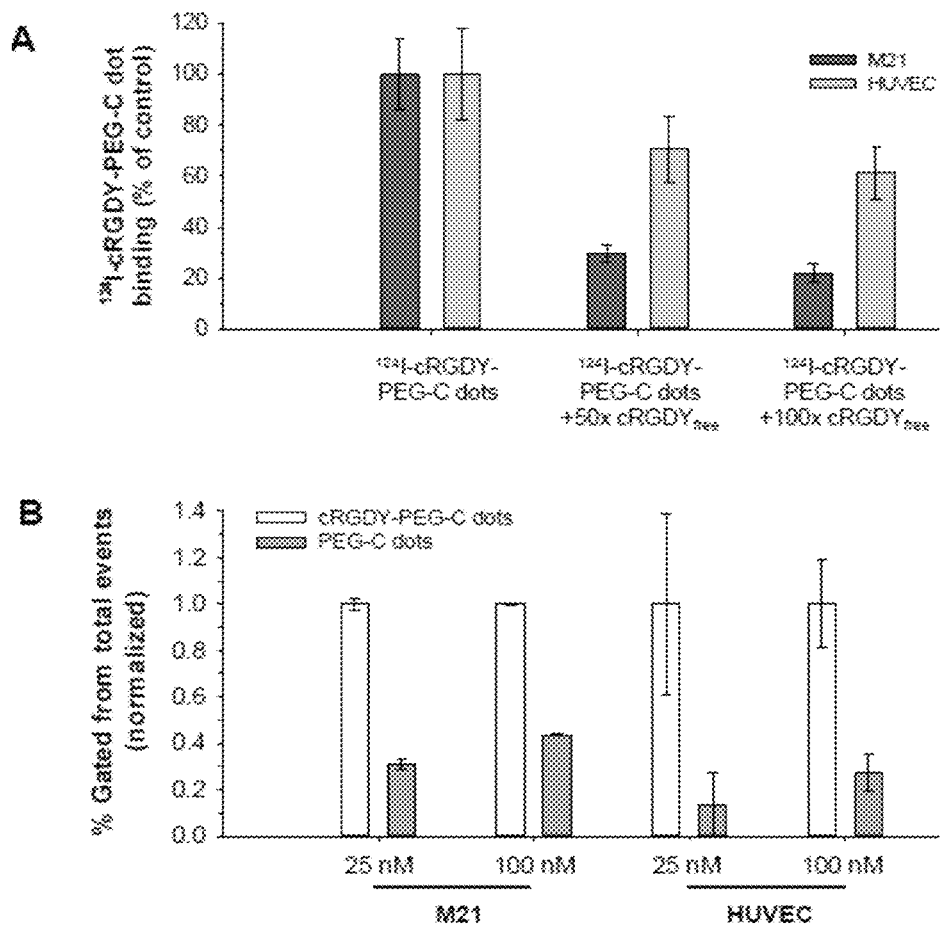
FIG. 48. Competitive integrin receptor binding with $^{124}$I-cRGDY-PEG-C dots and cRGDY peptide in two cell types. A. Specific binding of $^{124}$I-cRGDY-PEG-dots to M21 and HUVEC cells following incubation with excess cRGDY peptide using gamma counting. Monolayers of M21 and HUVEC cells were incubated (4 h, 25° C.) with 25 nM of $^{124}$I-cRGDY-PEG-dots in the presence and absence of cRGDY peptide (85, 170 nM). Binding is expressed as a percentage of the control (i.e., radioiodinated cRGDY-PEG-dots). B. Tumor-directed binding of non-radiolabeled cRGDY-PEG-C dots. M21 and HUVEC cells were incubated for 4 h at 25° C. with two targeted particle concentrations (25 nM, 100 nM) or particle controls (PEG-C dots) and assayed by flow cytometry.

Competitive $\alpha_v\beta_3$ Integrin Receptor Binding and Molecular Specificity Competitive binding assays showed blocking of receptor-mediated particle binding in M21 and HUVEC cells (FIG. 48A) by 80%-85% in the former and 30-40% in the latter using excess (×50-×100) cRGDY peptide and gamma counting of the radiolabeled particle tracer (124I-PEG-cRGDY-C dots). By contrast to cRGDY-PEG-C dots, significant reductions were seen in the magnitude of receptor binding in M21 (~30%-43%) and HUVEC (~13%-27%) cells after incubation with non-targeted (i.e., PEG-C dots) particle probes by flow cytometry (FIG. 48B).

Influence of cRGDY-PEG-C dots on Cell Viability and Proliferation

Figure 49:
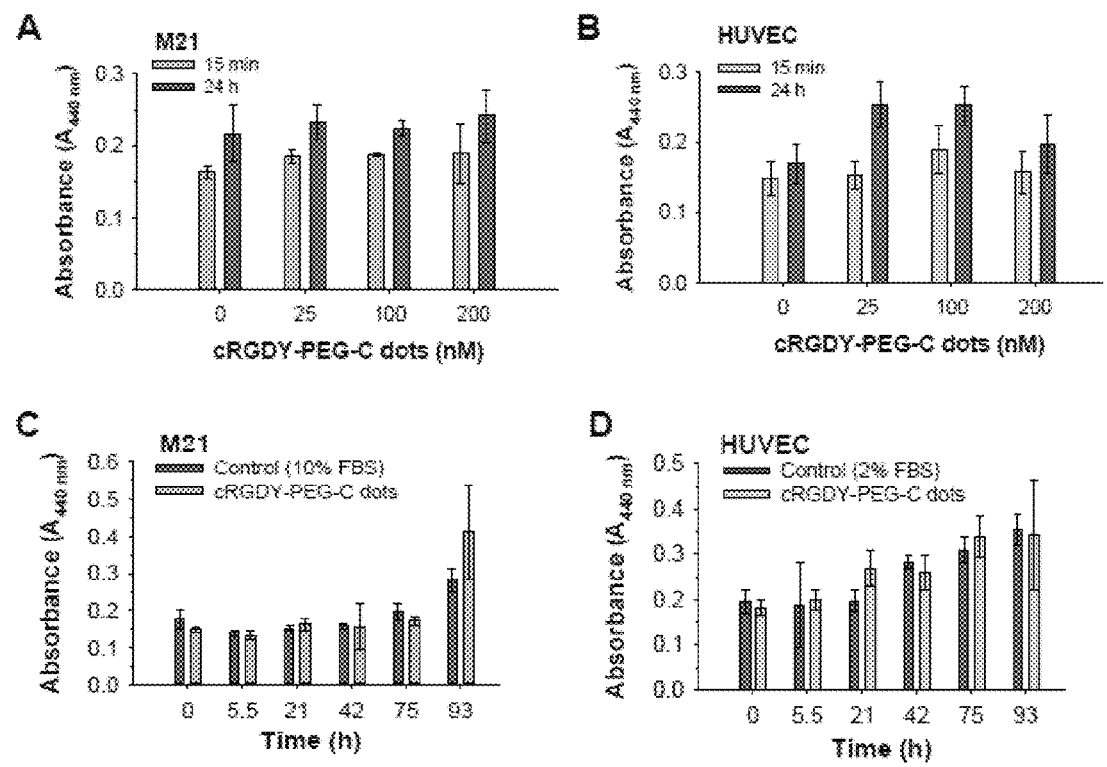
FIG. 49. Viability and proliferation of M21 and HUVEC cells as a function of particle concentration and incubation time. A, B. Absorbance ($\lambda_{ex}$=440 nm) as a measure of viability in subconfluent, $G_0/G_1$-phase-synchronized M21 (A) and HUVEC (B) cells over a 24 hour period using media supplemented with 10% or 2% FBS alone, respectively, or with addition of particles (25-200 nM). C, D. Cellular proliferative activity in M21 (C) and HUVEC (D) cells over a 93 h time interval using either media alone or particle-containing media, as specified in A, B.
Figure 50:
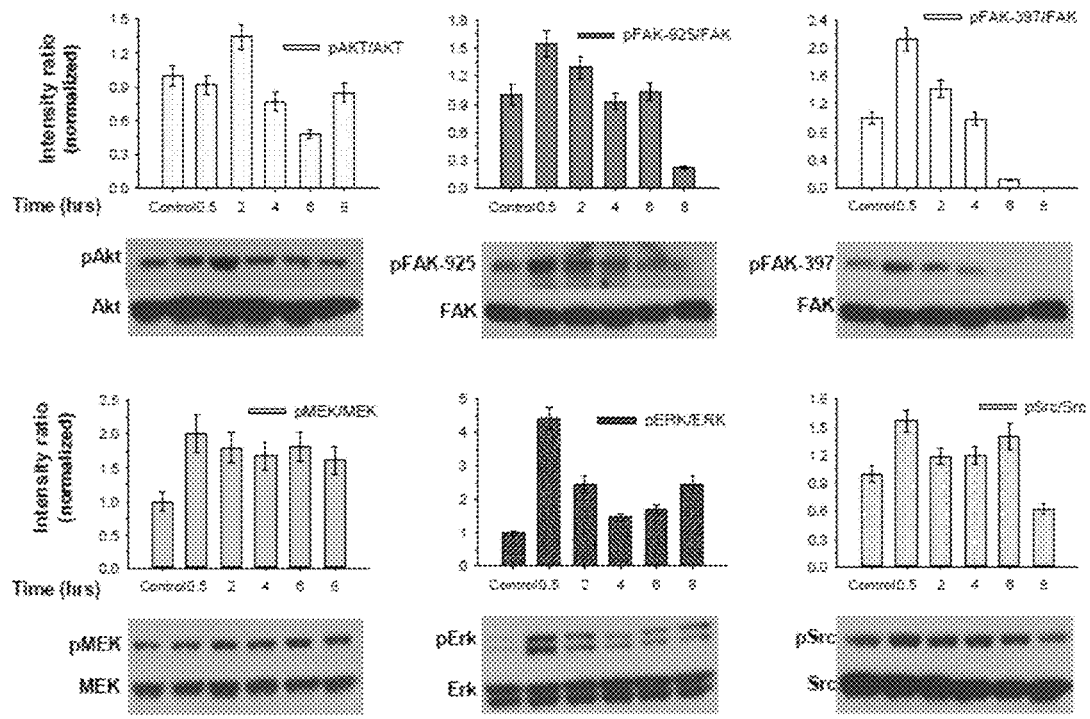
FIG. 50. Cell signaling changes as a function of particle incubation time in M21 cells. Western blots of selected phosphorylated and total protein intermediates over an 8 h time period. Normalized intensity ratios (i.e., difference of phospho-protein and total protein divided by the latter) are graphically illustrated.
Figure 51:
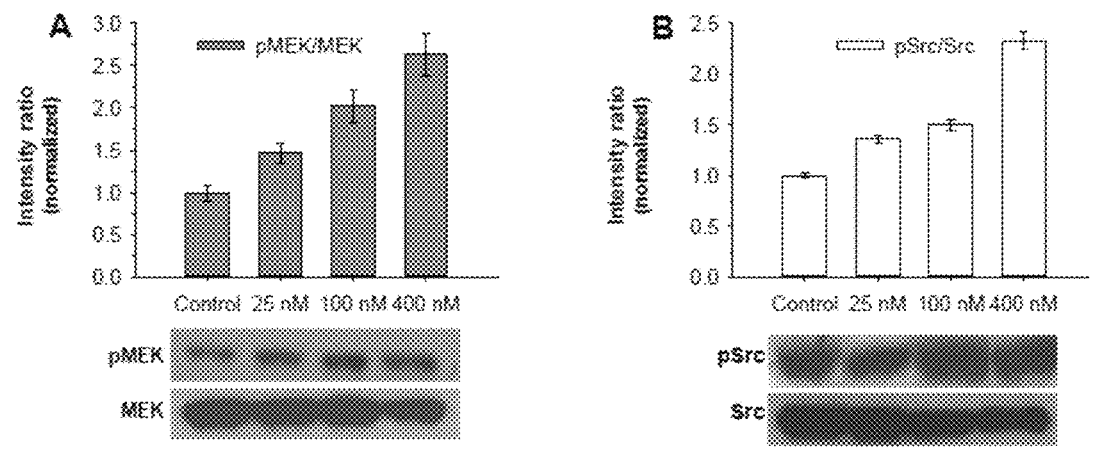
FIG. 51. Cell signaling modulation as a function of particle concentration in M21 cells. Western blots of selected phosphorylated and total protein intermediates over a range of particle concentrations (i.e., 0-400 nM).
Figure 52:
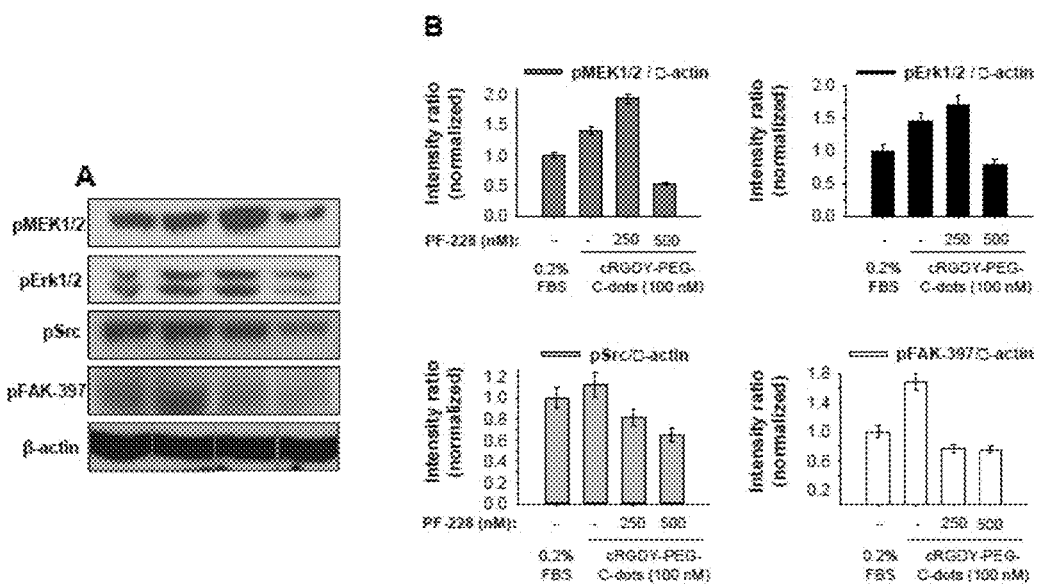
FIG. 52. Cell signaling inhibition studies in M21 cells. A. Western blots of selected phosphorylated and total protein intermediates (serum-deprived media, 100 nM particles alone, or 100 nM particles after addition of 250 nM or 500 nM inhibitor). B. Relative intensities of phospho-protein and $\beta$-actin blots in A relative to control cells (0.2% FBS).

To demonstrate that cRGDY-PEG-C dots did not adversely affect cell survival and proliferation, G0/G1 phase-synchronized M21 and HUVEC cells were exposed to a range of particle concentrations (25-200 nM cRGDY-PEG-C dots; 15 min or 24 hr) and incubation times (0-93 hrs) in serum-supplemented media (2%, 10% FBS) at 37° C., and time-dependent changes in absorbance were measured using an optical plate reader ($\lambda$=440 nm). Relative to controls (i.e., serum-supplemented media), absorbance measurements were seen to be relatively constant over the range of particle concentrations tested, suggesting no significant loss of cell survival (FIGS. 49A, 49B). Further, no time-dependent decreases in absorbance were found following multi-dose (n=5) addition of 100 nM cRGDY-PEG-C dots to M21 and HUVEC cells, suggesting no alteration in the proliferative properties of cells (FIGS. 49C, 49D).

Activation of the FAK Pathway by cRGDY-PEG-C-dots

Figure 40:
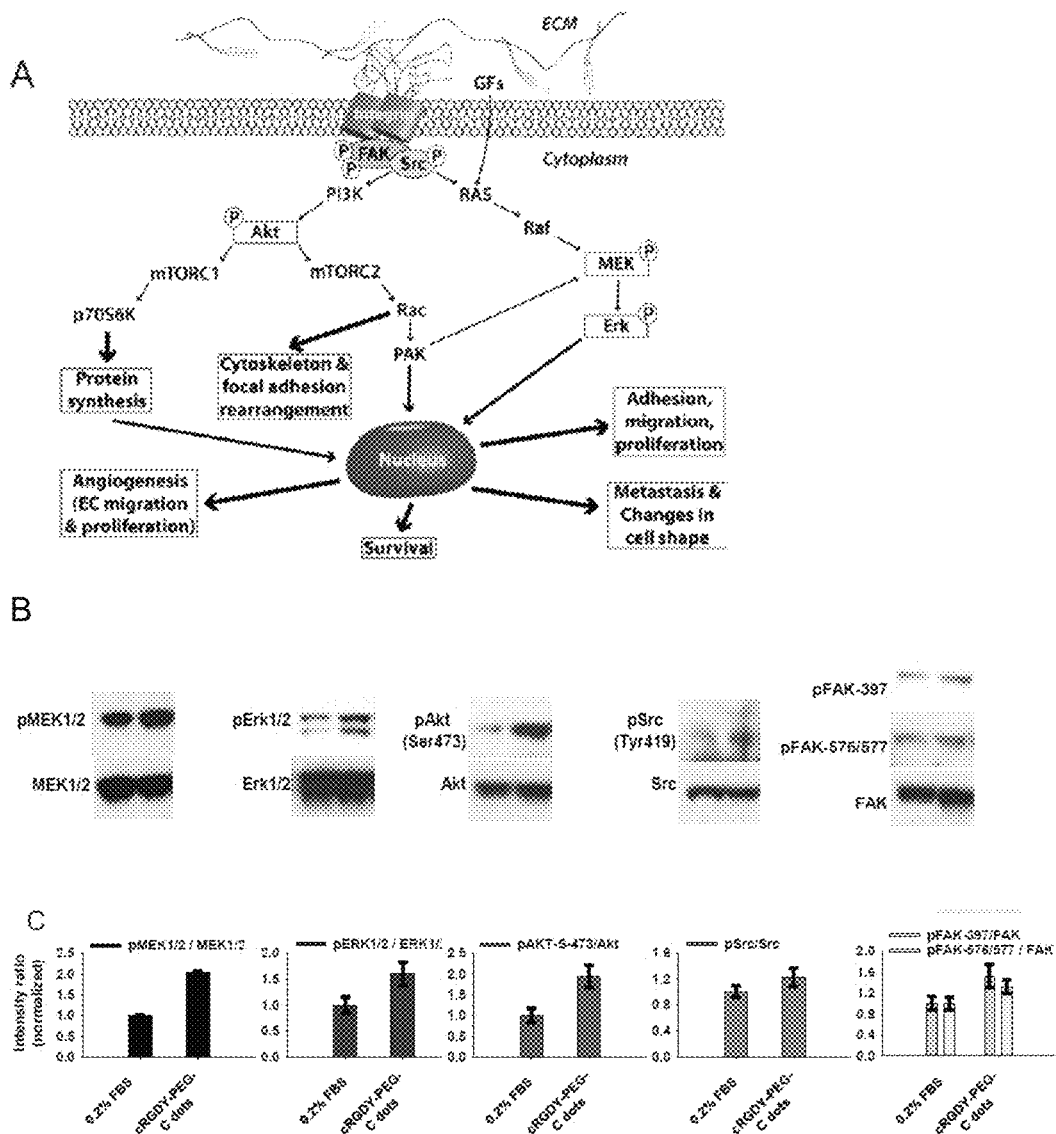
FIG. 40. Expression levels of phosphorylated FAK, Src, MEK, Erk1/2, and Akt in M21 cells. A. FAK/Src complex transduce signals from integrin cell surface receptors via activation of downstream signaling pathways (PI3K-Akt, Ras-MAPK) to elicit a range of biological responses (boxes indicate assayed protein intermediates). B. Western blots of phosphorylated and total protein expression levels of key pathway intermediates after exposure (2 h, 37° C.) of $G_0/G_1$ phase-synchronized M21 cells to 100 nM cRGDY-PEG-C-dots relative to cells in serum-deprived (0.2% FBS) media (i.e., control). After trypsinization of cells and re-suspension of the pellet in lysis buffer, proteins were resolved by 4-12% gradient SDS-PAGE and analyzed by anti-FAK 397, pFAK 576/577, p-Src, pMEK, pErk1/2, and pAkt antibodies. Antibodies against FAK, Src, MEK, Erk, and Akt were also used to detect the amount of total protein. C. Graphical summary of percent signal intensity changes in phosphorylated to total protein (Adobe Photoshop CS2; see Methods) for particle-exposed versus serum-deprived cells. GF, growth factors; EC, endothelial cell; ECM, extracellular matrix.

The binding of a ligand to the $\alpha_v\beta_3$ integrin receptor is known to initiate signal transduction pathways. Upon the binding, integrin clustering occurs which leads to autophosphorylation of the non-receptor kinase FAK at tyrosine 397, a binding site for the Src family kinases. Recruitment of Src kinase results in the phosphorylation of FAK at tyrosine 576/577 and FAK at tyrosine 925 in the carboxyl-terminal region. The phosphorylation of FAK at tyrosine 397 is also known to activate numerous signaling cascades and downstream pathway intermediates, such as the Ras-Mitogen Activated Protein (MAPK) signaling, which induces activation of Raf/MEK/Erk and phosphatidylinositol 3-kinase (PI3K)/AKT pathways (AKT, mTOR, S6K) (FIG. 40A).

To determine whether $\alpha_v\beta_3$ integrin-binding cRGDY-PEG-C-dots modulates the activity of these pathways, we treated serum-deprived (0.2% FCS) M21 cells with 100 nM of cRGDY-PEG-C-dots for 2 hrs at 37° C.; serum-deprived cells treated with 0.2% FCS alone served as controls. Western blot analyses of lysates from particle-exposed cells revealed enhancement of the phosphorylation levels of multiple protein intermediates: pFAK-397 and pFAK-576/577, Src, pMEK, pErk, and AkT (FIG. 40B), which suggested activation of downstream signaling pathways. These findings, depicted graphically as normalized intensity ratios, have been expressed relative to their respective total protein levels, and normalized to corresponding values measured under control conditions (FIG. 40C). Incubation of cells with PEG-C dots did not augment phosphorylation levels of the proteins tested (data not shown).

Figure 41:
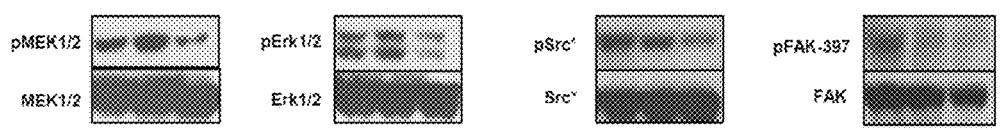
FIG. 41. Signaling induction and inhibition studies in M21 cells using PF-573228 (PF-228), a FAK inhibitor. A. Western blots of phosphorylated and total protein expression levels using the foregoing process of FIG. 2 with the addition of 250 nM or 500 nM PF-228 (0.5 h, 37° C.) to cells prior to particle exposure. B. Summary of percent intensity changes of phosphorylated to total protein expression levels in particle-exposed versus control cells with and without PF-228.
Figure 41:
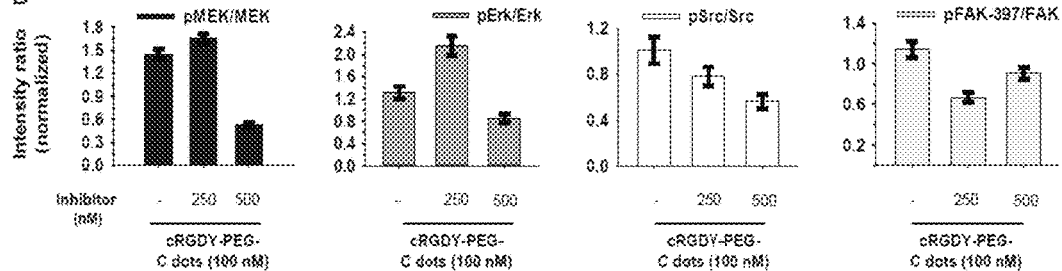

We evaluated whether the observed activation of downstream signaling pathways was dependent on the phosphorylation of FAK at tyrosine 397 by blocking this pathway with a small molecule inhibitor, PF-573228. This inhibitor interacts with FAK in the ATP-binding pocket and effectively blocks both the catalytic activity of FAK protein and subsequent FAK phosphorylation on $\text{Tyr}^{397}$. Following the addition of two concentrations of PF-573228 to serum-deprived M21 cells previously exposed to 100 nM cRGDY-PEG-C dots, Western blot analyses revealed inhibition of the phosphorylation of FAK on $\text{Tyr}^{397}$ and Src (FIG. 41A), graphically displayed in FIG. 41B Inhibition of MEK or Erk phosphorylation was observed only at the higher inhibitor concentration (FIGS. 41A, 41B).

Effect of cRGDY-PEG-C dots on Cellular Migration

Figure 42:
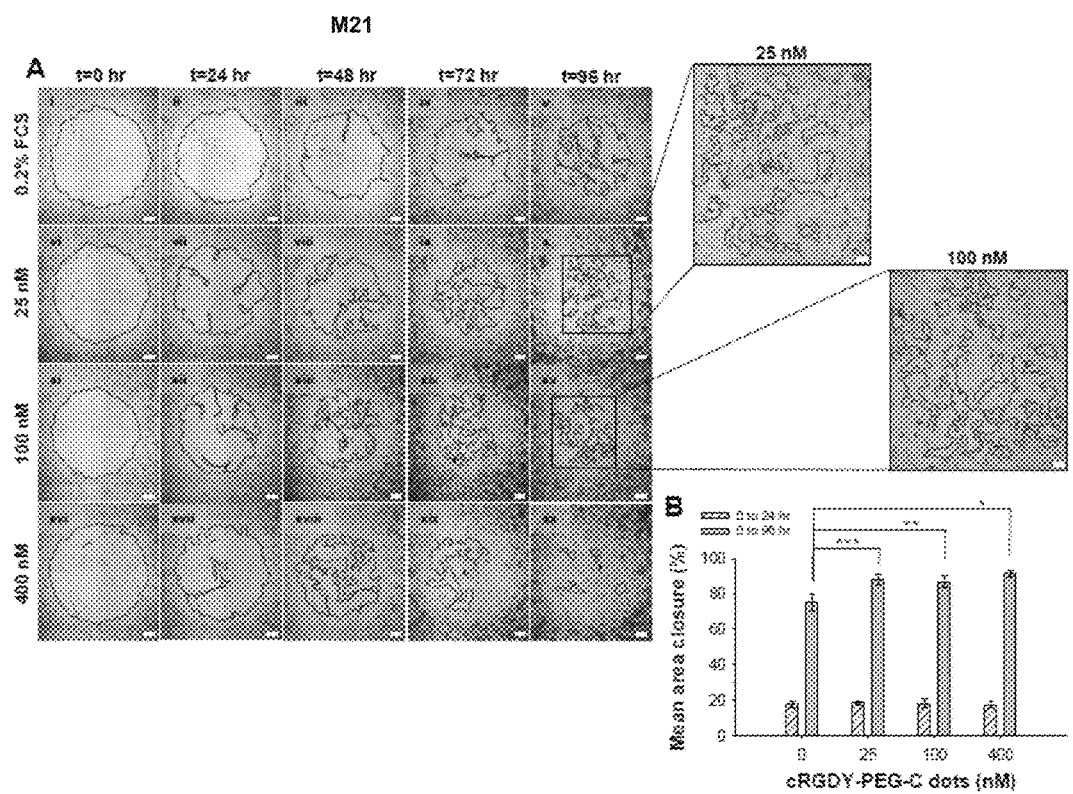
FIG. 42. Effect of cRGDY-PEG-C dots on M21 cellular migration using time lapse imaging. A. Time-dependent changes in cell migration using ORIS™ collagen coated plates for a range of particle concentrations (0-400 nM; 37° C.) in RPMI 1640 media supplemented with 0.2% FBS, as against supplemented media alone (controls). Images were captured at time t=0 (pre-migration) and at subsequent 24 h intervals following stopper removal by a Zeiss Axiovert 200M inverted microscope (5×/0.25NA objective) and a scan slide module (Metamorph® Microscopy Automation & Image Analysis Software) for a total of 96 hrs. B. Graphical plot of changes in the mean area of closure (%) as a function of concentration using ImageJ software. Mean area of closure represents the difference in the areas demarcated by the border of advancing cells (pixels) at arbitrary time points and after stopper removal (t=0), divided by the latter area. Quadruplicate samples were statistically tested for each group using a one-tailed t-test: *, p=0.011; , p=0.049; *, p=0.036. Scale bars=100 µm and 33 µm (magnified images of x and xv).

The $\alpha_v\beta_3$ integrin receptor, which is highly expressed on many types of tumor and angiogenic cells, is known to modulate a number of downstream biological processes, including cell migration, adhesion, proliferation, invasion, and angiogenesis. In the following experiments, we sought to determine whether cRGDY-PEG-C dots alter the migration of M21 and HUVEC cells. An initial set of experiments examined time-dependent changes in M21 cell migration, as reflected in mean areas of closure, using time-lapse imaging at three successively higher particle concentrations (0 nM-400 nM; 37° C.) during a 96-hour time period (FIG. 42A, i-xx). Statistically significant increases in mean area closure were observed over a 96-hr period, as a percentage of the baseline values (t=0), which were relatively constant for the particle concentration range used (i.e., ~87%-92%), as compared to control samples (73%; p<0.05) (FIG. 42A, B). No significant changes were seen at earlier time intervals (FIG. 42B).

Figure 43:
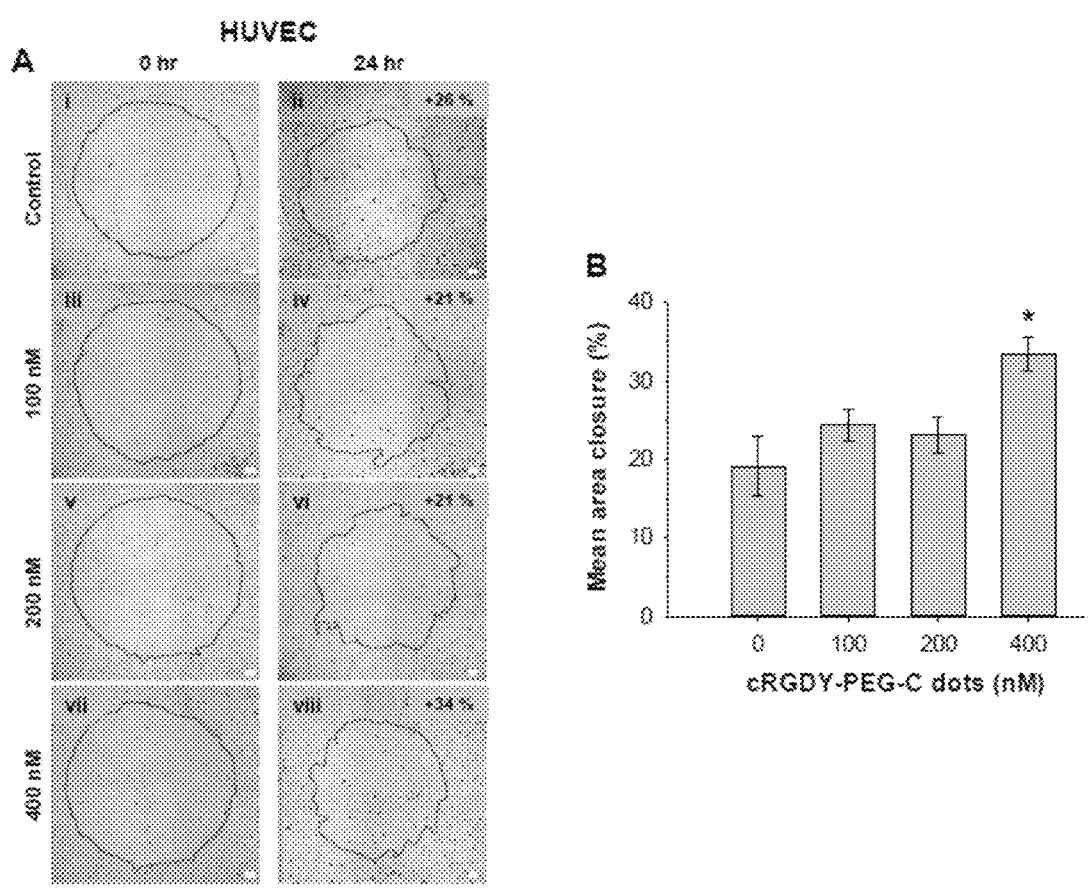
FIG. 43. Effect of cRGDY-PEG-C dots on the migration of HUVEC cells. A. Serial HUVEC migration was assayed using the same process in FIG. 4 over a 24-hr time interval. The displayed images and area of closure values indicated are representative of a single experiment. B. Mean areas of closure (%) were determined over this time interval for a range of particle concentrations (0-400 nM) using ImageJ software. Triplicate assays were performed for each concentration and time point. One-tailed t-test *, p<0.05. Scale bar=76 µm.

Incubation of HUVEC cells (37° C., 20 hours) with a range of cRGDY-PEG-C dot concentrations of (100-400 nM) in the presence of 0.2% FCS showed a statistically significant increase in the mean area closure for a concentration of 400 nM (i.e., 34%) (FIGS. 43A, 43B), as compared to 19% (p<0.05) for non-particle exposed cells. No appreciable change in migration was observed for the lower particle concentrations used (FIGS. 43A, 43B). Particle-exposed cells were seen to exhibit higher migration rates as compared to control cells.

Figure 44:
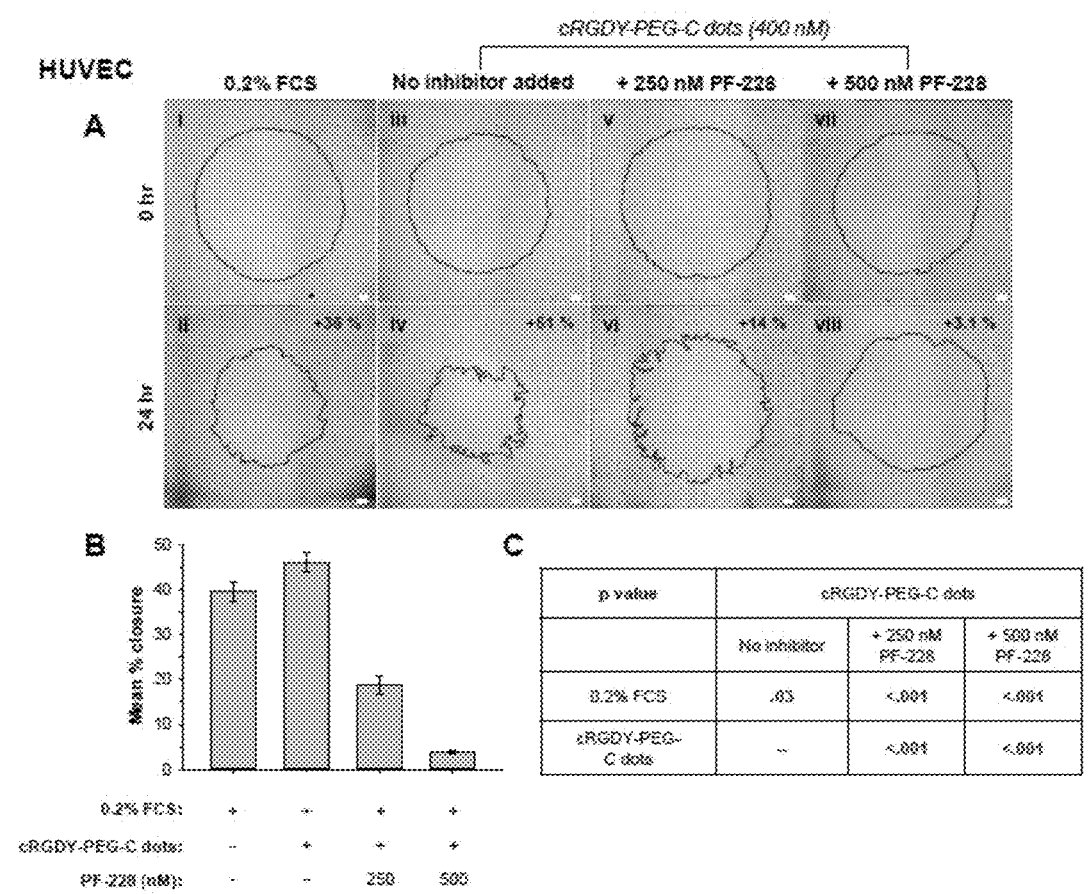
FIG. 44. Inhibition of HUVEC cell migration using PF-228. A. Same process as in FIG. 5, except cells were exposed to 250 nM and 500 nM PF-228 (0.5 h, 37° C.) prior to particle exposure or incubation in 0.2% FCS supplemented media. B. Mean area closure (%) for cells incubated under the foregoing conditions. C. Tabulated p values for each exposure condition using a one-tailed t-test. Quadruplicate samples were run for each inhibitor concentration. Scale bar=50 µm.

We further showed that increases in cell migration rates were attenuated by the addition of FAK inhibitor, PF-573228. Initial phase contrast images were acquired after incubating HUVEC cells with 400 nM particles over a 24 hour time interval (FIG. 44A, i-viii), and mean area closure was determined and graphically displayed relative to serum alone (FIG. 44B). Percentage change in mean areas of closure relative to controls, and before and after addition of an inhibitor, was seen to decrease from +34% to +3%. Statistically significant differences were found between values for particle-exposed cells without inhibitor ($p<0.03$) and particles treated with different inhibitor concentrations (250 nM, 500 nM; $p<0.001$) relative to serum-deprived controls; differences between the first two groups were also statistically significant (FIG. 44C).

Effect of cRGDY-PEG-C dots on Cellular Adhesion and Spreading

Figure 45:
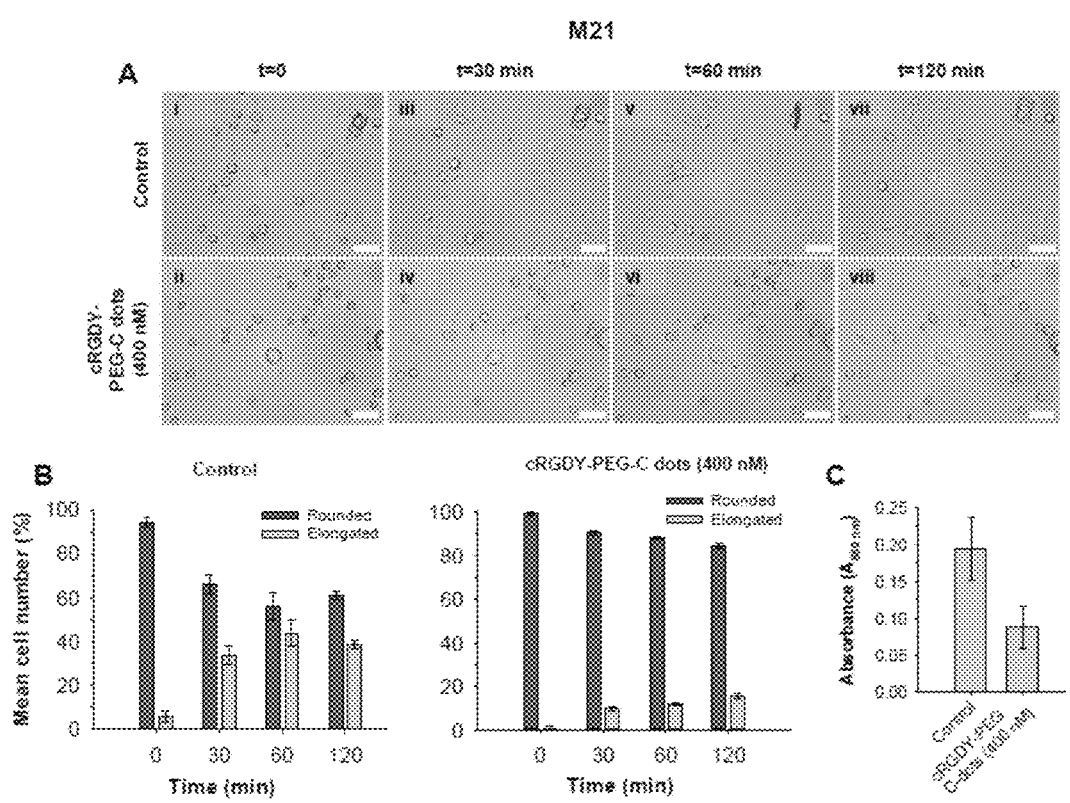
FIG. 45. Modulation of M21 cell spreading and adhesion using cRGDY-PEG-C dots. A. Time-lapse imaging showing changes in cellular attachment and spreading. Cells were pre-incubated in 0.2% FBS-supplemented RPMI (0.5 h, 25° C.), without and with particles (400 nM), followed by seeding in (5 µg/ml) fibronectin-coated 96-well plates. Images were captured at t=0, 0.5 h, 1 h, and 2 h using a Zeiss Axiovert 200M inverted microscope (20×/0.4NA objective) and a scan slide module in Metamorph®. B. Graphical plot showing the mean number of rounded and elongated cells within two groups as a function of time: non-particle exposed (elongated, graph #1) and particle exposed (rounded, graph #2). Cells in each of three wells of a 96-well plate were manually counted in a minimum of three high power fields (×200 magnification) and averaged. C. Absorbance ($\lambda$=650 nm; SpectroMax M5 microplate reader) values for 4% paraformaldehyde fixed cells, exposed to media or 400 nM cRGDY-PEG C-dots, and treated with methylene blue reagent (1 ml; 1 h, 37° C.), as a measure of cellular attachment. Scale bar=30 µm. Quadruplicate samples were run for each group.

The RGD tripeptide is known to be a component of extracellular matrix constituents, fibronectin and vitronectin. A competitive binding assay was performed using M21 cells ($10^4$ cells/well) pre-incubated (25° C., 30 minutes) with or without 400 nM cRGDY-PEG-C dots and fibronectin, after transferring cells to fibronectin-coated wells. About ~60% of the cells that were not pre-incubated with cRGDY-PEG-C-dots attached and spread on fibronectin coated plates in the first 30 minutes. By contrast, a very low percentage (15%) of M21 cells pre-incubated with 400 nM cRGDY-PEG-C-dots attached and spread on the fibronectin coated well, even 120 minutes after seeding (FIGS. 45A, 45B). Average cell counts of 'elongated' (spreading cells) versus 'rounded' cells over a 2 hour period revealed that in the absence of particles (i.e., control condition), cell spreading (elongated' cells) was observed in the majority of cells, while a predominantly 'rounded' appearance was seen in the case of particle-exposed cells (FIG. 45A). These results are graphically depicted in FIGS. 45B and 45C, respectively. Quantification of the optical densities of cells after addition of methylene blue (absorbance) revealed that cells which attached and spread on fibronectin (i.e., no particle pre-incubation) took up two times more methylene blue than particle-exposed cells (FIG. 45D). We observed the same phenomena if vitronectin-coated wells were used (data not shown). Altogether, these data demonstrate that cRGDY-PEG-C-dots enhanced the migration and spreading of cells through the binding to the integrin $\alpha_v\beta_3$ receptor found on M21 and HUVEC cells.

Influence of cRGDY-PEG-C dots on Cell Cycle in M21 Cells

Figure 46:
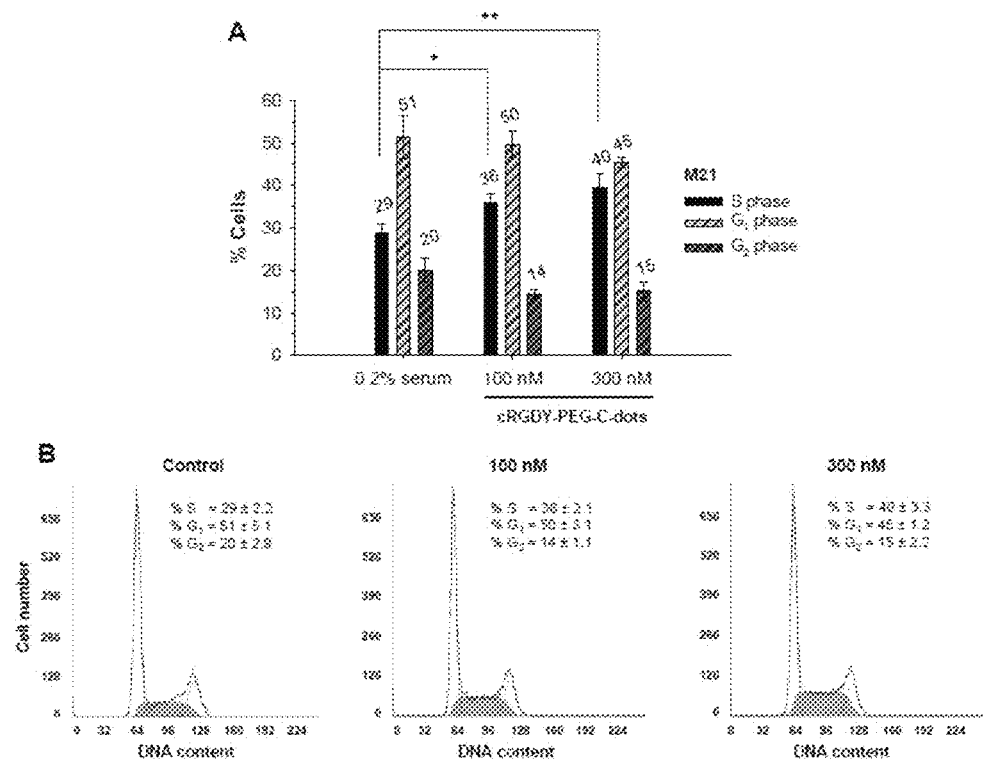
FIG. 46. Influence of cRGDY-PEG-C dots on cell cycle. A. Percentage (%) of viable cells in the $G_1$, S, and $G_2$ phases of the cell cycle as a function of particle concentration (0, 100, 300 nM) added to $G_0/G_1$-phase-synchronized M21 cells incubated for a total of 96 hours. Italicized numbers above each bar represent the percentage of cells (particle-incubated, control) in S, $G_1$ and $G_2$ phase, determined by flow cytometry. B. Representative cell cycle histograms are shown for cells under control (i.e., no particle) conditions and after incubation with 100 and 300 nM particles. One-way ANOVA: *, $p<0.05$; **, $p<0.005$ relative to S-phase control. Insets: Group mean values (n=3)±SD for each cell cycle phase. Experiments were performed in triplicate.

Since integrin receptors are involved in survival and proliferation of the cells, we analyzed the effect of cRGDY-PEG-C-dots on cell cycle. $G_0/G_1$-phase-synchronized M21 cells were incubated for 48 hours using two concentrations of cRGDY-PEG-C-dots (100 nM, 300 nM) in 0.2% FCS supplemented media. Over this range, the percentage of cells in the S phase rose by 11%, with statistical significance achieved at 100 nM ($p<0.05$) and 300 nM ($p<0.005$) in relation to controls (FIGS. 46A, 46B). Corresponding declines of 6% and 5% were seen in the G1 and G2 phases of the cell cycle, respectively. Taken together, these data indicate an enhancement in S phase in the presence of cRGDY-PEG-C dots.

Materials and Methods

Reagents, Antibodies and Chemicals.

RPMI 1640, fetal bovine serum (FBS), penicillin, streptomycin and HBSS (without calcium and magnesium containing 0.25% trypsin and 0.05% EDTA) were obtained from the Core Media Preparation Facility, Memorial Sloan Kettering Cancer Center (New York, N.Y.). Anti-polyclonal rabbit: phospho-Erk1/2 (p-Erk1/2$^{Thr\ 202/Tyr204}$), phospho-AKT (p-Akt$^{ser473}$)phospho-Src (p-Src$^{Tyr419}$)phospho-p70 S6 (p-p70S6$^{Thr389}$), phospho-MEK1/2 (p-MEK1/2$^{Ser217/221}$), phospho-FAK-$^{Tyr397}$, phospho-FAK-$^{Tyr576/577}$ phospho-FAK $^{Tyr925}$, Erk, AKT, Src, p70 S6, MEK1/2 (47E6) and FAK were obtained from Cell Signaling Technology (Danvers, Mass.). Goat anti-rabbit IgG, Goat anti-mouse IgG horseradish peroxidase (HRP) conjugates were acquired from Santa Cruz Biotechnology (Santa Cruz, Calif.). Propidium iodide, RNase A, Transferrin-Alexa Fluor 488 conjugate, FITC-Dextran, Fluorescein, LysoTracker Red DND-99, LysoTracker Green DND-26, pHrodo Red Dextran and Hoechst were procured from Invitrogen-Life Technologies (Carlsbad, Calif.). PF-573228 was obtained from TOCRIS bioscience (Ellisville, Mo.). Cyclo (Arg-Gly-Asp-D-Tyr-Cys) was from Peptides International (Louisville, Ky.).

Synthesis of cRGDY-PEG-C Dots and PEG-dots.

Fluorescent particles, containing the organic dye Cy5, were prepared by a modified Stöber-type silica condensation, as previously described. Tyrosine residues were conjugated to PEG chains for attachment of radioiodine. cRGDY peptides containing the sequence cyclo-(Arg-Gly-Asp-Tyr), and bearing cysteine residues (Peptide International), were attached to functionalized PEG chains via a cysteine-maleimide linkage. The number of cRGD ligands per nanoparticle was empirically calculated.

Mechanism of PEG Attachment to the C Dot Surface.

Bifunctional PEGs, MAL-dPEG®12-NHS ester (Quanta Biodesigns, Ltd) were derivatized with silanes, specifically 3-aminopropyl triethoxysilane (Gelest), for attachment to the silica surface and for peptide coupling via reactions between the sulfhydryl groups and maleimide moieties of the derivatized PEGs. In addition, methoxy-capped PEG chains were added to the particle surface using functional organosilicon compounds (Si compounds), specifically (MeO)3Si-PEG (Gelest), according to modified protocols. Briefly, (MeO)3Si-PEG was added, at approximately three molar excess, to particles in a water/alcohol basic mixture (~1:5 v/v), and the mixture stirred overnight at room temperature.

Hydrodynamic Size and Relative Brightness Comparison Measurements by Fluorescence Correlation Spectroscopy (FCS).

The hydrodynamic radius, brightness, and concentrations of cRGDY-PEG- and PEG-dots, as against free Cy5 dye, were initially determined by dialyzing these particle samples to water, diluting into physiological saline (0.15 M NaCl in $H_2O$), and analyzing the resulting specimens on a Zeiss LSM 510 Confocor 2 FCS using HeNe 633-nm excitation. The instrument was calibrated with respect to particle size prior to all measurements. Average hydrodynamic sizes of the dye and particle species were estimated based on diffusion time differences, while relative differences in brightness were assessed using count rates per molecule/particle.

Cells and Cell Culture:

Human melanoma cell line M21 and M21 variant M21L ($\alpha_v$ negative) were obtained from D. A. Cheresh (University of California, San Diego, Calif.). Cells were maintained in RPMI 1640 supplemented with 10% fetal bovine serum, 2 mM L-glutamine and Penicillin Streptomycin. Human Umbilical Vein Endothelial Cells (HUVECs) were obtained from LONZA (Walkersville, Md.) cultured in EGM-2 medium containing 2% FBS, and growth factors LONZA.

In Vitro Cell Binding Studies Using Optical Detection Methods:

To assay particle binding for M21, M21-L or HUVEC cells, 24-well plates were coated with 10 µg/ml collagen type I (BD Biosciences) in PBS, incubated at 37° C. for 30 minutes, and washed once with PBS. Cells ($3.0 \times 10^5$ cells/well to $4.0 \times 10^5$ cells/well) were grown to confluency. Differential binding of cRGDY-PEG-C-dots to M21 or HUVEC cells was evaluated over a range of incubation times (up to 4 hours) and particle concentrations (10-600 nM) using flow cytometry. After incubation, cells were washed with RPMI 1640 media/0.5% BSA, detached using 0.25% trypsin/EDTA, pelleted in a microcentrifuge tube (5 minutes at 153 g, 25° C.), re-suspended in BD FACSFlow solution (BD Biosciences), and analyzed in the Cy-5 channel to determine the percentage of particle-bound probe (FACSCalibur, Becton Dickinson, Mountain View, Calif.).

Internalization Study:

The experiment was done as above but incubated for 4 hours at three different temperatures: 4° C., 25° C. and 37° C. Co-incubation of excess (×250) cRGDY anti-human integrin $\alpha_v\beta_3$ fluorescein-conjugated antibody (Millipore, Billerica, Mass.) with cRGDY-PEG-C-dots was used for receptor blocking to assess specificity. Assays were performed with fixed and live cells. For fixed M21 cells, inverted confocal microscopy (Leica TCS SP2 AOBS) equipped with a HCX PL APO objective (63×1.2NA Water DIC D) was used and time-lapse imaging was used to track live M21 cells. Imaging was acquired following co-incubation of targeted (or control) particles at several concentrations with the following dye markers) for 4 hours: 70-kDa dextran—FITC conjugate (1 mg/mL, 37° C. for 30 min; Invitrogen) to label macropinosomes, Lysotracker Red (100 nM; Invitrogen) to label the endocytotic pathway (i.e., acidic organelles), and transferrin Alexa488 (2 µg/mL.

Competitive Binding Studies:

To assay specific binding M21 cells were incubated (25° C., 4 hours) with $^{124}$I-cRGDY-PEG-C-dots (25 nM) and excess cRGDY peptide. Cells were then washed with RPMI 1640 media/0.5% BSA, and dissolved in 0.5 ml of 0.2 M NaOH. Radioactivity was assayed using a 1480 Automatic Gamma Counter (Perkin Elmer) calibrated for iodine-124.

Western Blot (WB):

M21 cells ($1 \times 10^6$ cells/six wells plate) were grown in six wells coated with collagen (10 mg/ml), and made quiescent by growing under serum-deprived conditions. The medium was then changed to 0.2% FCS, and different concentrations (25-400 nM) of cRGDY-PEG-C-dots were added (37° C., 0.5-8 hours). Cells were rinsed twice in ice cold PBS, collected by trypsinization, and the pellet re-suspended in lysis buffer (10 mM Tris, pH-8.5, 150 mM NaCl, 1 mM EDTA, 1% Triton X-100; ACROS organics, NJ), 1% Na deoxycholate, 0.1% SDS, Complete™ protease inhibitors (Roche, Indianapolis, Ind.), and phosphatase inhibitor cocktail Tablet—PhosSTOP (Roche, Indianapolis, Ind.). Lysates were centrifuged (10 min, 4° C.). Protein concentrations were determined by the bicinchoninic acid assay (BCA, Thermo Scientific, Rockford, Ill.). A 50-µg protein aliquot of each fraction was separated by 4-12% gradient sodium dodecyl sulfate-polyacrylamide gel electrophoresis (SDS-PAGE) and transferred to a PVDF membrane (Invitrogen, Carlsbad, Calif.). Membranes were blocked with 5% non-fat dry milk (Bio-Rad, Hercules, Calif.) in Tris Buffered Saline (TBS)-Tween 0.1%, and signal visualized by ECL chemi-luminescence (Thermo Scientific, Rockford, Ill.) or Immobilon Western, (Millipore Billerica, Mass.) after applying primary (1:1000) and secondary (1:2000-1:5000) antibodies.

Cell Cycle Analysis:

$G_0/G_1$-phase-synchronized M21 cells were incubated for 48 hours using two concentrations (100 and 300 nM) of cRGDY-PEG-C-dots after changing the medium to 0.2% FCS. Following trypsinization, cells were centrifuged (1200 rpm, 5 min), and the pellet suspended in PBS, followed by fixation with 70% ethanol (4° C., 0.5-1 hour). Cells were successively re-suspended in 1 ml PBS containing 1% FCS and 0.1% Triton X-100, 200 µl PBS containing 25 µg/ml propidium iodide, and 100 mg/ml RNaseA (4° C., 60 minutes). Cell cycle analysis was performed by flow cytometry, FACSCalibur, (Mountain View, Calif.) and Phoenix Flow MultiCycle software (Phoenix Flow Systems, Inc., San Diego, Calif.).

Cell Proliferation:

Cells were split ($1 \times 10^4$ cells/well) in a 96-well plate coated with collagen as described in the in-vitro cell binding studies. Different concentrations of cRGDY-PEG-C-dots were added (25-200 nM) for 24-48 hours at 37° C. Then, 20 ml of the proliferation reagent WST-1 (Roche, Indianapolis, Ind.) was added to the plate (37° C., 1 hour). For determination of optical densities, we used a SpectraMax5 micro plate reader (Molecular Devices, Sunnyvale, Calif.). Absorbance was measured at 440 nm.

Migration Assay: M21 Cells:

M21 cells were seeded ($6 \times 10^4$ cells/well) using a migration kit (Oris™ Collagen I coated plate, PLATYPUS TEC). Twenty-four hours after seeding the cells, stoppers in the plate were removed. Fresh culture media (100 µl) supplemented with 0.2% FBS was introduced and cRGDY-PEG-C-dots were added at several concentrations: 25, 100 and 400 nM. Every 24 hours thereafter, media was replaced, along with new particles, over a 72 hr time interval. Prior to incubating the plate at 37° C. overnight, time zero images were captured by the Axiovert 200M microscope (Carl Zeiss) using a 5× (0.15NA) objective and using a scan slide module in the Metamorph software (molecular devices, PA). Serial microscopy was then performed and images captured every 24 hrs for a total of 96 hours post-incubation. The data were analyzed by using ImageJ software. HUVEC cells: HUVEC cells were additionally seeded ($5 \times 10^4$ cells/well) and, 24 hours later, incubated with several particle concentrations (100, 200, and 400 nM) after replacement of the media. A similar microscopy procedure was performed as that for M21 cells, with serial imaging acquired 20 hours later.

Adhesion and Spreading Assay:

The effect of cRGDY-PEG-C-dots on the binding of M21 cells to fibronectin coated plates was evaluated by initially coating 96-well micro titer plates with fibronectin in PBS (5 µg/ml), followed by 200 µl RPMI/0.5% BSA (37° C., 1 hour,). Cells ($1-3 \times 10^4$ cells/100 µl/well) were incubated (25° C., 30 minutes), with or without 400 nM of cRGDY-PEG-C-dots in RPMI/0.1% BSA, and added to fibronectin-coated wells (37° C., 30-120 minutes). For quantification of the number of attached cells, wells were rinsed with RPMI/0.1% BSA to remove non-adherent cells. Adherent cells were fixed with 4% PFA (25° C., 20 minutes) and stained with methylene blue (37° C., 1 hour). The methylene blue was extracted from cells by the addition of 200 ml of 0.1 M HCl (37° C., 1 hour). For determination of optical densities we used a SpectraMax5 micro plate reader and absorbance was measured at 650 nm. For spreading assay: Time lapse was performed (37° C., 2 hours) and images were captured by Axiovert 200M microscope (Carl Zeiss) using a 20× (0.15NA) objective and using a scan slide module in the Metamorph Software (Molecular Devices).

Quantitative Analyses:

In order to quantify the differences in the size and intensity between Western blot bands, we performed densitometry of phosphorylated and total protein intermediates using Photoshop CS2 (Adobe, San Jose, Calif.). Bands were scanned at 300 dpi (Scanjet 7650, Hewlett Packard, Palo Alto, Calif.), and converted to grayscale. The lasso tool was then used to draw a region of interest (ROI) within the boundaries of each band in order to derive the following: area (number of pixels), mean grayscale value within the selected area (0-255) and the associated standard deviation. The product of the first two values for each band was computed, and divided by the product for the initial band in each set (control band), yielding an intensity value for each sample relative to the control. Finally the ratio of phosphorylated protein to total protein and the corresponding propagated error (SD) were computed for each sample using the relative intensities.

Phase contrast images captured for migration studies were analyzed using ImageJ 1.45s (National Institutes of Health, rsbweb.nih.gov/ij/) in order to quantify the extent of cell migration (i.e., area closure) for M21 cells and HUVECs. At high power views, an enclosed area was drawn adjacent to the rim of attached cells seen in each image after stopper removal. The enclosed area for each image was measured (pixels) and used to calculate percent closure relative to time zero (following particle addition and media replacement) as follows: difference in area at a given time point (24, 48, 72 or 96 hr) and at time zero divided by the same area at time zero multiplied by 100. The resulting values were averaged and a standard error computed for each group.

Statistics:

All graphical values are plotted as mean±SE, except where noted. One-tailed Student's t-test was used to test the statistical significance of differences in cellular migration between HUVECs or M21 cells incubated with serum alone or cRGDY-PEG-C dots. One-way analysis of variance (ANOVA) was used to perform statistical pair-wise comparisons between the percentage of M21 cells in S phase that were incubated with serum alone, 100 nM or 300 nM cRGDY-PEG-C dots. We assigned statistical significance for all tests at $P<0.05$.

Example 17 Sphingomyelin Liposomes for Enhanced Tumor Delivery of Silica Diagnostic/Therapeutic Particles The therapeutic potential of sub-10 nm particles (e.g., C dots) as drug delivery vehicles is under investigation. Drug-bound particles have been developed by attaching drugs to particle-bound bifunctionalized PEG chains. Model drugs utilized for this proof-of-concept work are receptor tyrosine kinase (RTK) inhibitors. Delivery and accumulation of particles therapeutic payloads at the target site can be maximized by employing dose escalation strategies to assess for enhanced particle uptake and distribution within tumors by optical and/or PET imaging. An alternative approach to enhance particle load delivery utilizes liposomal formulations to encapsulate therapeutic particle probes. Liposomes passively target tumors via the enhanced permeability and retention (EPR) effect while protecting payloads from degradation in the circulation. Prior to particle encapsulation, either cRGDY or linker-drug conjugates will be attached to the particle surface as an active targeting mechanism to maximize delivery to the target site.

Once at the target site, release of particles from liposomal formulations into the tumor interstitium can occur as a result of upregulated enzymatic systems present in tumors. Extracellular release of acid sphingomyelinase (ASMase, acid SMase or SMase) from tumor cells in response to cellular stress, such as X-ray irradiation and toxins, leads to rapid ceramide-mediated cell injury and, subsequently, apoptosis. Acid SMase hydrolyzes sphingomyelin, present within the liposomal formulations, to ceramide. Ceramide has a role in biological systems as a secondary messenger in the apoptotic process. Ceramide has significantly different membrane properties than the parent molecule sphingomyelin. When sphingomyelin-containing liposomes are cleaved with SMase, there is a dramatic change in the membrane rigidity. Sphingomyelin is a suitable lipid for liposome formulation; this is not true for ceramide, as its incorporation as a liposome building block leads to liposome leakage. This leakage will lead to release of liposomal contents. This opens the possibility for the intracellular targeting of a large payload of silica nanoparticles, functionalized with drugs and/or cell-internalizing markers (i.e., peptide KLAKLAC and small molecule inhibitors) to monitor and/or treat disease.

To determine whether liposome encapsulation significantly increases particles delivery to the tumor site relative to non-encapsulated particle probes, we will utilize optical and PET imaging approaches to monitor uptake of both sphingomyelinase liposome encapsulated and non-encapsulated particle batches in EGFRmt+ expressing brain tumor xenograft models (i.e., H1650, A431) both liposomes and particle probes will contain optical markers for visualization.

Ref: Sochanik A1, Mitrus I, Smolarczyk R, Cichoń T, Snietura M, Czaja M, Szala S. Experimental anticancer therapy with vascular-disruptive peptide and liposome-entrapped chemotherapeutic agent. Arch Immunol Ther Exp (Warsz). 2010 June; 58(3):235-45.

The foregoing methods for detecting and targeting stressed cells involve a formulation comprised of bilayer liposomes each having an initial outer layer of liposome-forming lipids, sphingomyelin, or a mixture thereof; a second inner layer of liposome-forming lipids, sphingomyelin or a mixture thereof; the first and second layers forming a bilayer liposome and defining an interior space therein; wherein the interior space contains a silica nanoparticle. The silica nanoparticle and/or liposome will be compromised of optical markers and/or PET labels (dye, fluorophore, radiolabel, contrast agent), an enzyme substrate, and/or therapeutic agents, including cytotoxic drugs, DNA segments, or a radiotracer indicator label. The marker- and/or drug-labeled silica particles, contained within sphingomyelin liposomes, contact a cell sample under conditions wherein sphingomyelinase is present in or released by the cell. This enzymatic contact will, in turn, hydrolyze the sphingomyelin in the liposome to release the silica nanoparticle and/or marker label and/or drug from the hydrophilic (interior) or hydrophobic (bilayer) compartments of the liposome.

The scope of the present invention is not limited by what has been specifically shown and described hereinabove. Those skilled in the art will recognize that there are suitable alternatives to the depicted examples of materials, configurations, constructions and dimensions. Numerous references, including patents and various publications, are cited and discussed in the description of this invention. The citation and discussion of such references is provided merely to clarify the description of the present invention and is not an admission that any reference is prior art to the invention described herein. All references cited and discussed in this specification are incorporated herein by reference in their entirety. Variations, modifications and other implementations of what is described herein will occur to those of ordinary skill in the art without departing from the spirit and scope of the invention. While certain embodiments of the present invention have been shown and described, it will be obvious to those skilled in the art that changes and modifications may be made without departing from the spirit and scope of the invention. The matter set forth in the foregoing description and accompanying drawings is offered by way of illustration only and not as a limitation.

What is claimed is:

1. A method for detecting tumor cells in a human subject, comprising steps of:
   (a) administering to the human subject a plurality of multimodal silica-based nanoparticles in a dose ranging from about 0.01 nanomole/kg body weight to about 1 nanomole/kg body weight, each of the nanoparticles comprising:
      a silica-based core;
      a fluorescent compound within the core; and
      a silica shell surrounding at least a portion of the core, wherein each nanoparticle is coated with an organic polymer, wherein a plurality of discrete ligands no greater than 25 in number are attached to each polymer-coated nanoparticle for binding to a tumor marker, and wherein each of the polymer-coated nanoparticles with the ligands attached thereto has a hydrodynamic diameter within a range from 1 nm to 15 nm;
   (b) directing excitation light into the human subject to excite the fluorescent compound; and
   (c) imaging the nanoparticles,
the nanoparticles being excreted by renal clearance, by the human subject, within a range from 90% of initial dose (ID) to 100% ID in 24 hours after administration.

2. The method of claim 1, wherein the nanoparticles are administered subdermally, peritumorally, orally, intravenously, nasally, subcutaneously, intramuscularly or transdermally.

3. The method of claim 1, wherein the nanoparticle has a diameter between about 1 nm and about 8 nm.

4. The method of claim 1, wherein the organic polymer is selected from the group consisting of poly(ethylene glycol) (PEG), polylactate, polylactic acids, sugars, lipids, polyglutamic acid (PGA), polyglycolic acid, poly(lactic-co-glycolic acid) (PLGA), polyvinyl acetate (PVA), and the combinations thereof.

5. The method of claim 1, wherein the plurality of discrete ligands is not greater than 10 in number.

6. The method of claim 1, wherein each of the ligands is selected from the group consisting of a peptide, protein, biopolymer, synthetic polymer, antigen, antibody, microorganism, virus, receptor, hapten, enzyme, hormone, chemical compound, pathogen, toxin, surface modifier, and combinations thereof.

7. The method of claim 6, wherein each of the ligands is a peptide and the peptide is selected from the group consisting of tripeptide arginylglycylaspartic acid (RGD), cyclic peptide cRGD, octreotate, EPPT1 and peptide analogs of alpha-melanocyte-stimulating hormone (MSH).

8. The method of claim 1, wherein a contrast agent or a chelate is attached to the nanoparticle.

9. The method of claim 8, wherein the contrast agent is a radionuclide.

10. The method of claim 9, wherein the radionuclide is selected from the group consisting of $^{89}$Zr, $^{64}$Cu, $^{68}$Ga, $^{86}$Y, $^{124}$I and $^{177}$Lu.

11. The method of claim 8, wherein the chelate is adapted to bind a radionuclide.

12. The method of claim 8, wherein the chelate is selected from the group consisting of DFO, DOTA, TETA and DTPA.

13. The method of claim 1, wherein the nanoparticles are detectable by PET, SPECT, CT, MRI, optical imaging, bioluminescence imaging, or combinations thereof.

14. The method of claim 13, wherein the nanoparticles are detectable by optical imaging, wherein the optical imaging is fluorescence imaging.

15. The method of claim 1, wherein a therapeutic agent is attached to at least one of the nanoparticles.

16. The method of claim 15, wherein the therapeutic agent is selected from the group consisting of antibiotics, antimicrobials, antiproliferatives, antineoplastics, antioxidants, endothelial cell growth factors, thrombin inhibitors, immunosuppressants, anti-platelet aggregation agents, collagen synthesis inhibitors, therapeutic antibodies, nitric oxide donors, antisense oligonucleotides, wound healing agents, therapeutic gene transfer constructs, extracellular matrix components, vasodialators, thrombolytics, anti-metabolites, growth factor agonists, antimitotics, statin, steroids, steroidal and non-steroidal anti-inflammatory agents, angiotensin converting enzyme (ACE) inhibitors, free radical scavengers, PPAR-gamma agonists, small interfering RNA (siRNA), microRNA, and anti-cancer chemotherapeutic agents.

17. The method of claim 15, wherein the therapeutic agent is radiolabeled.

18. The method of claim 17, wherein the therapeutic agent is bound to radiofluorine $^{18}$F.

19. The method of claim 15, wherein the therapeutic agent is a radionuclide.

20. The method of claim 19, wherein the radionuclide is selected from the group consisting of $^{90}$Y, $^{131}$I and $^{177}$Lu.

21. The method of claim 1,
   wherein the nanoparticles are encapsulated by liposomes comprising sphingomyelin, and
   wherein at least of portion of the nanoparticles are released from the liposomes when the liposomes are exposed to acid sphingomyelinase released by the tumor cells.

22. The method of claim 1, further comprising at least one of:
   (i) detecting or monitoring a cellular abnormality or disease using at least one or more images of the human subject; and
   (ii) detecting or monitoring normal tissue structures by marking and discriminating the normal tissue structures, neural tissues, and/or vascular structures that are present within or lie adjacent to a surgical bed.

23. The method of claim 22, wherein the cellular abnormality or disease comprises at least one member selected from the group consisting of inflammation, cancer, cardiovascular disease, respiratory disease, dermatologic disease, ophthalmic disease, infectious disease, immunologic disease, central nervous system disease, inherited diseases, metabolic diseases, environmental diseases, bone-related disease, neurodegenerative disease, and surgery-related complications.

24. The method of claim 22, wherein the cellular abnormality or disease is metastatic melanoma in a sentinel lymph node.

25. The method of claim 22, wherein the cellular abnormality or disease is an abnormality of peripheral nerves or nodal disease.

26. The method of claim 14, wherein imaging the nanoparticles comprises detecting fluorescence from the nanoparticles with a portable detection device.

27. The method of claim 26, further comprising displaying at least one dual-channel image of a nodal basin to a user.

28. The method of claim 27, wherein the dual-channel image includes a red-green-blue (RGB) color image and a near infrared (NIR) image.

29. The method of claim 1, wherein the method further comprises ablating detected tumor cells using radiofrequency ablation (RFA).

30. The method of claim 1, wherein directing excitation light and using a gamma probe are performed simultaneously.

31. The method of claim 1, wherein the nanoparticles are excreted such that the nanoparticles in a liver of the human subject 4 hours after administering is less than 0.010% injected dose per gram (Dig).

32. The method of claim 1, wherein each of the nanoparticles is detected using a gamma probe.

33. The method of claim 1, wherein the organic polymer comprises polyethylene glycol, wherein the polyethylene glycol is attached to a silica surface of the nanoparticle via an amino-silane coupled to an activated ester group on the organic polymer leading to an amide bond.

34. The method of claim 6, wherein each of the ligands is a peptide and the peptide is an RGD-containing peptide.

35. The method of claim 34, wherein at least one of the nanoparticles is coated with maleimido-terminated polyethylene glycol chains for attachment of the plurality of RGD-containing peptide ligands no greater than 25 in number.

36. The method of claim 34, wherein the RGD-containing peptide is cyclic.

37. The method of claim 36, wherein at least one of the nanoparticles is coated with maleimido-terminated polyethylene glycol chains for attachment of the plurality of RGD-containing peptide ligands no greater than 25 in number, and wherein at least one cyclic RGD-containing peptide ligand is attached to a maleimido-terminated polyethylene glycol chain via a thiol group of a cysteine linker.

38. The method of claim 37, wherein the plurality of RGD-containing peptide ligands no greater than 25 in number are labeled with a radionuclide.

39. The method of claim 38, wherein the plurality of RGD-containing peptide ligands no greater than 25 in number are labeled with the radionuclide via a tyrosine (Y) linker.

40. The method of claim 1, wherein the fluorescent compound is Cy5.

41. The method of claim 1, wherein the fluorescent compound is Cy5.5.

42. A method for dual-channel optical imaging of a region within a human subject, the method comprising:
(a) administering to the human subject a plurality of multimodal silica nanoparticles, each of the nanoparticles comprising:
a silica-based core;
a fluorescent compound within the core; and
a silica shell surrounding at least a portion of the core, wherein each nanoparticle is coated with an organic polymer, wherein a plurality of discrete ligands no greater than 25 in number are attached to each polymer-coated nanoparticle for binding to a tumor marker, and wherein each of the polymer-coated nanoparticles with the ligands attached thereto has a hydrodynamic diameter within a range from 1 nm to 15 nm;
(b) directing light into the human subject;
(c) detecting light via a first channel and a second channel, wherein the first channel and the second channel of the dual channel optical imaging system are at different wavelengths; and
(d) processing the signals corresponding to the detected light to provide one or more images of the region of the human subject.

43. The method of claim 42, wherein the first channel detects red, green, and blue (RGB) light.

44. The method of claim 43, wherein the second channel detects near infrared (NIR) fluorescence.

45. The method of claim 42, wherein the images are provided in real time.

46. The method of claim 1, wherein a blood residence half time of the nanoparticle after administration is from 2 hours to 25 hours, from 3 hours to 15 hours, or from 4 hours to 10 hours.

47. The method of claim 1, wherein a tumor residence half time of the nanoparticle after administration is from 5 hours to 5 days, from 10 hours to 4 days, or from 15 hours to 3.5 days.

48. The method of claim 42, wherein a therapeutic agent is attached to at least one of the nanoparticles.

* * * * *

UNITED STATES PATENT AND TRADEMARK OFFICE
CERTIFICATE OF CORRECTION

PATENT NO. : 9,999,694 B2  
APPLICATION NO. : 14/215879  
DATED : June 19, 2018  
INVENTOR(S) : Bradbury et al.

Page 1 of 1

It is certified that error appears in the above-identified patent and that said Letters Patent is hereby corrected as shown below:

On the Title Page

In the "( * ) Notice" item, please delete the repeated "days.".

In the Claims

In Claim 31, Column 91, please delete "(Dig)" and replace with --(ID/g)--.

Signed and Sealed this  
Thirty-first Day of July, 2018

Andrei Iancu  
*Director of the United States Patent and Trademark Office*